United States Patent
Hupe et al.

(10) Patent No.: US 8,450,301 B2
(45) Date of Patent: May 28, 2013

(54) PIPERAZINE COMPOUNDS WITH A HERBICIDAL ACTION

(75) Inventors: Eike Hupe, Ludwigshafen (DE); Cyrill Zagar, Hong Kong (CN); Matthias Witschel, Bad Dürkheim (DE); Toralf Kühn, Mannheim (DE); William Karl Moberg, Haßloch (DE); Liliana Parra Rapado, Offenburg (DE); Frank Stelzer, Mannheim (DE); Andrea Vescovi, Mannheim (DE); Michael Puhl, Lampertheim (DE); Robert Reinhard, Limburgerhof (DE); Bernd Sievernich, Haßloch (DE); Klaus Großmann, Neuhofen (DE); Thomas Ehrhardt, Speyer (DE); Michael Rack, Eppelheim (DE)

(73) Assignee: BASF SE, Ludwigshafen (DE)

( * ) Notice: Subject to any disclaimer, the term of this patent is extended or adjusted under 35 U.S.C. 154(b) by 438 days.

(21) Appl. No.: 12/159,712

(22) PCT Filed: Dec. 29, 2006

(86) PCT No.: PCT/EP2006/070271
§ 371 (c)(1),
(2), (4) Date: Jun. 30, 2008

(87) PCT Pub. No.: WO2007/077201
PCT Pub. Date: Jul. 12, 2007

(65) Prior Publication Data
US 2009/0156553 A1    Jun. 18, 2009

(30) Foreign Application Priority Data
Jan. 2, 2006   (EP) ..................... 06000013

(51) Int. Cl.
*A01N 43/00* (2006.01)
*A61K 31/33* (2006.01)

(52) U.S. Cl.
USPC .......... 514/183; 514/63; 514/64; 514/255.02; 560/24; 544/229; 544/385

(58) Field of Classification Search
USPC .............. 514/255.02, 183, 358; 544/358
See application file for complete search history.

(56) References Cited

U.S. PATENT DOCUMENTS

| 6,972,289 | B1 * | 12/2005 | Kanzaki et al. | .......... 514/254.05 |
| 2003/0171379 | A1 | 9/2003 | Jacobs et al. | |

FOREIGN PATENT DOCUMENTS

| CN | 1557961 A | 12/2004 |
| EP | 0181152 A1 | 5/1986 |
| EP | 0243122 A2 | 10/1987 |
| WO | WO-99/48889 A1 | 9/1999 |
| WO | WO-01/53290 A1 | 7/2001 |
| WO | WO 0153290 A1 * | 7/2001 |
| WO | WO-2005/011699 A1 | 2/2005 |

OTHER PUBLICATIONS

STN accession No. 2005:62672 as evidenced by CN 1557961.*
Translation of CN1557961A.*
King, R.R., et al., "Herbicidal properties of the thaxtomin group phytotoxins," J. Agric. Food Chem., 2001, vol. 49, pp. 2298-2301.
King, R.R., et al., Chemistry of phytotoxins assoiciated with *Streptomyces scabies*, the causal organism of potato common scab, J. Agric. Food Chem., 1992, vol. 40, pp. 834-837.
Wang, L.X., et al., "A rapid and effective method for the declaration of 1,4-diaacetyl-2, 5-piperazinedione and its derivatives," Chinese Chemical Letters, 1993, vol. 4, No. 8, pp. 687-688.
Balboni, G., et al., "Opioid diketopiperazines: synthesis and activity of a prototypic class of opioid antagonists," Biol. Chem., 1997, vol. 378, pp. 19-29.

* cited by examiner

*Primary Examiner* — Brandon Fetterolf
*Assistant Examiner* — Jean Cornet
(74) *Attorney, Agent, or Firm* — Novak Druce Connolly Bove + Quigg LLP

(57) ABSTRACT

The invention relates to the use of piperazine compounds of formula (I) or the agriculturally useful salts of piperazine compounds of formula (I) as herbicides, the variables in formula (I) being defined as cited in the claims and the description.

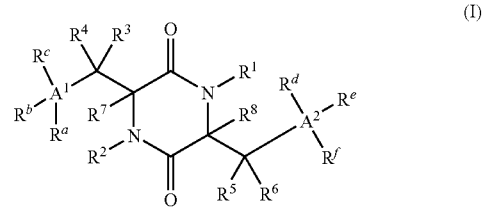

(I)

10 Claims, No Drawings

PIPERAZINE COMPOUNDS WITH A HERBICIDAL ACTION

RELATED APPLICATIONS

This application is a national stage application (under 35 U.S.C. §371) of PCT/EP2006/070271, filed Dec. 29, 2006, which claims benefit of European application 06000013.0, filed Jan. 2, 2006.

The present invention relates to the use of piperazine compounds of the formula I

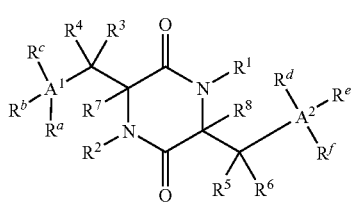

or of the agriculturally useful salts of piperazine compounds of the formula I as herbicides, where in formula I the variables are as defined below:

$R^1$ and $R^2$ independently of one another are:
cyano, $C_1$-$C_6$-alkyl, $C_3$-$C_6$-cycloalkyl, $C_3$-$C_6$-alkenyl, $C_3$-$C_6$-cycloalkenyl, $C_3$-$C_6$-alkynyl, $C_3$-$C_6$-cycloalkynyl, phenyl, phenyl-($C_1$-$C_6$)-alkyl, heterocyclyl, heterocyclyl-($C_1$-$C_6$)-alkyl; phenyl-[$C_1$-$C_6$-alkoxycarbonyl]-($C_1$-$C_6$)-alkyl or phenyl-heterocyclyl-($C_1$-$C_6$)-alkyl; or $COR^{21}$, where
$R^{21}$ is hydrogen, $C_1$-$C_6$-alkyl, $C_3$-$C_6$-cycloalkyl, $C_2$-$C_6$-alkenyl, $C_3$-$C_6$-cycloalkenyl, $C_2$-$C_6$-alkynyl, $C_3$-$C_6$-cycloalkynyl, hydroxyl, $C_1$-$C_6$-alkoxy, $C_3$-$C_6$-alkenyloxy, $C_3$-$C_6$-alkynyloxy, amino, $C_1$-$C_6$-alkylamino, [di-($C_1$-$C_6$)-alkyl]amino, $C_3$-$C_6$-alkenylamino, $C_3$-$C_6$-alkynylamino, $C_1$-$C_6$-alkylsulfonyl-amino, N—($C_2$-$C_6$-alkenyl)-N—($C_1$-$C_6$-alkyl)amino, N—($C_2$-$C_6$alkynyl)-N—($C_1$-$C_6$-alkyl)amino, N—($C_1$-$C_6$-alkoxy)-N—($C_1$-$C_6$-alkyl)amino, N—($C_2$-$C_6$-alkenyl)-N—($C_1$-$C_6$-alkoxy)amino, N—($C_2$-$C_6$-alkynyl)-N—($C_1$-$C_6$-alkoxy)amino, phenyl, phenylamino, phenoxy, naphthyl or heterocyclyl; or
$NR^{22}R^{23}$ where
$R^{22}$ and $R^{23}$ independently of one another are hydrogen, $C_1$-$C_6$-alkyl, $C_3$-$C_6$-cycloalkyl, $C_3$-$C_6$-alkenyl, $C_3$-$C_6$-cycloalkenyl, $C_3$-$C_6$-alkynyl, $C_3$-$C_6$-cycloalkynyl or $C_1$-$C_6$-alkylcarbonyl; or
$OR^{24}$ where
$R^{24}$ is $C_1$-$C_6$-alkyl, $C_3$-$C_6$-cycloalkyl, $C_3$-$C_6$-alkenyl, $C_3$-$C_6$-cycloalkenyl, $C_3$-$C_6$-alkynyl, $C_3$-$C_6$-cycloalkynyl, phenyl or phenyl-($C_1$-$C_6$)-alkyl; or
$SO_2R^{25}$, where
$R^{25}$ is $C_1$-$C_6$-alkyl or phenyl;
where the above-mentioned aliphatic, cyclic or aromatic moieties of the substituents of $R^1$ and $R^2$ may be partially or fully halogenated and/or may carry one to three of the following groups: cyano, hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-alkylthio, [di-($C_1$-$C_4$)-alkyl]amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, [di-($C_1$-$C_4$)-alkyl]aminocarbonyl or $C_1$-$C_4$-alkylcarbonyloxy;
and where $R^1$ may additionally be hydrogen, $R^3$ is a radical $R^{26}$, $OR^{27}$, $SR^{28}$, $NR^{29}R^{30}$ or $N(OR^{31})R^{32}$ where
$R^{25}$, $R^{27}$, $R^{28}$, $R^{79}$ and $R^{32}$ independently of one another are hydrogen, $C_1$-$C_6$-alkyl, $C_3$-$C_6$-cycloalkyl, $C_3$-$C_6$-alkenyl, $C_3$-$C_6$-alkynyl, $C_3$-$C_6$-haloalkynyl, formyl, $C_1$-$C_6$-alkylcarbonyl, $C_3$-$C_6$-cycloalkylcarbonyl, $C_2$-$C_6$-alkenylcarbonyl, $C_2$-$C_6$-alkynyl-carbonyl, $C_1$-$C_6$-alkoxy-($C_1$-$C_6$)-alkyl, $C_1$-$C_6$-alkoxycarbonyl, $C_2$-$C_6$-alkenyloxy-carbonyl, $C_3$-$C_6$-alkynyloxycarbonyl, $C_1$-$C_6$-alkylaminocarbonyl, $C_3$-$C_6$-alkenyl-aminocarbonyl, $C_3$-$C_6$-alkynylaminocarbonyl, $C_1$-$C_6$-alkylsulfonylaminocarbonyl, $C_1$-$C_6$-alkylaminocarbonyl, [di-($C_1$-$C_6$)-alkylamino]carbonyl, N—($C_3$-$C_6$-alkenyl)-N—($C_1$-$C_6$-alkyl)-aminocarbonyl, N—($C_3$-$C_6$-alkynyl)-N—($C_1$-$C_6$-alkyl)-aminocarbonyl, N—($C_1$-$C_6$-alkoxy)-N—($C_1$-$C_6$-alkyl)-aminocarbonyl, N—($C_3$-$C_6$-alkenyl)-N—($C_1$-$C_6$-alkoxy)-aminocarbonyl, N—($C_3$-$C_6$-alkynyl)-N—($C_1$-$C_6$-alkoxy)-aminocarbonyl, di-($C_1$-$C_6$-alkyl)-aminothiocarbonyl, $C_1$-$C_6$-alkylcarbonyl-$C_1$-$C_6$-alkyl, $C_1$-$C_6$-alkoxy-imino-$C_1$-$C_6$-alkyl, N—($C_1$-$C_6$-alkylamino)imino-$C_1$-$C_6$-alkyl, N-(di-$C_1$-$C_6$-alkyl-amino)imino-$C_1$-$C_6$-alkyl or [tri-($C_1$-$C_4$)-alkyl]silyl, where the above-mentioned aliphatic or isocyclic moieties of the substituents may be partially or fully halogenated and/or may carry one to three of the following groups: cyano, hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-alkylthio, [di-($C_1$-$C_4$)-alkyl]amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, [di-($C_1$-$C_4$)-alkyl]-aminocarbonyl or $C_1$-$C_4$-alkylcarbonyloxy; or
phenyl, phenyl-$C_1$-$C_6$-alkyl, phenylcarbonyl, phenylcarbonyl-$C_1$-$C_6$-alkyl, phenoxy-carbonyl, phenylaminocarbonyl, phenylsulfonylaminocarbonyl, N—($C_1$-$C_6$-alkyl)-N-(phenyl)aminocarbonyl, phenyl-$C_1$-$C_6$-alkylcarbonyl, heterocyclyl, heterocyclyl-$C_1$-$C_6$-alkyl, heterocyclylcarbonyl, heterocyclylcarbonyl-$C_1$-$C_6$-alkyl, heterocyclyloxycarbonyl, heterocyclylaminocarbonyl, heterocyclylsulfonyl-aminocarbonyl, N—($C_1$-$C_6$-alkyl)-N-(heterocyclyl)aminocarbonyl, or heterocyclyl-$C_1$-$C_6$-alkylcarbonyl, where the phenyl or heterocyclyl moieties of the substituents may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy; or
$S(O)_nR^{33}$, where
n is 1 or 2; and
$R^{33}$ is $C_1$-$C_6$-alkyl, $C_1$-$C_6$-haloalkyl or phenyl, and where the phenyl substituent may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy; and
$R^{30}$ and $R^{31}$ independently of one another are hydrogen, $C_1$-$C_6$-alkyl, $C_3$-$C_6$-cycloalkyl, $C_2$-$C_6$-alkenyl, $C_2$-$C_6$-alkynyl, where aliphatic or isocyclic moieties of the substituents may be partially or fully halogenated and/or may carry one to three of the following groups: cyano, hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-alkylthio, [di-($C_1$-$C_4$)-alkyl]amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, [di-($C_1$-$C_4$)-alkyl]aminocarbonyl or $C_1$-$C_4$-alkylcarbonyloxy,
phenyl, phenyl-$C_1$-$C_6$-alkyl, heterocyclyl or heterocyclyl-$C_1$-$C_6$-alkyl, where the phenyl or heterocyclyl moieties of the substituents may be partially or fully halogenated and/or may carry one to three of the following groups, nitro, cyano, $C_1$-$C_4$-alkyl, $C_1$-$C_4$-haloalkyl, $C_1$-$C_4$-alkoxy or $C_1$-$C_4$-haloalkoxy;

$R^4$, $R^5$, $R^6$ independently of one another are hydrogen, $C_1$-$C_6$-alkyl, $C_1$-$C_6$-alkoxy, where the above-mentioned aliphatic moieties of the substituents of $R^4$, $R^5$ or $R^6$ may be partially or fully halogenated and/or may carry one to three of the following groups: cyano, hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-alkylthio, [di-($C_1$-$C_4$)-alkyl]amino, $C_1$-$C_4$-alkylcarbonyl, hydroxycarbonyl, $C_1$-$C_4$-alkoxycarbonyl, aminocarbonyl, $C_1$-$C_4$-alkylamino-carbonyl, [di-($C_1$-$C_4$)-alkyl]aminocarbonyl or $C_1$-$C_4$-alkylcarbonyloxy;

$R^3$ and $R^4$ together may also be a keto group;

$R^7$, $R^8$ independently of one another are hydrogen, hydroxyl, $C_1$-$C_6$-alkyl which may be partially or fully halogenated and/or carry one to three of the following groups: cyano, hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-alkylthio, [di-($C_1$-$C_4$)-alkyl]amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, [di-($C_1$-$C_4$)-alkyl]aminocarbonyl or $C_1$-$C_4$-alkylcarbonyloxy;

$A^1$, $A^2$ independently of one another are aryl or heteroaryl, except for indolyl, where $R^a$ is attached in the ortho-position to the point of attachment of $A^1$ to a carbon atom or a nitrogen atom of $A^1$ and where $R^a$ has one of the meanings given below:

$R^a$ is halogen, cyano, nitro, $C_1$-$C_6$-alkyl, $C_3$-$C_6$-cycloalkyl, $C_2$-$C_6$-alkenyl, $C_3$-$C_6$-cycloalkenyl, $C_4$-$C_6$-alkadienyl, $C_2$-$C_6$-alkynyl, [tri-($C_1$-$C_6$)-alkylsilyl]-($C_2$-$C_6$)-alkynyl, $C_3$-$C_6$-cycloalkynyl, $C_1$-$C_6$-alkylthio, $C_1$-$C_6$-alkylsulfinyl, aryl, phenyl-($C_1$-$C_6$)-alkyl, phenyl-($C_2$-$C_6$)-alkenyl, phenylsulfonyl-($C_1$-$C_6$)-alkyl, heterocyclyl, heterocyclyl-($C_1$-$C_6$)-alkyl or phenyl-[$C_1$-$C_6$-alkoxycarbonyl]-($C_1$-$C_6$)-alkyl, $Z^1P(O)(OR^9)_2$, $Z^2B(OR^{10})_2$, where
$R^9$ and $R^{10}$ are each hydrogen or $C_1$-$C_6$-alkyl and the radicals $R^{10}$ in $Z^2B(OR^{10})_2$ together may form a $C_2$-$C_4$-alkylene chain; or $Z^3COR^{11}$ where
$R^{11}$ is hydrogen, $C_1$-$C_6$-alkyl, $C_3$-$C_6$-cycloalkyl, $C_2$-$C_6$-alkenyl, $C_3$-$C_6$-cycloalkenyl, $C_2$-$C_6$-alkynyl, $C_3$-$C_6$-cycloalkynyl, hydroxyl, $C_1$-$C_6$-alkoxy, $C_3$-$C_6$-alkenyloxy, $C_3$-$C_6$-alkynyloxy, amino, $C_1$-$C_6$-alkylamino, [di-($C_1$-$C_6$)-alkyl]amino, $C_1$-$C_6$-alkoxyamino, [di-($C_1$-$C_6$)-alkoxy]amino, $C_1$-$C_6$-alkyl-sulfonylamino, $C_1$-$C_6$-alkylaminosulfonylamino, [di-($C_1$-$C_6$)-alkylamino]-sulfonylamino, $C_3$-$C_6$-alkenylamino, $C_3$-$C_6$-alkynylamino, N—($C_2$-$C_6$-alkenyl)-N—($C_1$-$C_6$-alkyl)amino, N—($C_2$-$C_6$-alkynyl)-N—($C_1$-$C_6$-alkyl) amino, N—($C_1$-$C_6$-alkoxy)-N—($C_1$-$C_6$-alkyl) amino, N—($C_2$-$C_6$-alkenyl)-N—($C_1$-$C_6$-alkoxy) amino, N—($C_2$-$C_6$-alkynyl)-N—($C_1$-$C_6$-alkoxy) amino, phenyl, phenoxy, phenylamino, naphthyl or heterocyclyl; or $Z^4NR^{12}R^{13}$ where
$R^{12}$ and $R^{13}$ independently of one another are hydrogen, $C_1$-$C_6$-alkyl, $C_3$-$C_6$-cycloalkyl, $C_3$-$C_6$-alkenyl, $C_3$-$C_6$-cycloalkenyl, $C_3$-$C_6$-alkynyl, $C_3$-$C_6$-cycloalkynyl, $C_1$-$C_6$-alkylcarbonyl, $C_3$-$C_6$-cycloalkylcarbonyl, [di-($C_1$-$C_6$)-alkyl-amino]carbonyl, $C_1$-$C_6$-alkoxycarbonyl, $C_1$-$C_6$-alkoxycarbonyl-($C_1$-$C_6$)-alkyl, $C_1$-$C_6$-alkylsulfonyl, $C_1$-$C_6$-alkylaminosulfonyl, [di-($C_1$-$C_6$)-alkylamino]-sulfonyl, phenylcarbonyl, phenylaminocarbonyl, phenylsulfonyl, phenylsulfonylaminocarbonyl or heterocyclylcarbonyl; or $Z^5CH=N-O-R^{14}$, where $R^{14}$ is hydrogen or $C_1$-$C_6$alkyl; or $Z^6R^{15}$, where
$R^{15}$ is hydrogen, $C_1$-$C_6$-alkyl, $C_3$-$C_6$-cycloalkyl, $C_3$-$C_6$-alkenyl, $C_3$-$C_6$-cycloalkenyl, $C_3$-$C_6$-alkynyl, $C_3$-$C_6$-cycloalkynyl, $C_1$-$C_6$-alkylcarbonyl, $C_1$-$C_6$-alkoxycarbonyl-($C_1$-$C_6$)-alkyl, [di-($C_1$-$C_6$)-alkoxycarbonyl]-($C_1$-$C_6$)-alkyl, phenyl or phenyl-($C_1$-$C_6$)-alkyl; or $Z^7SO_2R^{16}$, where $R^{16}$ is $C_1$-$C_6$-alkyl or phenyl; and where $Z^1$, $Z^2$, $Z^3$, $Z^4$, $Z^5$, $Z^6$, $Z^7$ independently of one another are a bond, —$CH_2$—, —$CH_2$—$CH_2$—, —O—$CH(R^{17})$—, —S—$CH(R^{18})$—, —$S(O)$—$CH(R^{19})$— or —$SO_2CH$ ($R^2$—, and where $R^{17}$, $R^{18}$, $R^{19}$ and $R^{20}$ independently of one another are hydrogen or $C_1$-$C_6$-alkyl; and where the above-mentioned aliphatic, cyclic or aromatic moieties of the substituent $R^a$ may be partially or fully halogenated and/or may carry one to three of the following groups: cyano, hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-alkylthio, [di-($C_1$-$C_4$)-alkyl]amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, [di-($C_1$-$C_4$)-alkyl]aminocarbonyl or $C_1$-$C_4$-alkylcarbonyloxy; and $R^b$, $R^c$, $R^d$, $R^e$ and $R^f$ are each independently of one another hydrogen or have one of the meanings given for $R^a$ and where two radicals $R^a$, $R^b$ or $R^c$ attached to adjacent ring atoms of $A^1$ or two radicals $R^d$, $R^e$ or $R^f$ attached to adjacent ring atoms of $A^2$ may also be straight-chain $C_3$-$C_6$-alkylene which may be partially or fully halogenated and which may carry one to three of the following groups; cyano, hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-alkylthio, [di-($C_1$-$C_4$)-alkyl]amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, [di-($C_1$-$C_4$)-alkyl]aminocarbonyl or $C_1$-$C_4$-alkylcarbonyloxy, where one $CH_2$ group in $C_3$-$C_6$-alkylene may be replaced by a carbonyl group, thiocarbonyl group or sulfonyl group and in which one or two non-adjacent $CH_2$ groups in $C_3$-$C_6$-alkylene may in each case be replaced by oxygen, sulfur or a group $NR^{34}$ where $R^{34}$ has one of the meanings given for $R^{12}$.

The thaxtomins A and B produced by the plant pathogen *S. scabies* (King R. R. et al., J. Agric. Food Chem. (1992) 40, 834-837) are natural products having a central piperazine-2,5-dione ring which carries a 4-nitroindol-3-ylmethyl radical in the 3-position and an optionally OH-substituted benzyl radical in the 2-position. Owing to their plant-damaging action, these compound class was also investigated for a possible use as herbicides (King R. R. et al., J. Agric. Food Chem. (2001) 49, 2298-2301).

EP-A 181152 and EP-A 243122 describe structurally similar piperazine compounds and their use as antagonists of the platelet activating factor.

US 2003/0171379 A1 describes the use of mactanamide, a fungistatic diketopiperazine of the formula A,

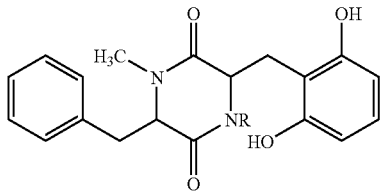

in which R is H or methyl as anti-inflammatory compounds in medicine.

WO 99/48889, WO 01/53290 and WO 2005/011699 describe 2,5-diketopiperazine compounds which have a 4-imidazolyl radical attached via a methylene or methyne group in the 3- or 6-position and in the other 3- or 6-position a benzyl radical. These compounds are antitumor compounds.

The compound 1,4-diacetyl-3,6-di(2-chlorophenyl)piperazine-2,5-dione is known (L. X. Wang, Y. Z. Shi, Z. M. Du, H. W. Hu, Chinese Chem. Lett. (1993) 4, 687-688).

It is an object of the present invention to provide compounds having herbicidal action. In particular the invention is to provide compounds having high herbicidal activity, in particular even at low application rates, and whose compatibility with crop plants is sufficient for commercial use.

This and further objects are achieved by the compounds of the formula I defined at the outset and by their agriculturally useful salts.

Accordingly, the present invention relates to the use of piperazine compounds of the general formula I or of the agriculturally useful salts of piperazine compounds of the formula I as herbicides, i.e. for controlling harmful plants.

The invention also relates to compositions comprising a herbicidally effective amount of at least one piperazine compound of the formula I or an agriculturally useful salt of I and auxiliaries customary for formulating crop protection agents.

Moreover, the invention relates to a process for controlling unwanted vegetation which comprises allowing a herbicidally effective amount of at least one piperazine compound of the formula I or an agriculturally useful salt of I to act on plants, their seeds and/or their habitat.

The piperazine compounds of the formula I are novel and also form part of the subject matter of the present invention,
except for compounds of the formula I in which $A^1$ and $A^2$ are phenyl, $R^1$ is methyl, $R^2$ is hydrogen or methyl, $R^3$, $R^4$, $R^5$, $R^6$, $R^7$, $R^8$ are hydrogen, the substituents $R^a$ and $R^b$ are each hydroxyl located in the two ortho-positions of the phenyl ring $A^1$ and $R^c$, $R^d$, $R^e$ and $R^f$ are hydrogen,
furthermore except for compounds of the formula I in which $A^1$ is phenyl and $A^2$ is 4-imidazolyl or $A^1$ is 4-imidazolyl and $A^2$ is phenyl, and
furthermore except for a compound of the formula I in which $A^1$ is phenyl, $R^a$ is chlorine, $R^b$ and $R^c$ are hydrogen, the group $A^2(R^d R^e R^f)$ is o-chlorophenyl, $R^1$ and $R^2$ are methylcarbonyl and $R^3$ to $R^8$ are each hydrogen.

Moreover, the invention relates to processes and intermediates for preparing compounds of the formula I.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

Depending on the substitution pattern, the compounds of the formula I may comprise one or more centers of chirality, in which case they are present as enantiomer or diastereomer mixtures. The invention provides both the pure enantiomers or diastereomers and their mixtures.

The compounds of the formula I may also be present in the form of their agriculturally useful salts, the nature of the salt generally being immaterial. Suitable salts are, in general, the cations or the acid addition salts of those acids whose cations and anions, respectively, have no adverse effect on the herbicidal action of the compounds I.

Suitable cations are in particular ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-yl-ammonium, di(2-hydroxyeth-1-yl)ammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$alkyl)sulfoxonium.

Anions of useful acid addition salts are primarily chloride, bromide, fluoride, hydrogensulfate, sulfate, dihydrogenphosphate, hydrogenphosphate, nitrate, bicarbonate, carbonate, hexafluorosilicate, hexafluorophosphate, benzoate, and the anions of $C_1$-$C_4$-alkanoic acids, preferably formate, acetate, propionate and butyrate.

The organic moieties mentioned for the substituents of the compounds according to the invention are collective terms for individual enumerations of the specific group members. All hydrocarbon chains, such as
alkyl, haloalkyl, and also the alkyl moieties in cyanoalkyl, alkoxy, haloalkoxy, alkylthio, haloalkylthio, alkylsulfinyl, haloalkylsulfinyl, alkylsulfonyl, haloalkylsulfonyl, N-alkylaminosulfonyl, N,N-dialkylaminosulfonyl, dialkylamino, N-alkylsulfonylamino, N-haloalkylsulfonylamino, N-alkyl-N-alkylsulfonylamino, N-alkyl-N-haloalkylsulfonylamino, alkylcarbonyl, haloalkylcarbonyl, alkoxycarbonyl, haloalkoxycarbonyl, alkylcarbonyloxy, alkylaminocarbonyl, dialkylaminocarbonyl, dialkylaminothiocarbonyl, alkoxyalkyl, dialkoxyalkyl, alkylthioalkyl, dialkylaminoalkyl, dialkylhydrazinoalkyl, alkyliminooxyalkyl, alkylcarbonylalkyl, alkoxyiminoalkyl, N-(alkylamino)-iminoalkyl, N-(dialkylamino)-iminoalkyl, alkoxycarbonylalkyl, dialkylaminocarbonylalkyl, phenylalkenylcarbonyl, heterocyclylalkenylcarbonyl, N-alkoxy-N-alkylaminocarbonyl, N-alkyl-N-phenylaminocarbonyl, N-alkyl-N-heterocyclylaminocarbonyl, phenylalkyl, heterocyclylalkyl, phenylcarbonylalkyl, heterocyclylcarbonylalkyl, dialkylaminoalkoxy-carbonyl, alkoxyalkoxycarbonyl, alkenylcarbonyl, alkenyloxycarbonyl, alkenyl-aminocarbonyl, N-alkenyl-N-alkylaminocarbonyl, N-alkenyl-N-alkoxyaminocarbonyl, alkynylcarbonyl, alkynyloxycarbonyl, alkynylaminocarbonyl, N-alkynyl-N-alkylaminocarbonyl, N-alkynyl-N-alkoxyaminocarbonyl, alkenyl, alkynyl, haloalkenyl, haloalkynyl and alkoxyalkoxy moieties may be straight-chain or branched. The prefix $C_n$-$C_m$-indicates the respective carbon number of the hydrocarbon moiety. Unless indicated otherwise, halogenated substituents preferably carry one to five identical or different halogen atoms, in particular fluorine atoms or chlorine atoms.

The term halogen denotes in each case fluorine, chlorine, bromine or iodine.

Examples of other meanings are:
alkyl and also the alkyl moieties, for example, in alkoxy, alkylthio, alkylsulfinyl and alkylsulfonyl, alkylcarbonyl, alkylamino, alkylsilyl, phenylalkyl, phenylsulfonylalkyl, heterocyclylalkyl: saturated straight-chain or branched hydrocarbon radicals having one or more carbon atoms, for example 1 to 2, 1 to 4 or 1 to 6 carbon atoms, for example $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethyl-butyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl. In one embodiment according to the invention, alkyl denotes small alkyl groups such as $C_1$-$C_4$-alkyl. In another embodiment according to the invention, alkyl denotes relatively large alkyl groups such as $C_5$-$C_6$-alkyl.

Haloalkyl; an alkyl radical as mentioned above whose hydrogen atoms are partially or fully substituted by halogen atoms such as fluorine, chlorine, bromine and/or iodine, for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoro-ethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-tri-chloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl.

Cycloalkyl and also the cycloalkyl moieties, for example, in cycloalkoxy or cycloalkylcarbonyl: monocyclic saturated hydrocarbon groups having three or more carbon atoms, for example 3 to 6 carbon ring members, such as cyclopropyl, cyclobutyl, cyclopentyl and cyclohexyl.

Alkenyl and also alkenyl moieties, for example, in phenyl-($C_2$-$C_6$-alkenyl or alkenylamino: monounsaturated straight-chain or branched hydrocarbon radicals having two or more carbon atoms, for example 2 to 4, 2 to 6, or 3 to 6 carbon atoms, and a double bond in any position, for example $C_2$-$C_6$-alkenyl, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-tri-methyl-2-propenyl, 1-ethyl-1-methyl-2-propenyl, 1-ethyl-2-methyl-1-propenyl, 1-ethyl-2-methyl-2-propenyl.

In one embodiment according to the invention, alkenyl groups such as $C_2$-$C_6$-alkenyl are employed. In another embodiment according to the invention, use is made of alkenyl groups such as $C_3$-$C_6$-alkenyl.

Cycloalkenyl and also cycloalkenyl moieties: monocyclic, monounsaturated hydrocarbon groups having three or more carbon atoms, for example 3 to 6, preferably 5 to 6, carbon ring members, such as cyclopenten-1-yl, cyclopenten-3-yl, cyclohexen-1-yl, cyclohexen-3-yl, cyclohexen-4-yl.

Alkynyl and also alkynyl moieties, for example, in [tri-($C_1$-$C_6$)-alkylsilyl-($C_2$-$C_6$)-alkynyl or alkynylamino: straight-chain or branched hydrocarbon groups having two or more carbon atoms, for example 2 to 4, 2 to 6, or 3 to 6 carbon atoms, and one or two triple bonds in any position, but not adjacent to one another, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl.

Cycloalkynyl and also cycloalkynyl moieties: monocyclic hydrocarbon groups having three or more carbon atoms, for example 3 to 6, preferably 5 to 6, carbon ring members and one triple bond, such as cyclohexyn-1-yl, cyclohexyn-3-yl, cyclohexyn-4-yl.

$C_4$-$C_{10}$-Alkadienyl; doubly unsaturated straight-chain or branched hydrocarbon radicals having four or more carbon atoms and two double bonds in any (but non-adjacent) position, for example 4 to 10 carbon atoms and two double bonds in any position, but not adjacent to one another, for example 1,3-butadienyl, 1-methyl-1,3-butadienyl, 2-methyl-1,3-butadienyl, penta-1,3-dien-1-yl, hexa-1,4-dien-1-yl, hexa-1,4-dien-3-yl, hexa-1,4-dien-6-yl, hexa-1,5-dien-1-yl, hexa-1,5-dien-3-yl, hexa-1,5-dien-4-yl, hepta-1,4-dien-1-yl, hepta-1,4-dien-3-yl, hepta-1,4-dien-6-yl, hepta-1,4-dien-7-yl, hepta-1,5-dien-1-yl, hepta-1,5-dien-3-yl, hepta-1,5-dien-4-yl, hepta-1,5-dien-7-yl, hepta-1,6-dien-1-yl, hepta-1,6-dien-3-yl, hepta-1,6-dien-4-yl, hepta-1,6-dien-5-yl, hepta-1,6-dien-2-yl, octa-1,4-dien-1-yl, octa-1,4-dien-2-yl, octa-1,4-dien-3-yl, octa-1,4-dien-6-yl, octa-1,4-dien-7-yl, octa-1,5-dien-1-yl, octa-1,5-dien-3-yl, octa-1,5-dien-4-yl, octa-1,5-dien-7-yl, octa-1,6-dien-1-yl, octa-1,6-dien-3-yl, octa-1,6-dien-4-yl, octa-1,6-dien-5-yl, octa-1,6-dien-2-yl, deca-1,4-dienyl, deca-1,5-dienyl, deca-1,6-dienyl, deca-1,7-dienyl, deca-1,8-dienyl, deca-2,5-dienyl, deca-2,6-dienyl, deca-2,7-dienyl, deca-2,8-dienyl.

Alkoxy or alkoxy moieties, for example, in phenylalkoxy, alkoxyamino, alkoxycarbonyl: alkyl, as defined above, which is attached via an oxygen atom: for example methoxy, ethoxy, n-propoxy, 1-methylethoxy, butoxy, 1-methylpropoxy, 2-methylpropoxy or 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethyl-propoxy, 1,2,2-trimethylpropoxy, 1-ethyl-1-methylpropoxy or 1-ethyl-2-methylpropoxy.

In one embodiment according to the invention, small alkoxy groups such as $C_1$-$C_4$-alkoxy are employed. In another embodiment according to the invention, use is made of relatively large alkoxy groups such as $C_5$-$C_6$-alkoxy.

Alkenyloxy: alkenyl as mentioned above which is attached via an oxygen atom, for example $C_3$-$C_6$-alkenyloxy, such as 1-propenyloxy, 2-propenyloxy, 1-methylethenyloxy, 1-butenyloxy, 2-butenyloxy, 3-butenyloxy, 1-methyl-1-propenyloxy, 2-methyl-1-propen-yloxy, 1-methyl-2-propenyloxy, 2-methyl-2-propenyloxy, 1-pentenyloxy, 2-pentenyloxy, 3-pentenyloxy, 4-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy, 5-hexenyloxy, 1-methyl-1-pentenyloxy, 2-methyl-1-pentenyloxy, 3-methyl-1-pentenyloxy, 4-methyl-1-pentenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-1-butenyloxy, 1,2-dimethyl-2-butenyloxy, 1,2-dimethyl-3-butenyloxy, 1,3-dimethyl-1-butenyloxy, 1,3-dimethyl-2-butenyloxy, 1,3-dimethyl-3-butenyloxy, 2,2-dimethyl-3-butenyloxy, 2,3-dimethyl-1-butenyloxy, 2,3-dimethyl-2-butenyloxy, 2,3-dimethyl-3-butenyloxy, 3,3-dimethyl-1-butenyloxy, 3,3-dimethyl-2-butenyl oxy, 1-ethyl-1-butenyloxy, 1-ethyl-2-butenyloxy, 1-ethyl-3-butenyloxy, 2-ethyl-1-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-1-propenyloxy and 1-ethyl-2-methyl-2-propenyloxy. In one embodiment according to the invention, small alkenyloxy groups such as $C_3$-$C_4$-alkenyloxy are employed. In another embodiment according to the invention, use is made of relatively large alkenyloxy groups such as $C_5$-$C_6$-alkenyloxy.

Alkynyloxy: alkynyl as mentioned above which is attached via an oxygen atom, for example $C_3$-$C_6$-alkynyloxy, such as 2-propynyloxy, 2-butynyloxy, 3-butynyloxy, 1-methyl-2-propynyloxy, 2-pentynyloxy, 3-pentynyloxy, 4-pentynyloxy, 1-methyl-2-butynyloxy, 1-methyl-3-butynyloxy, 2-methyl-3-butynyloxy 1,1-ethyl-2-propynyloxy, 2-hexynyloxy, 3-hexynyloxy, 4-hexynyloxy, 5-hexynyloxy, 1-methyl-2-pentynyloxy, 1-methyl-3-pentynyloxy. In one embodiment according to the invention, small alkynyloxy groups such as $C_3$-$C_4$-alkynyloxy are employed. In another embodiment according to the invention, use is made of relatively large alkynyloxy groups such as $C_5$-$C_6$-alkynyloxy.

Alkylthio: alkyl as defined above which is attached via a sulfur atom.

Alkylsulfinyl; alkyl as defined above which is attached via an SO group.

Alkylsulfonyl: alkyl as defined above which is attached via an $S(O)_2$ group.

Alkylcarbonyl: alkyl as defined above which is attached via a (C=O) group, for example methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl, pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, hexylcarbonyl, 1,1-dimethyl-propylcarbonyl, 1,2-dimethylpropylcarbonyl, 1-methylpentylcarbonyl, 2-methyl-pentylcarbonyl, 3-methylpentylcarbonyl, 4-methylpentylcarbonyl, 1,1-dimethyl-butylcarbonyl, 1,2-dimethylbutylcarbonyl, 1,3-dimethylbutylcarbonyl, 2,2-dimethyl-butylcarbonyl, 2,3-dimethylbutylcarbonyl, 3,3-dimethylbutylcarbonyl, 1-ethylbutyl-carbonyl, 2-ethylbutylcarbonyl, 1,1,2-trimethylpropylcarbonyl, 1,2,2-trimethylpropyl-carbonyl, 1-ethyl-1-methylpropylcarbonyl or 1-ethyl-2-methylpropylcarbonyl.

Alkenylcarbonyl: alkenyl as defined above which is attached via a (C=O) group, for example 1-ethenylcarbonyl.

Alkynylcarbonyl: alkynyl as defined above which is attached via a (C=O) group, for example 1-propynylcarbonyl.

Heterocyclyl: a mono- or bicyclic saturated, partially unsaturated or aromatic heterocyclic ring having three or more, for example 3 to 10, ring atoms, for example a monocyclic 3-, 4-, 5-, 6- or 7-membered heterocyclic ring which contains one to four identical or different heteroatoms selected from the group consisting of oxygen, sulfur and nitrogen and which may be attached via carbon or nitrogen, for example 3- or 4-membered saturated or unsaturated rings attached via carbon, such as 2-oxiranyl, 2-oxetanyl, 3-oxetanyl, 2-aziridinyl, 3-thiethanyl, 1-azetidinyl, 2-azetidinyl.

5-membered saturated rings attached via carbon, such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl.

6-membered saturated rings attached via carbon, such as: tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin- 2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl.

5-membered saturated rings attached via nitrogen, such as; tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl.

6-membered saturated rings attached via nitrogen, such as: piperidin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl.

5-membered partially unsaturated rings attached via carbon, such as: 2,3-dihydrofuran-2-yl, 2,3-dihydrofuran-3-yl, 2,5-dihydrofuran-2-yl, 2,5-di-hydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydro-isoxazol-5-yl, 2,5-dihydroisoxazol-3-yl, 2,5-dihydroisoxazol-4-yl, 2,5-dihydro-isoxazol-5-yl, 2,3-dihydroisoxazol-3-yl, 2,3-dihydroisoxazol-4-yl, 2,3-dihydro-isoxazol-5-yl, 4,5-dihydroisothiazol-3-yl, 4,5-dihydroisothiazol-4-yl, 4,5-dihydro-isothiazol-5-yl, 2,5-dihydroisothiazol-3-yl, 2,5-dihydroisothiazol-4-yl, 2,5-dihydro-isothiazol-5-yl, 2,3-dihydroisothiazol-3-yl, 2,3-dihydroisothiazol-4-yl, 2,3-dihydro-isothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, 1,2,3-$\Delta^2$-oxadiazolin-4-yl, 1,2,3-$\Delta^2$-oxadiazolin-5-yl, 1,2,3-$\Delta^4$-oxadiazolin-3-yl, 1,2,3-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,4-$\Delta^4$-thiadiazolin-3-yl, 1,2,4-$\Delta^4$-triazolin-3-yl, 1,2,4-$\Delta^3$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,2,3-$\Delta^2$-triazolin-4-yl, 1,2,3-$\Delta^2$-triazolin-5-yl, 1,2,4-$\Delta^2$-triazolin-3-yl, 1,2,4-$\Delta^2$-triazolin-5-yl, 1,2,4-$\Delta^3$-triazolin-3-yl, 1,2,4-$\Delta^3$-triazolin-5-yl, 1,2,4-$\Delta^1$-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl.

6-membered partially unsaturated rings attached via carbon, such as: 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydro-thiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydro-pyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydro-thiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2- oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetra-hydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydro-pyridazin-4-yl, 1,2,5,6-tetrahydropyridazin-5-yl, 2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetra-hydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetra-hydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 5H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-thiazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydro-pyridazin-3-yl, 1,4-dihydro-pyridazin-4-yl, 1,4-dihydropyridazin-5-yl, 1,4-dihydropyridazin-6-yl, 1,4-dihydro-pyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl.

5-membered partially unsaturated rings attached via nitrogen, such as: 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, 1,2,4-$\Delta^4$-oxa-diazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 1,2,4-$\Delta^5$-thiadiazolin-2-yl, 1,2,4-$\Delta^3$-thiadiazolin-2-yl, 1,2,4-$\Delta^2$-thiadiazolin-4-yl, 1,3,4-$\Delta^2$-thiadiazolin-4-yl, 1,2,3-$\Delta^2$-triazolin-1-yl, 1,2,4-$\Delta^2$-triazolin-1-yl, 1,2,4-$\Delta^2$-triazolin-4-yl, 1,2,4-$\Delta^3$-triazolin-1-yl, 1,2,4-$\Delta^1$-triazolin-4-yl.

6-membered partially unsaturated rings attached via nitrogen, such as: 1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydro-pyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetra-hydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

5-membered heteroaromatic rings, attached via carbon, having generally 1, 2, 3 or 4 nitrogen atoms or one heteroatom selected from the group consisting of oxygen and sulfur and, if appropriate, 1, 2 or 3 nitrogen atoms as ring members, such as:

2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,5-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl.

6-membered heteroaromatic rings, attached via carbon, having generally 1, 2, 3 or 4 nitrogen atoms as ring members, such as:

pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl.

5-membered heteroaromatic rings, attached via nitrogen, having generally 1, 2, 3 or 4 nitrogen atoms as ring members, such as:

pyrrol-1-yl, pyrazol-1-yl, imidazol-1-yl, 1,2,3-triazol-1-yl, 1,2,4-triazol-1-yl, tetrazol-1-yl.

or a bicyclic heterocycle which comprises one of the above-mentioned 5- or 6-membered heterocyclic rings and a further fused-on saturated, unsaturated or aromatic carbocycle, for example a benzene, cyclohexane, cyclohexene or cyclohexadiene ring, or a further fused-on 5- or 6-membered heterocyclic ring, where the latter may likewise be saturated, unsaturated or aromatic.

A sulfur atom in the heterocycles mentioned may be oxidized to S=O or S(=O)$_2$.

Accordingly, hetaryl or heteroaryl is a 5- or 6-membered heteroaromatic radical which has 1, 2, 3 or 4 identical or different heteroatoms selected from the group consisting of oxygen, sulfur and nitrogen as ring members, which may be attached via carbon or nitrogen and which, together with a further fused-on benzene ring or a 5- to 6-membered heteroaromatic may form a bicyclic ring system. Examples of hetaryl are the above-mentioned 5- and 6-membered heteroaromatic rings attached via carbon, the above-mentioned 5-membered heteroaromatic rings attached via nitrogen and bicyclic heteroaramatic radicals such as quinolinyl, isoquinolinyl, quinazolinyl, quinoxalinyl, indolyl, benzothienyl, benzofuryl, benzoxazolyl, benzothiazolyl, benzimidazolyl, benzopyrazolyl, benzotriazole, indolizinyl, 1,2,4-triazolo[1,5-a] pyrimidinyl, 1,2,4-triazolo[4,3-a]pyridinyl, pyrazolo[3,4-b] pyridinyl, 1,2,4-triazolo[1,5-a]pyridinyl, imidazo[1,2-a] pyridyl, imidazo[3,4-a]pyrimidinyl, and the like.

Aryl: a mono- or polycyclic aromatic carbocycle, for example a mono- or bicyclic or a mono- to tricyclic aromatic carbocycle having 6 to 14 ring members, such as, for example, phenyl, naphthyl or anthracenyl.

Arylalkyl: an aryl radical attached via an alkylene group, in particular via a methylene, 1,1-ethylene or 1,2-ethylene group, for example benzyl, 1-phenylethyl and 2-phenylethyl.

Heterocyclylalkyl and also hetarylalkyl: a heterocyclyl- or hetaryl radical attached via an alkylene group, in particular via a methylene, 1,1-ethylene or 1,2-ethylene group.

In a particular embodiment, the variables of the compounds of the formula I have the meanings below, these meanings—both on their own and in combination with one another—being particular embodiments of the compounds of the formula I:

$R^1$ is hydrogen, amino, cyano, $C_1$-$C_6$-alkyl, $C_3$-$C_6$-alkenyl, $C_3$-$C_6$-alkynyl, phenyl-($C_1$-$C_6$)-alkyl, heterocyclyl-($C_1$-$C_6$)-alkyl or $COR^2$, where $R^{21}$ is as defined above and is in particular $C_1$-$C_6$-alkyl, $C_1$-$C_6$-alkoxy, phenyl, phenylamino or heterocyclyl; where the above-mentioned aliphatic, cyclic or aromatic moieties of the substituents may be partially or fully halogenated. With particular preference, $R^1$ has the meanings hydrogen or $C_1$-$C_6$-alkyl, in particular methyl.

$R^2$ is amino, cyano, $C_1$-$C_6$-alkyl, $C_3$-$C_6$-alkenyl, $C_3$-$C_6$-alkynyl, phenyl-($C_1$-$C_6$)-alkyl, heterocyclyl-($C_1$-$C_6$)-alkyl or $COR^{21}$, where $R^{21}$ is as defined above and is in particular $C_1$-$C_6$-alkyl, $C_1$-$C_6$-alkoxy, phenyl, phenylamino or heterocyclyl; where the above-mentioned aliphatic, cyclic or aromatic moieties of the substituents may be partially or fully halogenated. With particular preference $R^2$ has the meaning $C_1$-$C_6$-alkyl, in particular methyl.

$R^3$ is a radical $R^{26}$ or a group $OR^{27}$, where $R^{26}$ and $R^{27}$ are as defined above and are in particular independently of one another hydrogen, $C_1$-$C_6$-alkyl, $C_1$-$C_6$-alkyl-carbonyl, phenyl-$C_1$-$C_6$-alkyl or phenylcarbonyl, where the above-mentioned aliphatic or aromatic moieties of the substituents may be partially or fully halogenated, or are $SO_2R^3$, where $R^{31}$ is $C_1$-$C_6$-alkyl or phenyl and where the phenyl substituent in $R^{31}$ may be partially or fully halogenated and/or may carry one to three $C_1$-$C_6$-alkyl groups. With particular preference $R^3$ has the meanings hydrogen, $C_1$-$C_6$-alkyl, phenyl-$C_1$-$C_6$-alkoxy or $C_1$-$C_6$-alkylsulfonyl.

$R^4$, $R^5$ and/or $R^6$ are hydrogen, $R^3$ and $R^4$ together may also be a keto group. In this case, $R^5$ and/or $R^6$ are preferably hydrogen.

$R^7$ and $R^8$ independently of one another are preferably hydrogen or methyl, in particular hydrogen.

$A^1$, $A^2$ independently of one another are aryl or heteroaryl selected from the group consisting of phenyl, naphthyl, furyl, thienyl, pyrrolyl, pyrazolyl, thiazolyl, isothiazolyl, oxazolyl, Isoxazolyl, triazolyl, tetrazolyl, pyridinyl, pyridazinyl, pyrimidinyl, pyrazinyl, triazinyl or tetrazinyl, in particular selected from the group consisting of phenyl, furyl, thienyl, triazolyl, tetrazolyl or pyridinyl. With particular preference, $A^1$ has the meaning phenyl or pyridinyl, in particular phenyl. With particular preference, $A^2$ has the meaning phenyl or thienyl, in particular phenyl.

According to the invention, $A^1$ has one to three substituents $R^a$, $R^b$, $R^c$ different from hydrogen, where $R^a$ is attached in the ortho-position to the point of attachment of $A^1$ to a nitrogen or a carbon atom of $A^1$, where $R^a$ has preferably one of the following meanings:

halogen, cyano, nitro, $C_1$-$C_6$-alkyl, $C_3$-$C_6$-cycloalkyl, $C_2$-$C_6$-alkenyl, $C_2$-$C_6$-alkynyl, [tri-($C_1$-$C_6$)-alkylsilyl]-($C_2$-$C_6$)-alkynyl, $C_1$-$C_6$-alkylthio, $C_1$-$C_6$-alkylsulfinyl, aryl, heterocyclyl, in particular 5- or 6-membered heterocyclyl, where aryl and heterocyclyl are unsubstituted or may have one or two radicals selected from the group consisting of $C_1$-$C_4$-alkyl, $C_1$-$C_4$-haloalkyl, $C_1$-$C_4$-alkoxy, $C_1$-$C_4$-haloalkoxy, CN, phenyl and halogen, $Z^1P(O)(OR^9)_2$, where $Z^1$ is a bond or —$CH_2$— and the radicals $R^9$ are each hydrogen or $C_1$-$C_6$-alkyl;

$Z^3COR^{11}$, where $Z^1$ is a bond and $R^{11}$ has the meanings given above and is in particular hydrogen, $C_1$-$C_6$-alkyl, hydroxyl, $C_1$-$C_6$-alkoxy, $C_3$-$C_6$-alkenyloxy, $C_3$-$C_6$-alkynyloxy, amino, $C_1$-$C_6$-alkylamino, [di-($C_1$-$C_6$)-alkyl]amino, $C_1$-$C_6$-alkoxyamino, N—$C_1$-$C_6$-alkoxy-N—$C_1$-$C_6$-alkylamino, [di-($C_1$-$C_6$)-alkoxy]amino, $C_1$-$C_6$-alkylsulfonyl-amino, $C_1$-$C_6$-alkylaminosulfonylamino, [di-($C_1$-$C_6$)-alkylamino]sulfonylamino, phenyl, phenoxy, phenylamino, naphthyl or heterocyclyl, especially 5- or 6-membered heteroaryl attached via carbon;

$Z^4NR^{12}R^{13}$, where $Z^4$ is a bond or —$CH_2$— and $R^{12}$ and $R^{13}$ have the meanings given above and are in particular independently of one another hydrogen, $C_1$-$C_6$-alkyl, $C_3$-$C_6$-cycloalkyl, $C_3$-$C_6$-alkenyl, $C_3$-$C_6$-alkynyl, $C_1$-$C_6$-alkylcarbonyl, [di-($C_1$-$C_6$)-alkylamino]carbonyl, $C_1$-$C_6$-alkoxycarbonyl, $C_1$-$C_6$-alkylsulfonyl, $C_1$-$C_6$-alkyl-aminosulfonyl, [di-($C_1$-$C_6$)-alkylamino]sulfonyl, $C_3$-$C_6$-cycloalkylcarbonyl, phenylcarbonyl, phenylaminocarbonyl, phenylsulfonyl, phenylsulfonylamino-carbonyl, or heterocyclylcarbonyl, especially 5- or 6-membered heteroaryl-carbonyl attached via carbon;

$Z^5CH=N$—$O$—$R^{14}$, where $Z^5$ is a bond and $R^{14}$ is hydrogen or $C_1$-$C_6$-alkyl; or $Z^6OR^{15}$, where $Z^6$ is a bond or —$CH_2$— and $R^{15}$ has the meanings given above and is in particular $C_3$-$C_6$-cycloalkyl, $C_3$-$C_6$-alkenyl, $C_3$-$C_6$-alkynyl, $C_1$-$C_6$-alkylcarbonyl, $C_1$-$C_6$-alkoxycarbonyl-($C_1$-$C_6$)-alkyl, di-($C_1$-$C_6$-alkoxycarbonyl)-$C_1$-$C_6$-alkyl, phenylcarbonyl, phenyl or phenyl-($C_1$-$C_6$)-alkyl, $R^{15}$ may also be hydrogen or $C_1$-$C_6$-alkyl; or $Z^7SO_2R^{16}$, where $Z^7$ is a bond or $CH_2$ and $R^{16}$ is $C_1$-$C_6$-alkyl or phenyl;

where the above-mentioned aliphatic, cyclic or aromatic moieties of the substituents $R^a$ may be partially or fully halogenated.

$R^b$, $R^c$, $R^d$, $R^e$ and $R^f$ are preferably hydrogen or independently of one another have one of the meanings mentioned as being preferred for $R^a$.

If $R^a$ is attached to a nitrogen atom, $R^a$ is preferably different from halogen, $C_1$-$C_6$-alkylthio, $C_1$-$C_6$-alkylsulfinyl, $Z^1P(O)(OR^9)_2$, where $Z^1$ is a bond. In a preferred embodiment of the invention, $R^a$ is attached to a carbon atom.

$R^a$ has in particular one of the following meanings:
halogen, cyano, nitro, $C_1$-$C_6$-alkylthio, $C_1$-$C_6$-alkylsulfinyl, aryl, heterocyclyl, where the last two radicals mentioned are unsubstituted or may have one or two radicals selected from the group consisting of $C_1$-$C_4$-alkyl, $C_1$-$C_4$-haloalkyl, $C_1$-$C_4$-alkoxy, $C_1$-$C_4$-haloalkoxy, CN, phenyl and halogen, $C_2$-$C_6$-alkenyl, $C_2$-$C_5$-alkynyl, $Z^1P(O)(OR^9)_2$, where $Z^1$ is a bond or —$CH_2$— and the radicals $R^9$ are each hydrogen or $C_1$-$C_6$-alkyl; or $Z^1COR^{11}$ where $Z^3$ is a bond and $R^{11}$ is hydrogen, $C_1$-$C_6$-alkyl, hydroxyl, $C_1$-$C_6$-alkoxy, $C_3$-$C_6$-alkenyloxy, $C_3$-$C_6$-alkynyloxy, amino, $C_1$-$C_6$-alkylamino, [di-($C_1$-$C_6$)-alkyl]amino, $C_1$-$C_6$-alkoxyamino, N—$C_1$-$C_6$-alkoxy-N—$C_1$-$C_6$-alkylamino, $C_1$-$C_6$-alkyl-sulfonylamino, $C_1$-$C_6$-alkylaminosulfonylamino, [di-($C_1$-$C_6$)-alkylamino]sulfonyl-amino, phenyl, phenoxy, phenylamino, naphthyl or heterocyclyl, especially 5- or 6-membered heteroaryl attached via carbon; or $Z^4NR^{12}R^{13}$, where $Z^4$ is a bond or —$CH_2$— and $R^{12}$ and $R^{13}$ independently of one another are hydrogen, $C_1$-$C_6$-alkyl, $C_3$-$C_6$-cycloalkyl, $C_3$-$C_6$-alkenyl, $C_3$-$C_6$-alkynyl, $C_1$-$C_6$-alkylcarbonyl, [di-($C_1$-$C_6$)-alkylamino]carbonyl, $C_1$-$C_6$-alkoxycarbonyl, $C_1$-$C_6$-alkylsulfonyl, phenylcarbonyl, phenylsulfonyl, or heterocyclylcarbonyl, especially 5- or 6-membered heteroarylcarbonyl attached via carbon; or $Z^5CH$=N—O—$R^{14}$, where $Z^5$ is a bond and $R^{14}$ is hydrogen or $C_1$-$C_6$-alkyl; or $Z^6OR^{15}$, where $Z^6$ is a bond or —$CH_2$— and $R^{15}$ is hydrogen, $C_1$-$C_6$-alkyl, $C_3$-$C_6$-cycloalkyl, $C_3$-$C_6$-alkenyl, $C_3$-$C_6$-alkynyl, $C_1$-$C_6$-alkylcarbonyl, $C_1$-$C_6$-alkoxycarbonyl-($C_1$-$C_6$)-alkyl, phenyl or phenyl-($C_1$-$C_6$)-alkyl; or $Z^7SO_2R^{16}$, where $R^{17}$ is a bond or $CH_2$ and $R^{16}$ is $C_1$-$C_6$-alkyl or phenyl;

and where the above-mentioned aliphatic, cyclic or aromatic moieties of the substituents $R^a$ may be partially or fully halogenated.

Very especially preferably, $R^a$ is a radical selected from the group consisting of halogen, cyano, nitro, $C_2$-$C_4$-alkenyl and $C_2$-$C_4$-alkynyl, NH—C(O)—$C_1$-$C_6$-alkyl, NH—S(O)$_2$—$C_1$-$C_6$-alkyl and 5-membered heteroaryl, for example oxazolyl, thiazolyl, isoxazolyl, isothiazolyl, where the heteroaryl radicals mentioned above may have one or 2 radicals selected from the group consisting of $C_1$-$C_2$-alkyl, $C_1$-$C_2$-haloalkyl and halogen, and which is attached in particular in one of the ortho positions of $A^1$.

$R^b$, $R^c$, $R^d$, $R^e$ and $R^f$ are in particular hydrogen or independently of one another have one of the meanings mentioned as being particularly preferred for $R^a$ or are: $C_1$-$C_6$-alkyl, $C_1$-$C_6$-haloalkyl, $C_3$-$C_6$-cycloalkyl which may be partially or fully halogenated, $C_2$-$C_6$-alkenyl which may be partially or fully halogenated, [tri-($C_1$-$C_6$)-alkylsilyl]-($C_2$-$C_6$)-alkynyl, or a group $Z^6OR^{15}$ in which $Z^6$ is a bond and $R^{15}$ is hydrogen, $C_1$-$C_6$-alkyl or haloalkyl.

In particular, the radicals $R^b$, $R^c$, $R^d$, $R^e$ and $R^f$ independently of one another are selected from the group consisting of hydrogen, halogen, $C_1$-$C_4$-alkyl, $C_2$-$C_4$-alkenyl, $C_2$-$C_4$-alkynyl, $C_1$-$C_4$-alkoxy, $C_1$-$C_4$-haloalkyl and $C_1$-$C_4$-haloalkoxy, where two groups $R^b$, $R^c$, $R^d$, $R^e$ or $R^f$ attached to adjacent carbon atoms of $A^1$ or $A^2$ may also be a group O—$CH_2$—O.

In particular, $R^e$ is a radical other than hydrogen. $R^r$ is preferably a radical attached in the ortho position of $A^1$, that is to say if $R^a$ is likewise attached in the ortho position, $R^b$ is in the second ortho position.

If one or both radicals $R^b$, $R^c$ are substituents different from hydrogen, they are selected in particular from among the substituents stated as being preferred, and especially from the group consisting of halogen, $C_1$-$C_4$-alkyl, $C_1$-$C_4$-alkoxy, $C_1$-$C_4$-haloalkyl, $C_2$-$C_4$-alkenyl, $C_2$-$C_4$-alkynyl and $C_1$-$C_4$-haloalkoxy, or $R^b$ and $R^c$ together are a group O—$CH_2$—O.

$A^2$ is in particular unsubstituted, or one or two of the substituents $R^d$, $R^e$ and $R^f$ are substituents different from hydrogen. If 1 or 2 of the substituents $R^d$, $R^e$ and $R^f$ are different from hydrogen, they are selected in particular from the group consisting of halogen, $C_1$-$C_4$-alkyl, $C_1$-$C_4$-alkoxy, $C_1$-$C_4$-haloalkyl and $C_1$-$C_4$-haloalkoxy.

The meaning that a substituent may assume in the context of the invention is completely independent of the meaning which another substituent may assume in the context of the invention.

The invention provides especially piperazine compounds of the general formula I in which $A^1$ and $A^2$ are phenyl, $R^1$ is methyl and $R^2$ is hydrogen, $C_1$-$C_6$-alkyl, $C_2$-$C_6$-alkenyl, $C_2$-$C_6$-alkynyl, aryl or $C_1$-$C_6$-alkoxy, in particular hydrogen or methyl, the substituents $R^a$ and $R^b$ independently of one another are each hydrogen, hydroxyl, $C_1$-$C_6$-alkyl, $C_2$-$C_6$-alkenyl, $C_2$-$C_6$-alkynyl or $C_1$-$C_6$-alkoxy, which are located in the two ortho-positions of the phenyl ring $A^1$, $R^3$, $R^4$, $R^5$, $R^6$, $R^7$, $R^8$ are hydrogen and $R^c$, $R^d$, $R^e$ and $R^f$ are likewise hydrogen. Among these, preference is given to those compounds in which $R^f$ is $C_2$-$C_6$-alkenyl or $C_2$-$C_6$-alkynyl.

The invention furthermore provides piperazine compounds of the formula I which are different from the compounds of the special subject matter mentioned above, i.e. compounds of the general formula I, except for those compounds of the formula I in which $R^1$ is methyl and $R^2$ is hydrogen, $C_1$-$C_6$-alkyl, $C_2$-$C_6$-alkenyl, $C_2$-$C_6$-alkynyl, aryl or $C_1$-$C_6$-alkoxy, in particular hydrogen or methyl, the substituents $R^a$ and $R^b$ independently of one another are each hydrogen, hydroxyl, $C_1$-$C_6$-alkyl, $C_2$-$C_6$-alkenyl, $C_2$-$C_6$-alkynyl or $C_1$-$C_6$-alkoxy which are located in the two ortho-positions of the phenyl ring $A^1$, $R^3$, $R^4$, $R^5$, $R^6$, $R^7$, $R^8$ are hydrogen and $R^c$, $R^d$, $R^e$ and $R^f$ are likewise hydrogen.

The invention furthermore preferably provides those compounds of the formula I (S,S) which have the S-configuration in both of the indicated positions (1) and (2).

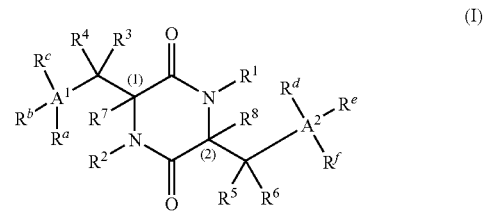

(I)

Preference is given to compounds of the formula I.1 in which $R^3$, $R^4$, $R^5$, $R^6$, $R^7$ and $R^8$ are hydrogen and $R^2$ is $CH_3$, particular preference is given to the compounds (S,S)-I.1 which have the S-configuration in both of the indicated positions (1) and (2). Examples of preferred compounds I.1 are those in which $A^1$, $R^a$, $R^b$ and $R^c$ have the meanings given in Table 1:

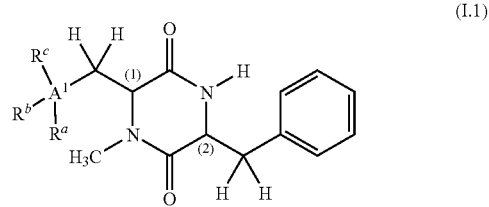

(I.1)

The compounds I.2 to I.252 listed below are per se preferred embodiments of the invention.

TABLE 1

| Comp. No. | A¹ | $R^a$ | $R^b$ or H | $R^c$ H |
|---|---|---|---|---|
| I.1.1 | phenyl | 2-NO$_2$ | H | H |
| I.1.2 | phenyl | 2-NO$_2$ | 3-Cl | H |
| I.1.3 | phenyl | 2-NO$_2$ | 4-Cl | H |
| I.1.4 | phenyl | 2-NO$_2$ | 5-Cl | H |
| I.1.5 | phenyl | 2-NO$_2$ | 6-Cl | H |
| I.1.6 | phenyl | 2-NO$_2$ | 3-F | H |
| I.1.7 | phenyl | 2-NO$_2$ | 4-F | H |
| I.1.8 | phenyl | 2-NO$_2$ | 5-F | H |
| I.1.9 | phenyl | 2-NO$_2$ | 6-F | H |
| I.1.10 | phenyl | 2-NO$_2$ | 3-CH$_3$ | H |
| I.1.11 | phenyl | 2-NO$_2$ | 4-CH$_3$ | H |
| I.1.12 | phenyl | 2-NO$_2$ | 5-CH$_3$ | H |
| I.1.13 | phenyl | 2-NO$_2$ | 6-CH$_3$ | H |
| I.1.14 | phenyl | 2-NO$_2$ | 5-vinyl | H |
| I.1.15 | phenyl | 2-NO$_2$ | 6-vinyl | H |
| I.1.16 | phenyl | 2-NO$_2$ | 5-CF$_3$ | 3-Cl |
| I.1.17 | phenyl | 2-NO$_2$ | 5-CF$_3$ | 4-Cl |
| I.1.18 | phenyl | 2-NO$_2$ | 4-CF$_3$ | 5-Cl |
| I.1.19 | phenyl | 2-NO$_2$ | 5-CF$_3$ | 6-Cl |
| I.1.20 | phenyl | 2-NO$_2$ | 5-CF$_3$ | 3-F |
| I.1.21 | phenyl | 2-NO$_2$ | 5-CF$_3$ | 4-F |
| I.1.22 | phenyl | 2-NO$_2$ | 4-CF$_3$ | 5-F |
| I.1.23 | phenyl | 2-NO$_2$ | 5-CF$_3$ | 6-F |
| I.1.24 | phenyl | 2-NO$_2$ | 5-CF$_3$ | 3-CH$_3$ |
| I.1.25 | phenyl | 2-NO$_2$ | 5-CF$_3$ | 4-CH$_3$ |
| I.1.26 | phenyl | 2-NO$_2$ | 4-CF$_3$ | 5-CH$_3$ |
| I.1.27 | phenyl | 2-NO$_2$ | 5-CF$_3$ | 6-CH$_3$ |
| I.1.28 | phenyl | 2-NO$_2$ | 4-CF$_3$ | 5-vinyl |
| I.1.29 | phenyl | 2-NO$_2$ | 4-CF$_3$ | 6-vinyl |
| I.1.30 | phenyl | 2-NO$_2$ | 3-Cl | 4-F |
| I.1.31 | phenyl | 2-NO$_2$ | 3-Cl | 5-F |
| I.1.32 | phenyl | 2-NO$_2$ | 3-Cl | 6-F |
| I.1.33 | phenyl | 2-NO$_2$ | 3-Cl | 4-Cl |
| I.1.34 | phenyl | 2-NO$_2$ | 3-Cl | 5-Cl |
| I.1.35 | phenyl | 2-NO$_2$ | 3-Cl | 6-Cl |
| I.1.36 | phenyl | 2-NO$_2$ | 3-Cl | 4-CH$_3$ |
| I.1.37 | phenyl | 2-NO$_2$ | 3-Cl | 5-CH$_3$ |
| I.1.38 | phenyl | 2-NO$_2$ | 3-Cl | 6-CH$_3$ |
| I.1.39 | phenyl | 2-NO$_2$ | 3-Cl | 5-vinyl |
| I.1.40 | phenyl | 2-NO$_2$ | 3-Cl | 6-vinyl |
| I.1.41 | phenyl | 2-NO$_2$ | 3-F | 4-F |
| I.1.42 | phenyl | 2-NO$_2$ | 3-F | 5-F |
| I.1.43 | phenyl | 2-NO$_2$ | 3-F | 6-F |
| I.1.44 | phenyl | 2-NO$_2$ | 3-F | 4-Cl |
| I.1.45 | phenyl | 2-NO$_2$ | 3-F | 5-Cl |
| I.1.46 | phenyl | 2-NO$_2$ | 3-F | 6-Cl |
| I.1.47 | phenyl | 2-NO$_2$ | 3-F | 4-CH$_3$ |
| I.1.48 | phenyl | 2-NO$_2$ | 3-F | 5-CH$_3$ |
| I.1.49 | phenyl | 2-NO$_2$ | 3-F | 6-CH$_3$ |
| I.1.50 | phenyl | 2-NO$_2$ | 3-F | 5-vinyl |
| I.1.51 | phenyl | 2-NO$_2$ | 3-F | 6-vinyl |
| I.1.52 | phenyl | 2-NO$_2$ | 3-CH$_3$ | 4-F |
| I.1.53 | phenyl | 2-NO$_2$ | 3-CH$_3$ | 5-F |
| I.1.54 | phenyl | 2-NO$_2$ | 3-CH$_3$ | 6-F |
| I.1.55 | phenyl | 2-NO$_2$ | 3-CH$_3$ | 4-Cl |
| I.1.56 | phenyl | 2-NO$_2$ | 3-CH$_3$ | 5-Cl |
| I.1.57 | phenyl | 2-NO$_2$ | 3-CH$_3$ | 6-Cl |
| I.1.58 | phenyl | 2-NO$_2$ | 3-CH$_3$ | 4-CH$_3$ |
| I.1.59 | phenyl | 2-NO$_2$ | 3-CH$_3$ | 5-CH$_3$ |
| I.1.60 | phenyl | 2-NO$_2$ | 3-CH$_3$ | 6-CH$_3$ |
| I.1.61 | phenyl | 2-NO$_2$ | 3-CH$_3$ | 5-vinyl |
| I.1.62 | phenyl | 2-NO$_2$ | 3-CH$_3$ | 6-vinyl |
| I.1.63 | phenyl | 2-NO$_2$ | 4-Cl | 5-F |
| I.1.64 | phenyl | 2-NO$_2$ | 4-Cl | 6-F |
| I.1.65 | phenyl | 2-NO$_2$ | 4-Cl | 5-Cl |
| I.1.66 | phenyl | 2-NO$_2$ | 4-Cl | 6-Cl |
| I.1.67 | phenyl | 2-NO$_2$ | 4-Cl | 5-CH$_3$ |
| I.1.68 | phenyl | 2-NO$_2$ | 4-Cl | 6-CH$_3$ |
| I.1.69 | phenyl | 2-NO$_2$ | 4-Cl | 5-vinyl |
| I.1.70 | phenyl | 2-NO$_2$ | 4-Cl | 6-vinyl |
| I.1.71 | phenyl | 2-NO$_2$ | 4-F | 5-F |
| I.1.72 | phenyl | 2-NO$_2$ | 4-F | 6-F |
| I.1.73 | phenyl | 2-NO$_2$ | 4-F | 5-Cl |
| I.1.74 | phenyl | 2-NO$_2$ | 4-F | 6-Cl |
| I.1.75 | phenyl | 2-NO$_2$ | 4-F | 5-CH$_3$ |
| I.1.76 | phenyl | 2-NO$_2$ | 4-F | 6-CH$_3$ |
| I.1.77 | phenyl | 2-NO$_2$ | 4-F | 5-vinyl |
| I.1.78 | phenyl | 2-NO$_2$ | 4-F | 6-vinyl |
| I.1.79 | phenyl | 2-NO$_2$ | 4-CH$_3$ | 5-F |
| I.1.80 | phenyl | 2-NO$_2$ | 4-CH$_3$ | 6-F |
| I.1.81 | phenyl | 2-NO$_2$ | 4-CH$_3$ | 5-Cl |
| I.1.82 | phenyl | 2-NO$_2$ | 4-CH$_3$ | 6-Cl |
| I.1.83 | phenyl | 2-NO$_2$ | 4-CH$_3$ | 5-CH$_3$ |
| I.1.84 | phenyl | 2-NO$_2$ | 4-CH$_3$ | 6-CH$_3$ |
| I.1.85 | phenyl | 2-NO$_2$ | 4-CH$_3$ | 5-vinyl |
| I.1.86 | phenyl | 2-NO$_2$ | 4-CH$_3$ | 6-vinyl |
| I.1.87 | phenyl | 2-NO$_2$ | 5-Cl | 6-Cl |
| I.1.88 | phenyl | 2-NO$_2$ | 5-Cl | 6-F |
| I.1.89 | phenyl | 2-NO$_2$ | 5-Cl | 6-CH$_3$ |
| I.1.90 | phenyl | 2-NO$_2$ | 5-Cl | 6-vinyl |
| I.1.91 | phenyl | 2-NO$_2$ | 5-F | 6-Cl |
| I.1.92 | phenyl | 2-NO$_2$ | 5-F | 6-F |
| I.1.93 | phenyl | 2-NO$_2$ | 5-F | 6-CH$_3$ |
| I.1.94 | phenyl | 2-NO$_2$ | 5-F | 6-vinyl |
| I.1.95 | phenyl | 2-NO$_2$ | 5-CH$_3$ | 6-Cl |
| I.1.96 | phenyl | 2-NO$_2$ | 5-CH$_3$ | 6-F |
| I.1.97 | phenyl | 2-NO$_2$ | 5-CH$_3$ | 6-CH$_3$ |
| I.1.98 | phenyl | 2-NO$_2$ | 5-CH$_3$ | 6-vinyl |
| I.1.99 | phenyl | 2-NO$_2$ | 5-vinyl | 6-Cl |
| I.1.100 | phenyl | 2-NO$_2$ | 5-vinyl | 6-F |
| I.1.101 | phenyl | 2-NO$_2$ | 5-vinyl | 6-CH$_3$ |
| I.1.102 | phenyl | 2-NO$_2$ | 5-vinyl | 6-vinyl |
| I.1.103 | phenyl | 2-CN | H | H |
| I.1.104 | phenyl | 2-CN | 3-Cl | H |
| I.1.105 | phenyl | 2-CN | 4-Cl | H |
| I.1.106 | phenyl | 2-CN | 5-Cl | H |
| I.1.107 | phenyl | 2-CN | 6-Cl | H |
| I.1.108 | phenyl | 2-CN | 3-F | H |
| I.1.109 | phenyl | 2-CN | 4-F | H |
| I.1.110 | phenyl | 2-CN | 5-F | H |
| I.1.111 | phenyl | 2-CN | 6-F | H |
| I.1.112 | phenyl | 2-CN | 3-CH$_3$ | H |
| I.1.113 | phenyl | 2-CN | 4-CH$_3$ | H |
| I.1.114 | phenyl | 2-CN | 5-CH$_3$ | H |
| I.1.115 | phenyl | 2-CN | 6-CH$_3$ | H |
| I.1.116 | phenyl | 2-CN | 5-vinyl | H |
| I.1.117 | phenyl | 2-CN | 6-vinyl | H |
| I.1.118 | phenyl | 2-CN | 5-CF$_3$ | 3-Cl |
| I.1.119 | phenyl | 2-CN | 5-CF$_3$ | 4-Cl |
| I.1.120 | phenyl | 2-CN | 4-CF$_3$ | 5-Cl |
| I.1.121 | phenyl | 2-CN | 5-CF$_3$ | 6-Cl |
| I.1.122 | phenyl | 2-CN | 5-CF$_3$ | 3-F |
| I.1.123 | phenyl | 2-CN | 5-CF$_3$ | 4-F |
| I.1.124 | phenyl | 2-CN | 4-CF$_3$ | 5-F |
| I.1.125 | phenyl | 2-CN | 5-CF$_3$ | 6-F |
| I.1.126 | phenyl | 2-CN | 5-CF$_3$ | 3-CH$_3$ |
| I.1.127 | phenyl | 2-CN | 5-CF$_3$ | 4-CH$_3$ |
| I.1.128 | phenyl | 2-CN | 4-CF$_3$ | 5-CH$_3$ |
| I.1.129 | phenyl | 2-CN | 5-CF$_3$ | 6-CH$_3$ |
| I.1.130 | phenyl | 2-CN | 4-CF$_3$ | 5-vinyl |
| I.1.131 | phenyl | 2-CN | 4-CF$_3$ | 6-vinyl |
| I.1.132 | phenyl | 2-CN | 3-Cl | 4-F |
| I.1.133 | phenyl | 2-CN | 3-Cl | 5-F |
| I.1.134 | phenyl | 2-CN | 3-Cl | 6-F |
| I.1.135 | phenyl | 2-CN | 3-Cl | 4-Cl |
| I.1.136 | phenyl | 2-CN | 3-Cl | 5-Cl |
| I.1.137 | phenyl | 2-CN | 3-Cl | 6-Cl |
| I.1.138 | phenyl | 2-CN | 3-Cl | 4-CH$_3$ |
| I.1.139 | phenyl | 2-CN | 3-Cl | 5-CH$_3$ |
| I.1.140 | phenyl | 2-CN | 3-Cl | 6-CH$_3$ |
| I.1.141 | phenyl | 2-CN | 3-Cl | 5-vinyl |
| I.1.142 | phenyl | 2-CN | 3-Cl | 6-vinyl |
| I.1.143 | phenyl | 2-CN | 3-F | 4-F |
| I.1.144 | phenyl | 2-CN | 3-F | 5-F |
| I.1.145 | phenyl | 2-CN | 3-F | 6-F |
| I.1.146 | phenyl | 2-CN | 3-F | 4-Cl |
| I.1.147 | phenyl | 2-CN | 3-F | 5-Cl |
| I.1.148 | phenyl | 2-CN | 3-F | 6-Cl |
| I.1.149 | phenyl | 2-CN | 3-F | 4-CH$_3$ |
| I.1.150 | phenyl | 2-CN | 3-F | 5-CH$_3$ |
| I.1.151 | phenyl | 2-CN | 3-F | 6-CH$_3$ |
| I.1.152 | phenyl | 2-CN | 3-F | 5-vinyl |

TABLE 1-continued

| Comp. No. | A¹ | $R^a$ | $R^b$ or H | $R^c$ H |
|---|---|---|---|---|
| I.1.153 | phenyl | 2-CN | 3-F | 6-vinyl |
| I.1.154 | phenyl | 2-CN | 3-CH₃ | 4-F |
| I.1.155 | phenyl | 2-CN | 3-CH₃ | 5-F |
| I.1.156 | phenyl | 2-CN | 3-CH₃ | 6-F |
| I.1.157 | phenyl | 2-CN | 3-CH₃ | 4-Cl |
| I.1.158 | phenyl | 2-CN | 3-CH₃ | 5-Cl |
| I.1.159 | phenyl | 2-CN | 3-CH₃ | 6-Cl |
| I.1.160 | phenyl | 2-CN | 3-CH₃ | 4-CH₃ |
| I.1.161 | phenyl | 2-CN | 3-CH₃ | 5-CH₃ |
| I.1.162 | phenyl | 2-CN | 3-CH₃ | 6-CH₃ |
| I.1.163 | phenyl | 2-CN | 3-CH₃ | 5-vinyl |
| I.1.164 | phenyl | 2-CN | 3-CH₃ | 6-vinyl |
| I.1.165 | phenyl | 2-CN | 4-Cl | 5-F |
| I.1.166 | phenyl | 2-CN | 4-Cl | 6-F |
| I.1.167 | phenyl | 2-CN | 4-Cl | 5-Cl |
| I.1.168 | phenyl | 2-CN | 4-Cl | 6-Cl |
| I.1.169 | phenyl | 2-CN | 4-Cl | 5-CH₃ |
| I.1.170 | phenyl | 2-CN | 4-Cl | 6-CH₃ |
| I.1.171 | phenyl | 2-CN | 4-Cl | 5-vinyl |
| I.1.172 | phenyl | 2-CN | 4-Cl | 6-vinyl |
| I.1.173 | phenyl | 2-CN | 4-F | 5-F |
| I.1.174 | phenyl | 2-CN | 4-F | 6-F |
| I.1.175 | phenyl | 2-CN | 4-F | 5-Cl |
| I.1.176 | phenyl | 2-CN | 4-F | 6-Cl |
| I.1.177 | phenyl | 2-CN | 4-F | 5-CH₃ |
| I.1.178 | phenyl | 2-CN | 4-F | 6-CH₃ |
| I.1.179 | phenyl | 2-CN | 4-F | 5-vinyl |
| I.1.180 | phenyl | 2-CN | 4-F | 6-vinyl |
| I.1.181 | phenyl | 2-CN | 4-CH₃ | 5-F |
| I.1.182 | phenyl | 2-CN | 4-CH₃ | 6-F |
| I.1.183 | phenyl | 2-CN | 4-CH₃ | 5-Cl |
| I.1.184 | phenyl | 2-CN | 4-CH₃ | 6-Cl |
| I.1.185 | phenyl | 2-CN | 4-CH₃ | 5-CH₃ |
| I.1.186 | phenyl | 2-CN | 4-CH₃ | 6-CH₃ |
| I.1.187 | phenyl | 2-CN | 4-CH₃ | 5-vinyl |
| I.1.188 | phenyl | 2-CN | 4-CH₃ | 6-vinyl |
| I.1.189 | phenyl | 2-CN | 5-Cl | 6-Cl |
| I.1.190 | phenyl | 2-CN | 5-Cl | 6-F |
| I.1.191 | phenyl | 2-CN | 5-Cl | 6-CH₃ |
| I.1.192 | phenyl | 2-CN | 5-Cl | 6-vinyl |
| I.1.193 | phenyl | 2-CN | 5-F | 6-Cl |
| I.1.194 | phenyl | 2-CN | 5-F | 6-F |
| I.1.195 | phenyl | 2-CN | 5-F | 6-CH₃ |
| I.1.196 | phenyl | 2-CN | 5-F | 6-vinyl |
| I.1.197 | phenyl | 2-CN | 5-CH₃ | 6-Cl |
| I.1.198 | phenyl | 2-CN | 5-CH₃ | 6-F |
| I.1.199 | phenyl | 2-CN | 5-CH₃ | 6-CH₃ |
| I.1.200 | phenyl | 2-CN | 5-CH₃ | 6-vinyl |
| I.1.201 | phenyl | 2-CN | 5-vinyl | 6-Cl |
| I.1.202 | phenyl | 2-CN | 5-vinyl | 6-F |
| I.1.203 | phenyl | 2-CN | 5-vinyl | 6-CH₃ |
| I.1.204 | phenyl | 2-CN | 5-vinyl | 6-vinyl |
| I.1.205 | phenyl | 2-ethynyl | H | H |
| I.1.206 | phenyl | 2-ethynyl | 3-Cl | H |
| I.1.207 | phenyl | 2-ethynyl | 4-Cl | H |
| I.1.208 | phenyl | 2-ethynyl | 5-Cl | H |
| I.1.209 | phenyl | 2-ethynyl | 6-Cl | H |
| I.1.210 | phenyl | 2-ethynyl | 3-F | H |
| I.1.211 | phenyl | 2-ethynyl | 4-F | H |
| I.1.212 | phenyl | 2-ethynyl | 5-F | H |
| I.1.213 | phenyl | 2-ethynyl | 6-F | H |
| I.1.214 | phenyl | 2-ethynyl | 3-CH₃ | H |
| I.1.215 | phenyl | 2-ethynyl | 4-CH₃ | H |
| I.1.216 | phenyl | 2-ethynyl | 5-CH₃ | H |
| I.1.217 | phenyl | 2-ethynyl | 6-CH₃ | H |
| I.1.218 | phenyl | 2-ethynyl | 5-vinyl | H |
| I.1.219 | phenyl | 2-ethynyl | 6-vinyl | H |
| I.1.220 | phenyl | 2-ethynyl | 5-CF₃ | 3-Cl |
| I.1.221 | phenyl | 2-ethynyl | 5-CF₃ | 4-Cl |
| I.1.222 | phenyl | 2-ethynyl | 4-CF₃ | 5-Cl |
| I.1.223 | phenyl | 2-ethynyl | 5-CF₃ | 6-Cl |
| I.1.224 | phenyl | 2-ethynyl | 5-CF₃ | 3-F |
| I.1.225 | phenyl | 2-ethynyl | 5-CF₃ | 4-F |
| I.1.226 | phenyl | 2-ethynyl | 4-CF₃ | 5-F |
| I.1.227 | phenyl | 2-ethynyl | 5-CF₃ | 6-F |
| I.1.228 | phenyl | 2-ethynyl | 5-CF₃ | 3-CH₃ |
| I.1.229 | phenyl | 2-ethynyl | 5-CF₃ | 4-CH₃ |
| I.1.230 | phenyl | 2-ethynyl | 4-CF₃ | 5-CH₃ |
| I.1.231 | phenyl | 2-ethynyl | 5-CF₃ | 6-CH₃ |
| I.1.232 | phenyl | 2-ethynyl | 4-CF₃ | 5-vinyl |
| I.1.233 | phenyl | 2-ethynyl | 4-CF₃ | 6-vinyl |
| I.1.234 | phenyl | 2-ethynyl | 3-Cl | 4-F |
| I.1.235 | phenyl | 2-ethynyl | 3-Cl | 5-F |
| I.1.236 | phenyl | 2-ethynyl | 3-Cl | 6-F |
| I.1.237 | phenyl | 2-ethynyl | 3-Cl | 4-Cl |
| I.1.238 | phenyl | 2-ethynyl | 3-Cl | 5-Cl |
| I.1.239 | phenyl | 2-ethynyl | 3-Cl | 6-Cl |
| I.1.240 | phenyl | 2-ethynyl | 3-Cl | 4-CH₃ |
| I.1.241 | phenyl | 2-ethynyl | 3-Cl | 5-CH₃ |
| I.1.242 | phenyl | 2-ethynyl | 3-Cl | 6-CH₃ |
| I.1.243 | phenyl | 2-ethynyl | 3-Cl | 5-vinyl |
| I.1.244 | phenyl | 2-ethynyl | 3-Cl | 6-vinyl |
| I.1.245 | phenyl | 2-ethynyl | 3-F | 4-F |
| I.1.246 | phenyl | 2-ethynyl | 3-F | 5-F |
| I.1.247 | phenyl | 2-ethynyl | 3-F | 6-F |
| I.1.248 | phenyl | 2-ethynyl | 3-F | 4-Cl |
| I.1.249 | phenyl | 2-ethynyl | 3-F | 5-Cl |
| I.1.250 | phenyl | 2-ethynyl | 3-F | 6-Cl |
| I.1.251 | phenyl | 2-ethynyl | 3-F | 4-CH₃ |
| I.1.252 | phenyl | 2-ethynyl | 3-F | 5-CH₃ |
| I.1.253 | phenyl | 2-ethynyl | 3-F | 6-CH₃ |
| I.1.254 | phenyl | 2-ethynyl | 3-F | 5-vinyl |
| I.1.255 | phenyl | 2-ethynyl | 3-F | 6-vinyl |
| I.1.256 | phenyl | 2-ethynyl | 3-CH₃ | 4-F |
| I.1.257 | phenyl | 2-ethynyl | 3-CH₃ | 5-F |
| I.1.258 | phenyl | 2-ethynyl | 3-CH₃ | 6-F |
| I.1.259 | phenyl | 2-ethynyl | 3-CH₃ | 4-Cl |
| I.1.260 | phenyl | 2-ethynyl | 3-CH₃ | 5-Cl |
| I.1.261 | phenyl | 2-ethynyl | 3-CH₃ | 6-Cl |
| I.1.262 | phenyl | 2-ethynyl | 3-CH₃ | 4-CH₃ |
| I.1.263 | phenyl | 2-ethynyl | 3-CH₃ | 5-CH₃ |
| I.1.264 | phenyl | 2-ethynyl | 3-CH₃ | 6-CH₃ |
| I.1.265 | phenyl | 2-ethynyl | 3-CH₃ | 5-vinyl |
| I.1.266 | phenyl | 2-ethynyl | 3-CH₃ | 6-vinyl |
| I.1.267 | phenyl | 2-ethynyl | 4-Cl | 5-F |
| I.1.268 | phenyl | 2-ethynyl | 4-Cl | 6-F |
| I.1.269 | phenyl | 2-ethynyl | 4-Cl | 5-Cl |
| I.1.270 | phenyl | 2-ethynyl | 4-Cl | 6-Cl |
| I.1.271 | phenyl | 2-ethynyl | 4-Cl | 5-CH₃ |
| I.1.272 | phenyl | 2-ethynyl | 4-Cl | 6-CH₃ |
| I.1.273 | phenyl | 2-ethynyl | 4-Cl | 5-vinyl |
| I.1.274 | phenyl | 2-ethynyl | 4-Cl | 6-vinyl |
| I.1.275 | phenyl | 2-ethynyl | 4-F | 5-F |
| I.1.276 | phenyl | 2-ethynyl | 4-F | 6-F |
| I.1.277 | phenyl | 2-ethynyl | 4-F | 5-Cl |
| I.1.278 | phenyl | 2-ethynyl | 4-F | 6-Cl |
| I.1.279 | phenyl | 2-ethynyl | 4-F | 5-CH₃ |
| I.1.280 | phenyl | 2-ethynyl | 4-F | 6-CH₃ |
| I.1.281 | phenyl | 2-ethynyl | 4-F | 5-vinyl |
| I.1.282 | phenyl | 2-ethynyl | 4-F | 6-vinyl |
| I.1.283 | phenyl | 2-ethynyl | 4-CH₃ | 5-F |
| I.1.284 | phenyl | 2-ethynyl | 4-CH₃ | 6-F |
| I.1.285 | phenyl | 2-ethynyl | 4-CH₃ | 5-Cl |
| I.1.286 | phenyl | 2-ethynyl | 4-CH₃ | 6-Cl |
| I.1.287 | phenyl | 2-ethynyl | 4-CH₃ | 5-CH₃ |
| I.1.288 | phenyl | 2-ethynyl | 4-CH₃ | 6-CH₃ |
| I.1.289 | phenyl | 2-ethynyl | 4-CH₃ | 5-vinyl |
| I.1.290 | phenyl | 2-ethynyl | 4-CH₃ | 6-vinyl |
| I.1.291 | phenyl | 2-ethynyl | 5-Cl | 6-F |
| I.1.292 | phenyl | 2-ethynyl | 5-Cl | 6-F |
| I.1.293 | phenyl | 2-ethynyl | 5-Cl | 6-CH₃ |
| I.1.294 | phenyl | 2-ethynyl | 5-Cl | 6-vinyl |
| I.1.295 | phenyl | 2-ethynyl | 5-F | 6-Cl |
| I.1.296 | phenyl | 2-ethynyl | 5-F | 6-F |
| I.1.297 | phenyl | 2-ethynyl | 5-F | 6-CH₃ |
| I.1.298 | phenyl | 2-ethynyl | 5-F | 6-vinyl |
| I.1.299 | phenyl | 2-ethynyl | 5-CH₃ | 6-Cl |
| I.1.300 | phenyl | 2-ethynyl | 5-CH₃ | 6-F |
| I.1.301 | phenyl | 2-ethynyl | 5-CH₃ | 6-CH₃ |
| I.1.302 | phenyl | 2-ethynyl | 5-CH₃ | 6-vinyl |
| I.1.303 | phenyl | 2-ethynyl | 5-vinyl | 6-Cl |
| I.1.304 | phenyl | 2-ethynyl | 5-vinyl | 6-F |
| I.1.305 | phenyl | 2-ethynyl | 5-vinyl | 6-CH₃ |
| I.1.306 | phenyl | 2-ethynyl | 5-vinyl | 6-vinyl |
| I.1.307 | phenyl | 2-COOCH₃ | H | H |
| I.1.308 | phenyl | 2-COOCH₃ | 3-Cl | H |

TABLE 1-continued

| Comp. No. | A¹ | Rᵃ | Rᵇ or H | Rᶜ H |
|---|---|---|---|---|
| I.1.309 | phenyl | 2-COOCH₃ | 4-Cl | H |
| I.1.310 | phenyl | 2-COOCH₃ | 5-Cl | H |
| I.1.311 | phenyl | 2-COOCH₃ | 6-Cl | H |
| I.1.312 | phenyl | 2-COOCH₃ | 3-F | H |
| I.1.313 | phenyl | 2-COOCH₃ | 4-F | H |
| I.1.314 | phenyl | 2-COOCH₃ | 5-F | H |
| I.1.315 | phenyl | 2-COOCH₃ | 6-F | H |
| I.1.316 | phenyl | 2-COOCH₃ | 3-CH₃ | H |
| I.1.317 | phenyl | 2-COOCH₃ | 4-CH₃ | H |
| I.1.318 | phenyl | 2-COOCH₃ | 5-CH₃ | H |
| I.1.319 | phenyl | 2-COOCH₃ | 6-CH₃ | H |
| I.1.320 | phenyl | 2-COOCH₃ | 5-vinyl | H |
| I.1.321 | phenyl | 2-COOCH₃ | 6-vinyl | H |
| I.1.322 | phenyl | 2-COOCH₃ | 5-CF₃ | 3-Cl |
| I.1.323 | phenyl | 2-COOCH₃ | 5-CF₃ | 4-Cl |
| I.1.324 | phenyl | 2-COOCH₃ | 4-CF₃ | 5-Cl |
| I.1.325 | phenyl | 2-COOCH₃ | 5-CF₃ | 6-Cl |
| I.1.326 | phenyl | 2-COOCH₃ | 5-CF₃ | 3-F |
| I.1.327 | phenyl | 2-COOCH₃ | 5-CF₃ | 4-F |
| I.1.328 | phenyl | 2-COOCH₃ | 4-CF₃ | 5-F |
| I.1.329 | phenyl | 2-COOCH₃ | 5-CF₃ | 6-F |
| I.1.330 | phenyl | 2-COOCH₃ | 5-CF₃ | 3-CH₃ |
| I.1.331 | phenyl | 2-COOCH₃ | 5-CF₃ | 4-CH₃ |
| I.1.332 | phenyl | 2-COOCH₃ | 4-CF₃ | 5-CH₃ |
| I.1.333 | phenyl | 2-COOCH₃ | 5-CF₃ | 6-CH₃ |
| I.1.334 | phenyl | 2-COOCH₃ | 4-CF₃ | 5-vinyl |
| I.1.335 | phenyl | 2-COOCH₃ | 4-CF₃ | 6-vinyl |
| I.1.336 | phenyl | 2-COOCH₃ | 3-Cl | 4-F |
| I.1.337 | phenyl | 2-COOCH₃ | 3-Cl | 5-F |
| I.1.338 | phenyl | 2-COOCH₃ | 3-Cl | 6-F |
| I.1.339 | phenyl | 2-COOCH₃ | 3-Cl | 4-Cl |
| I.1.340 | phenyl | 2-COOCH₃ | 3-Cl | 5-Cl |
| I.1.341 | phenyl | 2-COOCH₃ | 3-Cl | 6-Cl |
| I.1.342 | phenyl | 2-COOCH₃ | 3-Cl | 4-CH₃ |
| I.1.343 | phenyl | 2-COOCH₃ | 3-Cl | 5-CH₃ |
| I.1.344 | phenyl | 2-COOCH₃ | 3-Cl | 6-CH₃ |
| I.1.345 | phenyl | 2-COOCH₃ | 3-Cl | 5-vinyl |
| I.1.346 | phenyl | 2-COOCH₃ | 3-Cl | 6-vinyl |
| I.1.347 | phenyl | 2-COOCH₃ | 3-F | 4-F |
| I.1.348 | phenyl | 2-COOCH₃ | 3-F | 5-F |
| I.1.349 | phenyl | 2-COOCH₃ | 3-F | 6-F |
| I.1.350 | phenyl | 2-COOCH₃ | 3-F | 4-Cl |
| I.1.351 | phenyl | 2-COOCH₃ | 3-F | 5-Cl |
| I.1.352 | phenyl | 2-COOCH₃ | 3-F | 6-Cl |
| I.1.353 | phenyl | 2-COOCH₃ | 3-F | 4-CH₃ |
| I.1.354 | phenyl | 2-COOCH₃ | 3-F | 5-CH₃ |
| I.1.355 | phenyl | 2-COOCH₃ | 3-F | 6-CH₃ |
| I.1.356 | phenyl | 2-COOCH₃ | 3-F | 5-vinyl |
| I.1.357 | phenyl | 2-COOCH₃ | 3-F | 6-vinyl |
| I.1.358 | phenyl | 2-COOCH₃ | 3-CH₃ | 4-F |
| I.1.359 | phenyl | 2-COOCH₃ | 3-CH₃ | 5-F |
| I.1.360 | phenyl | 2-COOCH₃ | 3-CH₃ | 6-F |
| I.1.361 | phenyl | 2-COOCH₃ | 3-CH₃ | 4-Cl |
| I.1.362 | phenyl | 2-COOCH₃ | 3-CH₃ | 5-Cl |
| I.1.363 | phenyl | 2-COOCH₃ | 3-CH₃ | 6-Cl |
| I.1.364 | phenyl | 2-COOCH₃ | 3-CH₃ | 4-CH₃ |
| I.1.365 | phenyl | 2-COOCH₃ | 3-CH₃ | 5-CH₃ |
| I.1.366 | phenyl | 2-COOCH₃ | 3-CH₃ | 6-CH₃ |
| I.1.367 | phenyl | 2-COOCH₃ | 3-CH₃ | 5-vinyl |
| I.1.368 | phenyl | 2-COOCH₃ | 3-CH₃ | 6-vinyl |
| I.1.369 | phenyl | 2-COOCH₃ | 4-Cl | 5-F |
| I.1.370 | phenyl | 2-COOCH₃ | 4-Cl | 6-F |
| I.1.371 | phenyl | 2-COOCH₃ | 4-Cl | 5-Cl |
| I.1.372 | phenyl | 2-COOCH₃ | 4-Cl | 6-Cl |
| I.1.373 | phenyl | 2-COOCH₃ | 4-Cl | 5-CH₃ |
| I.1.374 | phenyl | 2-COOCH₃ | 4-Cl | 6-CH₃ |
| I.1.375 | phenyl | 2-COOCH₃ | 4-Cl | 5-vinyl |
| I.1.376 | phenyl | 2-COOCH₃ | 4-Cl | 6-vinyl |
| I.1.377 | phenyl | 2-COOCH₃ | 4-F | 5-F |
| I.1.378 | phenyl | 2-COOCH₃ | 4-F | 6-F |
| I.1.379 | phenyl | 2-COOCH₃ | 4-F | 5-Cl |
| I.1.380 | phenyl | 2-COOCH₃ | 4-F | 6-Cl |
| I.1.381 | phenyl | 2-COOCH₃ | 4-F | 5-CH₃ |
| I.1.382 | phenyl | 2-COOCH₃ | 4-F | 6-CH₃ |
| I.1.383 | phenyl | 2-COOCH₃ | 4-F | 5-vinyl |
| I.1.384 | phenyl | 2-COOCH₃ | 4-F | 6-vinyl |
| I.1.385 | phenyl | 2-COOCH₃ | 4-CH₃ | 5-F |
| I.1.386 | phenyl | 2-COOCH₃ | 4-CH₃ | 6-F |
| I.1.387 | phenyl | 2-COOCH₃ | 4-CH₃ | 5-Cl |
| I.1.388 | phenyl | 2-COOCH₃ | 4-CH₃ | 6-Cl |
| I.1.389 | phenyl | 2-COOCH₃ | 4-CH₃ | 5-CH₃ |
| I.1.390 | phenyl | 2-COOCH₃ | 4-CH₃ | 6-CH₃ |
| I.1.391 | phenyl | 2-COOCH₃ | 4-CH₃ | 5-vinyl |
| I.1.392 | phenyl | 2-COOCH₃ | 4-CH₃ | 6-vinyl |
| I.1.393 | phenyl | 2-COOCH₃ | 5-Cl | 6-Cl |
| I.1.394 | phenyl | 2-COOCH₃ | 5-Cl | 6-F |
| I.1.395 | phenyl | 2-COOCH₃ | 5-Cl | 6-CH₃ |
| I.1.396 | phenyl | 2-COOCH₃ | 5-Cl | 6-vinyl |
| I.1.397 | phenyl | 2-COOCH₃ | 5-F | 6-Cl |
| I.1.398 | phenyl | 2-COOCH₃ | 5-F | 6-F |
| I.1.399 | phenyl | 2-COOCH₃ | 5-F | 6-CH₃ |
| I.1.400 | phenyl | 2-COOCH₃ | 5-F | 6-vinyl |
| I.1.401 | phenyl | 2-COOCH₃ | 5-CH₃ | 6-Cl |
| I.1.402 | phenyl | 2-COOCH₃ | 5-CH₃ | 6-F |
| I.1.403 | phenyl | 2-COOCH₃ | 5-CH₃ | 6-CH₃ |
| I.1.404 | phenyl | 2-COOCH₃ | 5-CH₃ | 6-vinyl |
| I.1.405 | phenyl | 2-COOCH₃ | 5-vinyl | 6-Cl |
| I.1.406 | phenyl | 2-COOCH₃ | 5-vinyl | 6-F |
| I.1.407 | phenyl | 2-COOCH₃ | 5-vinyl | 6-CH₃ |
| I.1.408 | phenyl | 2-COOCH₃ | 5-vinyl | 6-vinyl |
| I.1.409 | phenyl | 2-COOH | H | H |
| I.1.410 | phenyl | 2-COOH | 3-Cl | H |
| I.1.411 | phenyl | 2-COOH | 4-Cl | H |
| I.1.412 | phenyl | 2-COOH | 5-Cl | H |
| I.1.413 | phenyl | 2-COOH | 6-Cl | H |
| I.1.414 | phenyl | 2-COOH | 3-F | H |
| I.1.415 | phenyl | 2-COOH | 4-F | H |
| I.1.416 | phenyl | 2-COOH | 5-F | H |
| I.1.417 | phenyl | 2-COOH | 6-F | H |
| I.1.418 | phenyl | 2-COOH | 3-CH₃ | H |
| I.1.419 | phenyl | 2-COOH | 4-CH₃ | H |
| I.1.420 | phenyl | 2-COOH | 5-CH₃ | H |
| I.1.421 | phenyl | 2-COOH | 6-CH₃ | H |
| I.1.422 | phenyl | 2-COOH | 5-vinyl | H |
| I.1.423 | phenyl | 2-COOH | 6-vinyl | H |
| I.1.424 | phenyl | 2-COOH | 5-CF₃ | 3-Cl |
| I.1.425 | phenyl | 2-COOH | 5-CF₃ | 4-Cl |
| I.1.426 | phenyl | 2-COOH | 4-CF₃ | 5-Cl |
| I.1.427 | phenyl | 2-COOH | 5-CF₃ | 6-Cl |
| I.1.428 | phenyl | 2-COOH | 5-CF₃ | 3-F |
| I.1.429 | phenyl | 2-COOH | 5-CF₃ | 4-F |
| I.1.430 | phenyl | 2-COOH | 4-CF₃ | 5-F |
| I.1.431 | phenyl | 2-COOH | 5-CF₃ | 6-F |
| I.1.432 | phenyl | 2-COOH | 5-CF₃ | 3-CH₃ |
| I.1.433 | phenyl | 2-COOH | 5-CF₃ | 4-CH₃ |
| I.1.434 | phenyl | 2-COOH | 4-CF₃ | 5-CH₃ |
| I.1.435 | phenyl | 2-COOH | 5-CF₃ | 6-CH₃ |
| I.1.436 | phenyl | 2-COOH | 4-CF₃ | 5-vinyl |
| I.1.437 | phenyl | 2-COOH | 4-CF₃ | 6-vinyl |
| I.1.438 | phenyl | 2-COOH | 3-Cl | 4-F |
| I.1.439 | phenyl | 2-COOH | 3-Cl | 5-F |
| I.1.440 | phenyl | 2-COOH | 3-Cl | 6-F |
| I.1.441 | phenyl | 2-COOH | 3-Cl | 4-Cl |
| I.1.442 | phenyl | 2-COOH | 3-Cl | 5-Cl |
| I.1.443 | phenyl | 2-COOH | 3-Cl | 6-Cl |
| I.1.444 | phenyl | 2-COOH | 3-Cl | 4-CH₃ |
| I.1.445 | phenyl | 2-COOH | 3-Cl | 5-CH₃ |
| I.1.446 | phenyl | 2-COOH | 3-Cl | 6-CH₃ |
| I.1.447 | phenyl | 2-COOH | 3-Cl | 5-vinyl |
| I.1.448 | phenyl | 2-COOH | 3-Cl | 6-vinyl |
| I.1.449 | phenyl | 2-COOH | 3-F | 4-F |
| I.1.450 | phenyl | 2-COOH | 3-F | 5-F |
| I.1.451 | phenyl | 2-COOH | 3-F | 6-F |
| I.1.452 | phenyl | 2-COOH | 3-F | 4-Cl |
| I.1.453 | phenyl | 2-COOH | 3-F | 5-Cl |
| I.1.454 | phenyl | 2-COOH | 3-F | 6-Cl |
| I.1.455 | phenyl | 2-COOH | 3-F | 4-CH₃ |
| I.1.456 | phenyl | 2-COOH | 3-F | 5-CH₃ |
| I.1.457 | phenyl | 2-COOH | 3-F | 6-CH₃ |
| I.1.458 | phenyl | 2-COOH | 3-F | 5-vinyl |
| I.1.459 | phenyl | 2-COOH | 3-F | 6-vinyl |
| I.1.460 | phenyl | 2-COOH | 3-CH₃ | 4-F |
| I.1.461 | phenyl | 2-COOH | 3-CH₃ | 5-F |
| I.1.462 | phenyl | 2-COOH | 3-CH₃ | 6-F |
| I.1.463 | phenyl | 2-COOH | 3-CH₃ | 4-Cl |
| I.1.464 | phenyl | 2-COOH | 3-CH₃ | 5-Cl |

TABLE 1-continued

| Comp. No. | A¹ | $R^a$ | $R^b$ or H | $R^c$ H |
|---|---|---|---|---|
| I.1.465 | phenyl | 2-COOH | 3-CH₃ | 6-Cl |
| I.1.466 | phenyl | 2-COOH | 3-CH₃ | 4-CH₃ |
| I.1.467 | phenyl | 2-COOH | 3-CH₃ | 5-CH₃ |
| I.1.468 | phenyl | 2-COOH | 3-CH₃ | 6-CH₃ |
| I.1.469 | phenyl | 2-COOH | 3-CH₃ | 5-vinyl |
| I.1.470 | phenyl | 2-COOH | 3-CH₃ | 6-vinyl |
| I.1.471 | phenyl | 2-COOH | 4-Cl | 5-F |
| I.1.472 | phenyl | 2-COOH | 4-Cl | 6-F |
| I.1.473 | phenyl | 2-COOH | 4-Cl | 5-Cl |
| I.1.474 | phenyl | 2-COOH | 4-Cl | 6-Cl |
| I.1.475 | phenyl | 2-COOH | 4-Cl | 5-CH₃ |
| I.1.476 | phenyl | 2-COOH | 4-Cl | 6-CH₃ |
| I.1.477 | phenyl | 2-COOH | 4-Cl | 5-vinyl |
| I.1.478 | phenyl | 2-COOH | 4-Cl | 6-vinyl |
| I.1.479 | phenyl | 2-COOH | 4-F | 5-F |
| I.1.480 | phenyl | 2-COOH | 4-F | 6-F |
| I.1.481 | phenyl | 2-COOH | 4-F | 5-Cl |
| I.1.482 | phenyl | 2-COOH | 4-F | 6-Cl |
| I.1.483 | phenyl | 2-COOH | 4-F | 5-CH₃ |
| I.1.484 | phenyl | 2-COOH | 4-F | 6-CH₃ |
| I.1.485 | phenyl | 2-COOH | 4-F | 5-vinyl |
| I.1.486 | phenyl | 2-COOH | 4-F | 6-vinyl |
| I.1.487 | phenyl | 2-COOH | 4-CH₃ | 5-F |
| I.1.488 | phenyl | 2-COOH | 4-CH₃ | 6-F |
| I.1.489 | phenyl | 2-COOH | 4-CH₃ | 5-Cl |
| I.1.490 | phenyl | 2-COOH | 4-CH₃ | 6-Cl |
| I.1.491 | phenyl | 2-COOH | 4-CH₃ | 5-CH₃ |
| I.1.492 | phenyl | 2-COOH | 4-CH₃ | 6-CH₃ |
| I.1.493 | phenyl | 2-COOH | 4-CH₃ | 5-vinyl |
| I.1.494 | phenyl | 2-COOH | 4-CH₃ | 6-vinyl |
| I.1.495 | phenyl | 2-COOH | 5-Cl | 6-Cl |
| I.1.496 | phenyl | 2-COOH | 5-Cl | 6-F |
| I.1.497 | phenyl | 2-COOH | 5-Cl | 6-CH₃ |
| I.1.498 | phenyl | 2-COOH | 5-Cl | 6-vinyl |
| I.1.499 | phenyl | 2-COOH | 5-F | 6-Cl |
| I.1.500 | phenyl | 2-COOH | 5-F | 6-F |
| I.1.501 | phenyl | 2-COOH | 5-F | 6-CH₃ |
| I.1.502 | phenyl | 2-COOH | 5-F | 6-vinyl |
| I.1.503 | phenyl | 2-COOH | 5-CH₃ | 6-Cl |
| I.1.504 | phenyl | 2-COOH | 5-CH₃ | 6-F |
| I.1.505 | phenyl | 2-COOH | 5-CH₃ | 6-CH₃ |
| I.1.506 | phenyl | 2-COOH | 5-CH₃ | 6-vinyl |
| I.1.507 | phenyl | 2-COOH | 5-vinyl | 6-Cl |
| I.1.508 | phenyl | 2-COOH | 5-vinyl | 6-F |
| I.1.509 | phenyl | 2-COOH | 5-vinyl | 6-CH₃ |
| I.1.510 | phenyl | 2-COOH | 5-vinyl | 6-vinyl |
| I.1.511 | phenyl | 2-CON(CH₃)₂ | H | H |
| I.1.512 | phenyl | 2-CON(CH₃)₂ | 3-Cl | H |
| I.1.513 | phenyl | 2-CON(CH₃)₂ | 4-Cl | H |
| I.1.514 | phenyl | 2-CON(CH₃)₂ | 5-Cl | H |
| I.1.515 | phenyl | 2-CON(CH₃)₂ | 6-Cl | H |
| I.1.516 | phenyl | 2-CON(CH₃)₂ | 3-F | H |
| I.1.517 | phenyl | 2-CON(CH₃)₂ | 4-F | H |
| I.1.518 | phenyl | 2-CON(CH₃)₂ | 5-F | H |
| I.1.519 | phenyl | 2-CON(CH₃)₂ | 6-F | H |
| I.1.520 | phenyl | 2-CON(CH₃)₂ | 3-CH₃ | H |
| I.1.521 | phenyl | 2-CON(CH₃)₂ | 4-CH₃ | H |
| I.1.522 | phenyl | 2-CON(CH₃)₂ | 5-CH₃ | H |
| I.1.523 | phenyl | 2-CON(CH₃)₂ | 6-CH₃ | H |
| I.1.524 | phenyl | 2-CON(CH₃)₂ | 5-vinyl | H |
| I.1.525 | phenyl | 2-CON(CH₃)₂ | 6-vinyl | H |
| I.1.526 | phenyl | 2-CON(CH₃)₂ | 5-CF₃ | 3-Cl |
| I.1.527 | phenyl | 2-CON(CH₃)₂ | 5-CF₃ | 4-Cl |
| I.1.528 | phenyl | 2-CON(CH₃)₂ | 4-CF₃ | 5-Cl |
| I.1.529 | phenyl | 2-CON(CH₃)₂ | 5-CF₃ | 6-Cl |
| I.1.530 | phenyl | 2-CON(CH₃)₂ | 5-CF₃ | 3-F |
| I.1.531 | phenyl | 2-CON(CH₃)₂ | 5-CF₃ | 4-F |
| I.1.532 | phenyl | 2-CON(CH₃)₂ | 4-CF₃ | 5-F |
| I.1.533 | phenyl | 2-CON(CH₃)₂ | 5-CF₃ | 6-F |
| I.1.534 | phenyl | 2-CON(CH₃)₂ | 5-CF₃ | 3-CH₃ |
| I.1.535 | phenyl | 2-CON(CH₃)₂ | 5-CF₃ | 4-CH₃ |
| I.1.536 | phenyl | 2-CON(CH₃)₂ | 4-CF₃ | 5-CH₃ |
| I.1.537 | phenyl | 2-CON(CH₃)₂ | 5-CF₃ | 6-CH₃ |
| I.1.538 | phenyl | 2-CON(CH₃)₂ | 4-CF₃ | 5-vinyl |
| I.1.539 | phenyl | 2-CON(CH₃)₂ | 4-CF₃ | 6-vinyl |
| I.1.540 | phenyl | 2-CON(CH₃)₂ | 3-Cl | 4-F |
| I.1.541 | phenyl | 2-CON(CH₃)₂ | 3-Cl | 5-F |
| I.1.542 | phenyl | 2-CON(CH₃)₂ | 3-Cl | 6-F |
| I.1.543 | phenyl | 2-CON(CH₃)₂ | 3-Cl | 4-Cl |
| I.1.544 | phenyl | 2-CON(CH₃)₂ | 3-Cl | 5-Cl |
| I.1.545 | phenyl | 2-CON(CH₃)₂ | 3-Cl | 6-Cl |
| I.1.546 | phenyl | 2-CON(CH₃)₂ | 3-Cl | 4-CH₃ |
| I.1.547 | phenyl | 2-CON(CH₃)₂ | 3-Cl | 5-CH₃ |
| I.1.548 | phenyl | 2-CON(CH₃)₂ | 3-Cl | 6-CH₃ |
| I.1.549 | phenyl | 2-CON(CH₃)₂ | 3-Cl | 5-vinyl |
| I.1.550 | phenyl | 2-CON(CH₃)₂ | 3-Cl | 6-vinyl |
| I.1.551 | phenyl | 2-CON(CH₃)₂ | 3-F | 4-F |
| I.1.552 | phenyl | 2-CON(CH₃)₂ | 3-F | 5-F |
| I.1.553 | phenyl | 2-CON(CH₃)₂ | 3-F | 6-F |
| I.1.554 | phenyl | 2-CON(CH₃)₂ | 3-F | 4-Cl |
| I.1.555 | phenyl | 2-CON(CH₃)₂ | 3-F | 5-Cl |
| I.1.556 | phenyl | 2-CON(CH₃)₂ | 3-F | 6-Cl |
| I.1.557 | phenyl | 2-CON(CH₃)₂ | 3-F | 4-CH₃ |
| I.1.558 | phenyl | 2-CON(CH₃)₂ | 3-F | 5-CH₃ |
| I.1.559 | phenyl | 2-CON(CH₃)₂ | 3-F | 6-CH₃ |
| I.1.560 | phenyl | 2-CON(CH₃)₂ | 3-F | 5-vinyl |
| I.1.561 | phenyl | 2-CON(CH₃)₂ | 3-F | 6-vinyl |
| I.1.562 | phenyl | 2-CON(CH₃)₂ | 3-CH₃ | 4-F |
| I.1.563 | phenyl | 2-CON(CH₃)₂ | 3-CH₃ | 5-F |
| I.1.564 | phenyl | 2-CON(CH₃)₂ | 3-CH₃ | 6-F |
| I.1.565 | phenyl | 2-CON(CH₃)₂ | 3-CH₃ | 4-Cl |
| I.1.566 | phenyl | 2-CON(CH₃)₂ | 3-CH₃ | 5-Cl |
| I.1.567 | phenyl | 2-CON(CH₃)₂ | 3-CH₃ | 6-Cl |
| I.1.568 | phenyl | 2-CON(CH₃)₂ | 3-CH₃ | 4-CH₃ |
| I.1.569 | phenyl | 2-CON(CH₃)₂ | 3-CH₃ | 5-CH₃ |
| I.1.570 | phenyl | 2-CON(CH₃)₂ | 3-CH₃ | 6-CH₃ |
| I.1.571 | phenyl | 2-CON(CH₃)₂ | 3-CH₃ | 5-vinyl |
| I.1.572 | phenyl | 2-CON(CH₃)₂ | 3-CH₃ | 6-vinyl |
| I.1.573 | phenyl | 2-CON(CH₃)₂ | 4-Cl | 5-F |
| I.1.574 | phenyl | 2-CON(CH₃)₂ | 4-Cl | 6-F |
| I.1.575 | phenyl | 2-CON(CH₃)₂ | 4-Cl | 5-Cl |
| I.1.576 | phenyl | 2-CON(CH₃)₂ | 4-Cl | 6-Cl |
| I.1.577 | phenyl | 2-CON(CH₃)₂ | 4-Cl | 5-CH₃ |
| I.1.578 | phenyl | 2-CON(CH₃)₂ | 4-Cl | 6-CH₃ |
| I.1.579 | phenyl | 2-CON(CH₃)₂ | 4-Cl | 5-vinyl |
| I.1.580 | phenyl | 2-CON(CH₃)₂ | 4-Cl | 6-vinyl |
| I.1.581 | phenyl | 2-CON(CH₃)₂ | 4-F | 5-F |
| I.1.582 | phenyl | 2-CON(CH₃)₂ | 4-F | 6-F |
| I.1.583 | phenyl | 2-CON(CH₃)₂ | 4-F | 5-Cl |
| I.1.584 | phenyl | 2-CON(CH₃)₂ | 4-F | 6-Cl |
| I.1.585 | phenyl | 2-CON(CH₃)₂ | 4-F | 5-CH₃ |
| I.1.586 | phenyl | 2-CON(CH₃)₂ | 4-F | 6-CH₃ |
| I.1.587 | phenyl | 2-CON(CH₃)₂ | 4-F | 5-vinyl |
| I.1.588 | phenyl | 2-CON(CH₃)₂ | 4-F | 6-vinyl |
| I.1.589 | phenyl | 2-CON(CH₃)₂ | 4-CH₃ | 5-F |
| I.1.590 | phenyl | 2-CON(CH₃)₂ | 4-CH₃ | 6-F |
| I.1.591 | phenyl | 2-CON(CH₃)₂ | 4-CH₃ | 5-Cl |
| I.1.592 | phenyl | 2-CON(CH₃)₂ | 4-CH₃ | 6-Cl |
| I.1.593 | phenyl | 2-CON(CH₃)₂ | 4-CH₃ | 5-CH₃ |
| I.1.594 | phenyl | 2-CON(CH₃)₂ | 4-CH₃ | 6-CH₃ |
| I.1.595 | phenyl | 2-CON(CH₃)₂ | 4-CH₃ | 5-vinyl |
| I.1.596 | phenyl | 2-CON(CH₃)₂ | 4-CH₃ | 6-vinyl |
| I.1.597 | phenyl | 2-CON(CH₃)₂ | 5-Cl | 6-Cl |
| I.1.598 | phenyl | 2-CON(CH₃)₂ | 5-Cl | 6-F |
| I.1.599 | phenyl | 2-CON(CH₃)₂ | 5-Cl | 6-CH₃ |
| I.1.600 | phenyl | 2-CON(CH₃)₂ | 5-Cl | 6-vinyl |
| I.1.601 | phenyl | 2-CON(CH₃)₂ | 5-F | 6-Cl |
| I.1.602 | phenyl | 2-CON(CH₃)₂ | 5-F | 6-F |
| I.1.603 | phenyl | 2-CON(CH₃)₂ | 5-F | 6-CH₃ |
| I.1.604 | phenyl | 2-CON(CH₃)₂ | 5-F | 6-vinyl |
| I.1.605 | phenyl | 2-CON(CH₃)₂ | 5-CH₃ | 6-Cl |
| I.1.606 | phenyl | 2-CON(CH₃)₂ | 5-CH₃ | 6-F |
| I.1.607 | phenyl | 2-CON(CH₃)₂ | 5-CH₃ | 6-CH₃ |
| I.1.608 | phenyl | 2-CON(CH₃)₂ | 5-CH₃ | 6-vinyl |
| I.1.609 | phenyl | 2-CON(CH₃)₂ | 5-vinyl | 6-Cl |
| I.1.610 | phenyl | 2-CON(CH₃)₂ | 5-vinyl | 6-F |
| I.1.611 | phenyl | 2-CON(CH₃)₂ | 5-vinyl | 6-CH₃ |
| I.1.612 | phenyl | 2-CON(CH₃)₂ | 5-vinyl | 6-vinyl |
| I.1.613 | phenyl | 2-I | H | H |
| I.1.614 | phenyl | 2-I | 3-Cl | H |
| I.1.615 | phenyl | 2-I | 4-Cl | H |
| I.1.616 | phenyl | 2-I | 5-Cl | H |
| I.1.617 | phenyl | 2-I | 6-Cl | H |
| I.1.618 | phenyl | 2-I | 3-F | H |
| I.1.619 | phenyl | 2-I | 4-F | H |
| I.1.620 | phenyl | 2-I | 5-F | H |

TABLE 1-continued

| Comp. No. | A¹ | Rᵃ | Rᵇ or H | Rᶜ H |
|---|---|---|---|---|
| I.1.621 | phenyl | 2-I | 6-F | H |
| I.1.622 | phenyl | 2-I | 3-CH₃ | H |
| I.1.623 | phenyl | 2-I | 4-CH₃ | H |
| I.1.624 | phenyl | 2-I | 5-CH₃ | H |
| I.1.625 | phenyl | 2-I | 6-CH₃ | H |
| I.1.626 | phenyl | 2-I | 5-vinyl | H |
| I.1.627 | phenyl | 2-I | 6-vinyl | H |
| I.1.628 | phenyl | 2-I | 5-CF₃ | 3-Cl |
| I.1.629 | phenyl | 2-I | 5-CF₃ | 4-Cl |
| I.1.630 | phenyl | 2-I | 4-CF₃ | 5-Cl |
| I.1.631 | phenyl | 2-I | 5-CF₃ | 6-Cl |
| I.1.632 | phenyl | 2-I | 5-CF₃ | 3-F |
| I.1.633 | phenyl | 2-I | 5-CF₃ | 4-F |
| I.1.634 | phenyl | 2-I | 4-CF₃ | 5-F |
| I.1.635 | phenyl | 2-I | 5-CF₃ | 6-F |
| I.1.636 | phenyl | 2-I | 5-CF₃ | 3-CH₃ |
| I.1.637 | phenyl | 2-I | 5-CF₃ | 4-CH₃ |
| I.1.638 | phenyl | 2-I | 4-CF₃ | 5-CH₃ |
| I.1.639 | phenyl | 2-I | 5-CF₃ | 6-CH₃ |
| I.1.640 | phenyl | 2-I | 4-CF₃ | 5-vinyl |
| I.1.641 | phenyl | 2-I | 4-CF₃ | 6-vinyl |
| I.1.642 | phenyl | 2-I | 3-Cl | 4-F |
| I.1.643 | phenyl | 2-I | 3-Cl | 5-F |
| I.1.644 | phenyl | 2-I | 3-Cl | 6-F |
| I.1.645 | phenyl | 2-I | 3-Cl | 4-Cl |
| I.1.646 | phenyl | 2-I | 3-Cl | 5-Cl |
| I.1.647 | phenyl | 2-I | 3-Cl | 6-Cl |
| I.1.648 | phenyl | 2-I | 3-Cl | 4-CH₃ |
| I.1.649 | phenyl | 2-I | 3-Cl | 5-CH₃ |
| I.1.650 | phenyl | 2-I | 3-Cl | 6-CH₃ |
| I.1.651 | phenyl | 2-I | 3-Cl | 5-vinyl |
| I.1.652 | phenyl | 2-I | 3-Cl | 6-vinyl |
| I.1.653 | phenyl | 2-I | 3-F | 4-F |
| I.1.654 | phenyl | 2-I | 3-F | 5-F |
| I.1.655 | phenyl | 2-I | 3-F | 6-F |
| I.1.656 | phenyl | 2-I | 3-F | 4-Cl |
| I.1.657 | phenyl | 2-I | 3-F | 5-Cl |
| I.1.658 | phenyl | 2-I | 3-F | 6-Cl |
| I.1.659 | phenyl | 2-I | 3-F | 4-CH₃ |
| I.1.660 | phenyl | 2-I | 3-F | 5-CH₃ |
| I.1.661 | phenyl | 2-I | 3-F | 6-CH₃ |
| I.1.662 | phenyl | 2-I | 3-F | 5-vinyl |
| I.1.663 | phenyl | 2-I | 3-F | 6-vinyl |
| I.1.664 | phenyl | 2-I | 3-CH₃ | 4-F |
| I.1.665 | phenyl | 2-I | 3-CH₃ | 5-F |
| I.1.666 | phenyl | 2-I | 3-CH₃ | 6-F |
| I.1.667 | phenyl | 2-I | 3-CH₃ | 4-Cl |
| I.1.668 | phenyl | 2-I | 3-CH₃ | 5-Cl |
| I.1.669 | phenyl | 2-I | 3-CH₃ | 6-Cl |
| I.1.670 | phenyl | 2-I | 3-CH₃ | 4-CH₃ |
| I.1.671 | phenyl | 2-I | 3-CH₃ | 5-CH₃ |
| I.1.672 | phenyl | 2-I | 3-CH₃ | 6-CH₃ |
| I.1.673 | phenyl | 2-I | 3-CH₃ | 5-vinyl |
| I.1.674 | phenyl | 2-I | 3-CH₃ | 6-vinyl |
| I.1.675 | phenyl | 2-I | 4-Cl | 5-F |
| I.1.676 | phenyl | 2-I | 4-Cl | 6-F |
| I.1.677 | phenyl | 2-I | 4-Cl | 5-Cl |
| I.1.678 | phenyl | 2-I | 4-Cl | 6-Cl |
| I.1.679 | phenyl | 2-I | 4-Cl | 5-CH₃ |
| I.1.680 | phenyl | 2-I | 4-Cl | 6-CH₃ |
| I.1.681 | phenyl | 2-I | 4-Cl | 5-vinyl |
| I.1.682 | phenyl | 2-I | 4-Cl | 6-vinyl |
| I.1.683 | phenyl | 2-I | 4-F | 5-F |
| I.1.684 | phenyl | 2-I | 4-F | 6-F |
| I.1.685 | phenyl | 2-I | 4-F | 5-Cl |
| I.1.686 | phenyl | 2-I | 4-F | 6-Cl |
| I.1.687 | phenyl | 2-I | 4-F | 5-CH₃ |
| I.1.688 | phenyl | 2-I | 4-F | 6-CH₃ |
| I.1.689 | phenyl | 2-I | 4-F | 5-vinyl |
| I.1.690 | phenyl | 2-I | 4-F | 6-vinyl |
| I.1.691 | phenyl | 2-I | 4-CH₃ | 5-F |
| I.1.692 | phenyl | 2-I | 4-CH₃ | 6-F |
| I.1.693 | phenyl | 2-I | 4-CH₃ | 5-Cl |
| I.1.694 | phenyl | 2-I | 4-CH₃ | 6-Cl |
| I.1.695 | phenyl | 2-I | 4-CH₃ | 5-CH₃ |
| I.1.696 | phenyl | 2-I | 4-CH₃ | 6-CH₃ |
| I.1.697 | phenyl | 2-I | 4-CH₃ | 5-vinyl |
| I.1.698 | phenyl | 2-I | 4-CH₃ | 6-vinyl |
| I.1.699 | phenyl | 2-I | 5-Cl | 6-Cl |
| I.1.700 | phenyl | 2-I | 5-Cl | 6-F |
| I.1.701 | phenyl | 2-I | 5-Cl | 6-CH₃ |
| I.1.702 | phenyl | 2-I | 5-Cl | 6-vinyl |
| I.1.703 | phenyl | 2-I | 5-F | 6-Cl |
| I.1.704 | phenyl | 2-I | 5-F | 6-F |
| I.1.705 | phenyl | 2-I | 5-F | 6-CH₃ |
| I.1.706 | phenyl | 2-I | 5-F | 6-vinyl |
| I.1.707 | phenyl | 2-I | 5-CH₃ | 6-Cl |
| I.1.708 | phenyl | 2-I | 5-CH₃ | 6-F |
| I.1.709 | phenyl | 2-I | 5-CH₃ | 6-CH₃ |
| I.1.710 | phenyl | 2-I | 5-CH₃ | 6-vinyl |
| I.1.711 | phenyl | 2-I | 5-vinyl | 6-Cl |
| I.1.712 | phenyl | 2-I | 5-vinyl | 6-F |
| I.1.713 | phenyl | 2-I | 5-vinyl | 6-CH₃ |
| I.1.714 | phenyl | 2-I | 5-vinyl | 6-vinyl |
| I.1.715 | phenyl | 2-Br | H | H |
| I.1.716 | phenyl | 2-Br | 3-Cl | H |
| I.1.717 | phenyl | 2-Br | 4-Cl | H |
| I.1.718 | phenyl | 2-Br | 5-Cl | H |
| I.1.719 | phenyl | 2-Br | 6-Cl | H |
| I.1.720 | phenyl | 2-Br | 3-F | H |
| I.1.721 | phenyl | 2-Br | 4-F | H |
| I.1.722 | phenyl | 2-Br | 5-F | H |
| I.1.723 | phenyl | 2-Br | 6-F | H |
| I.1.724 | phenyl | 2-Br | 3-CH₃ | H |
| I.1.725 | phenyl | 2-Br | 4-CH₃ | H |
| I.1.726 | phenyl | 2-Br | 5-CH₃ | H |
| I.1.727 | phenyl | 2-Br | 6-CH₃ | H |
| I.1.728 | phenyl | 2-Br | 5-vinyl | H |
| I.1.729 | phenyl | 2-Br | 6-vinyl | H |
| I.1.730 | phenyl | 2-Br | 5-CF₃ | 3-Cl |
| I.1.731 | phenyl | 2-Br | 5-CF₃ | 4-Cl |
| I.1.732 | phenyl | 2-Br | 4-CF₃ | 5-Cl |
| I.1.733 | phenyl | 2-Br | 5-CF₃ | 6-Cl |
| I.1.734 | phenyl | 2-Br | 5-CF₃ | 3-F |
| I.1.735 | phenyl | 2-Br | 5-CF₃ | 4-F |
| I.1.736 | phenyl | 2-Br | 4-CF₃ | 5-F |
| I.1.737 | phenyl | 2-Br | 5-CF₃ | 6-F |
| I.1.738 | phenyl | 2-Br | 5-CF₃ | 3-CH₃ |
| I.1.739 | phenyl | 2-Br | 5-CF₃ | 4-CH₃ |
| I.1.740 | phenyl | 2-Br | 4-CF₃ | 5-CH₃ |
| I.1.741 | phenyl | 2-Br | 5-CF₃ | 6-CH₃ |
| I.1.742 | phenyl | 2-Br | 4-CF₃ | 5-vinyl |
| I.1.743 | phenyl | 2-Br | 4-CF₃ | 6-vinyl |
| I.1.744 | phenyl | 2-Br | 3-Cl | 4-F |
| I.1.745 | phenyl | 2-Br | 3-Cl | 5-F |
| I.1.746 | phenyl | 2-Br | 3-Cl | 6-F |
| I.1.747 | phenyl | 2-Br | 3-Cl | 4-Cl |
| I.1.748 | phenyl | 2-Br | 3-Cl | 5-Cl |
| I.1.749 | phenyl | 2-Br | 3-Cl | 6-Cl |
| I.1.750 | phenyl | 2-Br | 3-Cl | 4-CH₃ |
| I.1.751 | phenyl | 2-Br | 3-Cl | 5-CH₃ |
| I.1.752 | phenyl | 2-Br | 3-Cl | 6-CH₃ |
| I.1.753 | phenyl | 2-Br | 3-Cl | 5-vinyl |
| I.1.754 | phenyl | 2-Br | 3-Cl | 6-vinyl |
| I.1.755 | phenyl | 2-Br | 3-F | 4-F |
| I.1.756 | phenyl | 2-Br | 3-F | 5-F |
| I.1.757 | phenyl | 2-Br | 3-F | 6-F |
| I.1.758 | phenyl | 2-Br | 3-F | 4-Cl |
| I.1.759 | phenyl | 2-Br | 3-F | 5-Cl |
| I.1.760 | phenyl | 2-Br | 3-F | 6-Cl |
| I.1.761 | phenyl | 2-Br | 3-F | 4-CH₃ |
| I.1.762 | phenyl | 2-Br | 3-F | 5-CH₃ |
| I.1.763 | phenyl | 2-Br | 3-F | 6-CH₃ |
| I.1.764 | phenyl | 2-Br | 3-F | 5-vinyl |
| I.1.765 | phenyl | 2-Br | 3-F | 6-vinyl |
| I.1.766 | phenyl | 2-Br | 3-CH₃ | 4-F |
| I.1.767 | phenyl | 2-Br | 3-CH₃ | 5-F |
| I.1.768 | phenyl | 2-Br | 3-CH₃ | 6-F |
| I.1.769 | phenyl | 2-Br | 3-CH₃ | 4-Cl |
| I.1.770 | phenyl | 2-Br | 3-CH₃ | 5-Cl |
| I.1.771 | phenyl | 2-Br | 3-CH₃ | 6-Cl |
| I.1.772 | phenyl | 2-Br | 3-CH₃ | 4-CH₃ |
| I.1.773 | phenyl | 2-Br | 3-CH₃ | 5-CH₃ |
| I.1.774 | phenyl | 2-Br | 3-CH₃ | 6-CH₃ |
| I.1.775 | phenyl | 2-Br | 3-CH₃ | 5-vinyl |
| I.1.776 | phenyl | 2-Br | 3-CH₃ | 6-vinyl |

TABLE 1-continued

| Comp. No. | A¹ | $R^a$ | $R^b$ or H | $R^c$ H |
|---|---|---|---|---|
| I.1.777 | phenyl | 2-Br | 4-Cl | 5-F |
| I.1.778 | phenyl | 2-Br | 4-Cl | 6-F |
| I.1.779 | phenyl | 2-Br | 4-Cl | 5-Cl |
| I.1.780 | phenyl | 2-Br | 4-Cl | 6-Cl |
| I.1.781 | phenyl | 2-Br | 4-Cl | 5-CH₃ |
| I.1.782 | phenyl | 2-Br | 4-Cl | 6-CH₃ |
| I.1.783 | phenyl | 2-Br | 4-Cl | 5-vinyl |
| I.1.784 | phenyl | 2-Br | 4-Cl | 6-vinyl |
| I.1.785 | phenyl | 2-Br | 4-F | 5-F |
| I.1.786 | phenyl | 2-Br | 4-F | 6-F |
| I.1.787 | phenyl | 2-Br | 4-F | 5-Cl |
| I.1.788 | phenyl | 2-Br | 4-F | 6-Cl |
| I.1.789 | phenyl | 2-Br | 4-F | 5-CH₃ |
| I.1.790 | phenyl | 2-Br | 4-F | 6-CH₃ |
| I.1.791 | phenyl | 2-Br | 4-F | 5-vinyl |
| I.1.792 | phenyl | 2-Br | 4-F | 6-vinyl |
| I.1.793 | phenyl | 2-Br | 4-CH₃ | 5-F |
| I.1.794 | phenyl | 2-Br | 4-CH₃ | 6-F |
| I.1.795 | phenyl | 2-Br | 4-CH₃ | 5-Cl |
| I.1.796 | phenyl | 2-Br | 4-CH₃ | 6-Cl |
| I.1.797 | phenyl | 2-Br | 4-CH₃ | 5-CH₃ |
| I.1.798 | phenyl | 2-Br | 4-CH₃ | 6-CH₃ |
| I.1.799 | phenyl | 2-Br | 4-CH₃ | 5-vinyl |
| I.1.800 | phenyl | 2-Br | 4-CH₃ | 6-vinyl |
| I.1.801 | phenyl | 2-Br | 5-Cl | 6-Cl |
| I.1.802 | phenyl | 2-Br | 5-Cl | 6-F |
| I.1.803 | phenyl | 2-Br | 5-Cl | 6-CH₃ |
| I.1.804 | phenyl | 2-Br | 5-Cl | 6-vinyl |
| I.1.805 | phenyl | 2-Br | 5-F | 6-Cl |
| I.1.806 | phenyl | 2-Br | 5-F | 6-F |
| I.1.807 | phenyl | 2-Br | 5-F | 6-CH₃ |
| I.1.808 | phenyl | 2-Br | 5-F | 6-vinyl |
| I.1.809 | phenyl | 2-Br | 5-CH₃ | 6-Cl |
| I.1.810 | phenyl | 2-Br | 5-CH₃ | 6-F |
| I.1.811 | phenyl | 2-Br | 5-CH₃ | 6-CH₃ |
| I.1.812 | phenyl | 2-Br | 5-CH₃ | 6-vinyl |
| I.1.813 | phenyl | 2-Br | 5-vinyl | 6-Cl |
| I.1.814 | phenyl | 2-Br | 5-vinyl | 6-F |
| I.1.815 | phenyl | 2-Br | 5-vinyl | 6-CH₃ |
| I.1.816 | phenyl | 2-Br | 5-vinyl | 6-vinyl |
| I.1.817 | phenyl | 2-Cl | H | H |
| I.1.818 | phenyl | 2-Cl | 3-Cl | H |
| I.1.819 | phenyl | 2-Cl | 4-Cl | H |
| I.1.820 | phenyl | 2-Cl | 5-Cl | H |
| I.1.821 | phenyl | 2-Cl | 6-Cl | H |
| I.1.822 | phenyl | 2-Cl | 3-F | H |
| I.1.823 | phenyl | 2-Cl | 4-F | H |
| I.1.824 | phenyl | 2-Cl | 5-F | H |
| I.1.825 | phenyl | 2-Cl | 6-F | H |
| I.1.826 | phenyl | 2-Cl | 3-CH₃ | H |
| I.1.827 | phenyl | 2-Cl | 4-CH₃ | H |
| I.1.828 | phenyl | 2-Cl | 5-CH₃ | H |
| I.1.829 | phenyl | 2-Cl | 6-CH₃ | H |
| I.1.830 | phenyl | 2-Cl | 5-vinyl | H |
| I.1.831 | phenyl | 2-Cl | 6-vinyl | H |
| I.1.832 | phenyl | 2-Cl | 5-CF₃ | 3-Cl |
| I.1.833 | phenyl | 2-Cl | 5-CF₃ | 4-Cl |
| I.1.834 | phenyl | 2-Cl | 4-CF₃ | 5-Cl |
| I.1.835 | phenyl | 2-Cl | 5-CF₃ | 6-Cl |
| I.1.836 | phenyl | 2-Cl | 5-CF₃ | 3-F |
| I.1.837 | phenyl | 2-Cl | 5-CF₃ | 4-F |
| I.1.838 | phenyl | 2-Cl | 4-CF₃ | 5-F |
| I.1.839 | phenyl | 2-Cl | 5-CF₃ | 6-F |
| I.1.840 | phenyl | 2-Cl | 5-CF₃ | 3-CH₃ |
| I.1.841 | phenyl | 2-Cl | 5-CF₃ | 4-CH₃ |
| I.1.842 | phenyl | 2-Cl | 4-CF₃ | 5-CH₃ |
| I.1.843 | phenyl | 2-Cl | 5-CF₃ | 6-CH₃ |
| I.1.844 | phenyl | 2-Cl | 4-CF₃ | 5-vinyl |
| I.1.845 | phenyl | 2-Cl | 4-CF₃ | 6-vinyl |
| I.1.846 | phenyl | 2-Cl | 3-Cl | 4-F |
| I.1.847 | phenyl | 2-Cl | 3-Cl | 5-F |
| I.1.848 | phenyl | 2-Cl | 3-Cl | 6-F |
| I.1.849 | phenyl | 2-Cl | 3-Cl | 4-Cl |
| I.1.850 | phenyl | 2-Cl | 3-Cl | 5-Cl |
| I.1.851 | phenyl | 2-Cl | 3-Cl | 6-Cl |
| I.1.852 | phenyl | 2-Cl | 3-Cl | 4-CH₃ |
| I.1.853 | phenyl | 2-Cl | 3-Cl | 5-CH₃ |
| I.1.854 | phenyl | 2-Cl | 3-Cl | 6-CH₃ |
| I.1.855 | phenyl | 2-Cl | 3-Cl | 5-vinyl |
| I.1.856 | phenyl | 2-Cl | 3-Cl | 6-vinyl |
| I.1.857 | phenyl | 2-Cl | 3-F | 4-F |
| I.1.858 | phenyl | 2-Cl | 3-F | 5-F |
| I.1.859 | phenyl | 2-Cl | 3-F | 6-F |
| I.1.860 | phenyl | 2-Cl | 3-F | 4-Cl |
| I.1.861 | phenyl | 2-Cl | 3-F | 5-Cl |
| I.1.862 | phenyl | 2-Cl | 3-F | 6-Cl |
| I.1.863 | phenyl | 2-Cl | 3-F | 4-CH₃ |
| I.1.864 | phenyl | 2-Cl | 3-F | 5-CH₃ |
| I.1.865 | phenyl | 2-Cl | 3-F | 6-CH₃ |
| I.1.866 | phenyl | 2-Cl | 3-F | 5-vinyl |
| I.1.867 | phenyl | 2-Cl | 3-F | 6-vinyl |
| I.1.868 | phenyl | 2-Cl | 3-CH₃ | 4-F |
| I.1.869 | phenyl | 2-Cl | 3-CH₃ | 5-F |
| I.1.870 | phenyl | 2-Cl | 3-CH₃ | 6-F |
| I.1.871 | phenyl | 2-Cl | 3-CH₃ | 4-Cl |
| I.1.872 | phenyl | 2-Cl | 3-CH₃ | 5-Cl |
| I.1.873 | phenyl | 2-Cl | 3-CH₃ | 6-Cl |
| I.1.874 | phenyl | 2-Cl | 3-CH₃ | 4-CH₃ |
| I.1.875 | phenyl | 2-Cl | 3-CH₃ | 5-CH₃ |
| I.1.876 | phenyl | 2-Cl | 3-CH₃ | 6-CH₃ |
| I.1.877 | phenyl | 2-Cl | 3-CH₃ | 5-vinyl |
| I.1.878 | phenyl | 2-Cl | 3-CH₃ | 6-vinyl |
| I.1.879 | phenyl | 2-Cl | 4-Cl | 5-F |
| I.1.880 | phenyl | 2-Cl | 4-Cl | 6-F |
| I.1.881 | phenyl | 2-Cl | 4-Cl | 5-Cl |
| I.1.882 | phenyl | 2-Cl | 4-Cl | 6-Cl |
| I.1.883 | phenyl | 2-Cl | 4-Cl | 5-CH₃ |
| I.1.884 | phenyl | 2-Cl | 4-Cl | 6-CH₃ |
| I.1.885 | phenyl | 2-Cl | 4-Cl | 5-vinyl |
| I.1.886 | phenyl | 2-Cl | 4-Cl | 6-vinyl |
| I.1.887 | phenyl | 2-Cl | 4-F | 5-F |
| I.1.888 | phenyl | 2-Cl | 4-F | 6-F |
| I.1.889 | phenyl | 2-Cl | 4-F | 5-Cl |
| I.1.890 | phenyl | 2-Cl | 4-F | 6-Cl |
| I.1.891 | phenyl | 2-Cl | 4-F | 5-CH₃ |
| I.1.892 | phenyl | 2-Cl | 4-F | 6-CH₃ |
| I.1.893 | phenyl | 2-Cl | 4-F | 5-vinyl |
| I.1.894 | phenyl | 2-Cl | 4-F | 6-vinyl |
| I.1.895 | phenyl | 2-Cl | 4-CH₃ | 5-F |
| I.1.896 | phenyl | 2-Cl | 4-CH₃ | 6-F |
| I.1.897 | phenyl | 2-Cl | 4-CH₃ | 5-Cl |
| I.1.898 | phenyl | 2-Cl | 4-CH₃ | 6-Cl |
| I.1.899 | phenyl | 2-Cl | 4-CH₃ | 5-CH₃ |
| I.1.900 | phenyl | 2-Cl | 4-CH₃ | 6-CH₃ |
| I.1.901 | phenyl | 2-Cl | 4-CH₃ | 5-vinyl |
| I.1.902 | phenyl | 2-Cl | 4-CH₃ | 6-vinyl |
| I.1.903 | phenyl | 2-Cl | 5-Cl | 6-Cl |
| I.1.904 | phenyl | 2-Cl | 5-Cl | 6-F |
| I.1.905 | phenyl | 2-Cl | 5-Cl | 6-CH₃ |
| I.1.906 | phenyl | 2-Cl | 5-Cl | 6-vinyl |
| I.1.907 | phenyl | 2-Cl | 5-F | 6-Cl |
| I.1.908 | phenyl | 2-Cl | 5-F | 6-F |
| I.1.909 | phenyl | 2-Cl | 5-F | 6-CH₃ |
| I.1.910 | phenyl | 2-Cl | 5-F | 6-vinyl |
| I.1.911 | phenyl | 2-Cl | 5-CH₃ | 6-Cl |
| I.1.912 | phenyl | 2-Cl | 5-CH₃ | 6-F |
| I.1.913 | phenyl | 2-Cl | 5-CH₃ | 6-CH₃ |
| I.1.914 | phenyl | 2-Cl | 5-CH₃ | 6-vinyl |
| I.1.915 | phenyl | 2-Cl | 5-vinyl | 6-Cl |
| I.1.916 | phenyl | 2-Cl | 5-vinyl | 6-F |
| I.1.917 | phenyl | 2-Cl | 5-vinyl | 6-CH₃ |
| I.1.918 | phenyl | 2-Cl | 5-vinyl | 6-vinyl |
| I.1.919 | phenyl | 2-COOCH₂CH₃ | H | H |
| I.1.920 | phenyl | 2-COOCH₂CH₃ | 3-Cl | H |
| I.1.921 | phenyl | 2-COOCH₂CH₃ | 4-Cl | H |
| I.1.922 | phenyl | 2-COOCH₂CH₃ | 5-Cl | H |
| I.1.923 | phenyl | 2-COOCH₂CH₃ | 6-Cl | H |
| I.1.924 | phenyl | 2-COOCH₂CH₃ | 3-F | H |
| I.1.925 | phenyl | 2-COOCH₂CH₃ | 4-F | H |
| I.1.926 | phenyl | 2-COOCH₂CH₃ | 5-F | H |
| I.1.927 | phenyl | 2-COOCH₂CH₃ | 6-F | H |
| I.1.928 | phenyl | 2-COOCH₂CH₃ | 3-CH₃ | H |
| I.1.929 | phenyl | 2-COOCH₂CH₃ | 4-CH₃ | H |
| I.1.930 | phenyl | 2-COOCH₂CH₃ | 5-CH₃ | H |
| I.1.931 | phenyl | 2-COOCH₂CH₃ | 6-CH₃ | H |
| I.1.932 | phenyl | 2-COOCH₂CH₃ | 5-vinyl | H |

TABLE 1-continued

| Comp. No. | A¹ | $R^a$ | $R^b$ or H | $R^c$ H |
|---|---|---|---|---|
| I.1.933 | phenyl | 2-COOCH$_2$CH$_3$ | 6-vinyl | H |
| I.1.934 | phenyl | 2-COOCH$_2$CH$_3$ | 5-CF$_3$ | 3-Cl |
| I.1.935 | phenyl | 2-COOCH$_2$CH$_3$ | 5-CF$_3$ | 4-Cl |
| I.1.936 | phenyl | 2-COOCH$_2$CH$_3$ | 4-CF$_3$ | 5-Cl |
| I.1.937 | phenyl | 2-COOCH$_2$CH$_3$ | 5-CF$_3$ | 6-Cl |
| I.1.938 | phenyl | 2-COOCH$_2$CH$_3$ | 5-CF$_3$ | 3-F |
| I.1.939 | phenyl | 2-COOCH$_2$CH$_3$ | 5-CF$_3$ | 4-F |
| I.1.940 | phenyl | 2-COOCH$_2$CH$_3$ | 4-CF$_3$ | 5-F |
| I.1.941 | phenyl | 2-COOCH$_2$CH$_3$ | 5-CF$_3$ | 6-F |
| I.1.942 | phenyl | 2-COOCH$_2$CH$_3$ | 5-CF$_3$ | 3-CH$_3$ |
| I.1.943 | phenyl | 2-COOCH$_2$CH$_3$ | 5-CF$_3$ | 4-CH$_3$ |
| I.1.944 | phenyl | 2-COOCH$_2$CH$_3$ | 4-CF$_3$ | 5-CH$_3$ |
| I.1.945 | phenyl | 2-COOCH$_2$CH$_3$ | 5-CF$_3$ | 6-CH$_3$ |
| I.1.946 | phenyl | 2-COOCH$_2$CH$_3$ | 4-CF$_3$ | 5-vinyl |
| I.1.947 | phenyl | 2-COOCH$_2$CH$_3$ | 4-CF$_3$ | 6-vinyl |
| I.1.948 | phenyl | 2-COOCH$_2$CH$_3$ | 3-Cl | 4-F |
| I.1.949 | phenyl | 2-COOCH$_2$CH$_3$ | 3-Cl | 5-F |
| I.1.950 | phenyl | 2-COOCH$_2$CH$_3$ | 3-Cl | 6-F |
| I.1.951 | phenyl | 2-COOCH$_2$CH$_3$ | 3-Cl | 4-Cl |
| I.1.952 | phenyl | 2-COOCH$_2$CH$_3$ | 3-Cl | 5-Cl |
| I.1.953 | phenyl | 2-COOCH$_2$CH$_3$ | 3-Cl | 6-Cl |
| I.1.954 | phenyl | 2-COOCH$_2$CH$_3$ | 3-Cl | 4-CH$_3$ |
| I.1.955 | phenyl | 2-COOCH$_2$CH$_3$ | 3-Cl | 5-CH$_3$ |
| I.1.956 | phenyl | 2-COOCH$_2$CH$_3$ | 3-Cl | 6-CH$_3$ |
| I.1.957 | phenyl | 2-COOCH$_2$CH$_3$ | 3-Cl | 5-vinyl |
| I.1.958 | phenyl | 2-COOCH$_2$CH$_3$ | 3-Cl | 6-vinyl |
| I.1.959 | phenyl | 2-COOCH$_2$CH$_3$ | 3-F | 4-F |
| I.1.960 | phenyl | 2-COOCH$_2$CH$_3$ | 3-F | 5-F |
| I.1.961 | phenyl | 2-COOCH$_2$CH$_3$ | 3-F | 6-F |
| I.1.962 | phenyl | 2-COOCH$_2$CH$_3$ | 3-F | 4-Cl |
| I.1.963 | phenyl | 2-COOCH$_2$CH$_3$ | 3-F | 5-Cl |
| I.1.964 | phenyl | 2-COOCH$_2$CH$_3$ | 3-F | 6-Cl |
| I.1.965 | phenyl | 2-COOCH$_2$CH$_3$ | 3-F | 4-CH$_3$ |
| I.1.966 | phenyl | 2-COOCH$_2$CH$_3$ | 3-F | 5-CH$_3$ |
| I.1.967 | phenyl | 2-COOCH$_2$CH$_3$ | 3-F | 6-CH$_3$ |
| I.1.968 | phenyl | 2-COOCH$_2$CH$_3$ | 3-F | 5-vinyl |
| I.1.969 | phenyl | 2-COOCH$_2$CH$_3$ | 3-F | 6-vinyl |
| I.1.970 | phenyl | 2-COOCH$_2$CH$_3$ | 3-CH$_3$ | 4-F |
| I.1.971 | phenyl | 2-COOCH$_2$CH$_3$ | 3-CH$_3$ | 5-F |
| I.1.972 | phenyl | 2-COOCH$_2$CH$_3$ | 3-CH$_3$ | 6-F |
| I.1.973 | phenyl | 2-COOCH$_2$CH$_3$ | 3-CH$_3$ | 4-Cl |
| I.1.974 | phenyl | 2-COOCH$_2$CH$_3$ | 3-CH$_3$ | 5-Cl |
| I.1.975 | phenyl | 2-COOCH$_2$CH$_3$ | 3-CH$_3$ | 6-Cl |
| I.1.976 | phenyl | 2-COOCH$_2$CH$_3$ | 3-CH$_3$ | 4-CH$_3$ |
| I.1.977 | phenyl | 2-COOCH$_2$CH$_3$ | 3-CH$_3$ | 5-CH$_3$ |
| I.1.978 | phenyl | 2-COOCH$_2$CH$_3$ | 3-CH$_3$ | 6-CH$_3$ |
| I.1.979 | phenyl | 2-COOCH$_2$CH$_3$ | 3-CH$_3$ | 5-vinyl |
| I.1.980 | phenyl | 2-COOCH$_2$CH$_3$ | 3-CH$_3$ | 6-vinyl |
| I.1.981 | phenyl | 2-COOCH$_2$CH$_3$ | 4-Cl | 5-F |
| I.1.982 | phenyl | 2-COOCH$_2$CH$_3$ | 4-Cl | 6-F |
| I.1.983 | phenyl | 2-COOCH$_2$CH$_3$ | 4-Cl | 5-Cl |
| I.1.984 | phenyl | 2-COOCH$_2$CH$_3$ | 4-Cl | 6-Cl |
| I.1.985 | phenyl | 2-COOCH$_2$CH$_3$ | 4-Cl | 5-CH$_3$ |
| I.1.986 | phenyl | 2-COOCH$_2$CH$_3$ | 4-Cl | 6-CH$_3$ |
| I.1.987 | phenyl | 2-COOCH$_2$CH$_3$ | 4-Cl | 5-vinyl |
| I.1.988 | phenyl | 2-COOCH$_2$CH$_3$ | 4-Cl | 6-vinyl |
| I.1.989 | phenyl | 2-COOCH$_2$CH$_3$ | 4-F | 5-F |
| I.1.990 | phenyl | 2-COOCH$_2$CH$_3$ | 4-F | 6-F |
| I.1.991 | phenyl | 2-COOCH$_2$CH$_3$ | 4-F | 5-Cl |
| I.1.992 | phenyl | 2-COOCH$_2$CH$_3$ | 4-F | 6-Cl |
| I.1.993 | phenyl | 2-COOCH$_2$CH$_3$ | 4-F | 5-CH$_3$ |
| I.1.994 | phenyl | 2-COOCH$_2$CH$_3$ | 4-F | 6-CH$_3$ |
| I.1.995 | phenyl | 2-COOCH$_2$CH$_3$ | 4-F | 5-vinyl |
| I.1.996 | phenyl | 2-COOCH$_2$CH$_3$ | 4-F | 6-vinyl |
| I.1.997 | phenyl | 2-COOCH$_2$CH$_3$ | 4-CH$_3$ | 5-F |
| I.1.998 | phenyl | 2-COOCH$_2$CH$_3$ | 4-CH$_3$ | 6-F |
| I.1.999 | phenyl | 2-COOCH$_2$CH$_3$ | 4-CH$_3$ | 5-Cl |
| I.1.1000 | phenyl | 2-COOCH$_2$CH$_3$ | 4-CH$_3$ | 6-Cl |
| I.1.1001 | phenyl | 2-COOCH$_2$CH$_3$ | 4-CH$_3$ | 5-CH$_3$ |
| I.1.1002 | phenyl | 2-COOCH$_2$CH$_3$ | 4-CH$_3$ | 6-CH$_3$ |
| I.1.1003 | phenyl | 2-COOCH$_2$CH$_3$ | 4-CH$_3$ | 5-vinyl |
| I.1.1004 | phenyl | 2-COOCH$_2$CH$_3$ | 4-CH$_3$ | 6-vinyl |
| I.1.1005 | phenyl | 2-COOCH$_2$CH$_3$ | 5-Cl | 6-Cl |
| I.1.1006 | phenyl | 2-COOCH$_2$CH$_3$ | 5-Cl | 6-F |
| I.1.1007 | phenyl | 2-COOCH$_2$CH$_3$ | 5-Cl | 6-CH$_3$ |
| I.1.1008 | phenyl | 2-COOCH$_2$CH$_3$ | 5-Cl | 6-vinyl |
| I.1.1009 | phenyl | 2-COOCH$_2$CH$_3$ | 5-F | 6-Cl |
| I.1.1010 | phenyl | 2-COOCH$_2$CH$_3$ | 5-F | 6-F |
| I.1.1011 | phenyl | 2-COOCH$_2$CH$_3$ | 5-F | 6-CH$_3$ |
| I.1.1012 | phenyl | 2-COOCH$_2$CH$_3$ | 5-F | 6-vinyl |
| I.1.1013 | phenyl | 2-COOCH$_2$CH$_3$ | 5-CH$_3$ | 6-Cl |
| I.1.1014 | phenyl | 2-COOCH$_2$CH$_3$ | 5-CH$_3$ | 6-F |
| I.1.1015 | phenyl | 2-COOCH$_2$CH$_3$ | 5-CH$_3$ | 6-CH$_3$ |
| I.1.1016 | phenyl | 2-COOCH$_2$CH$_3$ | 5-CH$_3$ | 6-vinyl |
| I.1.1017 | phenyl | 2-COOCH$_2$CH$_3$ | 5-vinyl | 6-Cl |
| I.1.1018 | phenyl | 2-COOCH$_2$CH$_3$ | 5-vinyl | 6-F |
| I.1.1019 | phenyl | 2-COOCH$_2$CH$_3$ | 5-vinyl | 6-CH$_3$ |
| I.1.1020 | phenyl | 2-COOCH$_2$CH$_3$ | 5-vinyl | 6-vinyl |
| I.1.1021 | phenyl | 2-COOCH$_2$CH$_3$ | H | H |
| I.1.1022 | phenyl | 2-COOCH$_2$CH$_3$ | 3-Cl | H |
| I.1.1023 | phenyl | 2-COOCH$_2$CH$_3$ | 4-Cl | H |
| I.1.1024 | phenyl | 2-COOCH$_2$CH$_3$ | 5-Cl | H |
| I.1.1025 | phenyl | 2-COOCH$_2$CH$_3$ | 6-Cl | H |
| I.1.1026 | phenyl | 2-COOCH$_2$CH$_3$ | 3-F | H |
| I.1.1027 | phenyl | 2-COOCH$_2$CH$_3$ | 4-F | H |
| I.1.1028 | phenyl | 2-COOCH$_2$CH$_3$ | 5-F | H |
| I.1.1029 | phenyl | 2-COOCH$_2$CH$_3$ | 6-F | H |
| I.1.1030 | phenyl | 2-COOCH$_2$CH$_3$ | 3-CH$_3$ | H |
| I.1.1031 | phenyl | 2-COOCH$_2$CH$_3$ | 4-CH$_3$ | H |
| I.1.1032 | phenyl | 2-COOCH$_2$CH$_3$ | 5-CH$_3$ | H |
| I.1.1033 | phenyl | 2-COOCH$_2$CH$_3$ | 6-CH$_3$ | H |
| I.1.1034 | phenyl | 2-COOCH$_2$CH$_3$ | 5-vinyl | H |
| I.1.1035 | phenyl | 2-COOCH$_2$CH$_3$ | 6-vinyl | H |
| I.1.1036 | phenyl | 2-COOCH$_2$CH$_3$ | 5-CF$_3$ | 3-Cl |
| I.1.1037 | phenyl | 2-COOCH$_2$CH$_3$ | 5-CF$_3$ | 4-Cl |
| I.1.1038 | phenyl | 2-COOCH$_2$CH$_3$ | 4-CF$_3$ | 5-Cl |
| I.1.1039 | phenyl | 2-COOCH$_2$CH$_3$ | 5-CF$_3$ | 6-Cl |
| I.1.1040 | phenyl | 2-COOCH$_2$CH$_3$ | 5-CF$_3$ | 3-F |
| I.1.1041 | phenyl | 2-COOCH$_2$CH$_3$ | 5-CF$_3$ | 4-F |
| I.1.1042 | phenyl | 2-COOCH$_2$CH$_3$ | 4-CF$_3$ | 5-F |
| I.1.1043 | phenyl | 2-COOCH$_2$CH$_3$ | 5-CF$_3$ | 6-F |
| I.1.1044 | phenyl | 2-COOCH$_2$CH$_3$ | 5-CF$_3$ | 3-CH$_3$ |
| I.1.1045 | phenyl | 2-COOCH$_2$CH$_3$ | 5-CF$_3$ | 4-CH$_3$ |
| I.1.1046 | phenyl | 2-COOCH$_2$CH$_3$ | 4-CF$_3$ | 5-CH$_3$ |
| I.1.1047 | phenyl | 2-COOCH$_2$CH$_3$ | 5-CF$_3$ | 6-CH$_3$ |
| I.1.1048 | phenyl | 2-COOCH$_2$CH$_3$ | 5-CF$_3$ | 5-vinyl |
| I.1.1049 | phenyl | 2-COOCH$_2$CH$_3$ | 4-CF$_3$ | 6-vinyl |
| I.1.1050 | phenyl | 2-COOCH$_2$CH$_3$ | 3-Cl | 4-F |
| I.1.1051 | phenyl | 2-COOCH$_2$CH$_3$ | 3-Cl | 5-F |
| I.1.1052 | phenyl | 2-COOCH$_2$CH$_3$ | 3-Cl | 6-F |
| I.1.1053 | phenyl | 2-COOCH$_2$CH$_3$ | 3-Cl | 4-Cl |
| I.1.1054 | phenyl | 2-COOCH$_2$CH$_3$ | 3-Cl | 5-Cl |
| I.1.1055 | phenyl | 2-COOCH$_2$CH$_3$ | 3-Cl | 6-Cl |
| I.1.1056 | phenyl | 2-COOCH$_2$CH$_3$ | 3-Cl | 4-CH$_3$ |
| I.1.1057 | phenyl | 2-COOCH$_2$CH$_3$ | 3-Cl | 5-CH$_3$ |
| I.1.1058 | phenyl | 2-COOCH$_2$CH$_3$ | 3-Cl | 6-CH$_3$ |
| I.1.1059 | phenyl | 2-COOCH$_2$CH$_3$ | 3-Cl | 5-vinyl |
| I.1.1060 | phenyl | 2-COOCH$_2$CH$_3$ | 3-Cl | 6-vinyl |
| I.1.1061 | phenyl | 2-COOCH$_2$CH$_3$ | 3-F | 4-F |
| I.1.1062 | phenyl | 2-COOCH$_2$CH$_3$ | 3-F | 5-F |
| I.1.1063 | phenyl | 2-COOCH$_2$CH$_3$ | 3-F | 6-F |
| I.1.1064 | phenyl | 2-COOCH$_2$CH$_3$ | 3-F | 4-Cl |
| I.1.1065 | phenyl | 2-COOCH$_2$CH$_3$ | 3-F | 5-Cl |
| I.1.1066 | phenyl | 2-COOCH$_2$CH$_3$ | 3-F | 6-Cl |
| I.1.1067 | phenyl | 2-COOCH$_2$CH$_3$ | 3-F | 4-CH$_3$ |
| I.1.1068 | phenyl | 2-COOCH$_2$CH$_3$ | 3-F | 5-CH$_3$ |
| I.1.1069 | phenyl | 2-COOCH$_2$CH$_3$ | 3-F | 6-CH$_3$ |
| I.1.1070 | phenyl | 2-COOCH$_2$CH$_3$ | 3-F | 5-vinyl |
| I.1.1071 | phenyl | 2-COOCH$_2$CH$_3$ | 3-F | 6-vinyl |
| I.1.1072 | phenyl | 2-COOCH$_2$CH$_3$ | 3-CH$_3$ | 4-F |
| I.1.1073 | phenyl | 2-COOCH$_2$CH$_3$ | 3-CH$_3$ | 5-F |
| I.1.1074 | phenyl | 2-COOCH$_2$CH$_3$ | 3-CH$_3$ | 6-F |
| I.1.1075 | phenyl | 2-COOCH$_2$CH$_3$ | 3-CH$_3$ | 4-Cl |
| I.1.1076 | phenyl | 2-COOCH$_2$CH$_3$ | 3-CH$_3$ | 5-Cl |
| I.1.1077 | phenyl | 2-COOCH$_2$CH$_3$ | 3-CH$_3$ | 6-Cl |
| I.1.1078 | phenyl | 2-COOCH$_2$CH$_3$ | 3-CH$_3$ | 4-CH$_3$ |
| I.1.1079 | phenyl | 2-COOCH$_2$CH$_3$ | 3-CH$_3$ | 5-CH$_3$ |
| I.1.1080 | phenyl | 2-COOCH$_2$CH$_3$ | 3-CH$_3$ | 6-CH$_3$ |
| I.1.1081 | phenyl | 2-COOCH$_2$CH$_3$ | 3-CH$_3$ | 5-vinyl |
| I.1.1082 | phenyl | 2-COOCH$_2$CH$_3$ | 3-CH$_3$ | 6-vinyl |
| I.1.1083 | phenyl | 2-COOCH$_2$CH$_3$ | 4-Cl | 5-F |
| I.1.1084 | phenyl | 2-COOCH$_2$CH$_3$ | 4-Cl | 6-F |
| I.1.1085 | phenyl | 2-COOCH$_2$CH$_3$ | 4-Cl | 5-Cl |
| I.1.1086 | phenyl | 2-COOCH$_2$CH$_3$ | 4-Cl | 6-Cl |
| I.1.1087 | phenyl | 2-COOCH$_2$CH$_3$ | 4-Cl | 5-CH$_3$ |
| I.1.1088 | phenyl | 2-COOCH$_2$CH$_3$ | 4-Cl | 6-CH$_3$ |

TABLE 1-continued

| Comp. No. | A¹ | $R^a$ | $R^b$ or H | $R^c$ H |
|---|---|---|---|---|
| I.1.1089 | phenyl | 2-COOCH$_2$CH$_3$ | 4-Cl | 5-vinyl |
| I.1.1090 | phenyl | 2-COOCH$_2$CH$_3$ | 4-Cl | 6-vinyl |
| I.1.1091 | phenyl | 2-COOCH$_2$CH$_3$ | 4-F | 5-F |
| I.1.1092 | phenyl | 2-COOCH$_2$CH$_3$ | 4-F | 6-F |
| I.1.1093 | phenyl | 2-COOCH$_2$CH$_3$ | 4-F | 5-Cl |
| I.1.1094 | phenyl | 2-COOCH$_2$CH$_3$ | 4-F | 6-Cl |
| I.1.1095 | phenyl | 2-COOCH$_2$CH$_3$ | 4-F | 5-CH$_3$ |
| I.1.1096 | phenyl | 2-COOCH$_2$CH$_3$ | 4-F | 6-CH$_3$ |
| I.1.1097 | phenyl | 2-COOCH$_2$CH$_3$ | 4-F | 5-vinyl |
| I.1.1098 | phenyl | 2-COOCH$_2$CH$_3$ | 4-F | 6-vinyl |
| I.1.1099 | phenyl | 2-COOCH$_2$CH$_3$ | 4-CH$_3$ | 5-F |
| I.1.1100 | phenyl | 2-COOCH$_2$CH$_3$ | 4-CH$_3$ | 6-F |
| I.1.1101 | phenyl | 2-COOCH$_2$CH$_3$ | 4-CH$_3$ | 5-Cl |
| I.1.1102 | phenyl | 2-COOCH$_2$CH$_3$ | 4-CH$_3$ | 6-Cl |
| I.1.1103 | phenyl | 2-COOCH$_2$CH$_3$ | 4-CH$_3$ | 5-CH$_3$ |
| I.1.1104 | phenyl | 2-COOCH$_2$CH$_3$ | 4-CH$_3$ | 6-CH$_3$ |
| I.1.1105 | phenyl | 2-COOCH$_2$CH$_3$ | 4-CH$_3$ | 5-vinyl |
| I.1.1106 | phenyl | 2-COOCH$_2$CH$_3$ | 4-CH$_3$ | 6-vinyl |
| I.1.1107 | phenyl | 2-COOCH$_2$CH$_3$ | 5-Cl | 6-Cl |
| I.1.1108 | phenyl | 2-COOCH$_2$CH$_3$ | 5-Cl | 6-F |
| I.1.1109 | phenyl | 2-COOCH$_2$CH$_3$ | 5-Cl | 6-CH$_3$ |
| I.1.1110 | phenyl | 2-COOCH$_2$CH$_3$ | 5-Cl | 6-vinyl |
| I.1.1111 | phenyl | 2-COOCH$_2$CH$_3$ | 5-F | 6-Cl |
| I.1.1112 | phenyl | 2-COOCH$_2$CH$_3$ | 5-F | 6-F |
| I.1.1113 | phenyl | 2-COOCH$_2$CH$_3$ | 5-F | 6-CH$_3$ |
| I.1.1114 | phenyl | 2-COOCH$_2$CH$_3$ | 5-F | 6-vinyl |
| I.1.1115 | phenyl | 2-COOCH$_2$CH$_3$ | 5-CH$_3$ | 6-Cl |
| I.1.1116 | phenyl | 2-COOCH$_2$CH$_3$ | 5-CH$_3$ | 6-F |
| I.1.1117 | phenyl | 2-COOCH$_2$CH$_3$ | 5-CH$_3$ | 6-CH$_3$ |
| I.1.1118 | phenyl | 2-COOCH$_2$CH$_3$ | 5-CH$_3$ | 6-vinyl |
| I.1.1119 | phenyl | 2-COOCH$_2$CH$_3$ | 5-vinyl | 6-Cl |
| I.1.1120 | phenyl | 2-COOCH$_2$CH$_3$ | 5-vinyl | 6-F |
| I.1.1121 | phenyl | 2-COOCH$_2$CH$_3$ | 5-vinyl | 6-CH$_3$ |
| I.1.1122 | phenyl | 2-COOCH$_2$CH$_3$ | 5-vinyl | 6-vinyl |
| I.1.1123 | pyridin-2-yl | 3-NO$_2$ | 4-Cl | 5-F |
| I.1.1124 | pyridin-2-yl | 3-NO$_2$ | 4-Cl | H |
| I.1.1125 | pyridin-2-yl | 3-NO$_2$ | 5-Cl | H |
| I.1.1126 | pyridin-2-yl | 3-NO$_2$ | 6-Cl | H |
| I.1.1127 | pyridin-2-yl | 3-NO$_2$ | 4-F | H |
| I.1.1128 | pyridin-2-yl | 3-NO$_2$ | 5-F | H |
| I.1.1129 | pyridin-2-yl | 3-NO$_2$ | 6-F | H |
| I.1.1130 | pyridin-2-yl | 3-NO$_2$ | 4-Br | H |
| I.1.1131 | pyridin-2-yl | 3-NO$_2$ | 5-Br | H |
| I.1.1132 | pyridin-2-yl | 3-NO$_2$ | 6-Br | H |
| I.1.1133 | pyridin-2-yl | 3-NO$_2$ | 4-CH$_3$ | H |
| I.1.1134 | pyridin-2-yl | 3-NO$_2$ | 5-CH$_3$ | H |
| I.1.1135 | pyridin-2-yl | 3-NO$_2$ | 6-CH$_3$ | H |
| I.1.1136 | pyridin-2-yl | 3-NO$_2$ | 4-CF$_3$ | H |
| I.1.1137 | pyridin-2-yl | 3-NO$_2$ | 5-CF$_3$ | H |
| I.1.1138 | pyridin-2-yl | 3-NO$_2$ | 6-CF$_3$ | H |
| I.1.1139 | pyridin-2-yl | 3-NO$_2$ | 4-vinyl | H |
| I.1.1140 | pyridin-2-yl | 3-NO$_2$ | 5-vinyl | H |
| I.1.1141 | pyridin-2-yl | 3-NO$_2$ | 6-vinyl | H |
| I.1.1142 | pyridin-2-yl | 3-NO$_2$ | 4-Cl | 6-F |
| I.1.1143 | pyridin-2-yl | 3-NO$_2$ | 5-Cl | 6-F |
| I.1.1144 | pyridin-2-yl | 3-CN | 4-Cl | 5-F |
| I.1.1145 | pyridin-2-yl | 3-CN | 4-Cl | H |
| I.1.1146 | pyridin-2-yl | 3-CN | 5-Cl | H |
| I.1.1147 | pyridin-2-yl | 3-CN | 6-Cl | H |
| I.1.1148 | pyridin-2-yl | 3-CN | 4-F | H |
| I.1.1149 | pyridin-2-yl | 3-CN | 5-F | H |
| I.1.1150 | pyridin-2-yl | 3-CN | 6-F | H |
| I.1.1151 | pyridin-2-yl | 3-CN | 4-Br | H |
| I.1.1152 | pyridin-2-yl | 3-CN | 5-Br | H |
| I.1.1153 | pyridin-2-yl | 3-CN | 6-Br | H |
| I.1.1154 | pyridin-2-yl | 3-CN | 4-CH$_3$ | H |
| I.1.1155 | pyridin-2-yl | 3-CN | 5-CH$_3$ | H |
| I.1.1156 | pyridin-2-yl | 3-CN | 6-CH$_3$ | H |
| I.1.1157 | pyridin-2-yl | 3-CN | 4-CF$_3$ | H |
| I.1.1158 | pyridin-2-yl | 3-CN | 5-CF$_3$ | H |
| I.1.1159 | pyridin-2-yl | 3-CN | 6-CF$_3$ | H |
| I.1.1160 | pyridin-2-yl | 3-CN | 4-vinyl | H |
| I.1.1161 | pyridin-2-yl | 3-CN | 5-vinyl | H |
| I.1.1162 | pyridin-2-yl | 3-CN | 6-vinyl | H |
| I.1.1163 | pyridin-2-yl | 3-CN | 4-Cl | 6-F |
| I.1.1164 | pyridin-2-yl | 3-CN | 5-Cl | 6-F |
| I.1.1165 | pyridin-2-yl | 3-Br | 4-Cl | 5-F |
| I.1.1166 | pyridin-2-yl | 3-Br | 4-Cl | H |
| I.1.1167 | pyridin-2-yl | 3-Br | 5-Cl | H |
| I.1.1168 | pyridin-2-yl | 3-Br | 6-Cl | H |
| I.1.1169 | pyridin-2-yl | 3-Br | 4-F | H |
| I.1.1170 | pyridin-2-yl | 3-Br | 5-F | H |
| I.1.1171 | pyridin-2-yl | 3-Br | 6-F | H |
| I.1.1172 | pyridin-2-yl | 3-Br | 4-Br | H |
| I.1.1173 | pyridin-2-yl | 3-Br | 5-Br | H |
| I.1.1174 | pyridin-2-yl | 3-Br | 6-Br | H |
| I.1.1175 | pyridin-2-yl | 3-Br | 4-CH$_3$ | H |
| I.1.1176 | pyridin-2-yl | 3-Br | 5-CH$_3$ | H |
| I.1.1177 | pyridin-2-yl | 3-Br | 6-CH$_3$ | H |
| I.1.1178 | pyridin-2-yl | 3-Br | 4-CF$_3$ | H |
| I.1.1179 | pyridin-2-yl | 3-Br | 5-CF$_3$ | H |
| I.1.1180 | pyridin-2-yl | 3-Br | 6-CF$_3$ | H |
| I.1.1181 | pyridin-2-yl | 3-Br | 4-vinyl | H |
| I.1.1182 | pyridin-2-yl | 3-Br | 5-vinyl | H |
| I.1.1183 | pyridin-2-yl | 3-Br | 6-vinyl | H |
| I.1.1184 | pyridin-2-yl | 3-Br | 4-Cl | 6-F |
| I.1.1185 | pyridin-2-yl | 3-Br | 5-Cl | 6-F |
| I.1.1186 | pyridin-2-yl | 3-Cl | 4-Cl | 5-F |
| I.1.1187 | pyridin-2-yl | 3-Cl | 4-Cl | H |
| I.1.1188 | pyridin-2-yl | 3-Cl | 5-Cl | H |
| I.1.1189 | pyridin-2-yl | 3-Cl | 6-Cl | H |
| I.1.1190 | pyridin-2-yl | 3-Cl | 4-F | H |
| I.1.1191 | pyridin-2-yl | 3-Cl | 5-F | H |
| I.1.1192 | pyridin-2-yl | 3-Cl | 6-F | H |
| I.1.1193 | pyridin-2-yl | 3-Cl | 4-Br | H |
| I.1.1194 | pyridin-2-yl | 3-Cl | 5-Br | H |
| I.1.1195 | pyridin-2-yl | 3-Cl | 6-Br | H |
| I.1.1196 | pyridin-2-yl | 3-Cl | 4-CH$_3$ | H |
| I.1.1197 | pyridin-2-yl | 3-Cl | 5-CH$_3$ | H |
| I.1.1198 | pyridin-2-yl | 3-Cl | 6-CH$_3$ | H |
| I.1.1199 | pyridin-2-yl | 3-Cl | 4-CF$_3$ | H |
| I.1.1200 | pyridin-2-yl | 3-Cl | 5-CF$_3$ | H |
| I.1.1201 | pyridin-2-yl | 3-Cl | 6-CF$_3$ | H |
| I.1.1202 | pyridin-2-yl | 3-Cl | 4-vinyl | H |
| I.1.1203 | pyridin-2-yl | 3-Cl | 5-vinyl | H |
| I.1.1204 | pyridin-2-yl | 3-Cl | 6-vinyl | H |
| I.1.1205 | pyridin-2-yl | 3-Cl | 4-Cl | 6-F |
| I.1.1206 | pyridin-2-yl | 3-Cl | 5-Cl | 6-F |
| I.1.1207 | pyridin-2-yl | 3-ethynyl | 4-Cl | 5-F |
| I.1.1208 | pyridin-2-yl | 3-ethynyl | 4-Cl | H |
| I.1.1209 | pyridin-2-yl | 3-ethynyl | 5-Cl | H |
| I.1.1210 | pyridin-2-yl | 3-ethynyl | 6-Cl | H |
| I.1.1211 | pyridin-2-yl | 3-ethynyl | 4-F | H |
| I.1.1212 | pyridin-2-yl | 3-ethynyl | 5-F | H |
| I.1.1213 | pyridin-2-yl | 3-ethynyl | 6-F | H |
| I.1.1214 | pyridin-2-yl | 3-ethynyl | 4-Br | H |
| I.1.1215 | pyridin-2-yl | 3-ethynyl | 5-Br | H |
| I.1.1216 | pyridin-2-yl | 3-ethynyl | 6-Br | H |
| I.1.1217 | pyridin-2-yl | 3-ethynyl | 4-CH$_3$ | H |
| I.1.1218 | pyridin-2-yl | 3-ethynyl | 5-CH$_3$ | H |
| I.1.1219 | pyridin-2-yl | 3-ethynyl | 6-CH$_3$ | H |
| I.1.1220 | pyridin-2-yl | 3-ethynyl | 4-CF$_3$ | H |
| I.1.1221 | pyridin-2-yl | 3-ethynyl | 5-CF$_3$ | H |
| I.1.1222 | pyridin-2-yl | 3-ethynyl | 6-CF$_3$ | H |
| I.1.1223 | pyridin-2-yl | 3-ethynyl | 4-vinyl | H |
| I.1.1224 | pyridin-2-yl | 3-ethynyl | 5-vinyl | H |
| I.1.1225 | pyridin-2-yl | 3-ethynyl | 6-vinyl | H |
| I.1.1226 | pyridin-2-yl | 3-ethynyl | 4-Cl | 6-F |
| I.1.1227 | pyridin-2-yl | 3-ethynyl | 5-Cl | 6-F |
| I.1.1228 | pyridin-2-yl | 3-I | 4-Cl | 5-F |
| I.1.1229 | pyridin-2-yl | 3-I | 4-Cl | H |
| I.1.1230 | pyridin-2-yl | 3-I | 5-Cl | H |
| I.1.1231 | pyridin-2-yl | 3-I | 6-Cl | H |
| I.1.1232 | pyridin-2-yl | 3-I | 4-F | H |
| I.1.1233 | pyridin-2-yl | 3-I | 5-F | H |
| I.1.1234 | pyridin-2-yl | 3-I | 6-F | H |
| I.1.1235 | pyridin-2-yl | 3-I | 4-Br | H |
| I.1.1236 | pyridin-2-yl | 3-I | 5-Br | H |
| I.1.1237 | pyridin-2-yl | 3-I | 6-Br | H |
| I.1.1238 | pyridin-2-yl | 3-I | 4-CH$_3$ | H |
| I.1.1239 | pyridin-2-yl | 3-I | 5-CH$_3$ | H |
| I.1.1240 | pyridin-2-yl | 3-I | 6-CH$_3$ | H |
| I.1.1241 | pyridin-2-yl | 3-I | 4-CF$_3$ | H |
| I.1.1242 | pyridin-2-yl | 3-I | 5-CF$_3$ | H |
| I.1.1243 | pyridin-2-yl | 3-I | 6-CF$_3$ | H |
| I.1.1244 | pyridin-2-yl | 3-I | 4-vinyl | H |

TABLE 1-continued

| Comp. No. | A¹ | $R^a$ | $R^b$ or H | $R^c$ H |
|---|---|---|---|---|
| I.1.1245 | pyridin-2-yl | 3-I | 5-vinyl | H |
| I.1.1246 | pyridin-2-yl | 3-I | 6-vinyl | H |
| I.1.1247 | pyridin-2-yl | 3-I | 4-Cl | 6-F |
| I.1.1248 | pyridin-2-yl | 3-I | 5-Cl | 6-F |
| I.1.1249 | pyridin-2-yl | 3-COOH | 4-Cl | 5-F |
| I.1.1250 | pyridin-2-yl | 3-COOH | 4-Cl | H |
| I.1.1251 | pyridin-2-yl | 3-COOH | 5-Cl | H |
| I.1.1252 | pyridin-2-yl | 3-COOH | 6-Cl | H |
| I.1.1253 | pyridin-2-yl | 3-COOH | 4-F | H |
| I.1.1254 | pyridin-2-yl | 3-COOH | 5-F | H |
| I.1.1255 | pyridin-2-yl | 3-COOH | 6-F | H |
| I.1.1256 | pyridin-2-yl | 3-COOH | 4-Br | H |
| I.1.1257 | pyridin-2-yl | 3-COOH | 5-Br | H |
| I.1.1258 | pyridin-2-yl | 3-COOH | 6-Br | H |
| I.1.1259 | pyridin-2-yl | 3-COOH | 4-CH₃ | H |
| I.1.1260 | pyridin-2-yl | 3-COOH | 5-CH₃ | H |
| I.1.1261 | pyridin-2-yl | 3-COOH | 6-CH₃ | H |
| I.1.1262 | pyridin-2-yl | 3-COOH | 4-CF₃ | H |
| I.1.1263 | pyridin-2-yl | 3-COOH | 5-CF₃ | H |
| I.1.1264 | pyridin-2-yl | 3-COOH | 6-CF₃ | H |
| I.1.1265 | pyridin-2-yl | 3-COOH | 4-vinyl | H |
| I.1.1266 | pyridin-2-yl | 3-COOH | 5-vinyl | H |
| I.1.1267 | pyridin-2-yl | 3-COOH | 6-vinyl | H |
| I.1.1268 | pyridin-2-yl | 3-COOH | 4-Cl | 6-F |
| I.1.1269 | pyridin-2-yl | 3-COOH | 5-Cl | 6-F |
| I.1.1270 | pyridin-2-yl | 3-COOCH₃ | 4-Cl | 5-F |
| I.1.1271 | pyridin-2-yl | 3-COOCH₃ | 4-Cl | H |
| I.1.1272 | pyridin-2-yl | 3-COOCH₃ | 5-Cl | H |
| I.1.1273 | pyridin-2-yl | 3-COOCH₃ | 6-Cl | H |
| I.1.1274 | pyridin-2-yl | 3-COOCH₃ | 4-F | H |
| I.1.1275 | pyridin-2-yl | 3-COOCH₃ | 5-F | H |
| I.1.1276 | pyridin-2-yl | 3-COOCH₃ | 6-F | H |
| I.1.1277 | pyridin-2-yl | 3-COOCH₃ | 4-Br | H |
| I.1.1278 | pyridin-2-yl | 3-COOCH₃ | 5-Br | H |
| I.1.1279 | pyridin-2-yl | 3-COOCH₃ | 6-Br | H |
| I.1.1280 | pyridin-2-yl | 3-COOCH₃ | 4-CH₃ | H |
| I.1.1281 | pyridin-2-yl | 3-COOCH₃ | 5-CH₃ | H |
| I.1.1282 | pyridin-2-yl | 3-COOCH₃ | 6-CH₃ | H |
| I.1.1283 | pyridin-2-yl | 3-COOCH₃ | 4-CF₃ | H |
| I.1.1284 | pyridin-2-yl | 3-COOCH₃ | 5-CF₃ | H |
| I.1.1285 | pyridin-2-yl | 3-COOCH₃ | 6-CF₃ | H |
| I.1.1286 | pyridin-2-yl | 3-COOCH₃ | 4-vinyl | H |
| I.1.1287 | pyridin-2-yl | 3-COOCH₃ | 5-vinyl | H |
| I.1.1288 | pyridin-2-yl | 3-COOCH₃ | 6-vinyl | H |
| I.1.1289 | pyridin-2-yl | 3-COOCH₃ | 4-Cl | 6-F |
| I.1.1290 | pyridin-2-yl | 3-COOCH₃ | 5-Cl | 6-F |
| I.1.1291 | pyridin-2-yl | 3-COOCH₂CH₃ | 4-Cl | 5-F |
| I.1.1292 | pyridin-2-yl | 3-COOCH₂CH₃ | 4-Cl | H |
| I.1.1293 | pyridin-2-yl | 3-COOCH₂CH₃ | 5-Cl | H |
| I.1.1294 | pyridin-2-yl | 3-COOCH₂CH₃ | 6-Cl | H |
| I.1.1295 | pyridin-2-yl | 3-COOCH₂CH₃ | 4-F | H |
| I.1.1296 | pyridin-2-yl | 3-COOCH₂CH₃ | 5-F | H |
| I.1.1297 | pyridin-2-yl | 3-COOCH₂CH₃ | 6-F | H |
| I.1.1298 | pyridin-2-yl | 3-COOCH₂CH₃ | 4-Br | H |
| I.1.1299 | pyridin-2-yl | 3-COOCH₂CH₃ | 5-Br | H |
| I.1.1300 | pyridin-2-yl | 3-COOCH₂CH₃ | 6-Br | H |
| I.1.1301 | pyridin-2-yl | 3-COOCH₂CH₃ | 4-CH₃ | H |
| I.1.1302 | pyridin-2-yl | 3-COOCH₂CH₃ | 5-CH₃ | H |
| I.1.1303 | pyridin-2-yl | 3-COOCH₂CH₃ | 6-CH₃ | H |
| I.1.1304 | pyridin-2-yl | 3-COOCH₂CH₃ | 4-CF₃ | H |
| I.1.1305 | pyridin-2-yl | 3-COOCH₂CH₃ | 5-CF₃ | H |
| I.1.1306 | pyridin-2-yl | 3-COOCH₂CH₃ | 6-CF₃ | H |
| I.1.1307 | pyridin-2-yl | 3-COOCH₂CH₃ | 4-vinyl | H |
| I.1.1308 | pyridin-2-yl | 3-COOCH₂CH₃ | 5-vinyl | H |
| I.1.1309 | pyridin-2-yl | 3-COOCH₂CH₃ | 6-vinyl | H |
| I.1.1310 | pyridin-2-yl | 3-COOCH₂CH₃ | 4-Cl | 6-F |
| I.1.1311 | pyridin-2-yl | 3-COOCH₂CH₃ | 5-Cl | 6-F |
| I.1.1312 | pyridin-2-yl | 3-CONHCH₃ | 4-Cl | 5-F |
| I.1.1313 | pyridin-2-yl | 3-CONHCH₃ | 4-Cl | H |
| I.1.1314 | pyridin-2-yl | 3-CONHCH₃ | 5-Cl | H |
| I.1.1315 | pyridin-2-yl | 3-CONHCH₃ | 6-Cl | H |
| I.1.1316 | pyridin-2-yl | 3-CONHCH₃ | 4-F | H |
| I.1.1317 | pyridin-2-yl | 3-CONHCH₃ | 5-F | H |
| I.1.1318 | pyridin-2-yl | 3-CONHCH₃ | 6-F | H |
| I.1.1319 | pyridin-2-yl | 3-CONHCH₃ | 4-Br | H |
| I.1.1320 | pyridin-2-yl | 3-CONHCH₃ | 5-Br | H |
| I.1.1321 | pyridin-2-yl | 3-CONHCH₃ | 6-Br | H |
| I.1.1322 | pyridin-2-yl | 3-CONHCH₃ | 4-CH₃ | H |
| I.1.1323 | pyridin-2-yl | 3-CONHCH₃ | 5-CH₃ | H |
| I.1.1324 | pyridin-2-yl | 3-CONHCH₃ | 6-CH₃ | H |
| I.1.1325 | pyridin-2-yl | 3-CONHCH₃ | 4-CF₃ | H |
| I.1.1326 | pyridin-2-yl | 3-CONHCH₃ | 5-CF₃ | H |
| I.1.1327 | pyridin-2-yl | 3-CONHCH₃ | 6-CF₃ | H |
| I.1.1328 | pyridin-2-yl | 3-CONHCH₃ | 4-vinyl | H |
| I.1.1329 | pyridin-2-yl | 3-CONHCH₃ | 5-vinyl | H |
| I.1.1330 | pyridin-2-yl | 3-CONHCH₃ | 6-vinyl | H |
| I.1.1331 | pyridin-2-yl | 3-CONHCH₃ | 4-Cl | 6-F |
| I.1.1332 | pyridin-2-yl | 3-CONHCH₃ | 5-Cl | 6-F |
| I.1.1333 | pyridin-2-yl | 3-CON(CH₃)₂ | 4-Cl | 5-F |
| I.1.1334 | pyridin-2-yl | 3-CON(CH₃)₂ | 4-Cl | H |
| I.1.1335 | pyridin-2-yl | 3-CON(CH₃)₂ | 5-Cl | H |
| I.1.1336 | pyridin-2-yl | 3-CON(CH₃)₂ | 6-Cl | H |
| I.1.1337 | pyridin-2-yl | 3-CON(CH₃)₂ | 4-F | H |
| I.1.1338 | pyridin-2-yl | 3-CON(CH₃)₂ | 5-F | H |
| I.1.1339 | pyridin-2-yl | 3-CON(CH₃)₂ | 6-F | H |
| I.1.1340 | pyridin-2-yl | 3-CON(CH₃)₂ | 4-Br | H |
| I.1.1341 | pyridin-2-yl | 3-CON(CH₃)₂ | 5-Br | H |
| I.1.1342 | pyridin-2-yl | 3-CON(CH₃)₂ | 6-Br | H |
| I.1.1343 | pyridin-2-yl | 3-CON(CH₃)₂ | 4-CH₃ | H |
| I.1.1344 | pyridin-2-yl | 3-CON(CH₃)₂ | 5-CH₃ | H |
| I.1.1345 | pyridin-2-yl | 3-CON(CH₃)₂ | 6-CH₃ | H |
| I.1.1346 | pyridin-2-yl | 3-CON(CH₃)₂ | 4-CF₃ | H |
| I.1.1347 | pyridin-2-yl | 3-CON(CH₃)₂ | 5-CF₃ | H |
| I.1.1348 | pyridin-2-yl | 3-CON(CH₃)₂ | 6-CF₃ | H |
| I.1.1349 | pyridin-2-yl | 3-CON(CH₃)₂ | 4-vinyl | H |
| I.1.1350 | pyridin-2-yl | 3-CON(CH₃)₂ | 5-vinyl | H |
| I.1.1351 | pyridin-2-yl | 3-CON(CH₃)₂ | 6-vinyl | H |
| I.1.1352 | pyridin-2-yl | 3-CON(CH₃)₂ | 4-Cl | 6-F |
| I.1.1353 | pyridin-2-yl | 3-CON(CH₃)₂ | 5-Cl | 6-F |
| I.1.1354 | pyridin-2-yl | 3-CON(CH₃)₂ | 4-Cl | 5-F |
| I.1.1355 | pyridin-3-yl | 2-NO₂ | 4-Cl | H |
| I.1.1356 | pyridin-3-yl | 2-NO₂ | 5-Cl | H |
| I.1.1357 | pyridin-3-yl | 2-NO₂ | 6-Cl | H |
| I.1.1358 | pyridin-3-yl | 2-NO₂ | 4-F | H |
| I.1.1359 | pyridin-3-yl | 2-NO₂ | 5-F | H |
| I.1.1360 | pyridin-3-yl | 2-NO₂ | 6-F | H |
| I.1.1361 | pyridin-3-yl | 2-NO₂ | 4-Br | H |
| I.1.1362 | pyridin-3-yl | 2-NO₂ | 5-Br | H |
| I.1.1363 | pyridin-3-yl | 2-NO₂ | 6-Br | H |
| I.1.1364 | pyridin-3-yl | 2-NO₂ | 4-CH₃ | H |
| I.1.1365 | pyridin-3-yl | 2-NO₂ | 5-CH₃ | H |
| I.1.1366 | pyridin-3-yl | 2-NO₂ | 6-CH₃ | H |
| I.1.1367 | pyridin-3-yl | 2-NO₂ | 4-CF₃ | H |
| I.1.1368 | pyridin-3-yl | 2-NO₂ | 5-CF₃ | H |
| I.1.1369 | pyridin-3-yl | 2-NO₂ | 6-CF₃ | H |
| I.1.1370 | pyridin-3-yl | 2-NO₂ | 4-vinyl | H |
| I.1.1371 | pyridin-3-yl | 2-NO₂ | 5-vinyl | H |
| I.1.1372 | pyridin-3-yl | 2-NO₂ | 6-vinyl | H |
| I.1.1373 | pyridin-3-yl | 2-NO₂ | 4-Cl | 6-F |
| I.1.1374 | pyridin-3-yl | 2-NO₂ | 5-Cl | 6-F |
| I.1.1375 | pyridin-3-yl | 2-CN | 4-Cl | 5-F |
| I.1.1376 | pyridin-3-yl | 2-CN | 4-Cl | H |
| I.1.1377 | pyridin-3-yl | 2-CN | 5-Cl | H |
| I.1.1378 | pyridin-3-yl | 2-CN | 6-Cl | H |
| I.1.1379 | pyridin-3-yl | 2-CN | 4-F | H |
| I.1.1380 | pyridin-3-yl | 2-CN | 5-F | H |
| I.1.1381 | pyridin-3-yl | 2-CN | 6-F | H |
| I.1.1382 | pyridin-3-yl | 2-CN | 4-Br | H |
| I.1.1383 | pyridin-3-yl | 2-CN | 5-Br | H |
| I.1.1384 | pyridin-3-yl | 2-CN | 6-Br | H |
| I.1.1385 | pyridin-3-yl | 2-CN | 4-CH₃ | H |
| I.1.1386 | pyridin-3-yl | 2-CN | 5-CH₃ | H |
| I.1.1387 | pyridin-3-yl | 2-CN | 6-CH₃ | H |
| I.1.1388 | pyridin-3-yl | 2-CN | 4-CF₃ | H |
| I.1.1389 | pyridin-3-yl | 2-CN | 5-CF₃ | H |
| I.1.1390 | pyridin-3-yl | 2-CN | 6-CF₃ | H |
| I.1.1391 | pyridin-3-yl | 2-CN | 4-vinyl | H |
| I.1.1392 | pyridin-3-yl | 2-CN | 5-vinyl | H |
| I.1.1393 | pyridin-3-yl | 2-CN | 6-vinyl | H |
| I.1.1394 | pyridin-3-yl | 2-CN | 4-Cl | 6-F |
| I.1.1395 | pyridin-3-yl | 2-CN | 5-Cl | 6-F |
| I.1.1396 | pyridin-3-yl | 2-Br | 4-Cl | 5-F |
| I.1.1397 | pyridin-3-yl | 2-Br | 4-Cl | H |
| I.1.1398 | pyridin-3-yl | 2-Br | 5-Cl | H |
| I.1.1399 | pyridin-3-yl | 2-Br | 6-Cl | H |
| I.1.1400 | pyridin-3-yl | 2-Br | 4-F | H |

TABLE 1-continued

| Comp. No. | A¹ | Rᵃ | Rᵇ or H | Rᶜ H |
|---|---|---|---|---|
| I.1.1401 | pyridin-3-yl | 2-Br | 5-F | H |
| I.1.1402 | pyridin-3-yl | 2-Br | 6-F | H |
| I.1.1403 | pyridin-3-yl | 2-Br | 4-Br | H |
| I.1.1404 | pyridin-3-yl | 2-Br | 5-Br | H |
| I.1.1405 | pyridin-3-yl | 2-Br | 6-Br | H |
| I.1.1406 | pyridin-3-yl | 2-Br | 4-CH₃ | H |
| I.1.1407 | pyridin-3-yl | 2-Br | 5-CH₃ | H |
| I.1.1408 | pyridin-3-yl | 2-Br | 6-CH₃ | H |
| I.1.1409 | pyridin-3-yl | 2-Br | 4-CF₃ | H |
| I.1.1410 | pyridin-3-yl | 2-Br | 5-CF₃ | H |
| I.1.1411 | pyridin-3-yl | 2-Br | 6-CF₃ | H |
| I.1.1412 | pyridin-3-yl | 2-Br | 4-vinyl | H |
| I.1.1413 | pyridin-3-yl | 2-Br | 5-vinyl | H |
| I.1.1414 | pyridin-3-yl | 2-Br | 6-vinyl | H |
| I.1.1415 | pyridin-3-yl | 2-Br | 4-Cl | 6-F |
| I.1.1416 | pyridin-3-yl | 2-Br | 5-Cl | 6-F |
| I.1.1417 | pyridin-3-yl | 2-Cl | 4-Cl | 5-F |
| I.1.1418 | pyridin-3-yl | 2-Cl | 4-Cl | H |
| I.1.1419 | pyridin-3-yl | 2-Cl | 5-Cl | H |
| I.1.1420 | pyridin-3-yl | 2-Cl | 6-Cl | H |
| I.1.1421 | pyridin-3-yl | 2-Cl | 4-F | H |
| I.1.1422 | pyridin-3-yl | 2-Cl | 5-F | H |
| I.1.1423 | pyridin-3-yl | 2-Cl | 6-F | H |
| I.1.1424 | pyridin-3-yl | 2-Cl | 4-Br | H |
| I.1.1425 | pyridin-3-yl | 2-Cl | 5-Br | H |
| I.1.1426 | pyridin-3-yl | 2-Cl | 6-Br | H |
| I.1.1427 | pyridin-3-yl | 2-Cl | 4-CH₃ | H |
| I.1.1428 | pyridin-3-yl | 2-Cl | 5-CH₃ | H |
| I.1.1429 | pyridin-3-yl | 2-Cl | 6-CH₃ | H |
| I.1.1430 | pyridin-3-yl | 2-Cl | 4-CF₃ | H |
| I.1.1431 | pyridin-3-yl | 2-Cl | 5-CF₃ | H |
| I.1.1432 | pyridin-3-yl | 2-Cl | 6-CF₃ | H |
| I.1.1433 | pyridin-3-yl | 2-Cl | 4-vinyl | H |
| I.1.1434 | pyridin-3-yl | 2-Cl | 5-vinyl | H |
| I.1.1435 | pyridin-3-yl | 2-Cl | 6-vinyl | H |
| I.1.1436 | pyridin-3-yl | 2-Cl | 4-Cl | 6-F |
| I.1.1437 | pyridin-3-yl | 2-Cl | 5-Cl | 6-F |
| I.1.1438 | pyridin-3-yl | 2-ethynyl | 4-Cl | 5-F |
| I.1.1439 | pyridin-3-yl | 2-ethynyl | 4-Cl | H |
| I.1.1440 | pyridin-3-yl | 2-ethynyl | 5-Cl | H |
| I.1.1441 | pyridin-3-yl | 2-ethynyl | 6-Cl | H |
| I.1.1442 | pyridin-3-yl | 2-ethynyl | 4-F | H |
| I.1.1443 | pyridin-3-yl | 2-ethynyl | 5-F | H |
| I.1.1444 | pyridin-3-yl | 2-ethynyl | 6-F | H |
| I.1.1445 | pyridin-3-yl | 2-ethynyl | 4-Br | H |
| I.1.1446 | pyridin-3-yl | 2-ethynyl | 5-Br | H |
| I.1.1447 | pyridin-3-yl | 2-ethynyl | 6-Br | H |
| I.1.1448 | pyridin-3-yl | 2-ethynyl | 4-CH₃ | H |
| I.1.1449 | pyridin-3-yl | 2-ethynyl | 5-CH₃ | H |
| I.1.1450 | pyridin-3-yl | 2-ethynyl | 6-CH₃ | H |
| I.1.1451 | pyridin-3-yl | 2-ethynyl | 4-CF₃ | H |
| I.1.1452 | pyridin-3-yl | 2-ethynyl | 5-CF₃ | H |
| I.1.1453 | pyridin-3-yl | 2-ethynyl | 6-CF₃ | H |
| I.1.1454 | pyridin-3-yl | 2-ethynyl | 4-vinyl | H |
| I.1.1455 | pyridin-3-yl | 2-ethynyl | 5-vinyl | H |
| I.1.1456 | pyridin-3-yl | 2-ethynyl | 6-vinyl | H |
| I.1.1457 | pyridin-3-yl | 2-ethynyl | 4-Cl | 6-F |
| I.1.1458 | pyridin-3-yl | 2-ethynyl | 5-Cl | 6-F |
| I.1.1459 | pyridin-3-yl | 2-I | 4-Cl | 5-F |
| I.1.1460 | pyridin-3-yl | 2-I | 4-Cl | H |
| I.1.1461 | pyridin-3-yl | 2-I | 5-Cl | H |
| I.1.1462 | pyridin-3-yl | 2-I | 6-Cl | H |
| I.1.1463 | pyridin-3-yl | 2-I | 4-F | H |
| I.1.1464 | pyridin-3-yl | 2-I | 5-F | H |
| I.1.1465 | pyridin-3-yl | 2-I | 6-F | H |
| I.1.1466 | pyridin-3-yl | 2-I | 4-Br | H |
| I.1.1467 | pyridin-3-yl | 2-I | 5-Br | H |
| I.1.1468 | pyridin-3-yl | 2-I | 6-Br | H |
| I.1.1469 | pyridin-3-yl | 2-I | 4-CH₃ | H |
| I.1.1470 | pyridin-3-yl | 2-I | 5-CH₃ | H |
| I.1.1471 | pyridin-3-yl | 2-I | 6-CH₃ | H |
| I.1.1472 | pyridin-3-yl | 2-I | 4-CF₃ | H |
| I.1.1473 | pyridin-3-yl | 2-I | 5-CF₃ | H |
| I.1.1474 | pyridin-3-yl | 2-I | 6-CF₃ | H |
| I.1.1475 | pyridin-3-yl | 2-I | 4-vinyl | H |
| I.1.1476 | pyridin-3-yl | 2-I | 5-vinyl | H |
| I.1.1477 | pyridin-3-yl | 2-I | 6-vinyl | H |
| I.1.1478 | pyridin-3-yl | 2-I | 4-Cl | 6-F |
| I.1.1479 | pyridin-3-yl | 2-I | 5-Cl | 6-F |
| I.1.1480 | pyridin-3-yl | 2-COOH | 4-Cl | 5-F |
| I.1.1481 | pyridin-3-yl | 2-COOH | 4-Cl | H |
| I.1.1482 | pyridin-3-yl | 2-COOH | 5-Cl | H |
| I.1.1483 | pyridin-3-yl | 2-COOH | 6-Cl | H |
| I.1.1484 | pyridin-3-yl | 2-COOH | 4-F | H |
| I.1.1485 | pyridin-3-yl | 2-COOH | 5-F | H |
| I.1.1486 | pyridin-3-yl | 2-COOH | 6-F | H |
| I.1.1487 | pyridin-3-yl | 2-COOH | 4-Br | H |
| I.1.1488 | pyridin-3-yl | 2-COOH | 5-Br | H |
| I.1.1489 | pyridin-3-yl | 2-COOH | 6-Br | H |
| I.1.1490 | pyridin-3-yl | 2-COOH | 4-CH₃ | H |
| I.1.1491 | pyridin-3-yl | 2-COOH | 5-CH₃ | H |
| I.1.1492 | pyridin-3-yl | 2-COOH | 6-CH₃ | H |
| I.1.1493 | pyridin-3-yl | 2-COOH | 4-CF₃ | H |
| I.1.1494 | pyridin-3-yl | 2-COOH | 5-CF₃ | H |
| I.1.1495 | pyridin-3-yl | 2-COOH | 6-CF₃ | H |
| I.1.1496 | pyridin-3-yl | 2-COOH | 4-vinyl | H |
| I.1.1497 | pyridin-3-yl | 2-COOH | 5-vinyl | H |
| I.1.1498 | pyridin-3-yl | 2-COOH | 6-vinyl | H |
| I.1.1499 | pyridin-3-yl | 2-COOH | 4-Cl | 6-F |
| I.1.1500 | pyridin-3-yl | 2-COOH | 5-Cl | 6-F |
| I.1.1501 | pyridin-3-yl | 2-COOCH₃ | 4-Cl | 5-F |
| I.1.1502 | pyridin-3-yl | 2-COOCH₃ | 4-Cl | H |
| I.1.1503 | pyridin-3-yl | 2-COOCH₃ | 5-Cl | H |
| I.1.1504 | pyridin-3-yl | 2-COOCH₃ | 6-Cl | H |
| I.1.1505 | pyridin-3-yl | 2-COOCH₃ | 4-F | H |
| I.1.1506 | pyridin-3-yl | 2-COOCH₃ | 5-F | H |
| I.1.1507 | pyridin-3-yl | 2-COOCH₃ | 6-F | H |
| I.1.1508 | pyridin-3-yl | 2-COOCH₃ | 4-Br | H |
| I.1.1509 | pyridin-3-yl | 2-COOCH₃ | 5-Br | H |
| I.1.1510 | pyridin-3-yl | 2-COOCH₃ | 6-Br | H |
| I.1.1511 | pyridin-3-yl | 2-COOCH₃ | 4-CH₃ | H |
| I.1.1512 | pyridin-3-yl | 2-COOCH₃ | 5-CH₃ | H |
| I.1.1513 | pyridin-3-yl | 2-COOCH₃ | 6-CH₃ | H |
| I.1.1514 | pyridin-3-yl | 2-COOCH₃ | 4-CF₃ | H |
| I.1.1515 | pyridin-3-yl | 2-COOCH₃ | 5-CF₃ | H |
| I.1.1516 | pyridin-3-yl | 2-COOCH₃ | 6-CF₃ | H |
| I.1.1517 | pyridin-3-yl | 2-COOCH₃ | 4-vinyl | H |
| I.1.1518 | pyridin-3-yl | 2-COOCH₃ | 5-vinyl | H |
| I.1.1519 | pyridin-3-yl | 2-COOCH₃ | 6-vinyl | H |
| I.1.1520 | pyridin-3-yl | 2-COOCH₃ | 4-Cl | 6-F |
| I.1.1521 | pyridin-3-yl | 2-COOCH₃ | 5-Cl | 6-F |
| I.1.1522 | pyridin-3-yl | 2-COOCH₂CH₃ | 4-Cl | 5-F |
| I.1.1523 | pyridin-3-yl | 2-COOCH₂CH₃ | 4-Cl | H |
| I.1.1524 | pyridin-3-yl | 2-COOCH₂CH₃ | 5-Cl | H |
| I.1.1525 | pyridin-3-yl | 2-COOCH₂CH₃ | 6-Cl | H |
| I.1.1526 | pyridin-3-yl | 2-COOCH₂CH₃ | 4-F | H |
| I.1.1527 | pyridin-3-yl | 2-COOCH₂CH₃ | 5-F | H |
| I.1.1528 | pyridin-3-yl | 2-COOCH₂CH₃ | 6-F | H |
| I.1.1529 | pyridin-3-yl | 2-COOCH₂CH₃ | 4-Br | H |
| I.1.1530 | pyridin-3-yl | 2-COOCH₂CH₃ | 5-Br | H |
| I.1.1531 | pyridin-3-yl | 2-COOCH₂CH₃ | 6-Br | H |
| I.1.1532 | pyridin-3-yl | 2-COOCH₂CH₃ | 4-CH₃ | H |
| I.1.1533 | pyridin-3-yl | 2-COOCH₂CH₃ | 5-CH₃ | H |
| I.1.1534 | pyridin-3-yl | 2-COOCH₂CH₃ | 6-CH₃ | H |
| I.1.1535 | pyridin-3-yl | 2-COOCH₂CH₃ | 4-CF₃ | H |
| I.1.1536 | pyridin-3-yl | 2-COOCH₂CH₃ | 5-CF₃ | H |
| I.1.1537 | pyridin-3-yl | 2-COOCH₂CH₃ | 6-CF₃ | H |
| I.1.1538 | pyridin-3-yl | 2-COOCH₂CH₃ | 4-vinyl | H |
| I.1.1539 | pyridin-3-yl | 2-COOCH₂CH₃ | 5-vinyl | H |
| I.1.1540 | pyridin-3-yl | 2-COOCH₂CH₃ | 6-vinyl | H |
| I.1.1541 | pyridin-3-yl | 2-COOCH₂CH₃ | 4-Cl | 6-F |
| I.1.1542 | pyridin-3-yl | 2-COOCH₂CH₃ | 5-Cl | 6-F |
| I.1.1543 | pyridin-3-yl | 2-CONHCH₃ | 4-Cl | 5-F |
| I.1.1544 | pyridin-3-yl | 2-CONHCH₃ | 4-Cl | H |
| I.1.1545 | pyridin-3-yl | 2-CONHCH₃ | 5-Cl | H |
| I.1.1546 | pyridin-3-yl | 2-CONHCH₃ | 6-Cl | H |
| I.1.1547 | pyridin-3-yl | 2-CONHCH₃ | 4-F | H |
| I.1.1548 | pyridin-3-yl | 2-CONHCH₃ | 5-F | H |
| I.1.1549 | pyridin-3-yl | 2-CONHCH₃ | 6-F | H |
| I.1.1550 | pyridin-3-yl | 2-CONHCH₃ | 4-Br | H |
| I.1.1551 | pyridin-3-yl | 2-CONHCH₃ | 5-Br | H |
| I.1.1552 | pyridin-3-yl | 2-CONHCH₃ | 6-Br | H |
| I.1.1553 | pyridin-3-yl | 2-CONHCH₃ | 4-CH₃ | H |
| I.1.1554 | pyridin-3-yl | 2-CONHCH₃ | 5-CH₃ | H |
| I.1.1555 | pyridin-3-yl | 2-CONHCH₃ | 6-CH₃ | H |
| I.1.1556 | pyridin-3-yl | 2-CONHCH₃ | 4-CF₃ | H |

TABLE 1-continued

| Comp. No. | A¹ | $R^a$ | $R^b$ or H | $R^c$ H |
|---|---|---|---|---|
| I.1.1557 | pyridin-3-yl | 2-CONHCH₃ | 5-CF₃ | H |
| I.1.1558 | pyridin-3-yl | 2-CONHCH₃ | 6-CF₃ | H |
| I.1.1559 | pyridin-3-yl | 2-CONHCH₃ | 4-vinyl | H |
| I.1.1560 | pyridin-3-yl | 2-CONHCH₃ | 5-vinyl | H |
| I.1.1561 | pyridin-3-yl | 2-CONHCH₃ | 6-vinyl | H |
| I.1.1562 | pyridin-3-yl | 2-CONHCH₃ | 4-Cl | 6-F |
| I.1.1563 | pyridin-3-yl | 2-CONHCH₃ | 5-Cl | 6-F |
| I.1.1564 | pyridin-3-yl | 2-CON(CH₃)₂ | 4-Cl | 5-F |
| I.1.1565 | pyridin-3-yl | 2-CON(CH₃)₂ | 4-Cl | H |
| I.1.1566 | pyridin-3-yl | 2-CON(CH₃)₂ | 5-Cl | H |
| I.1.1567 | pyridin-3-yl | 2-CON(CH₃)₂ | 6-Cl | H |
| I.1.1568 | pyridin-3-yl | 2-CON(CH₃)₂ | 4-F | H |
| I.1.1569 | pyridin-3-yl | 2-CON(CH₃)₂ | 5-F | H |
| I.1.1570 | pyridin-3-yl | 2-CON(CH₃)₂ | 6-F | H |
| I.1.1571 | pyridin-3-yl | 2-CON(CH₃)₂ | 4-Br | H |
| I.1.1572 | pyridin-3-yl | 2-CON(CH₃)₂ | 5-Br | H |
| I.1.1573 | pyridin-3-yl | 2-CON(CH₃)₂ | 6-Br | H |
| I.1.1574 | pyridin-3-yl | 2-CON(CH₃)₂ | 4-CH₃ | H |
| I.1.1575 | pyridin-3-yl | 2-CON(CH₃)₂ | 5-CH₃ | H |
| I.1.1576 | pyridin-3-yl | 2-CON(CH₃)₂ | 6-CH₃ | H |
| I.1.1577 | pyridin-3-yl | 2-CON(CH₃)₂ | 4-CF₃ | H |
| I.1.1578 | pyridin-3-yl | 2-CON(CH₃)₂ | 5-CF₃ | H |
| I.1.1579 | pyridin-3-yl | 2-CON(CH₃)₂ | 6-CF₃ | H |
| I.1.1580 | pyridin-3-yl | 2-CON(CH₃)₂ | 4-vinyl | H |
| I.1.1581 | pyridin-3-yl | 2-CON(CH₃)₂ | 5-vinyl | H |
| I.1.1582 | pyridin-3-yl | 2-CON(CH₃)₂ | 6-vinyl | H |
| I.1.1583 | pyridin-3-yl | 2-CON(CH₃)₂ | 4-Cl | 6-F |
| I.1.1584 | pyridin-3-yl | 2-CON(CH₃)₂ | 5-Cl | 6-F |
| I.1.1585 | pyridin-3-yl | 4-NO₂ | 2-Cl | 5-F |
| I.1.1586 | pyridin-3-yl | 4-NO₂ | 2-Cl | H |
| I.1.1587 | pyridin-3-yl | 4-NO₂ | 5-Cl | H |
| I.1.1588 | pyridin-3-yl | 4-NO₂ | 6-Cl | H |
| I.1.1589 | pyridin-3-yl | 4-NO₂ | 2-F | H |
| I.1.1590 | pyridin-3-yl | 4-NO₂ | 5-F | H |
| I.1.1591 | pyridin-3-yl | 4-NO₂ | 6-F | H |
| I.1.1592 | pyridin-3-yl | 4-NO₂ | 2-Br | H |
| I.1.1593 | pyridin-3-yl | 4-NO₂ | 5-Br | H |
| I.1.1594 | pyridin-3-yl | 4-NO₂ | 6-Br | H |
| I.1.1595 | pyridin-3-yl | 4-NO₂ | 2-CH₃ | H |
| I.1.1596 | pyridin-3-yl | 4-NO₂ | 5-CH₃ | H |
| I.1.1597 | pyridin-3-yl | 4-NO₂ | 6-CH₃ | H |
| I.1.1598 | pyridin-3-yl | 4-NO₂ | 2-CF₃ | H |
| I.1.1599 | pyridin-3-yl | 4-NO₂ | 5-CF₃ | H |
| I.1.1600 | pyridin-3-yl | 4-NO₂ | 6-CF₃ | H |
| I.1.1601 | pyridin-3-yl | 4-NO₂ | 2-vinyl | H |
| I.1.1602 | pyridin-3-yl | 4-NO₂ | 5-vinyl | H |
| I.1.1603 | pyridin-3-yl | 4-NO₂ | 6-vinyl | H |
| I.1.1604 | pyridin-3-yl | 4-NO₂ | 2-Cl | 6-F |
| I.1.1605 | pyridin-3-yl | 4-NO₂ | 5-Cl | 6-F |
| I.1.1606 | pyridin-3-yl | 4-CN | 2-Cl | 5-F |
| I.1.1607 | pyridin-3-yl | 4-CN | 2-Cl | H |
| I.1.1608 | pyridin-3-yl | 4-CN | 5-Cl | H |
| I.1.1609 | pyridin-3-yl | 4-CN | 6-Cl | H |
| I.1.1610 | pyridin-3-yl | 4-CN | 2-F | H |
| I.1.1611 | pyridin-3-yl | 4-CN | 5-F | H |
| I.1.1612 | pyridin-3-yl | 4-CN | 6-F | H |
| I.1.1613 | pyridin-3-yl | 4-CN | 2-Br | H |
| I.1.1614 | pyridin-3-yl | 4-CN | 5-Br | H |
| I.1.1615 | pyridin-3-yl | 4-CN | 6-Br | H |
| I.1.1616 | pyridin-3-yl | 4-CN | 2-CH₃ | H |
| I.1.1617 | pyridin-3-yl | 4-CN | 5-CH₃ | H |
| I.1.1618 | pyridin-3-yl | 4-CN | 6-CH₃ | H |
| I.1.1619 | pyridin-3-yl | 4-CN | 2-CF₃ | H |
| I.1.1620 | pyridin-3-yl | 4-CN | 5-CF₃ | H |
| I.1.1621 | pyridin-3-yl | 4-CN | 6-CF₃ | H |
| I.1.1622 | pyridin-3-yl | 4-CN | 2-vinyl | H |
| I.1.1623 | pyridin-3-yl | 4-CN | 5-vinyl | H |
| I.1.1624 | pyridin-3-yl | 4-CN | 6-vinyl | H |
| I.1.1625 | pyridin-3-yl | 4-CN | 2-Cl | 6-F |
| I.1.1626 | pyridin-3-yl | 4-CN | 5-Cl | 6-F |
| I.1.1627 | pyridin-3-yl | 4-Br | 2-Cl | 5-F |
| I.1.1628 | pyridin-3-yl | 4-Br | 2-Cl | H |
| I.1.1629 | pyridin-3-yl | 4-Br | 5-Cl | H |
| I.1.1630 | pyridin-3-yl | 4-Br | 6-Cl | H |
| I.1.1631 | pyridin-3-yl | 4-Br | 2-F | H |
| I.1.1632 | pyridin-3-yl | 4-Br | 5-F | H |
| I.1.1633 | pyridin-3-yl | 4-Br | 6-F | H |
| I.1.1634 | pyridin-3-yl | 4-Br | 2-Br | H |
| I.1.1635 | pyridin-3-yl | 4-Br | 5-Br | H |
| I.1.1636 | pyridin-3-yl | 4-Br | 6-Br | H |
| I.1.1637 | pyridin-3-yl | 4-Br | 2-CH₃ | H |
| I.1.1638 | pyridin-3-yl | 4-Br | 5-CH₃ | H |
| I.1.1639 | pyridin-3-yl | 4-Br | 6-CH₃ | H |
| I.1.1640 | pyridin-3-yl | 4-Br | 2-CF₃ | H |
| I.1.1641 | pyridin-3-yl | 4-Br | 5-CF₃ | H |
| I.1.1642 | pyridin-3-yl | 4-Br | 6-CF₃ | H |
| I.1.1643 | pyridin-3-yl | 4-Br | 2-vinyl | H |
| I.1.1644 | pyridin-3-yl | 4-Br | 5-vinyl | H |
| I.1.1645 | pyridin-3-yl | 4-Br | 6-vinyl | H |
| I.1.1646 | pyridin-3-yl | 4-Br | 2-Cl | 6-F |
| I.1.1647 | pyridin-3-yl | 4-Br | 5-Cl | 6-F |
| I.1.1648 | pyridin-3-yl | 4-Cl | 2-Cl | 5-F |
| I.1.1649 | pyridin-3-yl | 4-Cl | 2-Cl | H |
| I.1.1650 | pyridin-3-yl | 4-Cl | 5-Cl | H |
| I.1.1651 | pyridin-3-yl | 4-Cl | 6-Cl | H |
| I.1.1652 | pyridin-3-yl | 4-Cl | 2-F | H |
| I.1.1653 | pyridin-3-yl | 4-Cl | 5-F | H |
| I.1.1654 | pyridin-3-yl | 4-Cl | 6-F | H |
| I.1.1655 | pyridin-3-yl | 4-Cl | 2-Br | H |
| I.1.1656 | pyridin-3-yl | 4-Cl | 5-Br | H |
| I.1.1657 | pyridin-3-yl | 4-Cl | 6-Br | H |
| I.1.1658 | pyridin-3-yl | 4-Cl | 2-CH₃ | H |
| I.1.1659 | pyridin-3-yl | 4-Cl | 5-CH₃ | H |
| I.1.1660 | pyridin-3-yl | 4-Cl | 6-CH₃ | H |
| I.1.1661 | pyridin-3-yl | 4-Cl | 2-CF₃ | H |
| I.1.1662 | pyridin-3-yl | 4-Cl | 5-CF₃ | H |
| I.1.1663 | pyridin-3-yl | 4-Cl | 6-CF₃ | H |
| I.1.1664 | pyridin-3-yl | 4-Cl | 2-vinyl | H |
| I.1.1665 | pyridin-3-yl | 4-Cl | 5-vinyl | H |
| I.1.1666 | pyridin-3-yl | 4-Cl | 6-vinyl | H |
| I.1.1667 | pyridin-3-yl | 4-Cl | 2-Cl | 6-F |
| I.1.1668 | pyridin-3-yl | 4-Cl | 5-Cl | 6-F |
| I.1.1669 | pyridin-3-yl | 4-ethynyl | 2-Cl | 5-F |
| I.1.1670 | pyridin-3-yl | 4-ethynyl | 2-Cl | H |
| I.1.1671 | pyridin-3-yl | 4-ethynyl | 5-Cl | H |
| I.1.1672 | pyridin-3-yl | 4-ethynyl | 6-Cl | H |
| I.1.1673 | pyridin-3-yl | 4-ethynyl | 2-F | H |
| I.1.1674 | pyridin-3-yl | 4-ethynyl | 5-F | H |
| I.1.1675 | pyridin-3-yl | 4-ethynyl | 6-F | H |
| I.1.1676 | pyridin-3-yl | 4-ethynyl | 2-Br | H |
| I.1.1677 | pyridin-3-yl | 4-ethynyl | 5-Br | H |
| I.1.1678 | pyridin-3-yl | 4-ethynyl | 6-Br | H |
| I.1.1679 | pyridin-3-yl | 4-ethynyl | 2-CH₃ | H |
| I.1.1680 | pyridin-3-yl | 4-ethynyl | 5-CH₃ | H |
| I.1.1681 | pyridin-3-yl | 4-ethynyl | 6-CH₃ | H |
| I.1.1682 | pyridin-3-yl | 4-ethynyl | 2-CF₃ | H |
| I.1.1683 | pyridin-3-yl | 4-ethynyl | 5-CF₃ | H |
| I.1.1684 | pyridin-3-yl | 4-ethynyl | 6-CF₃ | H |
| I.1.1685 | pyridin-3-yl | 4-ethynyl | 2-vinyl | H |
| I.1.1686 | pyridin-3-yl | 4-ethynyl | 5-vinyl | H |
| I.1.1687 | pyridin-3-yl | 4-ethynyl | 6-vinyl | H |
| I.1.1688 | pyridin-3-yl | 4-ethynyl | 2-Cl | 6-F |
| I.1.1689 | pyridin-3-yl | 4-ethynyl | 5-Cl | 6-F |
| I.1.1690 | pyridin-3-yl | 4-I | 2-Cl | 5-F |
| I.1.1691 | pyridin-3-yl | 4-I | 2-Cl | H |
| I.1.1692 | pyridin-3-yl | 4-I | 5-Cl | H |
| I.1.1693 | pyridin-3-yl | 4-I | 6-Cl | H |
| I.1.1694 | pyridin-3-yl | 4-I | 2-F | H |
| I.1.1695 | pyridin-3-yl | 4-I | 5-F | H |
| I.1.1696 | pyridin-3-yl | 4-I | 6-F | H |
| I.1.1697 | pyridin-3-yl | 4-I | 2-Br | H |
| I.1.1698 | pyridin-3-yl | 4-I | 5-Br | H |
| I.1.1699 | pyridin-3-yl | 4-I | 6-Br | H |
| I.1.1700 | pyridin-3-yl | 4-I | 2-CH₃ | H |
| I.1.1701 | pyridin-3-yl | 4-I | 5-CH₃ | H |
| I.1.1702 | pyridin-3-yl | 4-I | 6-CH₃ | H |
| I.1.1703 | pyridin-3-yl | 4-I | 2-CF₃ | H |
| I.1.1704 | pyridin-3-yl | 4-I | 5-CF₃ | H |
| I.1.1705 | pyridin-3-yl | 4-I | 6-CF₃ | H |
| I.1.1706 | pyridin-3-yl | 4-I | 2-vinyl | H |
| I.1.1707 | pyridin-3-yl | 4-I | 5-vinyl | H |
| I.1.1708 | pyridin-3-yl | 4-I | 6-vinyl | H |
| I.1.1709 | pyridin-3-yl | 4-I | 2-Cl | 6-F |
| I.1.1710 | pyridin-3-yl | 4-I | 5-Cl | 6-F |
| I.1.1711 | pyridin-3-yl | 4-COOH | 2-Cl | 5-F |
| I.1.1712 | pyridin-3-yl | 4-COOH | 2-Cl | H |

TABLE 1-continued

| Comp. No. | A¹ | Rᵃ | Rᵇ or H | Rᶜ H |
|---|---|---|---|---|
| I.1.1713 | pyridin-3-yl | 4-COOH | 5-Cl | H |
| I.1.1714 | pyridin-3-yl | 4-COOH | 6-Cl | H |
| I.1.1715 | pyridin-3-yl | 4-COOH | 2-F | H |
| I.1.1716 | pyridin-3-yl | 4-COOH | 5-F | H |
| I.1.1717 | pyridin-3-yl | 4-COOH | 6-F | H |
| I.1.1718 | pyridin-3-yl | 4-COOH | 2-Br | H |
| I.1.1719 | pyridin-3-yl | 4-COOH | 5-Br | H |
| I.1.1720 | pyridin-3-yl | 4-COOH | 6-Br | H |
| I.1.1721 | pyridin-3-yl | 4-COOH | 2-CH₃ | H |
| I.1.1722 | pyridin-3-yl | 4-COOH | 5-CH₃ | H |
| I.1.1723 | pyridin-3-yl | 4-COOH | 6-CH₃ | H |
| I.1.1724 | pyridin-3-yl | 4-COOH | 2-CF₃ | H |
| I.1.1725 | pyridin-3-yl | 4-COOH | 5-CF₃ | H |
| I.1.1726 | pyridin-3-yl | 4-COOH | 6-CF₃ | H |
| I.1.1727 | pyridin-3-yl | 4-COOH | 2-vinyl | H |
| I.1.1728 | pyridin-3-yl | 4-COOH | 5-vinyl | H |
| I.1.1729 | pyridin-3-yl | 4-COOH | 6-vinyl | H |
| I.1.1730 | pyridin-3-yl | 4-COOH | 2-Cl | 6-F |
| I.1.1731 | pyridin-3-yl | 4-COOH | 5-Cl | 6-F |
| I.1.1732 | pyridin-3-yl | 4-COOCH₃ | 2-Cl | 5-F |
| I.1.1733 | pyridin-3-yl | 4-COOCH₃ | 2-Cl | H |
| I.1.1734 | pyridin-3-yl | 4-COOCH₃ | 5-Cl | H |
| I.1.1735 | pyridin-3-yl | 4-COOCH₃ | 6-Cl | H |
| I.1.1736 | pyridin-3-yl | 4-COOCH₃ | 2-F | H |
| I.1.1737 | pyridin-3-yl | 4-COOCH₃ | 5-F | H |
| I.1.1738 | pyridin-3-yl | 4-COOCH₃ | 6-F | H |
| I.1.1739 | pyridin-3-yl | 4-COOCH₃ | 2-Br | H |
| I.1.1740 | pyridin-3-yl | 4-COOCH₃ | 5-Br | H |
| I.1.1741 | pyridin-3-yl | 4-COOCH₃ | 6-Br | H |
| I.1.1742 | pyridin-3-yl | 4-COOCH₃ | 2-CH₃ | H |
| I.1.1743 | pyridin-3-yl | 4-COOCH₃ | 5-CH₃ | H |
| I.1.1744 | pyridin-3-yl | 4-COOCH₃ | 6-CH₃ | H |
| I.1.1745 | pyridin-3-yl | 4-COOCH₃ | 2-CF₃ | H |
| I.1.1746 | pyridin-3-yl | 4-COOCH₃ | 5-CF₃ | H |
| I.1.1747 | pyridin-3-yl | 4-COOCH₃ | 6-CF₃ | H |
| I.1.1748 | pyridin-3-yl | 4-COOCH₃ | 2-vinyl | H |
| I.1.1749 | pyridin-3-yl | 4-COOCH₃ | 5-vinyl | H |
| I.1.1750 | pyridin-3-yl | 4-COOCH₃ | 6-vinyl | H |
| I.1.1751 | pyridin-3-yl | 4-COOCH₃ | 2-Cl | 6-F |
| I.1.1752 | pyridin-3-yl | 4-COOCH₃ | 5-Cl | 6-F |
| I.1.1753 | pyridin-3-yl | 4-COOCH₂CH₃ | 2-Cl | 5-F |
| I.1.1754 | pyridin-3-yl | 4-COOCH₂CH₃ | 2-Cl | H |
| I.1.1755 | pyridin-3-yl | 4-COOCH₂CH₃ | 5-Cl | H |
| I.1.1756 | pyridin-3-yl | 4-COOCH₂CH₃ | 6-Cl | H |
| I.1.1757 | pyridin-3-yl | 4-COOCH₂CH₃ | 2-F | H |
| I.1.1758 | pyridin-3-yl | 4-COOCH₂CH₃ | 5-F | H |
| I.1.1759 | pyridin-3-yl | 4-COOCH₂CH₃ | 6-F | H |
| I.1.1760 | pyridin-3-yl | 4-COOCH₂CH₃ | 2-Br | H |
| I.1.1761 | pyridin-3-yl | 4-COOCH₂CH₃ | 5-Br | H |
| I.1.1762 | pyridin-3-yl | 4-COOCH₂CH₃ | 6-Br | H |
| I.1.1763 | pyridin-3-yl | 4-COOCH₂CH₃ | 2-CH₃ | H |
| I.1.1764 | pyridin-3-yl | 4-COOCH₂CH₃ | 5-CH₃ | H |
| I.1.1765 | pyridin-3-yl | 4-COOCH₂CH₃ | 6-CH₃ | H |
| I.1.1766 | pyridin-3-yl | 4-COOCH₂CH₃ | 2-CF₃ | H |
| I.1.1767 | pyridin-3-yl | 4-COOCH₂CH₃ | 5-CF₃ | H |
| I.1.1768 | pyridin-3-yl | 4-COOCH₂CH₃ | 6-CF₃ | H |
| I.1.1769 | pyridin-3-yl | 4-COOCH₂CH₃ | 2-vinyl | H |
| I.1.1770 | pyridin-3-yl | 4-COOCH₂CH₃ | 5-vinyl | H |
| I.1.1771 | pyridin-3-yl | 4-COOCH₂CH₃ | 6-vinyl | H |
| I.1.1772 | pyridin-3-yl | 4-COOCH₂CH₃ | 2-Cl | 6-F |
| I.1.1773 | pyridin-3-yl | 4-COOCH₂CH₃ | 5-Cl | 6-F |
| I.1.1774 | pyridin-3-yl | 4-CONHCH₃ | 2-Cl | 5-F |
| I.1.1775 | pyridin-3-yl | 4-CONHCH₃ | 2-Cl | H |
| I.1.1776 | pyridin-3-yl | 4-CONHCH₃ | 5-Cl | H |
| I.1.1777 | pyridin-3-yl | 4-CONHCH₃ | 6-Cl | H |
| I.1.1778 | pyridin-3-yl | 4-CONHCH₃ | 2-F | H |
| I.1.1779 | pyridin-3-yl | 4-CONHCH₃ | 5-F | H |
| I.1.1780 | pyridin-3-yl | 4-CONHCH₃ | 6-F | H |
| I.1.1781 | pyridin-3-yl | 4-CONHCH₃ | 2-Br | H |
| I.1.1782 | pyridin-3-yl | 4-CONHCH₃ | 5-Br | H |
| I.1.1783 | pyridin-3-yl | 4-CONHCH₃ | 6-Br | H |
| I.1.1784 | pyridin-3-yl | 4-CONHCH₃ | 2-CH₃ | H |
| I.1.1785 | pyridin-3-yl | 4-CONHCH₃ | 5-CH₃ | H |
| I.1.1786 | pyridin-3-yl | 4-CONHCH₃ | 6-CH₃ | H |
| I.1.1787 | pyridin-3-yl | 4-CONHCH₃ | 2-CF₃ | H |
| I.1.1788 | pyridin-3-yl | 4-CONHCH₃ | 5-CF₃ | H |
| I.1.1789 | pyridin-3-yl | 4-CONHCH₃ | 6-CF₃ | H |
| I.1.1790 | pyridin-3-yl | 4-CONHCH₃ | 2-vinyl | H |
| I.1.1791 | pyridin-3-yl | 4-CONHCH₃ | 5-vinyl | H |
| I.1.1792 | pyridin-3-yl | 4-CONHCH₃ | 6-vinyl | H |
| I.1.1793 | pyridin-3-yl | 4-CONHCH₃ | 2-Cl | 6-F |
| I.1.1794 | pyridin-3-yl | 4-CONHCH₃ | 5-Cl | 6-F |
| I.1.1795 | pyridin-3-yl | 4-CON(CH₃)₂ | 2-Cl | 5-F |
| I.1.1796 | pyridin-3-yl | 4-CON(CH₃)₂ | 2-Cl | H |
| I.1.1797 | pyridin-3-yl | 4-CON(CH₃)₂ | 5-Cl | H |
| I.1.1798 | pyridin-3-yl | 4-CON(CH₃)₂ | 6-Cl | H |
| I.1.1799 | pyridin-3-yl | 4-CON(CH₃)₂ | 2-F | H |
| I.1.1800 | pyridin-3-yl | 4-CON(CH₃)₂ | 5-F | H |
| I.1.1801 | pyridin-3-yl | 4-CON(CH₃)₂ | 6-F | H |
| I.1.1802 | pyridin-3-yl | 4-CON(CH₃)₂ | 2-Br | H |
| I.1.1803 | pyridin-3-yl | 4-CON(CH₃)₂ | 5-Br | H |
| I.1.1804 | pyridin-3-yl | 4-CON(CH₃)₂ | 6-Br | H |
| I.1.1805 | pyridin-3-yl | 4-CON(CH₃)₂ | 2-CH₃ | H |
| I.1.1806 | pyridin-3-yl | 4-CON(CH₃)₂ | 5-CH₃ | H |
| I.1.1807 | pyridin-3-yl | 4-CON(CH₃)₂ | 6-CH₃ | H |
| I.1.1808 | pyridin-3-yl | 4-CON(CH₃)₂ | 2-CF₃ | H |
| I.1.1809 | pyridin-3-yl | 4-CON(CH₃)₂ | 5-CF₃ | H |
| I.1.1810 | pyridin-3-yl | 4-CON(CH₃)₂ | 6-CF₃ | H |
| I.1.1811 | pyridin-3-yl | 4-CON(CH₃)₂ | 2-vinyl | H |
| I.1.1812 | pyridin-3-yl | 4-CON(CH₃)₂ | 5-vinyl | H |
| I.1.1813 | pyridin-3-yl | 4-CON(CH₃)₂ | 6-vinyl | H |
| I.1.1814 | pyridin-3-yl | 4-CON(CH₃)₂ | 2-Cl | 6-F |
| I.1.1815 | pyridin-3-yl | 4-CON(CH₃)₂ | 5-Cl | 6-F |
| I.1.1816 | pyridin-4-yl | 3-NO₂ | 2-Cl | 5-F |
| I.1.1817 | pyridin-4-yl | 3-NO₂ | 2-Cl | H |
| I.1.1818 | pyridin-4-yl | 3-NO₂ | 5-Cl | H |
| I.1.1819 | pyridin-4-yl | 3-NO₂ | 6-Cl | H |
| I.1.1820 | pyridin-4-yl | 3-NO₂ | 2-F | H |
| I.1.1821 | pyridin-4-yl | 3-NO₂ | 5-F | H |
| I.1.1822 | pyridin-4-yl | 3-NO₂ | 6-F | H |
| I.1.1823 | pyridin-4-yl | 3-NO₂ | 2-Br | H |
| I.1.1824 | pyridin-4-yl | 3-NO₂ | 5-Br | H |
| I.1.1825 | pyridin-4-yl | 3-NO₂ | 6-Br | H |
| I.1.1826 | pyridin-4-yl | 3-NO₂ | 2-CH₃ | H |
| I.1.1827 | pyridin-4-yl | 3-NO₂ | 5-CH₃ | H |
| I.1.1828 | pyridin-4-yl | 3-NO₂ | 6-CH₃ | H |
| I.1.1829 | pyridin-4-yl | 3-NO₂ | 2-CF₃ | H |
| I.1.1830 | pyridin-4-yl | 3-NO₂ | 5-CF₃ | H |
| I.1.1831 | pyridin-4-yl | 3-NO₂ | 6-CF₃ | H |
| I.1.1832 | pyridin-4-yl | 3-NO₂ | 2-vinyl | H |
| I.1.1833 | pyridin-4-yl | 3-NO₂ | 5-vinyl | H |
| I.1.1834 | pyridin-4-yl | 3-NO₂ | 6-vinyl | H |
| I.1.1835 | pyridin-4-yl | 3-NO₂ | 2-Cl | 6-F |
| I.1.1836 | pyridin-4-yl | 3-NO₂ | 5-Cl | 6-F |
| I.1.1837 | pyridin-4-yl | 3-CN | 2-Cl | 5-F |
| I.1.1838 | pyridin-4-yl | 3-CN | 2-Cl | H |
| I.1.1839 | pyridin-4-yl | 3-CN | 5-Cl | H |
| I.1.1840 | pyridin-4-yl | 3-CN | 6-Cl | H |
| I.1.1841 | pyridin-4-yl | 3-CN | 2-F | H |
| I.1.1842 | pyridin-4-yl | 3-CN | 5-F | H |
| I.1.1843 | pyridin-4-yl | 3-CN | 6-F | H |
| I.1.1844 | pyridin-4-yl | 3-CN | 2-Br | H |
| I.1.1845 | pyridin-4-yl | 3-CN | 5-Br | H |
| I.1.1846 | pyridin-4-yl | 3-CN | 6-Br | H |
| I.1.1847 | pyridin-4-yl | 3-CN | 2-CH₃ | H |
| I.1.1848 | pyridin-4-yl | 3-CN | 5-CH₃ | H |
| I.1.1849 | pyridin-4-yl | 3-CN | 6-CH₃ | H |
| I.1.1850 | pyridin-4-yl | 3-CN | 2-CF₃ | H |
| I.1.1851 | pyridin-4-yl | 3-CN | 5-CF₃ | H |
| I.1.1852 | pyridin-4-yl | 3-CN | 6-CF₃ | H |
| I.1.1853 | pyridin-4-yl | 3-CN | 2-vinyl | H |
| I.1.1854 | pyridin-4-yl | 3-CN | 5-vinyl | H |
| I.1.1855 | pyridin-4-yl | 3-CN | 6-vinyl | H |
| I.1.1856 | pyridin-4-yl | 3-CN | 2-Cl | 6-F |
| I.1.1857 | pyridin-4-yl | 3-CN | 5-Cl | 6-F |
| I.1.1858 | pyridin-4-yl | 3-Br | 2-Cl | 5-F |
| I.1.1859 | pyridin-4-yl | 3-Br | 2-Cl | H |
| I.1.1860 | pyridin-4-yl | 3-Br | 5-Cl | H |
| I.1.1861 | pyridin-4-yl | 3-Br | 6-Cl | H |
| I.1.1862 | pyridin-4-yl | 3-Br | 2-F | H |
| I.1.1863 | pyridin-4-yl | 3-Br | 5-F | H |
| I.1.1864 | pyridin-4-yl | 3-Br | 6-F | H |
| I.1.1865 | pyridin-4-yl | 3-Br | 2-Br | H |
| I.1.1866 | pyridin-4-yl | 3-Br | 5-Br | H |
| I.1.1867 | pyridin-4-yl | 3-Br | 6-Br | H |
| I.1.1868 | pyridin-4-yl | 3-Br | 2-CH₃ | H |

TABLE 1-continued

| Comp. No. | A¹ | $R^a$ | $R^b$ or H | $R^c$ H |
|---|---|---|---|---|
| I.1.1869 | pyridin-4-yl | 3-Br | 5-CH₃ | H |
| I.1.1870 | pyridin-4-yl | 3-Br | 6-CH₃ | H |
| I.1.1871 | pyridin-4-yl | 3-Br | 2-CF₃ | H |
| I.1.1872 | pyridin-4-yl | 3-Br | 5-CF₃ | H |
| I.1.1873 | pyridin-4-yl | 3-Br | 6-CF₃ | H |
| I.1.1874 | pyridin-4-yl | 3-Br | 2-vinyl | H |
| I.1.1875 | pyridin-4-yl | 3-Br | 5-vinyl | H |
| I.1.1876 | pyridin-4-yl | 3-Br | 6-vinyl | H |
| I.1.1877 | pyridin-4-yl | 3-Br | 2-Cl | 6-F |
| I.1.1878 | pyridin-4-yl | 3-Br | 5-Cl | 6-F |
| I.1.1879 | pyridin-4-yl | 3-Cl | 2-Cl | 5-F |
| I.1.1880 | pyridin-4-yl | 3-Cl | 2-Cl | H |
| I.1.1881 | pyridin-4-yl | 3-Cl | 5-Cl | H |
| I.1.1882 | pyridin-4-yl | 3-Cl | 6-Cl | H |
| I.1.1883 | pyridin-4-yl | 3-Cl | 2-F | H |
| I.1.1884 | pyridin-4-yl | 3-Cl | 5-F | H |
| I.1.1885 | pyridin-4-yl | 3-Cl | 6-F | H |
| I.1.1886 | pyridin-4-yl | 3-Cl | 2-Br | H |
| I.1.1887 | pyridin-4-yl | 3-Cl | 5-Br | H |
| I.1.1888 | pyridin-4-yl | 3-Cl | 6-Br | H |
| I.1.1889 | pyridin-4-yl | 3-Cl | 2-CH₃ | H |
| I.1.1890 | pyridin-4-yl | 3-Cl | 5-CH₃ | H |
| I.1.1891 | pyridin-4-yl | 3-Cl | 6-CH₃ | H |
| I.1.1892 | pyridin-4-yl | 3-Cl | 2-CF₃ | H |
| I.1.1893 | pyridin-4-yl | 3-Cl | 5-CF₃ | H |
| I.1.1894 | pyridin-4-yl | 3-Cl | 6-CF₃ | H |
| I.1.1895 | pyridin-4-yl | 3-Cl | 2-vinyl | H |
| I.1.1896 | pyridin-4-yl | 3-Cl | 5-vinyl | H |
| I.1.1897 | pyridin-4-yl | 3-Cl | 6-vinyl | H |
| I.1.1898 | pyridin-4-yl | 3-Cl | 2-Cl | 6-F |
| I.1.1899 | pyridin-4-yl | 3-Cl | 5-Cl | 6-F |
| I.1.1900 | pyridin-4-yl | 3-ethynyl | 2-Cl | 5-F |
| I.1.1901 | pyridin-4-yl | 3-ethynyl | 2-Cl | H |
| I.1.1902 | pyridin-4-yl | 3-ethynyl | 5-Cl | H |
| I.1.1903 | pyridin-4-yl | 3-ethynyl | 6-Cl | H |
| I.1.1904 | pyridin-4-yl | 3-ethynyl | 2-F | H |
| I.1.1905 | pyridin-4-yl | 3-ethynyl | 5-F | H |
| I.1.1906 | pyridin-4-yl | 3-ethynyl | 6-F | H |
| I.1.1907 | pyridin-4-yl | 3-ethynyl | 2-Br | H |
| I.1.1908 | pyridin-4-yl | 3-ethynyl | 5-Br | H |
| I.1.1909 | pyridin-4-yl | 3-ethynyl | 6-Br | H |
| I.1.1910 | pyridin-4-yl | 3-ethynyl | 2-CH₃ | H |
| I.1.1911 | pyridin-4-yl | 3-ethynyl | 5-CH₃ | H |
| I.1.1912 | pyridin-4-yl | 3-ethynyl | 6-CH₃ | H |
| I.1.1913 | pyridin-4-yl | 3-ethynyl | 2-CF₃ | H |
| I.1.1914 | pyridin-4-yl | 3-ethynyl | 5-CF₃ | H |
| I.1.1915 | pyridin-4-yl | 3-ethynyl | 6-CF₃ | H |
| I.1.1916 | pyridin-4-yl | 3-ethynyl | 2-vinyl | H |
| I.1.1917 | pyridin-4-yl | 3-ethynyl | 5-vinyl | H |
| I.1.1918 | pyridin-4-yl | 3-ethynyl | 6-vinyl | H |
| I.1.1919 | pyridin-4-yl | 3-ethynyl | 2-Cl | 6-F |
| I.1.1920 | pyridin-4-yl | 3-ethynyl | 5-Cl | 6-F |
| I.1.1921 | pyridin-4-yl | 3-I | 2-Cl | 5-F |
| I.1.1922 | pyridin-4-yl | 3-I | 2-Cl | H |
| I.1.1923 | pyridin-4-yl | 3-I | 5-Cl | H |
| I.1.1924 | pyridin-4-yl | 3-I | 6-Cl | H |
| I.1.1925 | pyridin-4-yl | 3-I | 2-F | H |
| I.1.1926 | pyridin-4-yl | 3-I | 5-F | H |
| I.1.1927 | pyridin-4-yl | 3-I | 6-F | H |
| I.1.1928 | pyridin-4-yl | 3-I | 2-Br | H |
| I.1.1929 | pyridin-4-yl | 3-I | 5-Br | H |
| I.1.1930 | pyridin-4-yl | 3-I | 6-Br | H |
| I.1.1931 | pyridin-4-yl | 3-I | 2-CH₃ | H |
| I.1.1932 | pyridin-4-yl | 3-I | 5-CH₃ | H |
| I.1.1933 | pyridin-4-yl | 3-I | 6-CH₃ | H |
| I.1.1934 | pyridin-4-yl | 3-I | 2-CF₃ | H |
| I.1.1935 | pyridin-4-yl | 3-I | 5-CF₃ | H |
| I.1.1936 | pyridin-4-yl | 3-I | 6-CF₃ | H |
| I.1.1937 | pyridin-4-yl | 3-I | 2-vinyl | H |
| I.1.1938 | pyridin-4-yl | 3-I | 5-vinyl | H |
| I.1.1939 | pyridin-4-yl | 3-I | 6-vinyl | H |
| I.1.1940 | pyridin-4-yl | 3-I | 2-Cl | 6-F |
| I.1.1941 | pyridin-4-yl | 3-I | 5-Cl | 6-F |
| I.1.1942 | pyridin-4-yl | 3-COOH | 2-Cl | 5-F |
| I.1.1943 | pyridin-4-yl | 3-COOH | 2-Cl | H |
| I.1.1944 | pyridin-4-yl | 3-COOH | 5-Cl | H |
| I.1.1945 | pyridin-4-yl | 3-COOH | 6-Cl | H |
| I.1.1946 | pyridin-4-yl | 3-COOH | 2-F | H |
| I.1.1947 | pyridin-4-yl | 3-COOH | 5-F | H |
| I.1.1948 | pyridin-4-yl | 3-COOH | 6-F | H |
| I.1.1949 | pyridin-4-yl | 3-COOH | 2-Br | H |
| I.1.1950 | pyridin-4-yl | 3-COOH | 5-Br | H |
| I.1.1951 | pyridin-4-yl | 3-COOH | 6-Br | H |
| I.1.1952 | pyridin-4-yl | 3-COOH | 2-CH₃ | H |
| I.1.1953 | pyridin-4-yl | 3-COOH | 5-CH₃ | H |
| I.1.1954 | pyridin-4-yl | 3-COOH | 6-CH₃ | H |
| I.1.1955 | pyridin-4-yl | 3-COOH | 2-CF₃ | H |
| I.1.1956 | pyridin-4-yl | 3-COOH | 5-CF₃ | H |
| I.1.1957 | pyridin-4-yl | 3-COOH | 6-CF₃ | H |
| I.1.1958 | pyridin-4-yl | 3-COOH | 2-vinyl | H |
| I.1.1959 | pyridin-4-yl | 3-COOH | 5-vinyl | H |
| I.1.1960 | pyridin-4-yl | 3-COOH | 6-vinyl | H |
| I.1.1961 | pyridin-4-yl | 3-COOH | 2-Cl | 6-F |
| I.1.1962 | pyridin-4-yl | 3-COOH | 5-Cl | 6-F |
| I.1.1963 | pyridin-4-yl | 3-COOCH₃ | 2-Cl | 5-F |
| I.1.1964 | pyridin-4-yl | 3-COOCH₃ | 2-Cl | H |
| I.1.1965 | pyridin-4-yl | 3-COOCH₃ | 5-Cl | H |
| I.1.1966 | pyridin-4-yl | 3-COOCH₃ | 6-Cl | H |
| I.1.1967 | pyridin-4-yl | 3-COOCH₃ | 2-F | H |
| I.1.1968 | pyridin-4-yl | 3-COOCH₃ | 5-F | H |
| I.1.1969 | pyridin-4-yl | 3-COOCH₃ | 6-F | H |
| I.1.1970 | pyridin-4-yl | 3-COOCH₃ | 2-Br | H |
| I.1.1971 | pyridin-4-yl | 3-COOCH₃ | 5-Br | H |
| I.1.1972 | pyridin-4-yl | 3-COOCH₃ | 6-Br | H |
| I.1.1973 | pyridin-4-yl | 3-COOCH₃ | 2-CH₃ | H |
| I.1.1974 | pyridin-4-yl | 3-COOCH₃ | 5-CH₃ | H |
| I.1.1975 | pyridin-4-yl | 3-COOCH₃ | 6-CH₃ | H |
| I.1.1976 | pyridin-4-yl | 3-COOCH₃ | 2-CF₃ | H |
| I.1.1977 | pyridin-4-yl | 3-COOCH₃ | 5-CF₃ | H |
| I.1.1978 | pyridin-4-yl | 3-COOCH₃ | 6-CF₃ | H |
| I.1.1979 | pyridin-4-yl | 3-COOCH₃ | 2-vinyl | H |
| I.1.1980 | pyridin-4-yl | 3-COOCH₃ | 5-vinyl | H |
| I.1.1981 | pyridin-4-yl | 3-COOCH₃ | 6-vinyl | H |
| I.1.1982 | pyridin-4-yl | 3-COOCH₃ | 2-Cl | 6-F |
| I.1.1983 | pyridin-4-yl | 3-COOCH₃ | 5-Cl | 6-F |
| I.1.1984 | pyridin-4-yl | 3-COOCH₂CH₃ | 2-Cl | 5-F |
| I.1.1985 | pyridin-4-yl | 3-COOCH₂CH₃ | 2-Cl | H |
| I.1.1986 | pyridin-4-yl | 3-COOCH₂CH₃ | 5-Cl | H |
| I.1.1987 | pyridin-4-yl | 3-COOCH₂CH₃ | 6-Cl | H |
| I.1.1988 | pyridin-4-yl | 3-COOCH₂CH₃ | 2-F | H |
| I.1.1989 | pyridin-4-yl | 3-COOCH₂CH₃ | 5-F | H |
| I.1.1990 | pyridin-4-yl | 3-COOCH₂CH₃ | 6-F | H |
| I.1.1991 | pyridin-4-yl | 3-COOCH₂CH₃ | 2-Br | H |
| I.1.1992 | pyridin-4-yl | 3-COOCH₂CH₃ | 5-Br | H |
| I.1.1993 | pyridin-4-yl | 3-COOCH₂CH₃ | 6-Br | H |
| I.1.1994 | pyridin-4-yl | 3-COOCH₂CH₃ | 2-CH₃ | H |
| I.1.1995 | pyridin-4-yl | 3-COOCH₂CH₃ | 5-CH₃ | H |
| I.1.1996 | pyridin-4-yl | 3-COOCH₂CH₃ | 6-CH₃ | H |
| I.1.1997 | pyridin-4-yl | 3-COOCH₂CH₃ | 2-CF₃ | H |
| I.1.1998 | pyridin-4-yl | 3-COOCH₂CH₃ | 5-CF₃ | H |
| I.1.1999 | pyridin-4-yl | 3-COOCH₂CH₃ | 6-CF₃ | H |
| I.1.2000 | pyridin-4-yl | 3-COOCH₂CH₃ | 2-vinyl | H |
| I.1.2001 | pyridin-4-yl | 3-COOCH₂CH₃ | 5-vinyl | H |
| I.1.2002 | pyridin-4-yl | 3-COOCH₂CH₃ | 6-vinyl | H |
| I.1.2003 | pyridin-4-yl | 3-COOCH₂CH₃ | 2-Cl | 6-F |
| I.1.2004 | pyridin-4-yl | 3-COOCH₂CH₃ | 5-Cl | 6-F |
| I.1.2005 | pyridin-4-yl | 3-CONHCH₃ | 2-Cl | 5-F |
| I.1.2006 | pyridin-4-yl | 3-CONHCH₃ | 2-Cl | H |
| I.1.2007 | pyridin-4-yl | 3-CONHCH₃ | 5-Cl | H |
| I.1.2008 | pyridin-4-yl | 3-CONHCH₃ | 6-Cl | H |
| I.1.2009 | pyridin-4-yl | 3-CONHCH₃ | 2-F | H |
| I.1.2010 | pyridin-4-yl | 3-CONHCH₃ | 5-F | H |
| I.1.2011 | pyridin-4-yl | 3-CONHCH₃ | 6-F | H |
| I.1.2012 | pyridin-4-yl | 3-CONHCH₃ | 2-Br | H |
| I.1.2013 | pyridin-4-yl | 3-CONHCH₃ | 5-Br | H |
| I.1.2014 | pyridin-4-yl | 3-CONHCH₃ | 6-Br | H |
| I.1.2015 | pyridin-4-yl | 3-CONHCH₃ | 2-CH₃ | H |
| I.1.2016 | pyridin-4-yl | 3-CONHCH₃ | 5-CH₃ | H |
| I.1.2017 | pyridin-4-yl | 3-CONHCH₃ | 6-CH₃ | H |
| I.1.2018 | pyridin-4-yl | 3-CONHCH₃ | 2-CF₃ | H |
| I.1.2019 | pyridin-4-yl | 3-CONHCH₃ | 5-CF₃ | H |
| I.1.2020 | pyridin-4-yl | 3-CONHCH₃ | 6-CF₃ | H |
| I.1.2021 | pyridin-4-yl | 3-CONHCH₃ | 2-vinyl | H |
| I.1.2022 | pyridin-4-yl | 3-CONHCH₃ | 5-vinyl | H |
| I.1.2023 | pyridin-4-yl | 3-CONHCH₃ | 6-vinyl | H |
| I.1.2024 | pyridin-4-yl | 3-CONHCH₃ | 2-Cl | 6-F |

TABLE 1-continued

| Comp. No. | A¹ | R$^a$ | R$^b$ or H | R$^c$ H |
|---|---|---|---|---|
| I.1.2025 | pyridin-4-yl | 3-CONHCH$_3$ | 5-Cl | 6-F |
| I.1.2026 | pyridin-4-yl | 3-CON(CH$_3$)$_2$ | 2-Cl | 5-F |
| I.1.2027 | pyridin-4-yl | 3-CON(CH$_3$)$_2$ | 2-Cl | H |
| I.1.2028 | pyridin-4-yl | 3-CON(CH$_3$)$_2$ | 5-Cl | H |
| I.1.2029 | pyridin-4-yl | 3-CON(CH$_3$)$_2$ | 6-Cl | H |
| I.1.2030 | pyridin-4-yl | 3-CON(CH$_3$)$_2$ | 2-F | H |
| I.1.2031 | pyridin-4-yl | 3-CON(CH$_3$)$_2$ | 5-F | H |
| I.1.2032 | pyridin-4-yl | 3-CON(CH$_3$)$_2$ | 6-F | H |
| I.1.2033 | pyridin-4-yl | 3-CON(CH$_3$)$_2$ | 2-Br | H |
| I.1.2034 | pyridin-4-yl | 3-CON(CH$_3$)$_2$ | 5-Br | H |
| I.1.2035 | pyridin-4-yl | 3-CON(CH$_3$)$_2$ | 6-Br | H |
| I.1.2036 | pyridin-4-yl | 3-CON(CH$_3$)$_2$ | 2-CH$_3$ | H |
| I.1.2037 | pyridin-4-yl | 3-CON(CH$_3$)$_2$ | 5-CH$_3$ | H |
| I.1.2038 | pyridin-4-yl | 3-CON(CH$_3$)$_2$ | 6-CH$_3$ | H |
| I.1.2039 | pyridin-4-yl | 3-CON(CH$_3$)$_2$ | 2-CF$_3$ | H |
| I.1.2040 | pyridin-4-yl | 3-CON(CH$_3$)$_2$ | 5-CF$_3$ | H |
| I.1.2041 | pyridin-4-yl | 3-CON(CH$_3$)$_2$ | 6-CF$_3$ | H |
| I.1.2042 | pyridin-4-yl | 3-CON(CH$_3$)$_2$ | 2-vinyl | H |
| I.1.2043 | pyridin-4-yl | 3-CON(CH$_3$)$_2$ | 5-vinyl | H |
| I.1.2044 | pyridin-4-yl | 3-CON(CH$_3$)$_2$ | 6-vinyl | H |
| I.1.2045 | pyridin-4-yl | 3-CON(CH$_3$)$_2$ | 2-Cl | 6-F |
| I.1.2046 | pyridin-4-yl | 3-CON(CH$_3$)$_2$ | 5-Cl | 6-F |
| I.1.2047 | furan-2-yl | 3-NO$_2$ | 4-Cl | 5-F |
| I.1.2048 | furan-2-yl | 3-NO$_2$ | 4-Cl | H |
| I.1.2049 | furan-2-yl | 3-NO$_2$ | 5-Cl | H |
| I.1.2050 | furan-2-yl | 3-NO$_2$ | 4-F | H |
| I.1.2051 | furan-2-yl | 3-NO$_2$ | 5-F | H |
| I.1.2052 | furan-2-yl | 3-NO$_2$ | 4-CH$_3$ | H |
| I.1.2053 | furan-2-yl | 3-NO$_2$ | 5-CH$_3$ | H |
| I.1.2054 | furan-2-yl | 3-NO$_2$ | 4-CN | H |
| I.1.2055 | furan-2-yl | 3-NO$_2$ | 5-CN | H |
| I.1.2056 | furan-2-yl | 3-NO$_2$ | 4-CF$_3$ | H |
| I.1.2057 | furan-2-yl | 3-NO$_2$ | 5-CF$_3$ | H |
| I.1.2058 | furan-2-yl | 3-CN | 4-Cl | 5-F |
| I.1.2059 | furan-2-yl | 3-CN | 4-Cl | H |
| I.1.2060 | furan-2-yl | 3-CN | 5-Cl | H |
| I.1.2061 | furan-2-yl | 3-CN | 4-F | H |
| I.1.2062 | furan-2-yl | 3-CN | 5-F | H |
| I.1.2063 | furan-2-yl | 3-CN | 4-CH$_3$ | H |
| I.1.2064 | furan-2-yl | 3-CN | 5-CH$_3$ | H |
| I.1.2065 | furan-2-yl | 3-CN | 4-CN | H |
| I.1.2066 | furan-2-yl | 3-CN | 5-CN | H |
| I.1.2067 | furan-2-yl | 3-CN | 4-CF$_3$ | H |
| I.1.2068 | furan-2-yl | 3-CN | 5-CF$_3$ | H |
| I.1.2069 | furan-2-yl | 3-COOH | 4-Cl | 5-F |
| I.1.2070 | furan-2-yl | 3-COOH | 4-Cl | H |
| I.1.2071 | furan-2-yl | 3-COOH | 5-Cl | H |
| I.1.2072 | furan-2-yl | 3-COOH | 4-F | H |
| I.1.2073 | furan-2-yl | 3-COOH | 5-F | H |
| I.1.2074 | furan-2-yl | 3-COOH | 4-CH$_3$ | H |
| I.1.2075 | furan-2-yl | 3-COOH | 5-CH$_3$ | H |
| I.1.2076 | furan-2-yl | 3-COOH | 4-CN | H |
| I.1.2077 | furan-2-yl | 3-COOH | 5-CN | H |
| I.1.2078 | furan-2-yl | 3-COOH | 4-CF$_3$ | H |
| I.1.2079 | furan-2-yl | 3-COOH | 5-CF$_3$ | H |
| I.1.2080 | furan-2-yl | 3-COOCH$_3$ | 4-Cl | 5-F |
| I.1.2081 | furan-2-yl | 3-COOCH$_3$ | 4-Cl | H |
| I.1.2082 | furan-2-yl | 3-COOCH$_3$ | 5-Cl | H |
| I.1.2083 | furan-2-yl | 3-COOCH$_3$ | 4-F | H |
| I.1.2084 | furan-2-yl | 3-COOCH$_3$ | 5-F | H |
| I.1.2085 | furan-2-yl | 3-COOCH$_3$ | 4-CH$_3$ | H |
| I.1.2086 | furan-2-yl | 3-COOCH$_3$ | 5-CH$_3$ | H |
| I.1.2087 | furan-2-yl | 3-COOCH$_3$ | 4-CN | H |
| I.1.2088 | furan-2-yl | 3-COOCH$_3$ | 5-CN | H |
| I.1.2089 | furan-2-yl | 3-COOCH$_3$ | 4-CF$_3$ | H |
| I.1.2090 | furan-2-yl | 3-COOCH$_3$ | 5-CF$_3$ | H |
| I.1.2091 | furan-2-yl | 3-COOCH$_2$CH$_3$ | 4-Cl | 5-F |
| I.1.2092 | furan-2-yl | 3-COOCH$_2$CH$_3$ | 4-Cl | H |
| I.1.2093 | furan-2-yl | 3-COOCH$_2$CH$_3$ | 5-Cl | H |
| I.1.2094 | furan-2-yl | 3-COOCH$_2$CH$_3$ | 4-F | H |
| I.1.2095 | furan-2-yl | 3-COOCH$_2$CH$_3$ | 5-F | H |
| I.1.2096 | furan-2-yl | 3-COOCH$_2$CH$_3$ | 4-CH$_3$ | H |
| I.1.2097 | furan-2-yl | 3-COOCH$_2$CH$_3$ | 5-CH$_3$ | H |
| I.1.2098 | furan-2-yl | 3-COOCH$_2$CH$_3$ | 4-CN | H |
| I.1.2099 | furan-2-yl | 3-COOCH$_2$CH$_3$ | 5-CN | H |
| I.1.2100 | furan-2-yl | 3-COOCH$_2$CH$_3$ | 4-CF$_3$ | H |
| I.1.2101 | furan-2-yl | 3-COOCH$_2$CH$_3$ | 5-CF$_3$ | H |
| I.1.2102 | furan-2-yl | 3-ethynyl | 4-Cl | 5-F |
| I.1.2103 | furan-2-yl | 3-ethynyl | 4-Cl | H |
| I.1.2104 | furan-2-yl | 3-ethynyl | 5-Cl | H |
| I.1.2105 | furan-2-yl | 3-ethynyl | 4-F | H |
| I.1.2106 | furan-2-yl | 3-ethynyl | 5-F | H |
| I.1.2107 | furan-2-yl | 3-ethynyl | 4-CH$_3$ | H |
| I.1.2108 | furan-2-yl | 3-ethynyl | 5-CH$_3$ | H |
| I.1.2109 | furan-2-yl | 3-ethynyl | 4-CN | H |
| I.1.2110 | furan-2-yl | 3-ethynyl | 5-CN | H |
| I.1.2111 | furan-2-yl | 3-ethynyl | 4-CF$_3$ | H |
| I.1.2112 | furan-2-yl | 3-ethynyl | 5-CF$_3$ | H |
| I.1.2113 | furan-2-yl | 3-I | 4-Cl | 5-F |
| I.1.2114 | furan-2-yl | 3-I | 4-Cl | H |
| I.1.2115 | furan-2-yl | 3-I | 5-Cl | H |
| I.1.2116 | furan-2-yl | 3-I | 4-F | H |
| I.1.2117 | furan-2-yl | 3-I | 5-F | H |
| I.1.2118 | furan-2-yl | 3-I | 4-CH$_3$ | H |
| I.1.2119 | furan-2-yl | 3-I | 5-CH$_3$ | H |
| I.1.2120 | furan-2-yl | 3-I | 4-CN | H |
| I.1.2121 | furan-2-yl | 3-I | 5-CN | H |
| I.1.2122 | furan-2-yl | 3-I | 4-CF$_3$ | H |
| I.1.2123 | furan-2-yl | 3-I | 5-CF$_3$ | H |
| I.1.2124 | furan-2-yl | 3-Cl | 4-Cl | 5-F |
| I.1.2125 | furan-2-yl | 3-Cl | 4-Cl | H |
| I.1.2126 | furan-2-yl | 3-Cl | 5-Cl | H |
| I.1.2127 | furan-2-yl | 3-Cl | 4-F | H |
| I.1.2128 | furan-2-yl | 3-Cl | 5-F | H |
| I.1.2129 | furan-2-yl | 3-Cl | 4-CH$_3$ | H |
| I.1.2130 | furan-2-yl | 3-Cl | 5-CH$_3$ | H |
| I.1.2131 | furan-2-yl | 3-Cl | 4-CN | H |
| I.1.2132 | furan-2-yl | 3-Cl | 5-CN | H |
| I.1.2133 | furan-2-yl | 3-Cl | 4-CF$_3$ | H |
| I.1.2134 | furan-2-yl | 3-Cl | 5-CF$_3$ | H |
| I.1.2135 | furan-2-yl | 3-Br | 4-Cl | 5-F |
| I.1.2136 | furan-2-yl | 3-Br | 4-Cl | H |
| I.1.2137 | furan-2-yl | 3-Br | 5-Cl | H |
| I.1.2138 | furan-2-yl | 3-Br | 4-F | H |
| I.1.2139 | furan-2-yl | 3-Br | 5-F | H |
| I.1.2140 | furan-2-yl | 3-Br | 4-CH$_3$ | H |
| I.1.2141 | furan-2-yl | 3-Br | 5-CH$_3$ | H |
| I.1.2142 | furan-2-yl | 3-Br | 4-CN | H |
| I.1.2143 | furan-2-yl | 3-Br | 5-CN | H |
| I.1.2144 | furan-2-yl | 3-Br | 4-CF$_3$ | H |
| I.1.2145 | furan-2-yl | 3-Br | 5-CF$_3$ | H |
| I.1.2146 | furan-2-yl | 3-CON(CH$_3$)$_2$ | 4-Cl | 5-F |
| I.1.2147 | furan-2-yl | 3-CON(CH$_3$)$_2$ | 4-Cl | H |
| I.1.2148 | furan-2-yl | 3-CON(CH$_3$)$_2$ | 5-Cl | H |
| I.1.2149 | furan-2-yl | 3-CON(CH$_3$)$_2$ | 4-F | H |
| I.1.2150 | furan-2-yl | 3-CON(CH$_3$)$_2$ | 5-F | H |
| I.1.2151 | furan-2-yl | 3-CON(CH$_3$)$_2$ | 4-CH$_3$ | H |
| I.1.2152 | furan-2-yl | 3-CON(CH$_3$)$_2$ | 5-CH$_3$ | H |
| I.1.2153 | furan-2-yl | 3-CON(CH$_3$)$_2$ | 4-CN | H |
| I.1.2154 | furan-2-yl | 3-CON(CH$_3$)$_2$ | 5-CN | H |
| I.1.2155 | furan-2-yl | 3-CON(CH$_3$)$_2$ | 4-CF$_3$ | H |
| I.1.2156 | furan-2-yl | 3-CON(CH$_3$)$_2$ | 5-CF$_3$ | H |
| I.1.2157 | furan-2-yl | 3-CONHCH$_3$ | 4-Cl | 5-F |
| I.1.2158 | furan-2-yl | 3-CONHCH$_3$ | 4-Cl | H |
| I.1.2159 | furan-2-yl | 3-CONHCH$_3$ | 5-Cl | H |
| I.1.2160 | furan-2-yl | 3-CONHCH$_3$ | 4-F | H |
| I.1.2161 | furan-2-yl | 3-CONHCH$_3$ | 5-F | H |
| I.1.2162 | furan-2-yl | 3-CONHCH$_3$ | 4-CH$_3$ | H |
| I.1.2163 | furan-2-yl | 3-CONHCH$_3$ | 5-CH$_3$ | H |
| I.1.2164 | furan-2-yl | 3-CONHCH$_3$ | 4-CN | H |
| I.1.2165 | furan-2-yl | 3-CONHCH$_3$ | 5-CN | H |
| I.1.2166 | furan-2-yl | 3-CONHCH$_3$ | 4-CF$_3$ | H |
| I.1.2167 | furan-2-yl | 3-CONHCH$_3$ | 5-CF$_3$ | H |
| I.1.2168 | furan-3-yl | 2-NO$_2$ | 4-Cl | 5-F |
| I.1.2169 | furan-3-yl | 2-NO$_2$ | 4-Cl | H |
| I.1.2170 | furan-3-yl | 2-NO$_2$ | 5-Cl | H |
| I.1.2171 | furan-3-yl | 2-NO$_2$ | 4-F | H |
| I.1.2172 | furan-3-yl | 2-NO$_2$ | 5-F | H |
| I.1.2173 | furan-3-yl | 2-NO$_2$ | 4-CH$_3$ | H |
| I.1.2174 | furan-3-yl | 2-NO$_2$ | 5-CH$_3$ | H |
| I.1.2175 | furan-3-yl | 2-NO$_2$ | 4-CN | H |
| I.1.2176 | furan-3-yl | 2-NO$_2$ | 5-CN | H |
| I.1.2177 | furan-3-yl | 2-NO$_2$ | 4-CF$_3$ | H |
| I.1.2178 | furan-3-yl | 2-NO$_2$ | 5-CF$_3$ | H |
| I.1.2179 | furan-3-yl | 2-CN | 4-Cl | 5-F |
| I.1.2180 | furan-3-yl | 2-CN | 4-Cl | H |

TABLE 1-continued

| Comp. No. | A¹ | $R^a$ | $R^b$ or H | $R^c$ H |
|---|---|---|---|---|
| I.1.2181 | furan-3-yl | 2-CN | 5-Cl | H |
| I.1.2182 | furan-3-yl | 2-CN | 4-F | H |
| I.1.2183 | furan-3-yl | 2-CN | 5-F | H |
| I.1.2184 | furan-3-yl | 2-CN | 4-CH₃ | H |
| I.1.2185 | furan-3-yl | 2-CN | 5-CH₃ | H |
| I.1.2186 | furan-3-yl | 2-CN | 4-CN | H |
| I.1.2187 | furan-3-yl | 2-CN | 5-CN | H |
| I.1.2188 | furan-3-yl | 2-CN | 4-CF₃ | H |
| I.1.2189 | furan-3-yl | 2-CN | 5-CF₃ | H |
| I.1.2190 | furan-3-yl | 2-COOH | 4-Cl | 5-F |
| I.1.2191 | furan-3-yl | 2-COOH | 4-Cl | H |
| I.1.2192 | furan-3-yl | 2-COOH | 5-Cl | H |
| I.1.2193 | furan-3-yl | 2-COOH | 4-F | H |
| I.1.2194 | furan-3-yl | 2-COOH | 5-F | H |
| I.1.2195 | furan-3-yl | 2-COOH | 4-CH₃ | H |
| I.1.2196 | furan-3-yl | 2-COOH | 5-CH₃ | H |
| I.1.2197 | furan-3-yl | 2-COOH | 4-CN | H |
| I.1.2198 | furan-3-yl | 2-COOH | 5-CN | H |
| I.1.2199 | furan-3-yl | 2-COOH | 4-CF₃ | H |
| I.1.2200 | furan-3-yl | 2-COOH | 5-CF₃ | H |
| I.1.2201 | furan-3-yl | 2-COOCH₃ | 4-Cl | 5-F |
| I.1.2202 | furan-3-yl | 2-COOCH₃ | 4-Cl | H |
| I.1.2203 | furan-3-yl | 2-COOCH₃ | 5-Cl | H |
| I.1.2204 | furan-3-yl | 2-COOCH₃ | 4-F | H |
| I.1.2205 | furan-3-yl | 2-COOCH₃ | 5-F | H |
| I.1.2206 | furan-3-yl | 2-COOCH₃ | 4-CH₃ | H |
| I.1.2207 | furan-3-yl | 2-COOCH₃ | 5-CH₃ | H |
| I.1.2208 | furan-3-yl | 2-COOCH₃ | 4-CN | H |
| I.1.2209 | furan-3-yl | 2-COOCH₃ | 5-CN | H |
| I.1.2210 | furan-3-yl | 2-COOCH₃ | 4-CF₃ | H |
| I.1.2211 | furan-3-yl | 2-COOCH₃ | 5-CF₃ | H |
| I.1.2212 | furan-3-yl | 2-COOCH₂CH₃ | 4-Cl | 5-F |
| I.1.2213 | furan-3-yl | 2-COOCH₂CH₃ | 4-Cl | H |
| I.1.2214 | furan-3-yl | 2-COOCH₂CH₃ | 5-Cl | H |
| I.1.2215 | furan-3-yl | 2-COOCH₂CH₃ | 4-F | H |
| I.1.2216 | furan-3-yl | 2-COOCH₂CH₃ | 5-F | H |
| I.1.2217 | furan-3-yl | 2-COOCH₂CH₃ | 4-CH₃ | H |
| I.1.2218 | furan-3-yl | 2-COOCH₂CH₃ | 5-CH₃ | H |
| I.1.2219 | furan-3-yl | 2-COOCH₂CH₃ | 4-CN | H |
| I.1.2220 | furan-3-yl | 2-COOCH₂CH₃ | 5-CN | H |
| I.1.2221 | furan-3-yl | 2-COOCH₂CH₃ | 4-CF₃ | H |
| I.1.2222 | furan-3-yl | 2-COOCH₂CH₃ | 5-CF₃ | H |
| I.1.2223 | furan-3-yl | 2-ethynyl | 4-Cl | 5-F |
| I.1.2224 | furan-3-yl | 2-ethynyl | 4-Cl | H |
| I.1.2225 | furan-3-yl | 2-ethynyl | 5-Cl | H |
| I.1.2226 | furan-3-yl | 2-ethynyl | 4-F | H |
| I.1.2227 | furan-3-yl | 2-ethynyl | 5-F | H |
| I.1.2228 | furan-3-yl | 2-ethynyl | 4-CH₃ | H |
| I.1.2229 | furan-3-yl | 2-ethynyl | 5-CH₃ | H |
| I.1.2230 | furan-3-yl | 2-ethynyl | 4-CN | H |
| I.1.2231 | furan-3-yl | 2-ethynyl | 5-CN | H |
| I.1.2232 | furan-3-yl | 2-ethynyl | 4-CF₃ | H |
| I.1.2233 | furan-3-yl | 2-ethynyl | 5-CF₃ | H |
| I.1.2234 | furan-3-yl | 2-I | 4-Cl | 5-F |
| I.1.2235 | furan-3-yl | 2-I | 4-Cl | H |
| I.1.2236 | furan-3-yl | 2-I | 5-Cl | H |
| I.1.2237 | furan-3-yl | 2-I | 4-F | H |
| I.1.2238 | furan-3-yl | 2-I | 5-F | H |
| I.1.2239 | furan-3-yl | 2-I | 4-CH₃ | H |
| I.1.2240 | furan-3-yl | 2-I | 5-CH₃ | H |
| I.1.2241 | furan-3-yl | 2-I | 4-CN | H |
| I.1.2242 | furan-3-yl | 2-I | 5-CN | H |
| I.1.2243 | furan-3-yl | 2-I | 4-CF₃ | H |
| I.1.2244 | furan-3-yl | 2-I | 5-CF₃ | H |
| I.1.2245 | furan-3-yl | 2-Cl | 4-Cl | 5-F |
| I.1.2246 | furan-3-yl | 2-Cl | 4-Cl | H |
| I.1.2247 | furan-3-yl | 2-Cl | 5-Cl | H |
| I.1.2248 | furan-3-yl | 2-Cl | 4-F | H |
| I.1.2249 | furan-3-yl | 2-Cl | 5-F | H |
| I.1.2250 | furan-3-yl | 2-Cl | 4-CH₃ | H |
| I.1.2251 | furan-3-yl | 2-Cl | 5-CH₃ | H |
| I.1.2252 | furan-3-yl | 2-Cl | 4-CN | H |
| I.1.2253 | furan-3-yl | 2-Cl | 5-CN | H |
| I.1.2254 | furan-3-yl | 2-Cl | 4-CF₃ | H |
| I.1.2255 | furan-3-yl | 2-Cl | 5-CF₃ | H |
| I.1.2256 | furan-3-yl | 2-Br | 4-Cl | 5-F |
| I.1.2257 | furan-3-yl | 2-Br | 4-Cl | H |
| I.1.2258 | furan-3-yl | 2-Br | 5-Cl | H |
| I.1.2259 | furan-3-yl | 2-Br | 4-F | H |
| I.1.2260 | furan-3-yl | 2-Br | 5-F | H |
| I.1.2261 | furan-3-yl | 2-Br | 4-CH₃ | H |
| I.1.2262 | furan-3-yl | 2-Br | 5-CH₃ | H |
| I.1.2263 | furan-3-yl | 2-Br | 4-CN | H |
| I.1.2264 | furan-3-yl | 2-Br | 5-CN | H |
| I.1.2265 | furan-3-yl | 2-Br | 4-CF₃ | H |
| I.1.2266 | furan-3-yl | 2-Br | 5-CF₃ | H |
| I.1.2267 | furan-3-yl | 2-CON(CH₃)₂ | 4-Cl | 5-F |
| I.1.2268 | furan-3-yl | 2-CON(CH₃)₂ | 4-Cl | H |
| I.1.2269 | furan-3-yl | 2-CON(CH₃)₂ | 5-Cl | H |
| I.1.2270 | furan-3-yl | 2-CON(CH₃)₂ | 4-F | H |
| I.1.2271 | furan-3-yl | 2-CON(CH₃)₂ | 5-F | H |
| I.1.2272 | furan-3-yl | 2-CON(CH₃)₂ | 4-CH₃ | H |
| I.1.2273 | furan-3-yl | 2-CON(CH₃)₂ | 5-CH₃ | H |
| I.1.2274 | furan-3-yl | 2-CON(CH₃)₂ | 4-CN | H |
| I.1.2275 | furan-3-yl | 2-CON(CH₃)₂ | 5-CN | H |
| I.1.2276 | furan-3-yl | 2-CON(CH₃)₂ | 4-CF₃ | H |
| I.1.2277 | furan-3-yl | 2-CON(CH₃)₂ | 5-CF₃ | H |
| I.1.2278 | furan-3-yl | 2-CONHCH₃ | 4-Cl | 5-F |
| I.1.2279 | furan-3-yl | 2-CONHCH₃ | 4-Cl | H |
| I.1.2280 | furan-3-yl | 2-CONHCH₃ | 5-Cl | H |
| I.1.2281 | furan-3-yl | 2-CONHCH₃ | 4-F | H |
| I.1.2282 | furan-3-yl | 2-CONHCH₃ | 5-F | H |
| I.1.2283 | furan-3-yl | 2-CONHCH₃ | 4-CH₃ | H |
| I.1.2284 | furan-3-yl | 2-CONHCH₃ | 5-CH₃ | H |
| I.1.2285 | furan-3-yl | 2-CONHCH₃ | 4-CN | H |
| I.1.2286 | furan-3-yl | 2-CONHCH₃ | 5-CN | H |
| I.1.2287 | furan-3-yl | 2-CONHCH₃ | 4-CF₃ | H |
| I.1.2288 | furan-3-yl | 2-CONHCH₃ | 5-CF₃ | H |
| I.1.2289 | furan-3-yl | 4-NO₂ | 5-Cl | 2-F |
| I.1.2290 | furan-3-yl | 4-NO₂ | 5-Cl | H |
| I.1.2291 | furan-3-yl | 4-NO₂ | 2-Cl | H |
| I.1.2292 | furan-3-yl | 4-NO₂ | 5-F | H |
| I.1.2293 | furan-3-yl | 4-NO₂ | 2-F | H |
| I.1.2294 | furan-3-yl | 4-NO₂ | 5-CH₃ | H |
| I.1.2295 | furan-3-yl | 4-NO₂ | 2-CH₃ | H |
| I.1.2296 | furan-3-yl | 4-NO₂ | 5-CN | H |
| I.1.2297 | furan-3-yl | 4-NO₂ | 2-CN | H |
| I.1.2298 | furan-3-yl | 4-NO₂ | 5-CF₃ | H |
| I.1.2299 | furan-3-yl | 4-NO₂ | 2-CF₃ | H |
| I.1.2300 | furan-3-yl | 4-CN | 5-Cl | 2-F |
| I.1.2301 | furan-3-yl | 4-CN | 5-Cl | H |
| I.1.2302 | furan-3-yl | 4-CN | 2-Cl | H |
| I.1.2303 | furan-3-yl | 4-CN | 5-F | H |
| I.1.2304 | furan-3-yl | 4-CN | 2-F | H |
| I.1.2305 | furan-3-yl | 4-CN | 5-CH₃ | H |
| I.1.2306 | furan-3-yl | 4-CN | 2-CH₃ | H |
| I.1.2307 | furan-3-yl | 4-CN | 5-CN | H |
| I.1.2308 | furan-3-yl | 4-CN | 2-CN | H |
| I.1.2309 | furan-3-yl | 4-CN | 5-CF₃ | H |
| I.1.2310 | furan-3-yl | 4-CN | 2-CF₃ | H |
| I.1.2311 | furan-3-yl | 4-COOH | 5-Cl | 2-F |
| I.1.2312 | furan-3-yl | 4-COOH | 5-Cl | H |
| I.1.2313 | furan-3-yl | 4-COOH | 2-Cl | H |
| I.1.2314 | furan-3-yl | 4-COOH | 5-F | H |
| I.1.2315 | furan-3-yl | 4-COOH | 2-F | H |
| I.1.2316 | furan-3-yl | 4-COOH | 5-CH₃ | H |
| I.1.2317 | furan-3-yl | 4-COOH | 2-CH₃ | H |
| I.1.2318 | furan-3-yl | 4-COOH | 5-CN | H |
| I.1.2319 | furan-3-yl | 4-COOH | 2-CN | H |
| I.1.2320 | furan-3-yl | 4-COOH | 5-CF₃ | H |
| I.1.2321 | furan-3-yl | 4-COOH | 2-CF₃ | H |
| I.1.2322 | furan-3-yl | 4-COOCH₃ | 5-Cl | 2-F |
| I.1.2323 | furan-3-yl | 4-COOCH₃ | 5-Cl | H |
| I.1.2324 | furan-3-yl | 4-COOCH₃ | 2-Cl | H |
| I.1.2325 | furan-3-yl | 4-COOCH₃ | 5-F | H |
| I.1.2326 | furan-3-yl | 4-COOCH₃ | 2-F | H |
| I.1.2327 | furan-3-yl | 4-COOCH₃ | 5-CH₃ | H |
| I.1.2328 | furan-3-yl | 4-COOCH₃ | 2-CH₃ | H |
| I.1.2329 | furan-3-yl | 4-COOCH₃ | 5-CN | H |
| I.1.2330 | furan-3-yl | 4-COOCH₃ | 2-CN | H |
| I.1.2331 | furan-3-yl | 4-COOCH₃ | 5-CF₃ | H |
| I.1.2332 | furan-3-yl | 4-COOCH₃ | 2-CF₃ | H |
| I.1.2333 | furan-3-yl | 4-COOCH₂CH₃ | 5-Cl | 2-F |
| I.1.2334 | furan-3-yl | 4-COOCH₂CH₃ | 5-Cl | H |
| I.1.2335 | furan-3-yl | 4-COOCH₂CH₃ | 2-Cl | H |
| I.1.2336 | furan-3-yl | 4-COOCH₂CH₃ | 5-F | H |

TABLE 1-continued

| Comp. No. | A¹ | $R^a$ | $R^b$ or H | $R^c$ H |
|---|---|---|---|---|
| I.1.2337 | furan-3-yl | 4-COOCH$_2$CH$_3$ | 2-F | H |
| I.1.2338 | furan-3-yl | 4-COOCH$_2$CH$_3$ | 5-CH$_3$ | H |
| I.1.2339 | furan-3-yl | 4-COOCH$_2$CH$_3$ | 2-CH$_3$ | H |
| I.1.2340 | furan-3-yl | 4-COOCH$_2$CH$_3$ | 5-CN | H |
| I.1.2341 | furan-3-yl | 4-COOCH$_2$CH$_3$ | 2-CN | H |
| I.1.2342 | furan-3-yl | 4-COOCH$_2$CH$_3$ | 5-CF$_3$ | H |
| I.1.2343 | furan-3-yl | 4-COOCH$_2$CH$_3$ | 2-CF$_3$ | H |
| I.1.2344 | furan-3-yl | 4-ethynyl | 5-Cl | 2-F |
| I.1.2345 | furan-3-yl | 4-ethynyl | 5-Cl | H |
| I.1.2346 | furan-3-yl | 4-ethynyl | 2-Cl | H |
| I.1.2347 | furan-3-yl | 4-ethynyl | 5-F | H |
| I.1.2348 | furan-3-yl | 4-ethynyl | 2-F | H |
| I.1.2349 | furan-3-yl | 4-ethynyl | 5-CH$_3$ | H |
| I.1.2350 | furan-3-yl | 4-ethynyl | 2-CH$_3$ | H |
| I.1.2351 | furan-3-yl | 4-ethynyl | 5-CN | H |
| I.1.2352 | furan-3-yl | 4-ethynyl | 2-CN | H |
| I.1.2353 | furan-3-yl | 4-ethynyl | 5-CF$_3$ | H |
| I.1.2354 | furan-3-yl | 4-ethynyl | 2-CF$_3$ | H |
| I.1.2355 | furan-3-yl | 4-I | 5-Cl | 2-F |
| I.1.2356 | furan-3-yl | 4-I | 5-Cl | H |
| I.1.2357 | furan-3-yl | 4-I | 2-Cl | H |
| I.1.2358 | furan-3-yl | 4-I | 5-F | H |
| I.1.2359 | furan-3-yl | 4-I | 2-F | H |
| I.1.2360 | furan-3-yl | 4-I | 5-CH$_3$ | H |
| I.1.2361 | furan-3-yl | 4-I | 2-CH$_3$ | H |
| I.1.2362 | furan-3-yl | 4-I | 5-CN | H |
| I.1.2363 | furan-3-yl | 4-I | 2-CN | H |
| I.1.2364 | furan-3-yl | 4-I | 5-CF$_3$ | H |
| I.1.2365 | furan-3-yl | 4-I | 2-CF$_3$ | H |
| I.1.2366 | furan-3-yl | 4-Cl | 5-Cl | 2-F |
| I.1.2367 | furan-3-yl | 4-Cl | 5-Cl | H |
| I.1.2368 | furan-3-yl | 4-Cl | 2-Cl | H |
| I.1.2369 | furan-3-yl | 4-Cl | 5-F | H |
| I.1.2370 | furan-3-yl | 4-Cl | 2-F | H |
| I.1.2371 | furan-3-yl | 4-Cl | 5-CH$_3$ | H |
| I.1.2372 | furan-3-yl | 4-Cl | 2-CH$_3$ | H |
| I.1.2373 | furan-3-yl | 4-Cl | 5-CN | H |
| I.1.2374 | furan-3-yl | 4-Cl | 2-CN | H |
| I.1.2375 | furan-3-yl | 4-Cl | 5-CF$_3$ | H |
| I.1.2376 | furan-3-yl | 4-Cl | 2-CF$_3$ | H |
| I.1.2377 | furan-3-yl | 4-Br | 5-Cl | 2-F |
| I.1.2378 | furan-3-yl | 4-Br | 5-Cl | H |
| I.1.2379 | furan-3-yl | 4-Br | 2-Cl | H |
| I.1.2380 | furan-3-yl | 4-Br | 5-F | H |
| I.1.2381 | furan-3-yl | 4-Br | 2-F | H |
| I.1.2382 | furan-3-yl | 4-Br | 5-CH$_3$ | H |
| I.1.2383 | furan-3-yl | 4-Br | 2-CH$_3$ | H |
| I.1.2384 | furan-3-yl | 4-Br | 5-CN | H |
| I.1.2385 | furan-3-yl | 4-Br | 2-CN | H |
| I.1.2386 | furan-3-yl | 4-Br | 5-CF$_3$ | H |
| I.1.2387 | furan-3-yl | 4-Br | 2-CF$_3$ | H |
| I.1.2388 | furan-3-yl | 4-CON(CH$_3$)$_2$ | 5-Cl | 2-F |
| I.1.2389 | furan-3-yl | 4-CON(CH$_3$)$_2$ | 5-Cl | H |
| I.1.2390 | furan-3-yl | 4-CON(CH$_3$)$_2$ | 2-Cl | H |
| I.1.2391 | furan-3-yl | 4-CON(CH$_3$)$_2$ | 5-F | H |
| I.1.2392 | furan-3-yl | 4-CON(CH$_3$)$_2$ | 2-F | H |
| I.1.2393 | furan-3-yl | 4-CON(CH$_3$)$_2$ | 5-CH$_3$ | H |
| I.1.2394 | furan-3-yl | 4-CON(CH$_3$)$_2$ | 2-CH$_3$ | H |
| I.1.2395 | furan-3-yl | 4-CON(CH$_3$)$_2$ | 5-CN | H |
| I.1.2396 | furan-3-yl | 4-CON(CH$_3$)$_2$ | 2-CN | H |
| I.1.2397 | furan-3-yl | 4-CON(CH$_3$)$_2$ | 5-CF$_3$ | H |
| I.1.2398 | furan-3-yl | 4-CON(CH$_3$)$_2$ | 2-CF$_3$ | H |
| I.1.2399 | furan-3-yl | 4-CONHCH$_3$ | 5-Cl | 2-F |
| I.1.2400 | furan-3-yl | 4-CONHCH$_3$ | 5-Cl | H |
| I.1.2401 | furan-3-yl | 4-CONHCH$_3$ | 2-Cl | H |
| I.1.2402 | furan-3-yl | 4-CONHCH$_3$ | 5-F | H |
| I.1.2403 | furan-3-yl | 4-CONHCH$_3$ | 2-F | H |
| I.1.2404 | furan-3-yl | 4-CONHCH$_3$ | 5-CH$_3$ | H |
| I.1.2405 | furan-3-yl | 4-CONHCH$_3$ | 2-CH$_3$ | H |
| I.1.2406 | furan-3-yl | 4-CONHCH$_3$ | 5-CN | H |
| I.1.2407 | furan-3-yl | 4-CONHCH$_3$ | 2-CN | H |
| I.1.2408 | furan-3-yl | 4-CONHCH$_3$ | 5-CF$_3$ | H |
| I.1.2409 | furan-3-yl | 4-CONHCH$_3$ | 2-CF$_3$ | H |
| I.1.2410 | thiophen-2-yl | 3-NO$_2$ | 4-Cl | 5-F |
| I.1.2411 | thiophen-2-yl | 3-NO$_2$ | 4-Cl | H |
| I.1.2412 | thiophen-2-yl | 3-NO$_2$ | 5-Cl | H |
| I.1.2413 | thiophen-2-yl | 3-NO$_2$ | 4-F | H |
| I.1.2414 | thiophen-2-yl | 3-NO$_2$ | 5-F | H |
| I.1.2415 | thiophen-2-yl | 3-NO$_2$ | 4-CH$_3$ | H |
| I.1.2416 | thiophen-2-yl | 3-NO$_2$ | 5-CH$_3$ | H |
| I.1.2417 | thiophen-2-yl | 3-NO$_2$ | 4-CN | H |
| I.1.2418 | thiophen-2-yl | 3-NO$_2$ | 5-CN | H |
| I.1.2419 | thiophen-2-yl | 3-NO$_2$ | 4-CF$_3$ | H |
| I.1.2420 | thiophen-2-yl | 3-NO$_2$ | 5-CF$_3$ | H |
| I.1.2421 | thiophen-2-yl | 3-CN | 4-Cl | 5-F |
| I.1.2422 | thiophen-2-yl | 3-CN | 4-Cl | H |
| I.1.2423 | thiophen-2-yl | 3-CN | 5-Cl | H |
| I.1.2424 | thiophen-2-yl | 3-CN | 4-F | H |
| I.1.2425 | thiophen-2-yl | 3-CN | 5-F | H |
| I.1.2426 | thiophen-2-yl | 3-CN | 4-CH$_3$ | H |
| I.1.2427 | thiophen-2-yl | 3-CN | 5-CH$_3$ | H |
| I.1.2428 | thiophen-2-yl | 3-CN | 4-CN | H |
| I.1.2429 | thiophen-2-yl | 3-CN | 5-CN | H |
| I.1.2430 | thiophen-2-yl | 3-CN | 4-CF$_3$ | H |
| I.1.2431 | thiophen-2-yl | 3-CN | 5-CF$_3$ | H |
| I.1.2432 | thiophen-2-yl | 3-COOH | 4-Cl | 5-F |
| I.1.2433 | thiophen-2-yl | 3-COOH | 4-Cl | H |
| I.1.2434 | thiophen-2-yl | 3-COOH | 5-Cl | H |
| I.1.2435 | thiophen-2-yl | 3-COOH | 4-F | H |
| I.1.2436 | thiophen-2-yl | 3-COOH | 5-F | H |
| I.1.2437 | thiophen-2-yl | 3-COOH | 4-CH$_3$ | H |
| I.1.2438 | thiophen-2-yl | 3-COOH | 5-CH$_3$ | H |
| I.1.2439 | thiophen-2-yl | 3-COOH | 4-CN | H |
| I.1.2440 | thiophen-2-yl | 3-COOH | 5-CN | H |
| I.1.2441 | thiophen-2-yl | 3-COOH | 4-CF$_3$ | H |
| I.1.2442 | thiophen-2-yl | 3-COOH | 5-CF$_3$ | H |
| I.1.2443 | thiophen-2-yl | 3-COOCH$_3$ | 4-Cl | 5-F |
| I.1.2444 | thiophen-2-yl | 3-COOCH$_3$ | 4-Cl | H |
| I.1.2445 | thiophen-2-yl | 3-COOCH$_3$ | 5-Cl | H |
| I.1.2446 | thiophen-2-yl | 3-COOCH$_3$ | 4-F | H |
| I.1.2447 | thiophen-2-yl | 3-COOCH$_3$ | 5-F | H |
| I.1.2448 | thiophen-2-yl | 3-COOCH$_3$ | 4-CH$_3$ | H |
| I.1.2449 | thiophen-2-yl | 3-COOCH$_3$ | 5-CH$_3$ | H |
| I.1.2450 | thiophen-2-yl | 3-COOCH$_3$ | 4-CN | H |
| I.1.2451 | thiophen-2-yl | 3-COOCH$_3$ | 5-CN | H |
| I.1.2452 | thiophen-2-yl | 3-COOCH$_3$ | 4-CF$_3$ | H |
| I.1.2453 | thiophen-2-yl | 3-COOCH$_3$ | 5-CF$_3$ | H |
| I.1.2454 | thiophen-2-yl | 3-COOCH$_2$CH$_3$ | 4-Cl | 5-F |
| I.1.2455 | thiophen-2-yl | 3-COOCH$_2$CH$_3$ | 4-Cl | H |
| I.1.2456 | thiophen-2-yl | 3-COOCH$_2$CH$_3$ | 5-Cl | H |
| I.1.2457 | thiophen-2-yl | 3-COOCH$_2$CH$_3$ | 4-F | H |
| I.1.2458 | thiophen-2-yl | 3-COOCH$_2$CH$_3$ | 5-F | H |
| I.1.2459 | thiophen-2-yl | 3-COOCH$_2$CH$_3$ | 4-CH$_3$ | H |
| I.1.2460 | thiophen-2-yl | 3-COOCH$_2$CH$_3$ | 5-CH$_3$ | H |
| I.1.2461 | thiophen-2-yl | 3-COOCH$_2$CH$_3$ | 4-CN | H |
| I.1.2462 | thiophen-2-yl | 3-COOCH$_2$CH$_3$ | 5-CN | H |
| I.1.2463 | thiophen-2-yl | 3-COOCH$_2$CH$_3$ | 4-CF$_3$ | H |
| I.1.2464 | thiophen-2-yl | 3-COOCH$_2$CH$_3$ | 5-CF$_3$ | H |
| I.1.2465 | thiophen-2-yl | 3-ethynyl | 4-Cl | 5-F |
| I.1.2466 | thiophen-2-yl | 3-ethynyl | 4-Cl | H |
| I.1.2467 | thiophen-2-yl | 3-ethynyl | 5-Cl | H |
| I.1.2468 | thiophen-2-yl | 3-ethynyl | 4-F | H |
| I.1.2469 | thiophen-2-yl | 3-ethynyl | 5-F | H |
| I.1.2470 | thiophen-2-yl | 3-ethynyl | 4-CH$_3$ | H |
| I.1.2471 | thiophen-2-yl | 3-ethynyl | 5-CH$_3$ | H |
| I.1.2472 | thiophen-2-yl | 3-ethynyl | 4-CN | H |
| I.1.2473 | thiophen-2-yl | 3-ethynyl | 5-CN | H |
| I.1.2474 | thiophen-2-yl | 3-ethynyl | 4-CF$_3$ | H |
| I.1.2475 | thiophen-2-yl | 3-ethynyl | 5-CF$_3$ | H |
| I.1.2476 | thiophen-2-yl | 3-I | 4-Cl | 5-F |
| I.1.2477 | thiophen-2-yl | 3-I | 4-Cl | H |
| I.1.2478 | thiophen-2-yl | 3-I | 5-Cl | H |
| I.1.2479 | thiophen-2-yl | 3-I | 4-F | H |
| I.1.2480 | thiophen-2-yl | 3-I | 5-F | H |
| I.1.2481 | thiophen-2-yl | 3-I | 4-CH$_3$ | H |
| I.1.2482 | thiophen-2-yl | 3-I | 5-CH$_3$ | H |
| I.1.2483 | thiophen-2-yl | 3-I | 4-CN | H |
| I.1.2484 | thiophen-2-yl | 3-I | 5-CN | H |
| I.1.2485 | thiophen-2-yl | 3-I | 4-CF$_3$ | H |
| I.1.2486 | thiophen-2-yl | 3-I | 5-CF$_3$ | H |
| I.1.2487 | thiophen-2-yl | 3-Cl | 4-Cl | 5-F |
| I.1.2488 | thiophen-2-yl | 3-Cl | 4-Cl | H |
| I.1.2489 | thiophen-2-yl | 3-Cl | 5-Cl | H |
| I.1.2490 | thiophen-2-yl | 3-Cl | 4-F | H |
| I.1.2491 | thiophen-2-yl | 3-Cl | 5-F | H |
| I.1.2492 | thiophen-2-yl | 3-Cl | 4-CH$_3$ | H |

TABLE 1-continued

| Comp. No. | A$^1$ | R$^a$ | R$^b$ or H | R$^c$ H |
|---|---|---|---|---|
| I.1.2493 | thiophen-2-yl | 3-Cl | 5-CH$_3$ | H |
| I.1.2494 | thiophen-2-yl | 3-Cl | 4-CN | H |
| I.1.2495 | thiophen-2-yl | 3-Cl | 5-CN | H |
| I.1.2496 | thiophen-2-yl | 3-Cl | 4-CF$_3$ | H |
| I.1.2497 | thiophen-2-yl | 3-Cl | 5-CF$_3$ | H |
| I.1.2498 | thiophen-2-yl | 3-Br | 4-Cl | 5-F |
| I.1.2499 | thiophen-2-yl | 3-Br | 4-Cl | H |
| I.1.2500 | thiophen-2-yl | 3-Br | 5-Cl | H |
| I.1.2501 | thiophen-2-yl | 3-Br | 4-F | H |
| I.1.2502 | thiophen-2-yl | 3-Br | 5-F | H |
| I.1.2503 | thiophen-2-yl | 3-Br | 4-CH$_3$ | H |
| I.1.2504 | thiophen-2-yl | 3-Br | 5-CH$_3$ | H |
| I.1.2505 | thiophen-2-yl | 3-Br | 4-CN | H |
| I.1.2506 | thiophen-2-yl | 3-Br | 5-CN | H |
| I.1.2507 | thiophen-2-yl | 3-Br | 4-CF$_3$ | H |
| I.1.2508 | thiophen-2-yl | 3-Br | 5-CF$_3$ | H |
| I.1.2509 | thiophen-2-yl | 3-CON(CH$_3$)$_2$ | 4-Cl | 5-F |
| I.1.2510 | thiophen-2-yl | 3-CON(CH$_3$)$_2$ | 4-Cl | H |
| I.1.2511 | thiophen-2-yl | 3-CON(CH$_3$)$_2$ | 5-Cl | H |
| I.1.2512 | thiophen-2-yl | 3-CON(CH$_3$)$_2$ | 4-F | H |
| I.1.2513 | thiophen-2-yl | 3-CON(CH$_3$)$_2$ | 5-F | H |
| I.1.2514 | thiophen-2-yl | 3-CON(CH$_3$)$_2$ | 4-CH$_3$ | H |
| I.1.2515 | thiophen-2-yl | 3-CON(CH$_3$)$_2$ | 5-CH$_3$ | H |
| I.1.2516 | thiophen-2-yl | 3-CON(CH$_3$)$_2$ | 4-CN | H |
| I.1.2517 | thiophen-2-yl | 3-CON(CH$_3$)$_2$ | 5-CN | H |
| I.1.2518 | thiophen-2-yl | 3-CON(CH$_3$)$_2$ | 4-CF$_3$ | H |
| I.1.2519 | thiophen-2-yl | 3-CON(CH$_3$)$_2$ | 5-CF$_3$ | H |
| I.1.2520 | thiophen-2-yl | 3-CONHCH$_3$ | 4-Cl | 5-F |
| I.1.2521 | thiophen-2-yl | 3-CONHCH$_3$ | 4-Cl | H |
| I.1.2522 | thiophen-2-yl | 3-CONHCH$_3$ | 5-Cl | H |
| I.1.2523 | thiophen-2-yl | 3-CONHCH$_3$ | 4-F | H |
| I.1.2524 | thiophen-2-yl | 3-CONHCH$_3$ | 5-F | H |
| I.1.2525 | thiophen-2-yl | 3-CONHCH$_3$ | 4-CH$_3$ | H |
| I.1.2526 | thiophen-2-yl | 3-CONHCH$_3$ | 5-CH$_3$ | H |
| I.1.2527 | thiophen-2-yl | 3-CONHCH$_3$ | 4-CN | H |
| I.1.2528 | thiophen-2-yl | 3-CONHCH$_3$ | 5-CN | H |
| I.1.2529 | thiophen-2-yl | 3-CONHCH$_3$ | 4-CF$_3$ | H |
| I.1.2530 | thiophen-2-yl | 3-CONHCH$_3$ | 5-CF$_3$ | H |
| I.1.2531 | thiophen-3-yl | 2-NO$_2$ | 4-Cl | 5-F |
| I.1.2532 | thiophen-3-yl | 2-NO$_2$ | 4-Cl | H |
| I.1.2533 | thiophen-3-yl | 2-NO$_2$ | 5-Cl | H |
| I.1.2534 | thiophen-3-yl | 2-NO$_2$ | 4-F | H |
| I.1.2535 | thiophen-3-yl | 2-NO$_2$ | 5-F | H |
| I.1.2536 | thiophen-3-yl | 2-NO$_2$ | 4-CH$_3$ | H |
| I.1.2537 | thiophen-3-yl | 2-NO$_2$ | 5-CH$_3$ | H |
| I.1.2538 | thiophen-3-yl | 2-NO$_2$ | 4-CN | H |
| I.1.2539 | thiophen-3-yl | 2-NO$_2$ | 5-CN | H |
| I.1.2540 | thiophen-3-yl | 2-NO$_2$ | 4-CF$_3$ | H |
| I.1.2541 | thiophen-3-yl | 2-NO$_2$ | 5-CF$_3$ | H |
| I.1.2542 | thiophen-3-yl | 2-CN | 4-Cl | 5-F |
| I.1.2543 | thiophen-3-yl | 2-CN | 4-Cl | H |
| I.1.2544 | thiophen-3-yl | 2-CN | 5-Cl | H |
| I.1.2545 | thiophen-3-yl | 2-CN | 4-F | H |
| I.1.2546 | thiophen-3-yl | 2-CN | 5-F | H |
| I.1.2547 | thiophen-3-yl | 2-CN | 4-CH$_3$ | H |
| I.1.2548 | thiophen-3-yl | 2-CN | 5-CH$_3$ | H |
| I.1.2549 | thiophen-3-yl | 2-CN | 4-CN | H |
| I.1.2550 | thiophen-3-yl | 2-CN | 5-CN | H |
| I.1.2551 | thiophen-3-yl | 2-CN | 4-CF$_3$ | H |
| I.1.2552 | thiophen-3-yl | 2-CN | 5-CF$_3$ | H |
| I.1.2553 | thiophen-3-yl | 2-COOH | 4-Cl | 5-F |
| I.1.2554 | thiophen-3-yl | 2-COOH | 4-Cl | H |
| I.1.2555 | thiophen-3-yl | 2-COOH | 5-Cl | H |
| I.1.2556 | thiophen-3-yl | 2-COOH | 4-F | H |
| I.1.2557 | thiophen-3-yl | 2-COOH | 5-F | H |
| I.1.2558 | thiophen-3-yl | 2-COOH | 4-CH$_3$ | H |
| I.1.2559 | thiophen-3-yl | 2-COOH | 5-CH$_3$ | H |
| I.1.2560 | thiophen-3-yl | 2-COOH | 4-CN | H |
| I.1.2561 | thiophen-3-yl | 2-COOH | 5-CN | H |
| I.1.2562 | thiophen-3-yl | 2-COOH | 4-CF$_3$ | H |
| I.1.2563 | thiophen-3-yl | 2-COOH | 5-CF$_3$ | H |
| I.1.2564 | thiophen-3-yl | 2-COOCH$_3$ | 4-Cl | 5-F |
| I.1.2565 | thiophen-3-yl | 2-COOCH$_3$ | 4-Cl | H |
| I.1.2566 | thiophen-3-yl | 2-COOCH$_3$ | 5-Cl | H |
| I.1.2567 | thiophen-3-yl | 2-COOCH$_3$ | 4-F | H |
| I.1.2568 | thiophen-3-yl | 2-COOCH$_3$ | 5-F | H |
| I.1.2569 | thiophen-3-yl | 2-COOCH$_3$ | 4-CH$_3$ | H |
| I.1.2570 | thiophen-3-yl | 2-COOCH$_3$ | 5-CH$_3$ | H |
| I.1.2571 | thiophen-3-yl | 2-COOCH$_3$ | 4-CN | H |
| I.1.2572 | thiophen-3-yl | 2-COOCH$_3$ | 5-CN | H |
| I.1.2573 | thiophen-3-yl | 2-COOCH$_3$ | 4-CF$_3$ | H |
| I.1.2574 | thiophen-3-yl | 2-COOCH$_3$ | 5-CF$_3$ | H |
| I.1.2575 | thiophen-3-yl | 2-COOCH$_2$CH$_3$ | 4-Cl | 5-F |
| I.1.2576 | thiophen-3-yl | 2-COOCH$_2$CH$_3$ | 4-Cl | H |
| I.1.2577 | thiophen-3-yl | 2-COOCH$_2$CH$_3$ | 5-Cl | H |
| I.1.2578 | thiophen-3-yl | 2-COOCH$_2$CH$_3$ | 4-F | H |
| I.1.2579 | thiophen-3-yl | 2-COOCH$_2$CH$_3$ | 5-F | H |
| I.1.2580 | thiophen-3-yl | 2-COOCH$_2$CH$_3$ | 4-CH$_3$ | H |
| I.1.2581 | thiophen-3-yl | 2-COOCH$_2$CH$_3$ | 5-CH$_3$ | H |
| I.1.2582 | thiophen-3-yl | 2-COOCH$_2$CH$_3$ | 4-CN | H |
| I.1.2583 | thiophen-3-yl | 2-COOCH$_2$CH$_3$ | 5-CN | H |
| I.1.2584 | thiophen-3-yl | 2-COOCH$_2$CH$_3$ | 4-CF$_3$ | H |
| I.1.2585 | thiophen-3-yl | 2-COOCH$_2$CH$_3$ | 5-CF$_3$ | H |
| I.1.2586 | thiophen-3-yl | 2-ethynyl | 4-Cl | 5-F |
| I.1.2587 | thiophen-3-yl | 2-ethynyl | 4-Cl | H |
| I.1.2588 | thiophen-3-yl | 2-ethynyl | 5-Cl | H |
| I.1.2589 | thiophen-3-yl | 2-ethynyl | 4-F | H |
| I.1.2590 | thiophen-3-yl | 2-ethynyl | 5-F | H |
| I.1.2591 | thiophen-3-yl | 2-ethynyl | 4-CH$_3$ | H |
| I.1.2592 | thiophen-3-yl | 2-ethynyl | 5-CH$_3$ | H |
| I.1.2593 | thiophen-3-yl | 2-ethynyl | 4-CN | H |
| I.1.2594 | thiophen-3-yl | 2-ethynyl | 5-CN | H |
| I.1.2595 | thiophen-3-yl | 2-ethynyl | 4-CF$_3$ | H |
| I.1.2596 | thiophen-3-yl | 2-ethynyl | 5-CF$_3$ | H |
| I.1.2597 | thiophen-3-yl | 2-I | 4-Cl | 5-F |
| I.1.2598 | thiophen-3-yl | 2-I | 4-Cl | H |
| I.1.2599 | thiophen-3-yl | 2-I | 5-Cl | H |
| I.1.2600 | thiophen-3-yl | 2-I | 4-F | H |
| I.1.2601 | thiophen-3-yl | 2-I | 5-F | H |
| I.1.2602 | thiophen-3-yl | 2-I | 4-CH$_3$ | H |
| I.1.2603 | thiophen-3-yl | 2-I | 5-CH$_3$ | H |
| I.1.2604 | thiophen-3-yl | 2-I | 4-CN | H |
| I.1.2605 | thiophen-3-yl | 2-I | 5-CN | H |
| I.1.2606 | thiophen-3-yl | 2-I | 4-CF$_3$ | H |
| I.1.2607 | thiophen-3-yl | 2-I | 5-CF$_3$ | H |
| I.1.2608 | thiophen-3-yl | 2-Cl | 4-Cl | 5-F |
| I.1.2609 | thiophen-3-yl | 2-Cl | 4-Cl | H |
| I.1.2610 | thiophen-3-yl | 2-Cl | 5-Cl | H |
| I.1.2611 | thiophen-3-yl | 2-Cl | 4-F | H |
| I.1.2612 | thiophen-3-yl | 2-Cl | 5-F | H |
| I.1.2613 | thiophen-3-yl | 2-Cl | 4-CH$_3$ | H |
| I.1.2614 | thiophen-3-yl | 2-Cl | 5-CH$_3$ | H |
| I.1.2615 | thiophen-3-yl | 2-Cl | 4-CN | H |
| I.1.2616 | thiophen-3-yl | 2-Cl | 5-CN | H |
| I.1.2617 | thiophen-3-yl | 2-Cl | 4-CF$_3$ | H |
| I.1.2618 | thiophen-3-yl | 2-Cl | 5-CF$_3$ | H |
| I.1.2619 | thiophen-3-yl | 2-Br | 4-Cl | 5-F |
| I.1.2620 | thiophen-3-yl | 2-Br | 4-Cl | H |
| I.1.2621 | thiophen-3-yl | 2-Br | 5-Cl | H |
| I.1.2622 | thiophen-3-yl | 2-Br | 4-F | H |
| I.1.2623 | thiophen-3-yl | 2-Br | 5-F | H |
| I.1.2624 | thiophen-3-yl | 2-Br | 4-CH$_3$ | H |
| I.1.2625 | thiophen-3-yl | 2-Br | 5-CH$_3$ | H |
| I.1.2626 | thiophen-3-yl | 2-Br | 4-CN | H |
| I.1.2627 | thiophen-3-yl | 2-Br | 5-CN | H |
| I.1.2628 | thiophen-3-yl | 2-Br | 4-CF$_3$ | H |
| I.1.2629 | thiophen-3-yl | 2-Br | 5-CF$_3$ | H |
| I.1.2630 | thiophen-3-yl | 2-CON(CH$_3$)$_2$ | 4-Cl | 5-F |
| I.1.2631 | thiophen-3-yl | 2-CON(CH$_3$)$_2$ | 4-Cl | H |
| I.1.2632 | thiophen-3-yl | 2-CON(CH$_3$)$_2$ | 5-Cl | H |
| I.1.2633 | thiophen-3-yl | 2-CON(CH$_3$)$_2$ | 4-F | H |
| I.1.2634 | thiophen-3-yl | 2-CON(CH$_3$)$_2$ | 5-F | H |
| I.1.2635 | thiophen-3-yl | 2-CON(CH$_3$)$_2$ | 4-CH$_3$ | H |
| I.1.2636 | thiophen-3-yl | 2-CON(CH$_3$)$_2$ | 5-CH$_3$ | H |
| I.1.2637 | thiophen-3-yl | 2-CON(CH$_3$)$_2$ | 4-CN | H |
| I.1.2638 | thiophen-3-yl | 2-CON(CH$_3$)$_2$ | 5-CN | H |
| I.1.2639 | thiophen-3-yl | 2-CON(CH$_3$)$_2$ | 4-CF$_3$ | H |
| I.1.2640 | thiophen-3-yl | 2-CON(CH$_3$)$_2$ | 5-CF$_3$ | H |
| I.1.2641 | thiophen-3-yl | 2-CONHCH$_3$ | 4-Cl | 5-F |
| I.1.2642 | thiophen-3-yl | 2-CONHCH$_3$ | 4-Cl | H |
| I.1.2643 | thiophen-3-yl | 2-CONHCH$_3$ | 5-Cl | H |
| I.1.2644 | thiophen-3-yl | 2-CONHCH$_3$ | 4-F | H |
| I.1.2645 | thiophen-3-yl | 2-CONHCH$_3$ | 5-F | H |
| I.1.2646 | thiophen-3-yl | 2-CONHCH$_3$ | 4-CH$_3$ | H |
| I.1.2647 | thiophen-3-yl | 2-CONHCH$_3$ | 5-CH$_3$ | H |
| I.1.2648 | thiophen-3-yl | 2-CONHCH$_3$ | 4-CN | H |

TABLE 1-continued

| Comp. No. | A¹ | $R^a$ | $R^b$ or H | $R^c$ H |
|---|---|---|---|---|
| I.1.2649 | thiophen-3-yl | 2-CONHCH$_3$ | 5-CN | H |
| I.1.2650 | thiophen-3-yl | 2-CONHCH$_3$ | 4-CF$_3$ | H |
| I.1.2651 | thiophen-3-yl | 2-CONHCH$_3$ | 5-CF$_3$ | H |
| I.1.2652 | thiophen-3-yl | 4-NO$_2$ | 5-Cl | 2-F |
| I.1.2653 | thiophen-3-yl | 4-NO$_2$ | 5-Cl | H |
| I.1.2654 | thiophen-3-yl | 4-NO$_2$ | 2-Cl | H |
| I.1.2655 | thiophen-3-yl | 4-NO$_2$ | 5-F | H |
| I.1.2656 | thiophen-3-yl | 4-NO$_2$ | 2-F | H |
| I.1.2657 | thiophen-3-yl | 4-NO$_2$ | 5-CH$_3$ | H |
| I.1.2658 | thiophen-3-yl | 4-NO$_2$ | 2-CH$_3$ | H |
| I.1.2659 | thiophen-3-yl | 4-NO$_2$ | 5-CN | H |
| I.1.2660 | thiophen-3-yl | 4-NO$_2$ | 2-CN | H |
| I.1.2661 | thiophen-3-yl | 4-NO$_2$ | 5-CF$_3$ | H |
| I.1.2662 | thiophen-3-yl | 4-NO$_2$ | 2-CF$_3$ | H |
| I.1.2663 | thiophen-3-yl | 4-CN | 5-Cl | 2-F |
| I.1.2664 | thiophen-3-yl | 4-CN | 5-Cl | H |
| I.1.2665 | thiophen-3-yl | 4-CN | 2-Cl | H |
| I.1.2666 | thiophen-3-yl | 4-CN | 5-F | H |
| I.1.2667 | thiophen-3-yl | 4-CN | 2-F | H |
| I.1.2668 | thiophen-3-yl | 4-CN | 5-CH$_3$ | H |
| I.1.2669 | thiophen-3-yl | 4-CN | 2-CH$_3$ | H |
| I.1.2670 | thiophen-3-yl | 4-CN | 5-CN | H |
| I.1.2671 | thiophen-3-yl | 4-CN | 2-CN | H |
| I.1.2672 | thiophen-3-yl | 4-CN | 5-CF$_3$ | H |
| I.1.2673 | thiophen-3-yl | 4-CN | 2-CF$_3$ | H |
| I.1.2674 | thiophen-3-yl | 4-COOH | 5-Cl | 2-F |
| I.1.2675 | thiophen-3-yl | 4-COOH | 5-Cl | H |
| I.1.2676 | thiophen-3-yl | 4-COOH | 2-Cl | H |
| I.1.2677 | thiophen-3-yl | 4-COOH | 5-F | H |
| I.1.2678 | thiophen-3-yl | 4-COOH | 2-F | H |
| I.1.2679 | thiophen-3-yl | 4-COOH | 5-CH$_3$ | H |
| I.1.2680 | thiophen-3-yl | 4-COOH | 2-CH$_3$ | H |
| I.1.2681 | thiophen-3-yl | 4-COOH | 5-CN | H |
| I.1.2682 | thiophen-3-yl | 4-COOH | 2-CN | H |
| I.1.2683 | thiophen-3-yl | 4-COOH | 5-CF$_3$ | H |
| I.1.2684 | thiophen-3-yl | 4-COOH | 2-CF$_3$ | H |
| I.1.2685 | thiophen-3-yl | 4-COOCH$_3$ | 5-Cl | 2-F |
| I.1.2686 | thiophen-3-yl | 4-COOCH$_3$ | 5-Cl | H |
| I.1.2687 | thiophen-3-yl | 4-COOCH$_3$ | 2-Cl | H |
| I.1.2688 | thiophen-3-yl | 4-COOCH$_3$ | 5-F | H |
| I.1.2689 | thiophen-3-yl | 4-COOCH$_3$ | 2-F | H |
| I.1.2690 | thiophen-3-yl | 4-COOCH$_3$ | 5-CH$_3$ | H |
| I.1.2691 | thiophen-3-yl | 4-COOCH$_3$ | 2-CH$_3$ | H |
| I.1.2692 | thiophen-3-yl | 4-COOCH$_3$ | 5-CN | H |
| I.1.2693 | thiophen-3-yl | 4-COOCH$_3$ | 2-CN | H |
| I.1.2694 | thiophen-3-yl | 4-COOCH$_3$ | 5-CF$_3$ | H |
| I.1.2695 | thiophen-3-yl | 4-COOCH$_3$ | 2-CF$_3$ | H |
| I.1.2696 | thiophen-3-yl | 4-COOCH$_2$CH$_3$ | 5-Cl | 2-F |
| I.1.2697 | thiophen-3-yl | 4-COOCH$_2$CH$_3$ | 5-Cl | H |
| I.1.2698 | thiophen-3-yl | 4-COOCH$_2$CH$_3$ | 2-Cl | H |
| I.1.2699 | thiophen-3-yl | 4-COOCH$_2$CH$_3$ | 5-F | H |
| I.1.2700 | thiophen-3-yl | 4-COOCH$_2$CH$_3$ | 2-F | H |
| I.1.2701 | thiophen-3-yl | 4-COOCH$_2$CH$_3$ | 5-CH$_3$ | H |
| I.1.2702 | thiophen-3-yl | 4-COOCH$_2$CH$_3$ | 2-CH$_3$ | H |
| I.1.2703 | thiophen-3-yl | 4-COOCH$_2$CH$_3$ | 5-CN | H |
| I.1.2704 | thiophen-3-yl | 4-COOCH$_2$CH$_3$ | 2-CN | H |
| I.1.2705 | thiophen-3-yl | 4-COOCH$_2$CH$_3$ | 5-CF$_3$ | H |
| I.1.2706 | thiophen-3-yl | 4-COOCH$_2$CH$_3$ | 2-CF$_3$ | H |
| I.1.2707 | thiophen-3-yl | 4-ethynyl | 5-Cl | 2-F |
| I.1.2708 | thiophen-3-yl | 4-ethynyl | 5-Cl | H |
| I.1.2709 | thiophen-3-yl | 4-ethynyl | 2-Cl | H |
| I.1.2710 | thiophen-3-yl | 4-ethynyl | 5-F | H |
| I.1.2711 | thiophen-3-yl | 4-ethynyl | 2-F | H |
| I.1.2712 | thiophen-3-yl | 4-ethynyl | 5-CH$_3$ | H |
| I.1.2713 | thiophen-3-yl | 4-ethynyl | 2-CH$_3$ | H |
| I.1.2714 | thiophen-3-yl | 4-ethynyl | 5-CN | H |
| I.1.2715 | thiophen-3-yl | 4-ethynyl | 2-CN | H |
| I.1.2716 | thiophen-3-yl | 4-ethynyl | 5-CF$_3$ | H |
| I.1.2717 | thiophen-3-yl | 4-ethynyl | 2-CF$_3$ | H |
| I.1.2718 | thiophen-3-yl | 4-I | 5-Cl | 2-F |
| I.1.2719 | thiophen-3-yl | 4-I | 5-Cl | H |
| I.1.2720 | thiophen-3-yl | 4-I | 2-Cl | H |
| I.1.2721 | thiophen-3-yl | 4-I | 5-F | H |
| I.1.2722 | thiophen-3-yl | 4-I | 2-F | H |
| I.1.2723 | thiophen-3-yl | 4-I | 5-CH$_3$ | H |
| I.1.2724 | thiophen-3-yl | 4-I | 2-CH$_3$ | H |
| I.1.2725 | thiophen-3-yl | 4-I | 5-CN | H |
| I.1.2726 | thiophen-3-yl | 4-I | 2-CN | H |
| I.1.2727 | thiophen-3-yl | 4-I | 5-CF$_3$ | H |
| I.1.2728 | thiophen-3-yl | 4-I | 2-CF$_3$ | H |
| I.1.2729 | thiophen-3-yl | 4-Cl | 5-Cl | 2-F |
| I.1.2730 | thiophen-3-yl | 4-Cl | 5-Cl | H |
| I.1.2731 | thiophen-3-yl | 4-Cl | 2-Cl | H |
| I.1.2732 | thiophen-3-yl | 4-Cl | 5-F | H |
| I.1.2733 | thiophen-3-yl | 4-Cl | 2-F | H |
| I.1.2734 | thiophen-3-yl | 4-Cl | 5-CH$_3$ | H |
| I.1.2735 | thiophen-3-yl | 4-Cl | 2-CH$_3$ | H |
| I.1.2736 | thiophen-3-yl | 4-Cl | 5-CN | H |
| I.1.2737 | thiophen-3-yl | 4-Cl | 2-CN | H |
| I.1.2738 | thiophen-3-yl | 4-Cl | 5-CF$_3$ | H |
| I.1.2739 | thiophen-3-yl | 4-Cl | 2-CF$_3$ | H |
| I.1.2740 | thiophen-3-yl | 4-Br | 5-Cl | 2-F |
| I.1.2741 | thiophen-3-yl | 4-Br | 5-Cl | H |
| I.1.2742 | thiophen-3-yl | 4-Br | 2-Cl | H |
| I.1.2743 | thiophen-3-yl | 4-Br | 5-F | H |
| I.1.2744 | thiophen-3-yl | 4-Br | 2-F | H |
| I.1.2745 | thiophen-3-yl | 4-Br | 5-CH$_3$ | H |
| I.1.2746 | thiophen-3-yl | 4-Br | 2-CH$_3$ | H |
| I.1.2747 | thiophen-3-yl | 4-Br | 5-CN | H |
| I.1.2748 | thiophen-3-yl | 4-Br | 2-CN | H |
| I.1.2749 | thiophen-3-yl | 4-Br | 5-CF$_3$ | H |
| I.1.2750 | thiophen-3-yl | 4-Br | 2-CF$_3$ | H |
| I.1.2751 | thiophen-3-yl | 4-CON(CH$_3$)$_2$ | 5-Cl | 2-F |
| I.1.2752 | thiophen-3-yl | 4-CON(CH$_3$)$_2$ | 5-Cl | H |
| I.1.2753 | thiophen-3-yl | 4-CON(CH$_3$)$_2$ | 2-Cl | H |
| I.1.2754 | thiophen-3-yl | 4-CON(CH$_3$)$_2$ | 5-F | H |
| I.1.2755 | thiophen-3-yl | 4-CON(CH$_3$)$_2$ | 2-F | H |
| I.1.2756 | thiophen-3-yl | 4-CON(CH$_3$)$_2$ | 5-CH$_3$ | H |
| I.1.2757 | thiophen-3-yl | 4-CON(CH$_3$)$_2$ | 2-CH$_3$ | H |
| I.1.2758 | thiophen-3-yl | 4-CON(CH$_3$)$_2$ | 5-CN | H |
| I.1.2759 | thiophen-3-yl | 4-CON(CH$_3$)$_2$ | 2-CN | H |
| I.1.2760 | thiophen-3-yl | 4-CON(CH$_3$)$_2$ | 5-CF$_3$ | H |
| I.1.2761 | thiophen-3-yl | 4-CON(CH$_3$)$_2$ | 2-CF$_3$ | H |
| I.1.2762 | thiophen-3-yl | 4-CONHCH$_3$ | 5-Cl | 2-F |
| I.1.2763 | thiophen-3-yl | 4-CONHCH$_3$ | 5-Cl | H |
| I.1.2764 | thiophen-3-yl | 4-CONHCH$_3$ | 2-Cl | H |
| I.1.2765 | thiophen-3-yl | 4-CONHCH$_3$ | 5-F | H |
| I.1.2766 | thiophen-3-yl | 4-CONHCH$_3$ | 2-F | H |
| I.1.2767 | thiophen-3-yl | 4-CONHCH$_3$ | 5-CH$_3$ | H |
| I.1.2768 | thiophen-3-yl | 4-CONHCH$_3$ | 2-CH$_3$ | H |
| I.1.2769 | thiophen-3-yl | 4-CONHCH$_3$ | 5-CN | H |
| I.1.2770 | thiophen-3-yl | 4-CONHCH$_3$ | 2-CN | H |
| I.1.2771 | thiophen-3-yl | 4-CONHCH$_3$ | 5-CF$_3$ | H |
| I.1.2772 | thiophen-3-yl | 4-CONHCH$_3$ | 2-CF$_3$ | H |
| I.1.2773 | phenyl | 3-methylisoxazol-5-yl | H | H |
| I.1.2774 | phenyl | 3-methylisoxazol-5-yl | 3-Cl | H |
| I.1.2775 | phenyl | 3-methylisoxazol-5-yl | 4-Cl | H |
| I.1.2776 | phenyl | 3-methylisoxazol-5-yl | 5-Cl | H |
| I.1.2777 | phenyl | 3-methylisoxazol-5-yl | 6-Cl | H |
| I.1.2778 | phenyl | 3-methylisoxazol-5-yl | 3-F | H |
| I.1.2779 | phenyl | 3-methylisoxazol-5-yl | 4-F | H |
| I.1.2780 | phenyl | 3-methylisoxazol-5-yl | 5-F | H |
| I.1.2781 | phenyl | 3-methylisoxazol-5-yl | 6-F | H |
| I.1.2782 | phenyl | 3-methylisoxazol-5-yl | 3-CH$_3$ | H |
| I.1.2783 | phenyl | 3-methylisoxazol-5-yl | 4-CH$_3$ | H |
| I.1.2784 | phenyl | 3-methylisoxazol-5-yl | 5-CH$_3$ | H |
| I.1.2785 | phenyl | 3-methylisoxazol-5-yl | 6-CH$_3$ | H |
| I.1.2786 | phenyl | 3-methylisoxazol-5-yl | 5-vinyl | H |
| I.1.2787 | phenyl | 3-methylisoxazol-5-yl | 6-vinyl | H |
| I.1.2788 | phenyl | 2-furyl | H | H |
| I.1.2789 | phenyl | 2-furyl | 3-Cl | H |

TABLE 1-continued

| Comp. No. | A¹ | $R^a$ | $R^b$ or H | $R^c$ H |
|---|---|---|---|---|
| I.1.2790 | phenyl | 2-furyl | 4-Cl | H |
| I.1.2791 | phenyl | 2-furyl | 5-Cl | H |
| I.1.2792 | phenyl | 2-furyl | 6-Cl | H |
| I.1.2793 | phenyl | 2-furyl | 3-F | H |
| I.1.2794 | phenyl | 2-furyl | 4-F | H |
| I.1.2795 | phenyl | 2-furyl | 5-F | H |
| I.1.2796 | phenyl | 2-furyl | 6-F | H |
| I.1.2797 | phenyl | 2-furyl | 3-CH₃ | H |
| I.1.2798 | phenyl | 2-furyl | 4-CH₃ | H |
| I.1.2799 | phenyl | 2-furyl | 5-CH₃ | H |
| I.1.2800 | phenyl | 2-furyl | 6-CH₃ | H |
| I.1.2801 | phenyl | 2-furyl | 5-vinyl | H |
| I.1.2802 | phenyl | 2-furyl | 6-vinyl | H |
| I.1.2803 | phenyl | 2-thienyl | H | H |
| I.1.2804 | phenyl | 2-thienyl | 3-Cl | H |
| I.1.2805 | phenyl | 2-thienyl | 4-Cl | H |
| I.1.2806 | phenyl | 2-thienyl | 5-Cl | H |
| I.1.2807 | phenyl | 2-thienyl | 6-Cl | H |
| I.1.2808 | phenyl | 2-thienyl | 3-F | H |
| I.1.2809 | phenyl | 2-thienyl | 4-F | H |
| I.1.2810 | phenyl | 2-thienyl | 5-F | H |
| I.1.2811 | phenyl | 2-thienyl | 6-F | H |
| I.1.2812 | phenyl | 2-thienyl | 3-CH₃ | H |
| I.1.2813 | phenyl | 2-thienyl | 4-CH₃ | H |
| I.1.2814 | phenyl | 2-thienyl | 5-CH₃ | H |
| I.1.2815 | phenyl | 2-thienyl | 6-CH₃ | H |
| I.1.2816 | phenyl | 2-thienyl | 5-vinyl | H |
| I.1.2817 | phenyl | 2-thienyl | 6-vinyl | H |
| I.1.2818 | phenyl | 2-oxazolyl | H | H |
| I.1.2819 | phenyl | 2-oxazolyl | 3-Cl | H |
| I.1.2820 | phenyl | 2-oxazolyl | 4-Cl | H |
| I.1.2821 | phenyl | 2-oxazolyl | 5-Cl | H |
| I.1.2822 | phenyl | 2-oxazolyl | 6-Cl | H |
| I.1.2823 | phenyl | 2-oxazolyl | 3-F | H |
| I.1.2824 | phenyl | 2-oxazolyl | 4-F | H |
| I.1.2825 | phenyl | 2-oxazolyl | 5-F | H |
| I.1.2826 | phenyl | 2-oxazolyl | 6-F | H |
| I.1.2827 | phenyl | 2-oxazolyl | 3-CH₃ | H |
| I.1.2828 | phenyl | 2-oxazolyl | 4-CH₃ | H |
| I.1.2829 | phenyl | 2-oxazolyl | 5-CH₃ | H |
| I.1.2830 | phenyl | 2-oxazolyl | 6-CH₃ | H |
| I.1.2831 | phenyl | 2-oxazolyl | 5-vinyl | H |
| I.1.2832 | phenyl | 2-oxazolyl | 6-vinyl | H |
| I.1.2833 | phenyl | 4-methyloxazol-2-yl | H | H |
| I.1.2834 | phenyl | 4-methyloxazol-2-yl | 3-Cl | H |
| I.1.2835 | phenyl | 4-methyloxazol-2-yl | 4-Cl | H |
| I.1.2836 | phenyl | 4-methyloxazol-2-yl | 5-Cl | H |
| I.1.2837 | phenyl | 4-methyloxazol-2-yl | 6-Cl | H |
| I.1.2838 | phenyl | 4-methyloxazol-2-yl | 3-F | H |
| I.1.2839 | phenyl | 4-methyloxazol-2-yl | 4-F | H |
| I.1.2840 | phenyl | 4-methyloxazol-2-yl | 5-F | H |
| I.1.2841 | phenyl | 4-methyloxazol-2-yl | 6-F | H |
| I.1.2842 | phenyl | 4-methyloxazol-2-yl | 3-CH₃ | H |
| I.1.2843 | phenyl | 4-methyloxazol-2-yl | 4-CH₃ | H |
| I.1.2844 | phenyl | 4-methyloxazol-2-yl | 5-CH₃ | H |
| I.1.2845 | phenyl | 4-methyloxazol-2-yl | 6-CH₃ | H |
| I.1.2846 | phenyl | 4-methyloxazol-2-yl | 5-vinyl | H |
| I.1.2847 | phenyl | 4-methyloxazol-2-yl | 6-vinyl | H |
| I.1.2848 | phenyl | 2-thiazolyl | H | H |
| I.1.2849 | phenyl | 2-thiazolyl | 3-Cl | H |
| I.1.2850 | phenyl | 2-thiazolyl | 4-Cl | H |
| I.1.2851 | phenyl | 2-thiazolyl | 5-Cl | H |
| I.1.2852 | phenyl | 2-thiazolyl | 6-Cl | H |
| I.1.2853 | phenyl | 2-thiazolyl | 3-F | H |
| I.1.2854 | phenyl | 2-thiazolyl | 4-F | H |
| I.1.2855 | phenyl | 2-thiazolyl | 5-F | H |
| I.1.2856 | phenyl | 2-thiazolyl | 6-F | H |
| I.1.2857 | phenyl | 2-thiazolyl | 3-CH₃ | H |
| I.1.2858 | phenyl | 2-thiazolyl | 4-CH₃ | H |
| I.1.2859 | phenyl | 2-thiazolyl | 5-CH₃ | H |
| I.1.2860 | phenyl | 2-thiazolyl | 6-CH₃ | H |
| I.1.2861 | phenyl | 2-thiazolyl | 5-vinyl | H |
| I.1.2862 | phenyl | 2-thiazolyl | 6-vinyl | H |
| I.1.2863 | phenyl | 2-pyridinyl | H | H |
| I.1.2864 | phenyl | 2-pyridinyl | 3-Cl | H |
| I.1.2865 | phenyl | 2-pyridinyl | 4-Cl | H |
| I.1.2866 | phenyl | 2-pyridinyl | 5-Cl | H |
| I.1.2867 | phenyl | 2-pyridinyl | 6-Cl | H |
| I.1.2868 | phenyl | 2-pyridinyl | 3-F | H |
| I.1.2869 | phenyl | 2-pyridinyl | 4-F | H |
| I.1.2870 | phenyl | 2-pyridinyl | 5-F | H |
| I.1.2871 | phenyl | 2-pyridinyl | 6-F | H |
| I.1.2872 | phenyl | 2-pyridinyl | 3-CH₃ | H |
| I.1.2873 | phenyl | 2-pyridinyl | 4-CH₃ | H |
| I.1.2874 | phenyl | 2-pyridinyl | 5-CH₃ | H |
| I.1.2875 | phenyl | 2-pyridinyl | 6-CH₃ | H |
| I.1.2876 | phenyl | 2-pyridinyl | 5-vinyl | H |
| I.1.2877 | phenyl | 2-pyridinyl | 6-vinyl | H |
| I.1.2878 | phenyl | 3-pyridinyl | H | H |
| I.1.2879 | phenyl | 3-pyridinyl | 3-Cl | H |
| I.1.2880 | phenyl | 3-pyridinyl | 4-Cl | H |
| I.1.2881 | phenyl | 3-pyridinyl | 5-Cl | H |
| I.1.2882 | phenyl | 3-pyridinyl | 6-Cl | H |
| I.1.2883 | phenyl | 3-pyridinyl | 3-F | H |
| I.1.2884 | phenyl | 3-pyridinyl | 4-F | H |
| I.1.2885 | phenyl | 3-pyridinyl | 5-F | H |
| I.1.2886 | phenyl | 3-pyridinyl | 6-F | H |
| I.1.2887 | phenyl | 3-pyridinyl | 3-CH₃ | H |
| I.1.2888 | phenyl | 3-pyridinyl | 4-CH₃ | H |
| I.1.2889 | phenyl | 3-pyridinyl | 5-CH₃ | H |
| I.1.2890 | phenyl | 3-pyridinyl | 6-CH₃ | H |
| I.1.2891 | phenyl | 3-pyridinyl | 5-vinyl | H |
| I.1.2892 | phenyl | 3-pyridinyl | 6-vinyl | H |
| I.1.2893 | phenyl | 2-pyrimidinyl | H | H |
| I.1.2894 | phenyl | 2-pyrimidinyl | 3-Cl | H |
| I.1.2895 | phenyl | 2-pyrimidinyl | 4-Cl | H |
| I.1.2896 | phenyl | 2-pyrimidinyl | 5-Cl | H |
| I.1.2897 | phenyl | 2-pyrimidinyl | 6-Cl | H |
| I.1.2898 | phenyl | 2-pyrimidinyl | 3-F | H |
| I.1.2899 | phenyl | 2-pyrimidinyl | 4-F | H |
| I.1.2900 | phenyl | 2-pyrimidinyl | 5-F | H |
| I.1.2901 | phenyl | 2-pyrimidinyl | 6-F | H |
| I.1.2902 | phenyl | 2-pyrimidinyl | 3-CH₃ | H |
| I.1.2903 | phenyl | 2-pyrimidinyl | 4-CH₃ | H |
| I.1.2904 | phenyl | 2-pyrimidinyl | 5-CH₃ | H |
| I.1.2905 | phenyl | 2-pyrimidinyl | 6-CH₃ | H |
| I.1.2906 | phenyl | 2-pyrimidinyl | 5-vinyl | H |
| I.1.2907 | phenyl | 2-pyrimidinyl | 6-vinyl | H |
| I.1.2908 | phenyl | 2-pyrazinyl | H | H |
| I.1.2909 | phenyl | 2-pyrazinyl | 3-Cl | H |
| I.1.2910 | phenyl | 2-pyrazinyl | 4-Cl | H |
| I.1.2911 | phenyl | 2-pyrazinyl | 5-Cl | H |
| I.1.2912 | phenyl | 2-pyrazinyl | 6-Cl | H |
| I.1.2913 | phenyl | 2-pyrazinyl | 3-F | H |
| I.1.2914 | phenyl | 2-pyrazinyl | 4-F | H |
| I.1.2915 | phenyl | 2-pyrazinyl | 5-F | H |
| I.1.2916 | phenyl | 2-pyrazinyl | 6-F | H |
| I.1.2917 | phenyl | 2-pyrazinyl | 3-CH₃ | H |
| I.1.2918 | phenyl | 2-pyrazinyl | 4-CH₃ | H |
| I.1.2919 | phenyl | 2-pyrazinyl | 5-CH₃ | H |
| I.1.2920 | phenyl | 2-pyrazinyl | 6-CH₃ | H |
| I.1.2921 | phenyl | 2-pyrazinyl | 5-vinyl | H |
| I.1.2922 | phenyl | 2-pyrazinyl | 6-vinyl | H |

Preference is likewise given to the compounds of the formula I.2, particularly preferably the compounds I.2.1-I.2.2922, in particular the compounds (S,S)-I.2.1-I.2.2922, which differ from the corresponding compounds I.1.1-I.1.2922 or (S,S)-I.1.1-I.1.2922 in that the group $A^2R^dR^eR^f$ is 2-chlorophenyl.

Preference is likewise given to the compounds of the formula I.3, particularly preferably the compounds I.3.1-I.3.2922, in particular the compounds (S,S)-I.3.1-I.3.2922, which differ from the corresponding compounds I.1.1-I.1.2922 or (S,S)-I.1.1-I.1.2922 in that the group $A^2R^dR^eR^f$ is 3-chlorophenyl.

Preference is likewise given to the compounds of the formula I.4, particularly preferably the compounds I.4.1-I.4.2922, in particular the compounds (S,S)-I.4.1-I.4.2922, which differ from the corresponding compounds I.1.1-I.1.2922 or (S,S)-I.1.1-I.1.2922 in that the group $A^2R^dR^eR^f$ is 4-chlorophenyl.

Preference is likewise given to the compounds of the formula I.5, particularly preferably the compounds I.5.1-I.5.2922, in particular the compounds (S,S)-I.5.1-I.5.2922, which differ from the corresponding compounds I.1.1-I.1.2922 or (S,S)-I.1.1-I.1.2922 in that the group $A^2R^dR^eR^f$ is 2-trifluoromethylphenyl.

Preference is likewise given to the compounds of the formula I.6, particularly preferably the compounds I.6.1-I.6.2922, in particular the compounds (S,S)-I.6.1-I.6.2922, which differ from the corresponding compounds I.1.1-I.1.2922 or (S,S)-I.1.1-I.1.2922 in that the group $A^2R^dR^eR^f$ is 3-trifluoromethylphenyl.

Preference is likewise given to the compounds of the formula I.7, particularly preferably the compounds I.7.1-I.7.2922, in particular the compounds (S,S)-I.7.1-I.7.2922, which differ from the corresponding compounds I.1.1-I.1.2922 or (S,S)-I.1.1-I.1.2922 in that the group $A^2R^dR^eR^f$ is 4-trifluoromethylphenyl.

Preference is likewise given to the compounds of the formula I.8, particularly preferably the compounds I.8.1-I.8.2922, in particular the compounds (S,S)-I.8.1-I.8.2922, which differ from the corresponding compounds I.1.1-I.1.2922 or (S,S)-I.1.1-I.1.2922 in that the group $A^2R^dR^eR^f$ is 2-methoxyphenyl.

Preference is likewise given to the compounds of the formula I.9, particularly preferably the compounds I.9.1-I.9.2922, in particular the compounds (S,S)-I.9.1-I.9.2922, which differ from the corresponding compounds I.1.1-I.1.2922 or (S,S)-I.1.1-I.1.2922 in that the group $A^2R^dR^eR^f$ is 3-methoxyphenyl.

Preference is likewise given to the compounds of the formula I.10, particularly preferably the compounds I.10.1-I.10.2922, in particular the compounds (S,S)-I.10.1-I.10.2922, which differ from the corresponding compounds I.1.1-I.1.2922 or (S,S)-I.1.1-I.1.2922 in that the group $A^2R^dR^eR^f$ is 4-methoxyphenyl.

Preference is likewise given to the compounds of the formula I.11, particularly preferably the compounds I.11.1-I.11.2922, in particular the compounds (S,S)-I.11.1-I.11.2922, which differ from the corresponding compounds I.1.1-I.1.2922 or (S,S)-I.1.1-I.1.2922 in that the group $A^2R^dR^eR^f$ is 2-fluorophenyl.

Preference is likewise given to the compounds of the formula I.12, particularly preferably the compounds I.12.1-I.12.2922, in particular the compounds (S,S)-I.12.1-I.12.2922, which differ from the corresponding compounds I.1.1-I.1.2922 or (S,S)-I.1.1-I.1.2922 in that the group $A^2R^dR^eR^f$ is 3-fluorophenyl.

Preference is likewise given to the compounds of the formula 0.113, particularly preferably the compounds I.13.1-I.13.2922, in particular the compounds (S,S)-I.13.1-I.13.2922, which differ from the corresponding compounds I.1.1-I.1.2922 or (S,S)-I.1.1-I.1.2922 in that $A^2$ is 4-fluorophenyl.

Preference is likewise given to the compounds of the formula I.14, particularly preferably the compounds I.14.1-I.14.2922, in particular the compounds (S,S)-I.14.1-I.14.2922, which differ from the corresponding compounds I.1.1-I.1.2922 or (S,S)-I.1.1-I.1.2922 in that the group 2-methylphenyl.

Preference is likewise given to the compounds of the formula I.15, particularly preferably the compounds I.15.1-I.15.2922, in particular the compounds (S,S)-I.15.1-I.15.2922, which differ from the corresponding compounds I.1.1-I.1.2922 or (S,S)-I.1.1-I.1.2922 in that the group $A^2R^dR^eR^f$ is 3-methylphenyl.

Preference is likewise given to the compounds of the formula I.16, particularly preferably the compounds I.16.1-I.16.2922, in particular the compounds (S,S)-I.16.1-I.16.2922, which differ from the corresponding compounds I.1.1-I.1.2922 or (S,S)-I.1.1-I.1.2922 in that the group $A^2R^dR^eR^f$ is 4-methylphenyl.

Preference is likewise given to the compounds of the formula I.17, particularly preferably the compounds I.17.1-I.17.2922, in particular the compounds (S,S)-I.17.1-I.17.2922, which differ from the corresponding compounds I.1.1-I.1.2922 or (S,S)-I.1.1-I.1.2922 in that the group $A^2R^dR^eR^f$ is 2-chloro-3-methylphenyl.

Preference is likewise given to the compounds of the formula I.18, particularly preferably the compounds I.18.1-I.18.2922, in particular the compounds (S,S)-I.18.1-I.18.2922, which differ from the corresponding compounds I.1.1-I.1.2922 or (S,S)-I.1.1-I.1.2922 in that the group $A^2R^dR^eR^f$ is 2-chloro-4-methylphenyl.

Preference is likewise given to the compounds of the formula I.19, particularly preferably the compounds I.19.1-I.19.2922, in particular the compounds (S,S)-I.19.1-I.19.2922, which differ from the corresponding compounds I.1.1-I.1.2922 or (S,S)-I.1.1-I.1.2922 in that the group $A^2R^dR^eR^f$ is 2-chloro-5-methylphenyl.

Preference is likewise given to the compounds of the formula I.20, particularly preferably the compounds I.20.1-I.20.2922, in particular the compounds (S,S)-I.20.1-I.20.2922, which differ from the corresponding compounds I.1.1-I.1.2922 or (S,S)-I.1.1-I.1.2922 in that the group $A^2R^dR^eR^f$ is 2-chloro-6-methylphenyl.

Preference is likewise given to the compounds of the formula I.21, particularly preferably the compounds I.21.1-I.21.2922, in particular the compounds (S,S)-I.21.1-I.21.2922, which differ from the corresponding compounds I.1.1-I.1.2922 or (S,S)-I.1.1-I.1.2922 in that the group $A^2R^dR^eR^f$ is 2,3-dichlorophenyl.

Preference is likewise given to the compounds of the formula I.22, particularly preferably the compounds I.22.1-I.22.2922, in particular the compounds (S,S)-I.22.1-I.22.2922, which differ from the corresponding compounds I.1.1-I.1.2922 or (S,S)-I.1.1-I.1.2922 in that the group $A^2R^dR^eR^f$ is 2,4-dichlorophenyl.

Preference is likewise given to the compounds of the formula I.23, particularly preferably the compounds I.23.1-I.23.2922, in particular the compounds (S,S)-I.23.1-I.23.2922, which differ from the corresponding compounds I.1.1-I.1.2922 or (S,S)-I.1.1-I.1.2922 in that the group $A^2R^dR^eR^f$ is 2,5-dichlorophenyl.

Preference is likewise given to the compounds of the formula I.24, particularly preferably the compounds I.24.1-I.24.2922, in particular the compounds (S,S)-I.24.1-I.24.2922, which differ from the corresponding compounds I.1.1-I.1.2922 or (S,S)-I.1.1-I.1.2922 in that the group $A^2R^dR^eR^f$ is 2,6-dichlorophenyl.

Preference is likewise given to the compounds of the formula I.25, particularly preferably the compounds I.25.1-I.25.2922, in particular the compounds (S,S)-I.25.1-I.25.2922, which differ from the corresponding compounds I.1.1-I.1.2922 or (S,S)-I.1.1-I.1.2922 in that the group $A^2R^dR^eR^f$ is 2-chloro-3-fluorophenyl.

Preference is likewise given to the compounds of the formula I.26, particularly preferably the compounds I.26.1-I.26.2922, in particular the compounds (S,S)-I.26.1-I.26.2922, which differ from the corresponding compounds I.1.1-I.1.2922 or (S,S)-I.1.1-I.1.2922 in that the group $A^2R^dR^eR^f$ is 2-chloro-4-fluorophenyl.

Preference is likewise given to the compounds of the formula I.27, particularly preferably the compounds I.27.1-I.27.2922, in particular the compounds (S,S)-I.27.1-I.27.2922, which differ from the corresponding compounds I.1.1-I.1.2922 or (S,S)-I.1.1-I.1.2922 in that the group $A^2R^dR^eR^f$ is 2-chloro-5-fluorophenyl.

Preference is likewise given to the compounds of the formula I.28, particularly preferably the compounds I.28.1-I.28.2922, in particular the compounds (S,S)-I.28.1-I.28.2922, which differ from the corresponding compounds I.1.1-I.1.2922 or (S,S)-I.1.1-I.1.2922 in that the group $A^2R^dR^eR^f$ is 2-chloro-6-fluorophenyl.

Preference is likewise given to the compounds of the formula I.29, particularly preferably the compounds I.29.1-I.29.2922, in particular the compounds (S,S)-I.29.1-I.29.2922, which differ from the corresponding compounds I.1.1-I.1.2922 or (S,S)-I.1.1-I.1.2922 in that the group $A^2R^dR^eR^f$ is 2,3-difluorophenyl.

Preference is likewise given to the compounds of the formula I.30, particularly preferably the compounds I.30.1-I.30.2922, in particular the compounds (S,S)-I.30.1-I.30.2922, which differ from the corresponding compounds I.1.1-I.1.2922 or (S,S)-I.1.1-I.1.2922 in that the group $A^2R^dR^eR^f$ is 2,4-difluorophenyl.

Preference is likewise given to the compounds of the formula I.31, particularly preferably the compounds I.31.1-I.31.2922, in particular the compounds (S,S)-I.31.1-I.31.2922, which differ from the corresponding compounds I.1.1-I.1.2922 or (S,S)-I.1.1-I.1.2922 in that the group $A^2R^dR^eR^f$ is 2,5-difluorophenyl.

Preference is likewise given to the compounds of the formula I.32, particularly preferably the compounds I.32.1-I.32.2922, in particular the compounds (S,S)-I.32.1-I.32.2922, which differ from the corresponding compounds I.1.1-I.1.2922 or (S,S)-I.1.1-I.1.2922 in that the group $A^2R^dR^eR^f$ is 2,6-difluorophenyl.

Preference is likewise given to the compounds of the formula I.33, particularly preferably the compounds I.33.1-I.33.2922, in particular the compounds (S,S)-I.33.1-I.33.2922, which differ from the corresponding compounds I.1.1-I.1.2922 or (S,S)-I.1.1-I.1.2922 in that the group $A^2R^dR^eR^f$ is 2-fluoro-3-chlorophenyl.

Preference is likewise given to the compounds of the formula I.34, particularly preferably the compounds I.34.1-I.34.2922, in particular the compounds (S,S)-I.34.1-I.34.2922, which differ from the corresponding compounds I.1.1-I.1.2922 or (S,S)-I.1.1-I.1.2922 in that the group $A^2R^dR^eR^f$ is 2-fluoro-4-chlorophenyl.

Preference is likewise given to the compounds of the formula I.35, particularly preferably the compounds I.35.1-I.35.2922, in particular the compounds (S,S)-I.35.1-I.35.2922, which differ from the corresponding compounds I.1.1-I.1.2922 or (S,S)-I.1.1-I.1.2922 in that the group $A^2R^dR^eR^f$ is 2-fluoro-5-chlorophenyl.

Preference is likewise given to the compounds of the formula I.36, particularly preferably the compounds I.36.1-I.36.2922, in particular the compounds (S,S)-I.36.1-I.36.2922, which differ from the corresponding compounds I.1.1-I.1.2922 or (S,S)-I.1.1-I.1.2922 in that the group $A^2R^dR^eR^f$ is 3,4-difluorophenyl.

Preference is likewise given to the compounds of the formula I.37, particularly preferably the compounds I.37.1-I.37.2922, in particular the compounds (S,S)-I.37.1-I.37.2922, which differ from the corresponding compounds I.1.1-I.1.2922 or (S,S)-I.1.1-I.1.2922 in that the group $A^2R^dR^eR^f$ is 3,5-difluorophenyl.

Preference is likewise given to the compounds of the formula I.38, particularly preferably the compounds I.38.1-I.38.2922, in particular the compounds (S,S)-I.38.1-I.38.2922, which differ from the corresponding compounds I.1.1-I.1.2922 or (S,S)-I.1.1-I.1.2922 in that the group $A^2R^dR^eR^f$ is 3,4-dichlorophenyl.

Preference is likewise given to the compounds of the formula I.39, particularly preferably the compounds I.39.1-I.39.2922, in particular the compounds (S,S)-I.39.1-I.39.2922, which differ from the corresponding compounds I.1.1-I.1.2922 or (S,S)-I.1.1-I.1.2922 in that the group $A^2R^dR^eR^f$ is 3,5-dichlorophenyl.

Preference is likewise given to the compounds of the formula I.40, particularly preferably the compounds I.40.1-I.40.2922, in particular the compounds (S,S)-I.40.1-I.40.2922, which differ from the corresponding compounds I.1.1-I.1.2922 or (S,S)-I.1.1-I.1.2922 in that the group $A^2R^dR^eR^f$ is 3-fluoro-4-chlorophenyl.

Preference is likewise given to the compounds of the formula I.41, particularly preferably the compounds I.41.1-I.41.2922, in particular the compounds (S,S)-I.41.1-I.41.2922, which differ from the corresponding compounds I.1.1-I.1.2922 or (S,S)-I.1.1-I.1.2922 in that the group $A^2R^dR^eR^f$ is 4-fluoro-3-chlorophenyl.

Preference is likewise given to the compounds of the formula I.42, particularly preferably the compounds I.42.1-I.42.2922, in particular the compounds (S,S)-I.42.1-I.42.2922, which differ from the corresponding compounds I.1.1-I.1.2922 or (S,S)-I.1.1-I.1.2922 in that the group $A^2R^dR^eR^f$ is 3-fluoro-5-chlorophenyl.

Preference is likewise given to the compounds of the formula I.43, particularly preferably the compounds I.43.1-I.43.2922, in particular the compounds (S,S)-I.43.1-I.43.2922, which differ from the corresponding compounds I.1.1-I.1.2922 or (S,S)-I.1.1-I.1.2922 in that the group $A^2R^dR^eR^f$ is pyridin-2-yl.

Preference is likewise given to the compounds of the formula I.44, particularly preferably the compounds I.44.1-I.44.2922, in particular the compounds (S,S)-I.44.1-I.44.2922, which differ from the corresponding compounds I.1.1-I.1.2922 or (S,S)-I.1.1-I.1.2922 in that the group $A^2R^dR^eR^f$ is 3-chloropyridin-2-yl.

Preference is likewise given to the compounds of the formula I.45, particularly preferably the compounds I.45.1-I.45.2922, in particular the compounds (S,S)-I.45.1-I.45.2922, which differ from the corresponding compounds I.1.1-I.1.2922 or (S,S)-1.1-I.1.2922 in that the group $A^2R^dR^eR^f$ is 4-chloropyridin-2-yl.

Preference is likewise given to the compounds of the formula I.46, particularly preferably the compounds I.46.1-I.46.2922, in particular the compounds (S,S)-I.46.1-I.46.2922, which differ from the corresponding compounds I.1.1-I.1.2922 or (S,S)-I.1.1-I.1.2922 in that the group $A^2R^dR^eR^f$ is 5-chloropyridin-2-yl.

Preference is likewise given to the compounds of the formula I.47, particularly preferably the compounds I.47.1-I.47.2922, in particular the compounds (S,S)-I.47.1-I.47.2922, which differ from the corresponding compounds I.1.1-I.1.2922 or (S,S)-I.1.1-I.1.2922 in that the group $A^2R^dR^eR^f$ is 6-chloropyridin-2-yl.

Preference is likewise given to the compounds of the formula I.48, particularly preferably the compounds I.48.1-I.48.2922, in particular the compounds (S,S)-I.48.1-I.48.2922, which differ from the corresponding compounds I.1.1-I.1.2922 or (S,S)-I.1.1-I.1.2922 in that the group $A^2R^dR^eR^f$ is 3-trifluoromethylpyridin-2-yl.

Preference is likewise given to the compounds of the formula I.49, particularly preferably the compounds I.49.1-I.49.2922, in particular the compounds (S,S)-I.49.1-I.49.2922, which differ from the corresponding compounds I.1.1-I.1.2922 or (S,S)-I.1.1-I.1.2922 in that the group $A^2R^dR^eR^f$ is 4-trifluoromethylpyridin-2-yl.

Preference is likewise given to the compounds of the formula I.50, particularly preferably the compounds I.50.1-I.50.2922, in particular the compounds (S,S)-I.50.1-I.50.2922, which differ from the corresponding compounds I.1.1-I.1.2922 or (S,S)-I.1.1-I.1.2922 in that the group $A^2R^dR^eR^f$ is 5-trifluoromethylpyridin-2-yl.

Preference is likewise given to the compounds of the formula I.51, particularly preferably the compounds I.51.1-I.51.2922, in particular the compounds (S,S)-I.51.1-I.51.2922, which differ from the corresponding compounds I.1.1-I.1.2922 or (S,S)-I.1.1-I.1.2922 in that the group $A^2R^dR^eR^f$ is 6-trifluoromethylpyridin-2-yl.

Preference is likewise given to the compounds of the formula I.52, particularly preferably the compounds I.52.1-I.52.2922, in particular the compounds (S,S)-I.52.1-I.52.2922, which differ from the corresponding compounds I.1.1-I.1.2922 or (S,S)-I.1.1-I.1.2922 in that the group $A^2R^dR^eR^f$ is 3-methoxypyridin-2-yl.

Preference is likewise given to the compounds of the formula I.53, particularly preferably the compounds I.53.1-I.53.2922, in particular the compounds (S,S)-I.53.1-I.53.2922, which differ from the corresponding compounds I.1.1-I.1.2922 or (S,S)-I.1.1-I.1.2922 in that the group $A^2R^dR^eR^f$ is 4-methoxypyridin-2-yl.

Preference is likewise given to the compounds of the formula I.54, particularly preferably the compounds I.54.1-I.54.2922, in particular the compounds (S,S)-I.54.1-I.54.2922, which differ from the corresponding compounds I.1.1-I.1.2922 or (S,S)-I.1.1-I.1.2922 in that the group $A^2R^dR^eR^f$ is 5-methoxypyridin-2-yl.

Preference is likewise given to the compounds of the formula I.55, particularly preferably the compounds I.55.1-I.55.2922, in particular the compounds (S,S)-I.55.1-I.55.2922, which differ from the corresponding compounds I.1.1-I.1.2922 or (S,S)-I.1.1-I.1.2922 in that the group $A^2R^dR^eR^f$ is 6-methoxypyridin-2-yl.

Preference is likewise given to the compounds of the formula I.56, particularly preferably the compounds I.56.1-I.56.2922, in particular the compounds (S,S)-I.56.1-I.56.2922, which differ from the corresponding compounds I.1.1-I.1.2922 or (S,S)-I.1.1-I.1.2922 in that the group $A^2R^dR^eR^f$ is 3-fluoropyridin-2-yl.

Preference is likewise given to the compounds of the formula I.57, particularly preferably the compounds I.57.1-I.57.2922, in particular the compounds (S,S)-I.57.1-I.57.2922, which differ from the corresponding compounds I.1.1-I.1.2922 or (S,S)-I.1.1-I.1.2922 in that the group $A^2R^dR^eR^f$ is 4-fluoropyridin-2-yl.

Preference is likewise given to the compounds of the formula I.58, particularly preferably the compounds I.58.1-I.58.2922, in particular the compounds (S,S)-I.58.1-I.58.2922, which differ from the corresponding compounds I.1.1-I.1.2922 or (S,S)-I.1.1-I.1.2922 in that the group $A^2R^dR^eR^f$ is 5-fluoropyridin-2-yl.

Preference is likewise given to the compounds of the formula I.59, particularly preferably the compounds I.59.1-I.59.2922, in particular the compounds (S,S)-I.59.1-I.59.2922, which differ from the corresponding compounds I.1.1-I.1.2922 or (S,S)-I.1.1-I.1.2922 in that the group $A^2R^dR^eR^f$ is 6-fluoropyridin-2-yl.

Preference is likewise given to the compounds of the formula I.60, particularly preferably the compounds I.60.1-I.60.2922, in particular the compounds (S,S)-I.60.1-I.60.2922, which differ from the corresponding compounds I.1.1-I.1.2922 or (S,S)-I.1.1-I.1.2922 in that the group $A^2R^dR^eR^f$ is pyridin-3-yl.

Preference is likewise given to the compounds of the formula I.61, particularly preferably the compounds I.61.1-I.61.2922, in particular the compounds (S,S)-I.61.1-I.61.2922, which differ from the corresponding compounds I.1.1-I.1.2922 or (S,S)-I.1.1-I.1.2922 in that the group $A^2R^dR^eR^f$ is 2-chloropyridin-3-yl.

Preference is likewise given to the compounds of the formula I.62, particularly preferably the compounds I.62.1-I.62.2922, in particular the compounds (S,S)-I.62.1-I.62.2922, which differ from the corresponding compounds I.1.1-I.1.2922 or (S,S)-I.1.1-I.1.2922 in that the group $A^2R^dR^eR^f$ is 4-chloropyridin-3-yl.

Preference is likewise given to the compounds of the formula I.63, particularly preferably the compounds I.63.1-I.63.2922, in particular the compounds (S,S)-I.63.1-I.63.2922, which differ from the corresponding compounds I.1.1-I.1.2922 or (S,S)-I.1.1-I.1.2922 in that the group $A^2R^dR^eR^f$ is 5-chloropyridin-3-yl.

Preference is likewise given to the compounds of the formula I.64, particularly preferably the compounds I.64.1-I.64.2922, in particular the compounds (S,S)-I.64.1-I.64.2922, which differ from the corresponding compounds I.1.1-I.1.2922 or (S,S)-I.1.1-I.1.2922 in that the group $A^2R^dR^eR^f$ is 6-chloropyridin-3-yl.

Preference is likewise given to the compounds of the formula I.65, particularly preferably the compounds I.65.1-I.65.2922, in particular the compounds (S,S)-I.65.1-I.65.2922, which differ from the corresponding compounds I.1.1-I.1.2922 or (S,S)-I.1.1-I.1.2922 in that the group $A^2R^dR^eR^f$ is 2-trifluoromethylpyridin-3-yl.

Preference is likewise given to the compounds of the formula I.66, particularly preferably the compounds I.66.1-I.66.2922, in particular the compounds (S,S)-I.66.1-I.66.2922, which differ from the corresponding compounds I.1.1-I.1.2922 or (S,S)-I.1.1-I.1.2922 in that the group $A^2R^dR^eR^f$ is 4-trifluoromethylpyridin-3-yl.

Preference is likewise given to the compounds of the formula I.67, particularly preferably the compounds I.67.1-I.67.2922, in particular the compounds (S,S)-I.67.1-I.67.2922, which differ from the corresponding compounds I.1.1-I.1.2922 or (S,S)-I.1.1-I.1.2922 in that the group $A^2R^dR^eR^f$ is 5-trifluoromethylpyridin-3-yl.

Preference is likewise given to the compounds of the formula I.68, particularly preferably the compounds I.68.1-I.68.2922, in particular the compounds (S,S)-I.68.1-I.68.2922, which differ from the corresponding compounds I.1.1-I.1.2922 or (S,S)-I.1.1-I.1.2922 in that the group $A^2R^dR^eR^f$ is 6-trifluoromethylpyridin-3-yl.

Preference is likewise given to the compounds of the formula I.69, particularly preferably the compounds I.69.1-I.69.2922, in particular the compounds (S,S)-I.69.1-I.69.2922, which differ from the corresponding compounds I.1.1-I.1.2922 or (S,S)-I.1.1-I.1.2922 in that the group $A^2R^dR^eR^f$ is 2-methoxypyridin-3-yl.

Preference is likewise given to the compounds of the formula I.70, particularly preferably the compounds I.70.1-I.70.2922, in particular the compounds (S,S)-I.70.1-I.70.2922, which differ from the corresponding compounds I.1.1-I.1.2922 or (S,S)-I.1.1-I.1.2922 in that the group $A^2R^dR^eR^f$ is 4-methoxypyridin-3-yl.

Preference is likewise given to the compounds of the formula I.71, particularly preferably the compounds I.71.1-I.71.2922, in particular the compounds (S,S)-I.71.1-I.71.2922, which differ from the corresponding compounds I.1.1-I.1.2922 or (S,S)-I.1.1-I.1.2922 in that the group $A^2R^dR^eR^f$ is 5-methoxypyridin-3-yl.

Preference is likewise given to the compounds of the formula I.72, particularly preferably the compounds I.72.1-I.72.2922, in particular the compounds (S,S)-I.72.1-I.72.2922, which differ from the corresponding compounds I.1.1-I.1.2922 or (S,S)-I.1.1-I.1.2922 in that the group $A^2R^dR^eR^f$ is 6-methoxypyridin-3-yl.

Preference is likewise given to the compounds of the formula I.73, particularly preferably the compounds I.73.1-I.73.2922, in particular the compounds (S,S)-I.73.1-I.73.2922, which differ from the corresponding compounds I.1.1-I.1.2922 or (S,S)-I.1.1-I.1.2922 in that the group $A^2R^dR^eR^f$ is 2-fluoropyridin-3-yl.

Preference is likewise given to the compounds of the formula I.74, particularly preferably the compounds I.74.1-I.74.2922, in particular the compounds (S,S)-I.74.1-I.74.2922, which differ from the corresponding compounds I.1.1-I.1.2922 or (S,S)-I.1.1-I.1.2922 in that the group $A^2R^dR^eR^f$ is 4-fluoropyridin-3-yl.

Preference is likewise given to the compounds of the formula I.75, particularly preferably the compounds I.75.1-I.75.2922, in particular the compounds (S,S)-I.75.1-I.75.2922, which differ from the corresponding compounds I.1.1-I.1.2922 or (S,S)-I.1.1-I.1.2922 in that the group $A^2R^dR^eR^f$ is 5-fluoropyridin-3-yl.

Preference is likewise given to the compounds of the formula I.76, particularly preferably the compounds I.76.1-I.76.2922, in particular the compounds (S,S)-I.76.1-I.76.2922, which differ from the corresponding compounds I.1.1-I.1.2922 or (S,S)-I.1.1-I.1.2922 in that the group $A^2R^dR^eR^f$ is 6-fluoropyridin-3-yl.

Preference is likewise given to the compounds of the formula I.77, particularly preferably the compounds I.77.1-I.77.2922, in particular the compounds (S,S)-I.77.1-I.77.2922, which differ from the corresponding compounds I.1.1-I.1.2922 or (S,S)-I.1.1-I.1.2922 in that the group $A^2R^dR^eR^f$ is pyridin-4-yl.

Preference is likewise given to the compounds of the formula I.78, particularly preferably the compounds I.78.1-I.78.2922, in particular the compounds (S,S)-I.78.1-I.78.2922, which differ from the corresponding compounds I.1.1-I.1.2922 or (S,S)-I.1.1-I.1.2922 in that the group $A^2R^dR^eR^f$ is 2-fluoropyridin-4-yl.

Preference is likewise given to the compounds of the formula I.79, particularly preferably the compounds I.79.1-I.79.2922, in particular the compounds (S,S)-I.79.1-I.79.2922, which differ from the corresponding compounds I.1.1-I.1.2922 or (S,S)-I.1.1-I.1.2922 in that the group $A^2R^dR^eR^f$ is 3-fluoropyridin-4-yl.

Preference is likewise given to the compounds of the formula I.80, particularly preferably the compounds I.80.1-I.80.2922, in particular the compounds (S,S)-I.80.1-I.80.2922, which differ from the corresponding compounds I.1.1-I.1.2922 or (S,S)-I.1.1-I.1.2922 in that the group $A^2R^dR^eR^f$ is 2-methoxypyridin-4-yl.

Preference is likewise given to the compounds of the formula I.81, particularly preferably the compounds I.81.1-I.81.2922, in particular the compounds (S,S)-I.81.1-I.81.2922, which differ from the corresponding compounds I.1.1-I.1.2922 or (S,S)-I.1.1-I.1.2922 in that the group $A^2R^dR^eR^f$ is 3-methoxypyridin-4-yl.

Preference is likewise given to the compounds of the formula I.82, particularly preferably the compounds I.82.1-I.82.2922, in particular the compounds (S,S)-I.82.1-I.82.2922, which differ from the corresponding compounds I.1.1-I.1.2922 or (S,S)-I.1.1-I.1.2922 in that the group $A^2R^dR^eR^f$ is 2-trifluoromethylpyridin-4-yl.

Preference is likewise given to the compounds of the formula I.83, particularly preferably the compounds I.83.1-I.83.2922, in particular the compounds (S,S)-I.83.1-I.83.2922, which differ from the corresponding compounds I.1.1-I.1.2922 or (S,S)-I.1.1-I.1.2922 in that the group $A^2R^dR^eR^f$ is 3-trifluoromethylpyridin-4-yl.

Preference is likewise given to the compounds of the formula I.84, particularly preferably the compounds I.84.1-I.84.2922, in particular the compounds (S,S)-I.84.1-I.84.2922, which differ from the corresponding compounds I.1.1-I.1.2922 or (S,S)-I.1.1-I.1.2922 in that the group $A^2R^dR^eR^f$ is 2-chloropyridin-4-yl.

Preference is likewise given to the compounds of the formula I.85, particularly preferably the compounds I.85.1-I.85.2922, in particular the compounds (S,S)-I.85.1-I.85.2922, which differ from the corresponding compounds I.1.1-I.1.2922 or (S,S)-I.1.1-I.1.2922 in that the group $A^2R^dR^eR^f$ is 3-chloropyridin-4-yl.

Preference is likewise given to the compounds of the formula I.86, particularly preferably the compounds I.86.1-I.86.29225 in particular the compounds (S,S)-I.86.1-I.86.2922, which differ from the corresponding compounds I.1.1-I.1.2922 or (S,S)-I.1.1-I.1.2922 in that the group $A^2R^dR^eR^f$ is thiophen-2-yl.

Preference is likewise given to the compounds of the formula I.87, particularly preferably the compounds I.87.1-I.87.2922, in particular the compounds (S,S)-I.87.1-I.87.2922, which differ from the corresponding compounds I.1.1-I.1.2922 or (S,S)-I.1.1-I.1.2922 in that the group $A^2R^dR^eR^f$ is 3-chlorothiophen-2-yl.

Preference is likewise given to the compounds of the formula I.88, particularly preferably the compounds I.88.1-I.88.2922, in particular the compounds (S,S)-I.88.1-I.88.2922, which differ from the corresponding compounds I.1.1-I.1.2922 or (S,S)-I.1.1-I.1.2922 in that the group $A^2R^dR^eR^f$ is 4-chlorothiophen-2-yl.

Preference is likewise given to the compounds of the formula I.89, particularly preferably the compounds I.89.1-I.89.2922, in particular the compounds (S,S)-I.89.1-I.89.2922, which differ from the corresponding compounds I.1.1-I.1.2922 or (S,S)-I.1.1-I.1.2922 in that the group $A^2R^dR^eR^f$ is 5-chlorothiophen-2-yl.

Preference is likewise given to the compounds of the formula I.90, particularly preferably the compounds I.90.1-I.90.2922, in particular the compounds (S,S)-I.90.1-I.90.2922, which differ from the corresponding compounds I.1.1-I.1.2922 or (S,S)-I.1.1-I.1.2922 in that the group $A^2R^dR^eR^f$ is 3-trifluoromethylthiophen-2-yl.

Preference is likewise given to the compounds of the formula I.91, particularly preferably the compounds I.91.1-I.91.2922, in particular the compounds (S,S)-I.91.1-I.91.2922, which differ from the corresponding compounds I.1.1-I.1.2922 or (S,S)-I.1.1-I.1.2922 in that the group $A^2R^dR^eR^f$ is 4-trifluoromethylthiophen-2-yl.

Preference is likewise given to the compounds of the formula I.92, particularly preferably the compounds I.92.1-I.92.2922, in particular the compounds (S,S)-I.92.1-I.92.29227 which differ from the corresponding compounds I.1.1-I.1.2922 or (S,S)-I.1.1-I.1.2922 in that the group $A^2R^dR^eR^f$ is 5-trifluoromethylthiophen-2-yl.

Preference is likewise given to the compounds of the formula I.93, particularly preferably the compounds I.93.1-I.93.2922, in particular the compounds (S,S)-I.93.1-I.93.2922, which differ from the corresponding compounds I.1.1-I.1.2922 or (S,S)-I.1.1-I.1.2922 in that the group $A^2R^dR^eR^f$ is 3-methoxythiophen-2-yl.

Preference is likewise given to the compounds of the formula I.94, particularly preferably the compounds I.94.1-I.94.2922, in particular the compounds (S,S)-I.94.1-I.94.2922, which differ from the corresponding compounds I.1.1-I.1.2922 or (S,S)-I.1.1-I.1.2922 in that the group $A^2R^dR^eR^f$ is 4-methoxythiophen-2-yl.

Preference is likewise given to the compounds of the formula I.95, particularly preferably the compounds I.95.1-I.95.2922, in particular the compounds (S,S)-I.95.1-I.95.2922, which differ from the corresponding compounds I.1.1-I.1.2922 or (S,S)-I.1.1-I.1.2922 in that the group $A^2R^dR^eR^f$ is 5-methoxythiophen-2-yl.

Preference is likewise given to the compounds of the formula I.96, particularly preferably the compounds I.96.1-I.96.2922, in particular the compounds (S,S)-I.96.1-I.96.2922, which differ from the corresponding compounds I.1.1-I.1.2922 or (S,S)-I.1.1-I.1.2922 in that the group $A^2R^dR^eR^f$ is 3-fluorothiophen-2-yl.

Preference is likewise given to the compounds of the formula I.97, particularly preferably the compounds I.97.1-I.97.2922, in particular the compounds (S,S)-I.97.1-I.97.2922, which differ from the corresponding compounds I.1.1-I.1.2922 or (S,S)-I.1.1-I.1.2922 in that the group $A^2R^dR^eR^f$ is 4-fluorothiophen-2-yl.

Preference is likewise given to the compounds of the formula I.98, particularly preferably the compounds I.98.1-I.98.2922, in particular the compounds (S,S)-I.98.1-I.98.2922, which differ from the corresponding compounds I.1.1-I.1.2922 or (S,S)-I.1.1-I.1.2922 in that the group $A^2R^dR^eR^f$ is 5-fluorothiophen-2-yl.

Preference is likewise given to the compounds of the formula I.99, particularly preferably the compounds I.99.1-I.99.2922, in particular the compounds (S,S)-I.99.1-I.99.2922, which differ from the corresponding compounds I.1.1-I.1.2922 or (S,S)-I.1.1-I.1.2922 in that the group $A^2R^dR^eR^f$ is thiophen-3-yl.

Preference is likewise given to the compounds of the formula I.100, particularly preferably the compounds I.100.1-I.100.2922, in particular the compounds (S,S)-I.100.1-I.100.2922, which differ from the corresponding compounds I.1.1-I.1.2922 or (S,S)-I.1.1-I.1.2922 in that the group $A^2R^dR^eR^f$ is 2-chlorothiophen-3-yl.

Preference is likewise given to the compounds of the formula I.101, particularly preferably the compounds I.101.1-I.101.2922, in particular the compounds (S,S)-I.101.1-I.101.2922, which differ from the corresponding compounds I.1.1-I.1.2922 or (S,S)-I.1.1-I.1.2922 in that the group $A^2R^dR^eR^f$ is 4-chlorothiophen-3-yl.

Preference is likewise given to the compounds of the formula I.102, particularly preferably the compounds I.102.1-I.102.2922, in particular the compounds (S,S)-I.102.1-I.102.2922, which differ from the corresponding compounds I.1.1-I.1.2922 or (S,S)-I.1.1-I.1.2922 in that the group $A^2R^dR^eR^r$ is 5-chlorothiophen-3-yl.

Preference is likewise given to the compounds of the formula I.103, particularly preferably the compounds I.103.1-I.103.2922, in particular the compounds (S,S)-I.103.1-I.103.2922, which differ from the corresponding compounds I.1.1-I.1.2922 or (S,S)-I.1.1-I.1.2922 in that the group $A^2R^dR^eR^f$ is 2-fluorothiophen-3-yl.

Preference is likewise given to the compounds of the formula I.104, particularly preferably the compounds I.104.1-I.104.2922, in particular the compounds (S,S)-I.104.1-I.104.2922, which differ from the corresponding compounds I.1.1-I.1.2922 or (S,S)-I.1.1-I.1.2922 in that the group $A^2R^dR^eR^f$ is 4-fluorothiophen-3-yl.

Preference is likewise given to the compounds of the formula I.105, particularly preferably the compounds I.105.1-I.105.2922, in particular the compounds (S,S)-I.105.1-I.105.2922, which differ from the corresponding compounds I.1.1-I.1.2922 or (S,S)-I.1.1-I.1.2922 in that the group $A^2R^dR^eR^f$ is 5-fluorothiophen-3-yl.

Preference is likewise given to the compounds of the formula I.106, particularly preferably the compounds I.106.1-I.106.2922, in particular the compounds (S,S)-I.106.1-I.106.2922, which differ from the corresponding compounds I.1.1-I.1.2922 or (S,S)-I.1.1-I.1.2922 in that the group $A^2R^dR^eR^f$ is 2-methoxythiophen-3-yl.

Preference is likewise given to the compounds of the formula I.107, particularly preferably the compounds I.107.1-I.107.2922, in particular the compounds (S,S)-I.107.1-I.107.2922, which differ from the corresponding compounds I.1.1-I.1.2922 or (S,S)-I.1.1-I.1.2922 in that the group $A^2R^dR^eR^f$ is 4-methoxythiophen-3-yl.

Preference is likewise given to the compounds of the formula I.108, particularly preferably the compounds I.108.1-I.108.2922, in particular the compounds (S,S)-I.108.1-I.108.2922, which differ from the corresponding compounds I.1.1-I.1.2922 or (S,S)-I.1.1-I.1.2922 in that the group $A^2R^dR^eR^f$ is 5-methoxythiophen-3-yl.

Preference is likewise given to the compounds of the formula I.109, particularly preferably the compounds I.109.1-I.109.2922, in particular the compounds (S,S)-I.109.1-I.109.2922, which differ from the corresponding compounds I.1.1-I.1.2922 or (S,S)-I.1.1-I.1.2922 in that the group $A^2R^dR^eR^f$ is 2-trifluoromethylthiophen-3-yl.

Preference is likewise given to the compounds of the formula I.110, particularly preferably the compounds I.110.1-I.110.2922, in particular the compounds (S,S)-I.110.1-I.110.2922, which differ from the corresponding compounds I.1.1-I.1.2922 or (S,S)-I.1.1-I.1.2922 in that the group $A^2R^dR^eR^f$ is 4-trifluoromethylthiophen-3-yl.

Preference is likewise given to the compounds of the formula I.111, particularly preferably the compounds I.111.1-I.111.2922, in particular the compounds (S,S)-I.111.1-I.111.2922, which differ from the corresponding compounds I.1.1-I.1.2922 or (S,S)-I.1.1-I.1.2922 in that the group $A^2R^dR^eR^f$ is 5-trifluoromethylthiophen-3-yl.

Preference is likewise given to the compounds of the formula I.112, particularly preferably the compounds I.112.1-I.112.2922, in particular the compounds (S,S)-I.112.1-I.112.2922, which differ from the corresponding compounds I.1.1-I.1.2922 or (S,S)-I.1.1-I.1.2922 in that the group $A^2R^dR^eR^f$ is furan-2-yl.

Preference is likewise given to the compounds of the formula I.113, particularly preferably the compounds I.113.1-I.113.2922, in particular the compounds (S,S)-I.113.1-I.113.2922, which differ from the corresponding compounds I.1.1-I.1.2922 or (S,S)-I.1.1-I.1.2922 in that the group $A^2R^dR^eR^f$ is 3-chlorofuran-2-yl.

Preference is likewise given to the compounds of the formula I.114, particularly preferably the compounds I.114.1-I.114.2922, in particular the compounds (S,S)-I.114.1-I.114.2922, which differ from the corresponding compounds I.1.1-I.1.2922 or (S,S)-I.1.1-I.1.2922 in that the group $A^2R^dR^eR^f$ is 4-chlorofuran-2-yl.

Preference is likewise given to the compounds of the formula I.115, particularly preferably the compounds I.115.1-I.115.2922, in particular the compounds (S,S)-I.115.1-I.115.2922, which differ from the corresponding compounds I.1.1-I.1.2922 or (S,S)-I.1.1-I.1.2922 in that the group $A^2R^dR^eR^f$ is 5-chlorofuran-2-yl.

Preference is likewise given to the compounds of the formula I.116, particularly preferably the compounds I.116.1-I.116.2922, in particular the compounds (S,S)-I.116.1-I.116.2922, which differ from the corresponding compounds I.1.1-I.1.2922 or (S,S)-I.1.1-I.1.2922 in that the group $A^2R^dR^eR^f$ is 3-fluorofuran-2-yl.

Preference is likewise given to the compounds of the formula I.117, particularly preferably the compounds I.117.1-I.117.2922, in particular the compounds (S,S)-I.117.1-I.117.2922, which differ from the corresponding compounds I.1.1-I.1.2922 or (S,S)-I.1.1-I.1.2922 in that the group $A^2R^dR^eR^f$ is 4-fluorofuran-2-yl.

Preference is likewise given to the compounds of the formula I.118, particularly preferably the compounds I.118.1-I.118.2922, in particular the compounds (S,S)-I.118.1-I.118.2922, which differ from the corresponding compounds I.1.1-I.1.2922 or (S,S)-I.1.1-I.1.2922 in that the group $A^2R^dR^eR^f$ is 5-fluorofuran-2-yl.

Preference is likewise given to the compounds of the formula I.119, particularly preferably the compounds I.1119.1-I.119.2922, in particular the compounds (S,S)-I.119.1-I.119.2922, which differ from the corresponding compounds I.1.1-I.1.2922 or (S,S)-I.1.1-I.1.2922 in that the group $A^2R^dR^eR^f$ is furan-3-yl.

Preference is likewise given to the compounds of the formula I.120, particularly preferably the compounds I.120.1-I.120.2922, in particular the compounds (S,S)-I.120.1-I.120.2922, which differ from the corresponding compounds I.1.1-I.1.2922 or (S,S)-I.1.1-I.1.2922 in that the group $A^2R^dR^eR^f$ is 2-chlorofuran-3-yl.

Preference is likewise given to the compounds of the formula I.121, particularly preferably the compounds I.121.1-I.121.2922, in particular the compounds (S,S)-I.121.1-I.121.2922, which differ from the corresponding compounds I.1.1-I.1.2922 or (S,S)-I.1.1-I.1.2922 in that the group $A^2R^dR^eR^f$ is 4-chlorofuran-3-yl.

Preference is likewise given to the compounds of the formula I.122, particularly preferably the compounds I.122.1-I.122.2922, in particular the compounds (S,S)-I.122.1-I.122.2922, which differ from the corresponding compounds I.1.1-I.1.2922 or (S,S)-I.1.1-I.1.2922 in that the group $A^2R^dR^eR^f$ is 5-chlorofuran-3-yl.

Preference is likewise given to the compounds of the formula I.123, particularly preferably the compounds I.123.1-I.123.2922, in particular the compounds (S,S)-I.123.1-I.123.2922, which differ from the corresponding compounds I.1.1-I.1.2922 or (S,S)-I.1.1-I.1.2922 in that the group $A^2R^dR^eR^f$ is 2-fluorofuran-3-yl.

Preference is likewise given to the compounds of the formula I.124, particularly preferably the compounds I.124.1-I.124.2922, in particular the compounds (S,S)-I.124.1-I.124.2922, which differ from the corresponding compounds I.1.1-I.1.2922 or (S,S)-I.1.1-I.1.2922 in that the group $A^2R^dR^eR^f$ is 4-fluorofuran-3-yl.

Preference is likewise given to the compounds of the formula I.125, particularly preferably the compounds I.125.1-I.125.2922, in particular the compounds (S,S)-1125.1-I.125.2922, which differ from the corresponding compounds I.1.1-I.1.2922 or (S,S)-I.1.1-I.1.2922 in that the group $A^2R^dR^eR^f$ is 5-fluorofuran-3-yl.

Preference is likewise given to the compounds of the formula I.126, particularly preferably the compounds I.126.1-I.126.2922, in particular the compounds (S,S)-I.126.1-I.126.2922, which differ from the corresponding compounds I.1.1-I.1.2922 or (S,S)-I.1.1-I.1.2922 in that the group $A^2R^dR^eR^f$ is 5-fluorofuran-3-yl.

Preference is likewise given to the compounds of the formula I.127, particularly preferably the compounds I.127.1-I.127.2922, in particular the compounds (S,S)-I.127.1-I.127.2922, which differ from the corresponding compounds I.1.1-I.1.2922 or (S,S)-I.1.1-I.1.2922 in that $R^1$ is $CH_3$.

Preference is likewise given to the compounds of the formula I.128, particularly preferably the compounds I.128.1-I.128.2922, in particular the compounds (S,S)-I.128.1-I.128.2922, which differ from the corresponding compounds I.1.1-I.1.2922 or (S,S)-I.1.1-I.1.2922 in that the group $A^2R^dR^eR^O$ is 2-chlorophenyl and $R^1$ is $CH_3$.

Preference is likewise given to the compounds of the formula I.129, particularly preferably the compounds I.129.1-I.129.2922, in particular the compounds (S,S)-I.129.1-I.129.2922, which differ from the corresponding compounds I.1.1-I.1.2922 or (S,S)-I.1.1-I.1.2922 in that the group $A^2R^dR^eR^f$ is 3-chlorophenyl and $R^1$ is $CH_3$.

Preference is likewise given to the compounds of the formula I.130, particularly preferably the compounds I.130.1-I.130.2922, in particular the compounds (S,S)-I.130.1-I.130.2922, which differ from the corresponding compounds I.1.1-I.1.2922 or (S,S)-I.1.1-I.1.2922 in that the group $A^2R^dR^eR^f$ is 4-chlorophenyl and $R^1$ is $CH_3$.

Preference is likewise given to the compounds of the formula I.131, particularly preferably the compounds I.131.1-I.131.2922, in particular the compounds (S,S)-I.131.1-I.131.2922, which differ from the corresponding compounds I.1.1-I.1.2922 or (S,S)-I.1.1-I.1.2922 in that the group $A^2R^dR^eR^f$ is 2-trifluoromethylphenyl and $R^1$ is $CH_3$.

Preference is likewise given to the compounds of the formula I.132, particularly preferably the compounds I.132.1-I.132.2922, in particular the compounds (S,S)-I.132.1-I.132.2922, which differ from the corresponding compounds I.1.1-I.1.2922 or (S,S)-I.1.1-I.1.2922 in that the group $A^2R^dR^eR^f$ is 3-trifluoromethylphenyl and $R^1$ is $CH_3$.

Preference is likewise given to the compounds of the formula I.133, particularly preferably the compounds I.133.1-I.133.2922, in particular the compounds (S,S)-I.133.1-I.133.2922, which differ from the corresponding compounds I.1.1-I.1.2922 or (S,S)-I.1.1-I.1.2922 in that the group $A^2R^dR^eR^f$ is 4-trifluoromethylphenyl and $R^1$ is $CH_3$.

Preference is likewise given to the compounds of the formula I.134, particularly preferably the compounds I.134.1-I.134.2922, in particular the compounds (S,S)-I.134.1-I.134.2922, which differ from the corresponding compounds I.1.1-I.1.2922 or (S,S)-I.1.1-I.1.2922 in that the group $A^2R^dR^eR^f$ is 2-methoxyphenyl and $R^1$ is $CH_3$.

Preference is likewise given to the compounds of the formula I.135, particularly preferably the compounds I.135.1-

I.135.2922, in particular the compounds (S,S)-I.135.1-I.135.2922, which differ from the corresponding compounds I.1.1-I.1.2922 or (S,S)-I.1.1-I.1.2922 in that the group $A^2R^dR^eR^f$ is 3-methoxyphenyl and $R^1$ is $CH_3$.

Preference is likewise given to the compounds of the formula I.136, particularly preferably the compounds I.136.1-I.136.2922, in particular the compounds (S,S)-I.136.1-I.136.2922, which differ from the corresponding compounds I.1.1-I.1.2922 or (S,S)-I.1.1-I.1.2922 in that the group $A^2R^dR^eR^f$ is 4-methoxyphenyl and $R^1$ is $CH_3$.

Preference is likewise given to the compounds of the formula I.137, particularly preferably the compounds I.137.1-I.137.2922, in particular the compounds (S,S)-I.137.1-I.137.2922, which differ from the corresponding compounds I.1.1-I.1.2922 or (S,S)-I.1.1-I.1.2922 in that the group $A^2R^dR^eR^f$ is 2-fluorophenyl and $R^1$ is $CH_3$.

Preference is likewise given to the compounds of the formula I.138, particularly preferably the compounds I.138.1-I.138.2922, in particular the compounds (S,S)-I.138.1-I.138.2922, which differ from the corresponding compounds I.1.1-I.1.2922 or (S,S)-I.1.1-I.1.2922 in that the group $A^2R^dR^eR^f$ is 3-fluorophenyl and $R^1$ is $CH_3$.

Preference is likewise given to the compounds of the formula I.139, particularly preferably the compounds I.139.1-I.139.2922, in particular the compounds (S,S)-I.139.1-I.139.2922, which differ from the corresponding compounds I.1.1-I.1.2922 or (S,S)-I.1.1-I.1.2922 in that the group $A^2R^dR^eR^f$ is 4-fluorophenyl and $R^1$ is $CH_3$.

Preference is likewise given to the compounds of the formula I.140, particularly preferably the compounds I.140.1-I.140.2922, in particular the compounds (S,S)-I.140.1-I.140.2922, which differ from the corresponding compounds I.1.1-I.1.2922 or (S,S)-I.1.1-I.1.2922 in that the group $A^2R^dR^eR^f$ is 2-methylphenyl and $R^1$ is $CH_3$.

Preference is likewise given to the compounds of the formula I.141, particularly preferably the compounds I.141.1-I.141.2922, in particular the compounds (S,S)-I.141.1-I.141.2922, which differ from the corresponding compounds I.1.1-I.1.2922 or (S,S)-I.1.1-I.1.2922 in that the group $A^2R^dR^eR^f$ is 3-methylphenyl and $R^1$ is $CH_3$.

Preference is likewise given to the compounds of the formula I.142, particularly preferably the compounds I.142.1-I.142.2922, in particular the compounds (S,S)-I.142.1-I.142.2922, which differ from the corresponding compounds I.1.1-I.1.2922 or (S,S)-I.1.1-I.1.2922 in that the group $A^2R^dR^eR^f$ is 4-methylphenyl and $R^1$ is $CH_3$.

Preference is likewise given to the compounds of the formula I.143, particularly preferably the compounds I.143.1-I.143.2922, in particular the compounds (S,S)-I.143.1-I.143.2922, which differ from the corresponding compounds I.1.1-I.1.2922 or (S,S)-I.1.1-I.1.2922 in that the group $A^2R^dR^eR^f$ is 2-chloro-3-methylphenyl and $R^1$ is $CH_3$.

Preference is likewise given to the compounds of the formula I.144, particularly preferably the compounds I.144.1-I.144.2922, in particular the compounds (S,S)-I.144.1-I.144.2922, which differ from the corresponding compounds I.1.1-I.1.2922 or (S,S)-I.1.1-I.1.2922 in that the group $A^2R^dR^eR^f$ is 2-chloro-4-methylphenyl and $R^1$ is $CH_3$.

Preference is likewise given to the compounds of the formula I.145, particularly preferably the compounds I.145.1-I.145.2922, which differ from the corresponding compounds I.1.1-I.1.2922 or (S,S)-I.1.1-I.1.2922 in that the group $A^2R^dR^eR^f$ is 2-chloro-5-methylphenyl and $R^1$ is $CH_3$.

Preference is likewise given to the compounds of the formula I.146, particularly preferably the compounds I.146.1-I.146.29225 in particular the compounds (S,S)-I.146.1-I.146.2922, which differ from the corresponding compounds I.1.1-I.1.2922 or (S,S)-I.1.1-I.1.2922 in that the group $A^2R^dR^eR^f$ is 2-chloro-6-methylphenyl and $R^1$ is $CH_3$.

Preference is likewise given to the compounds of the formula I.147, particularly preferably the compounds I.147.1-I.147.2922, in particular the compounds (S,S)-I.147.1-I.147.2922, which differ from the corresponding compounds I.1.1-I.1.2922 or (S,S)-I.1.1-I.1.2922 in that the group $A^2R^dR^eR^r$ is 2,3-dichlorophenyl and $R^1$ is $CH_3$.

Preference is likewise given to the compounds of the formula I.148, particularly preferably the compounds I.148.1-I.148.2922, in particular the compounds (S,S)-I.148.1-I.148.2922, which differ from the corresponding compounds I.1.1-I.1.2922 or (S,S)-I.1.1-I.1.2922 in that the group $A^2R^dR^eR^f$ is 2,4-dichlorophenyl and $R^1$ is $CH_3$.

Preference is likewise given to the compounds of the formula I.149, particularly preferably the compounds I.149.1-I.149.2922, in particular the compounds (S,S)-I.149.1-I.149.2922, which differ from the corresponding compounds I.1.1-I.1.2922 or (S,S)-I.1.1-I.1.2922 in that the group $A^2R^dR^eR^f$ is 2,5-dichlorophenyl and $R^1$ is $CH_3$.

Preference is likewise given to the compounds of the formula I.150, particularly preferably the compounds I.150.1-I.150.2922, in particular the compounds (S,S)-I.150.1-I.150.2922, which differ from the corresponding compounds I.1.1-I.1.2922 or (S,S)-I.1.1-I.1.2922 in that the group $A^2R^dR^eR^f$ is 2,6-dichlorophenyl and $R^1$ is $CH_3$.

Preference is likewise given to the compounds of the formula I.151, particularly preferably the compounds I.151.1-I.151.2922, in particular the compounds (S,S)-I.151.1-I.151.2922, which differ from the corresponding compounds I.1.1-I.1.2922 or (S,S)-I.1.1-I.1.2922 in that the group $A^2R^dR^eR^f$ is 2-chloro-3-fluorophenyl and $R^1$ is $CH_3$.

Preference is likewise given to the compounds of the formula I.152, particularly preferably the compounds I.152.1-I.152.2922, in particular the compounds (S,S)-I.152.1-I.152.2922, which differ from the corresponding compounds I.1.1-I.1.2922 or (S,S)-I.1.1-I.1.2922 in that the group $A^2R^dR^eR^f$ is 2-chloro-4-fluorophenyl and $R^1$ is $CH_3$.

Preference is likewise given to the compounds of the formula I.153, particularly preferably the compounds I.153.1-I.153.2922, in particular the compounds (S,S)-I.153.1-I.153.2922, which differ from the corresponding compounds I.1.1-I.1.2922 or (S,S)-I.1.1-I.1.2922 in that the group $A^2R^dR^eR^f$ is 2-chloro-5-fluorophenyl and $R^1$ is $CH_3$.

Preference is likewise given to the compounds of the formula I.154, particularly preferably the compounds I.154.1-I.154.2922, in particular the compounds (S,S)-I.154.1-I.154.2922, which differ from the corresponding compounds I.1.1-I.1.2922 or (S,S)-I.1.1-I.1.2922 in that the group $A^2R^dR^eR^f$ is 2-chloro-6-fluorophenyl and $R^1$ is $CH_3$.

Preference is likewise given to the compounds of the formula I.155, particularly preferably the compounds I.155.1-I.155.2922, in particular the compounds (S,S)-I.155.1-I.155.2922, which differ from the corresponding compounds I.1.1-I.1.2922 or (S,S)-I.1.1-I.1.2922 in that the group $A^2R^dR^eR^f$ is 2,3-difluorophenyl and $R^1$ is $CH_3$.

Preference is likewise given to the compounds of the formula I.156, particularly preferably the compounds I.156.1-I.156.2922, in particular the compounds (S,S)-I.156.1-I.156.2922, which differ from the corresponding compounds I.1.1-I.1.2922 or (S,S)-I.1.1-I.1.2922 in that the group $A^2R^dR^eR^f$ is 2,4-difluorophenyl and $R^1$ is $CH_3$.

Preference is likewise given to the compounds of the formula I.157, particularly preferably the compounds I.57.1-I.157.2922, in particular the compounds (S,S)-I.157.1-I.157.2922, which differ from the corresponding compounds I.1.1-I.1.2922 or (S,S)-I.1.1-I.1.2922 in that the group $A^2R^dR^eR^f$ is 2,5-difluorophenyl and $R^1$ is $CH_3$.

Preference is likewise given to the compounds of the formula I.158, particularly preferably the compounds I.158.1-I.158.2922, in particular the compounds (S,S)-I.158.1-I.158.2922, which differ from the corresponding compounds I.1.1-I.1.2922 or (S,S)-I.1.1-I.1.2922 in that the group $A^2R^dR^eR^f$ is 2,6-difluorophenyl and $R^1$ is $CH_3$.

Preference is likewise given to the compounds of the formula I.159, particularly preferably the compounds I.159.1-I.159.2922, in particular the compounds (S,S)-I.159.1-I.159.2922, which differ from the corresponding compounds I.1.1-I.1.2922 or (S,S)-I.1.1-I.1.2922 in that the group $A^2R^dR^eR^f$ is 2-fluoro-3-chlorophenyl and $R^1$ is $CH_3$.

Preference is likewise given to the compounds of the formula I.160, particularly preferably the compounds I.160.1-I.160.2922, in particular the compounds (S,S)-I.160.1-I.160.2922, which differ from the corresponding compounds I.1.1-I.1.2922 or (S,S)-I.1.1-I.1.2922 in that the group $A^2R^dR^eR^f$ is 2-fluoro-4-chlorophenyl and $R^1$ is $CH_3$.

Preference is likewise given to the compounds of the formula I.161, particularly preferably the compounds I.161.1-I.161.2922, in particular the compounds (S,S)-I.161.1-I.161.2922, which differ from the corresponding compounds I.1.1-I.1.2922 or (S,S)-I.1.1-I.1.2922 in that the group $A^2R^dR^eR^f$ is 2-fluoro-5-chlorophenyl and $R^1$ is $CH_3$.

Preference is likewise given to the compounds of the formula I.162, particularly preferably the compounds I.162.1-I.162.2922, in particular the compounds (S,S)-I.162.1-I.162.2922, which differ from the corresponding compounds I.1.1-I.1.2922 or (S,S)-I.1.1-I.1.2922 in that the group $A^2R^dR^eR^f$ is 3,4-difluorophenyl and $R^1$ is $CH_3$.

Preference is likewise given to the compounds of the formula I.163, particularly preferably the compounds I.163.1-I.163.2922, in particular the compounds (S,S)-I.163.1-I.163.2922, which differ from the corresponding compounds I.1.1-I.1.2922 or (S,S)-I.1.1-I.1.2922 in that the group $A^2R^dR^eR^f$ is 3,5-difluorophenyl and $R^1$ is $CH_3$.

Preference is likewise given to the compounds of the formula I.164, particularly preferably the compounds I.164.1-I.164.2922, in particular the compounds (S,S)-I.164.1-I.164.2922, which differ from the corresponding compounds I.1.1-I.1.2922 or (S,S)-I.1.1-I.1.2922 in that the group $A^2R^dR^eR^f$ is 3,4-dichlorophenyl and $R^1$ is $CH_3$.

Preference is likewise given to the compounds of the formula I.165, particularly preferably the compounds I.165.1-I.165.2922, in particular the compounds (S,S)-I.165.1-I.165.2922, which differ from the corresponding compounds I.1.1-I.1.2922 or (S,S)-I.1.1-I.1.2922 in that the group $A^2R^dR^eR^f$ is 3,5-dichlorophenyl and $R^1$ is $CH_3$.

Preference is likewise given to the compounds of the formula I.166, particularly preferably the compounds I.166.1-I.166.2922, in particular the compounds (S,S)-I.166.1-I.166.2922, which differ from the corresponding compounds I.1.1-I.1.2922 or (S,S)-I.1.1-I.1.2922 in that the group $A^2R^dR^eR^f$ is 3-fluoro,4-chlorophenyl and $R^1$ is $CH_3$.

Preference is likewise given to the compounds of the formula I.167, particularly preferably the compounds I.167.1-I.167.2922, in particular the compounds (S,S)-I.167.1-I.167.2922, which differ from the corresponding compounds I.1.1-I.1.2922 or (S,S)-I.1.1-I.1.2922 in that the group $A^2R^dR^eR^f$ is 4-fluoro,3-chlorophenyl and $R^1$ is $CH_3$.

Preference is likewise given to the compounds of the formula I.168, particularly preferably the compounds I.168.1-I.168.2922, in particular the compounds (S,S)-I.168.1-I.168.2922, which differ from the corresponding compounds I.1.1-I.1.2922 or (S,S)-I.1.1-I.1.2922 in that the group $A^2R^dR^eR^f$ is 3-fluoro,5-chlorophenyl and $R^1$ is $CH_3$.

Preference is likewise given to the compounds of the formula I.169, particularly preferably the compounds I.169.1-I.169.2922, in particular the compounds (S,S)-I.169.1-I.169.2922, which differ from the corresponding compounds I.1-I.1.2922 or (S,S)-I.1.1-I.1.2922 in that the group $A^2R^dR^eR^f$ is pyridin-2-yl and $R^1$ is $CH_3$.

Preference is likewise given to the compounds of the formula I.170, particularly preferably the compounds I.170.1-I.170.2922, in particular the compounds (S,S)-I.170.1-I.170.2922, which differ from the corresponding compounds I.1.1-I.1.2922 or (S,S)-I.1.1-I.1.2922 in that the group $A^2R^dR^eR^f$ is 3-chloropyridin-2-yl and $R^1$ is $CH_3$.

Preference is likewise given to the compounds of the formula I.171, particularly preferably the compounds I.171.1-I.171.2922, in particular the compounds (S,S)-I.171.1-I.171.2922, which differ from the corresponding compounds I.1.1-I.1.2922 or (S,S)-I.1.1-I.1.2922 in that the group $A^2R^dR^eR^f$ is 4-chloropyridin-2-yl and $R^1$ is $CH_3$.

Preference is likewise given to the compounds of the formula I.172, particularly preferably the compounds I.172.1-I.172.2922, in particular the compounds (S,S)-I.172.1-I.172.2922, which differ from the corresponding compounds I.1.1-I.1.2922 or (S,S)-I.1.1-I.1.2922 in that the group $A^2R^dR^eR^f$ is 5-chloropyridin-2-yl and $R^1$ is $CH_3$.

Preference is likewise given to the compounds of the formula I.173, particularly preferably the compounds I.173.1-I.173.2922, in particular the compounds (S,S)-I.173.1-I.173.2922, which differ from the corresponding compounds I.1.1-I.1.2922 or (S,S)-I.1.1-I.1.2922 in that the group $A^2R^dR^eR^f$ is 6-chloropyridin-2-yl and $R^1$ is $CH_3$.

Preference is likewise given to the compounds of the formula I.174, particularly preferably the compounds I.174.1-I.174.2922, in particular the compounds (S,S)-I.174.1-I.174.2922, which differ from the corresponding compounds I.1.1-I.1.2922 or (S,S)-I.1.1-I.1.2922 in that the group $A^2R^dR^eR^f$ is 3-trifluoromethylpyridin-2-yl and $R^1$ is $CH_3$.

Preference is likewise given to the compounds of the formula I.175, particularly preferably the compounds I.175.1-I.175.2922, in particular the compounds (S,S)-I.175.1-I.175.2922, which differ from the corresponding compounds I.1.1-I.1.2922 or (S,S)-I.1.1-I.1.2922 in that the group $A^2R^dR^dR^f$ is 4-trifluoromethylpyridin-2-yl and $R^1$ is $CH_3$.

Preference is likewise given to the compounds of the formula I.176, particularly preferably the compounds I.176.1-I.176.2922, in particular the compounds (S,S)-I.176.1-I.176.2922, which differ from the corresponding compounds I.1-I.1.2922 or (S,S)-I.1.1-I.1.2922 in that the group $A^2R^dR^eR^f$ is 5-trifluoromethylpyridin-2-yl and $R^1$ is $CH_3$.

Preference is likewise given to the compounds of the formula I.177, particularly preferably the compounds I.177.1-I.177.2922, in particular the compounds (S,S)-I.177.1-I.177.2922, which differ from the corresponding compounds I.1.1-I.1.2922 or (S,S)-I.1.1-I.1.2922 in that the group $A^2R^dR^eR^f$ is 6-trifluoromethylpyridin-2-yl and $R^1$ is $CH_3$.

Preference is likewise given to the compounds of the formula I.178, particularly preferably the compounds I.178.1-I.178.2922, in particular the compounds (S,S)-I.178.1-I.178.2922, which differ from the corresponding compounds I.1.1-I.1.2922 or (S,S)-I.1.1-I.1.2922 in that the group $A^2R^dR^eR^f$ is 3-methoxypyridin-2-yl and $R^1$ is $CH_3$.

Preference is likewise given to the compounds of the formula I.179, particularly preferably the compounds I.179.1-I.179.2922, in particular the compounds (S,S)-I.179.1-I.179.2922, which differ from the corresponding compounds Preference is likewise given to the compounds of the formula I.180, particularly preferably the compounds I.180.1-I.180.2922, in particular the compounds (S,S)-I.180.1-I.180.2922, which differ from the corresponding compounds I.1.1-I.1.2922 or (S,S)-I.1.1-I.1.2922 in that the group $A^2R^dR^eR^f$ is 5-methoxypyridin-2-yl and $R^1$ is $CH_3$.

Preference is likewise given to the compounds of the formula I.181, particularly preferably the compounds I.181.1-I.181.2922, in particular the compounds (S,S)-I.181.1-I.181.2922, which differ from the corresponding compounds I.1.1-I.1.2922 or (S,S)-I.1.1-I.1.2922 in that the group $A^2R^dR^eR^f$ is 6-methoxypyridin-2-yl and $R^1$ is $CH_3$.

Preference is likewise given to the compounds of the formula I.182, particularly preferably the compounds I.182.1-I.182.2922, in particular the compounds (S,S)-I.182.1-I.182.2922, which differ from the corresponding compounds I.1.1-I.1.2922 or (S,S)-I.1.1-I.1.2922 in that the group $A^2R^dR^eR^f$ is 3-fluoropyridin-2-yl and $R^1$ is $CH_3$.

Preference is likewise given to the compounds of the formula I.183, particularly preferably the compounds I.183.1-I.183.2922, in particular the compounds (S,S)-I.183.1-I.183.2922, which differ from the corresponding compounds I.1.1-I.1.2922 or (S,S)-I.1.1-I.1.2922 in that the group $A^2R^dR^eR^f$ is 4-fluoropyridin-2-yl and $R^1$ is $CH_3$.

Preference is likewise given to the compounds of the formula I.184, particularly preferably the compounds I.184.1-I.184.2922, in particular the compounds (S,S)-I.184.1-I.184.2922, which differ from the corresponding compounds I.1.1-I.1.2922 or (S,S)-I.1.1-I.1.2922 in that the group $A^2R^dR^eR^f$ is 5-fluoropyridin-2-yl and $R^1$ is $CH_3$.

Preference is likewise given to the compounds of the formula I.185, particularly preferably the compounds I.185.1-I.185.2922, in particular the compounds (S,S)-I.185.1-I.185.2922, which differ from the corresponding compounds I.1.1-I.1.2922 or (S,S)-I.1.1-I.1.2922 in that the group $A^2R^dR^eR^f$ is 6-fluoropyridin-2-yl and $R^1$ is $CH_3$.

Preference is likewise given to the compounds of the formula I.186, particularly preferably the compounds I.186.1-I.186.2922, in particular the compounds (S,S)-I.186.1-I.186.2922, which differ from the corresponding compounds I.1.1-I.1.2922 or (S,S)-I.1.1-I.1.2922 in that the group $A^2R^dR^eR^f$ is pyridin-3-yl and $R^1$ is $CH_3$.

Preference is likewise given to the compounds of the formula I.187, particularly preferably the compounds I.187.1-I.187.2922, in particular the compounds (S,S)-I.187.1-I.187.2922, which differ from the corresponding compounds I.1.1-I.1.2922 or (S,S)-I.1.1-I.1.2922 in that the group $A^2R^dR^eR^f$ is 2-chloropyridin-3-yl and $R^1$ is $CH_3$.

Preference is likewise given to the compounds of the formula I.188, particularly preferably the compounds I.188.1-I.188.2922, in particular the compounds (S,S)-I.188.1-I.188.2922, which differ from the corresponding compounds I.1.1-I.1.2922 or (S,S)-I.1.1-I.1.2922 in that the group $A^2R^dR^eR^f$ is 4-chloropyridin-3-yl and $R^1$ is $CH_3$.

Preference is likewise given to the compounds of the formula I.189, particularly preferably the compounds I.189.1-I.189.2922, in particular the compounds (S,S)-I.189.1-I.189.2922, which differ from the corresponding compounds I.1.1-I.1.2922 or (S,S)-I.1.1-I.1.2922 in that the group $A^2R^dR^eR^f$ is 5-chloropyridin-3-yl and $R^1$ is $CH_3$.

Preference is likewise given to the compounds of the formula I.190, particularly preferably the compounds I.190.1-I.190.2922, in particular the compounds (S,S)-I.190.1-I.190.2922, which differ from the corresponding compounds I.1.1-I.1.2922 or (S,S)-I.1.1-I.1.2922 in that the group $A^2R^dR^eR^f$ is 6-chloropyridin-3-yl and $R^1$ is $CH_3$.

Preference is likewise given to the compounds of the formula I.191, particularly preferably the compounds I.191.1-I.191.2922, in particular the compounds (S,S)-I.191.1-I.191.2922, which differ from the corresponding compounds I.1.1-I.1.2922 or (S,S)-I.1.1-I.1.2922 in that the group $A^2R^dR^eR^f$ is 2-trifluoromethylpyridin-3-yl and $R^1$ is $CH_3$.

Preference is likewise given to the compounds of the formula I.192, particularly preferably the compounds I.192.1-I.192.2922, in particular the compounds (S,S)-I.192.1-I.192.2922, which differ from the corresponding compounds I.1.1-I.1.2922 or (S,S)-I.1.1-I.1.2922 in that the group $A^2R^dR^eR^f$ is 4-trifluoromethylpyridin-3-yl and $R^1$ is $CH_3$.

Preference is likewise given to the compounds of the formula I.193, particularly preferably the compounds I.193.1-I.193.2922, in particular the compounds (S,S)-I.193.1-I.193.2922, which differ from the corresponding compounds I.1.1-I.1.2922 or (S,S)-I.1.1-I.1.2922 in that the group $A^2R^dR^eR^f$ is 5-trifluoromethylpyridin-3-yl and $R^1$ is $CH_3$.

Preference is likewise given to the compounds of the formula I.194, particularly preferably the compounds I.194.1-I.194.2922, in particular the compounds (S,S)-I.194.1-I.194.2922, which differ from the corresponding compounds I.1.1-I.1.2922 or (S,S)-I.1.1-I.1.2922 in that the group $A^2R^dR^eR^f$ is 6-trifluoromethylpyridin-3-yl and $R^1$ is $CH_3$.

Preference is likewise given to the compounds of the formula I.195, particularly preferably the compounds I.195.1-I.195.2922, in particular the compounds (S,S)-I.195.1-I.195.2922, which differ from the corresponding compounds I.1.1-I.1.2922 or (S,S)-I.1.1-I.1.2922 in that the group $A^2R^dR^eR^f$ is 2-methoxypyridin-3-yl and $R^1$ is $CH_3$.

Preference is likewise given to the compounds of the formula I.196, particularly preferably the compounds I.196.1-I.196.2922, in particular the compounds (S,S)-I.196.1-I.196.2922, which differ from the corresponding compounds I.1.1-I.1.2922 or (S,S)-I.1.1-I.1.2922 in that the group $A^2R^dR^eR^f$ is 4-methoxypyridin-3-yl and $R^1$ is $CH_3$.

Preference is likewise given to the compounds of the formula I.197, particularly preferably the compounds I.197.1-I.197.2922, in particular the compounds (S,S)-I.197.1-I.197.2922, which differ from the corresponding compounds I.1.1-I.1.2922 or (S,S)-I.1.1-I.1.2922 in that the group $A^2R^dR^eR^f$ is 5-methoxypyridin-3-yl and $R^1$ is $CH_3$.

Preference is likewise given to the compounds of the formula I.198, particularly preferably the compounds I.198.1-I.198.2922, in particular the compounds (S,S)-I.198.1-I.198.2922, which differ from the corresponding compounds I.1.1-I.1.2922 or (S,S)-I.1.1-I.1.2922 in that the group $A^2R^dR^eR^f$ is 6-methoxypyridin-3-yl and $R^1$ is $CH_3$.

Preference is likewise given to the compounds of the formula I.199, particularly preferably the compounds I.199.1-I.199.2922, in particular the compounds (S,S)-I.199.1-I.199.2922, which differ from the corresponding compounds I.1.1-I.1.2922 or (S,S)-I.1.1-I.1.2922 in that the group $A^2R^dR^eR^f$ is 2-fluoropyridin-3-yl and $R^1$ is $CH_3$.

Preference is likewise given to the compounds of the formula I.200, particularly preferably the compounds I.200.1-I.200.2922, in particular the compounds (S,S)-I.200.1-I.200.2922, which differ from the corresponding compounds I.1.1-I.1.2922 or (S,S)-I.1.1-I.1.2922 in that the group $A^2R^dR^eR^f$ is 4-fluoropyridin-3-yl and $R^1$ is $CH_3$.

Preference is likewise given to the compounds of the formula I.201, particularly preferably the compounds I.201.1-I.201.2922, in particular the compounds (S,S)-I.201.1-I.201.2922, which differ from the corresponding compounds I.1.1-I.1.2922 or (S,S)-I.1.1-I.1.2922 in that the group $A^2R^dR^eR^f$ is 5-fluoropyridin-3-yl and $R^1$ is $CH_3$.

Preference is likewise given to the compounds of the formula I.202, particularly preferably the compounds I.202.1-I.202.2922, in particular the compounds (S,S)-I.202.1-I.202.2922, which differ from the corresponding compounds I.1.1-I.1.2922 or (S,S)-I.1.1-I.1.2922 in that the group $A^2R^dR^eR^f$ is 6-fluoropyridin-3-yl and $R^1$ is $CH_3$ Preference is likewise given to the compounds of the formula I.203, particularly preferably the compounds I.203.1-I.203.2922, in particular the compounds (S,S)-I.203.1-I.203.2922, which differ from the corresponding compounds I.1.1-I.1.2922 or (S,S)-I.1.1-I.1.2922 in that the group $A^2R^dR^eR^f$ is pyridin-4-yl and $R^1$ is $CH_3$.

Preference is likewise given to the compounds of the formula I.204, particularly preferably the compounds I.204.1-I.204.2922, in particular the compounds (S,S)-I.204.1-I.204.2922, which differ from the corresponding compounds I.1.1-I.1.2922 or (S,S)-I.1.1-I.1.2922 in that the group $A^2R^dR^eR^f$ is 2-fluoropyridin-4-yl and $R^1$ is $CH_3$.

Preference is likewise given to the compounds of the formula I.205, particularly preferably the compounds I.205.1-I.205.2922, in particular the compounds (S,S)-I.205.1-I.205.2922, which differ from the corresponding compounds I.1.1-I.1.2922 or (S,S)-I.1.1-I.1.2922 in that the group $A^2R^dR^dR^f$ is 3-fluoropyridin-4-yl and $R^1$ is $CH_3$.

Preference is likewise given to the compounds of the formula I.206, particularly preferably the compounds I.206.1-I.206.2922, in particular the compounds (S,S)-I.206.1-I.206.2922, which differ from the corresponding compounds I.1.1-I.1.2922 or (S,S)-I.1.1-I.1.2922 in that the group $A^2R^dR^eR^f$ is 2-methoxypyridin-4-yl and $R^1$ is $CH_3$.

Preference is likewise given to the compounds of the formula I.207, particularly preferably the compounds I.207.1-I.207.2922, in particular the compounds (S,S)-I.207.1-I.207.2922, which differ from the corresponding compounds I.1.1-I.1.2922 or (S,S)-I.1.1-I.1.2922 in that the group $A^2R^dR^eR^f$ is 3-methoxypyridin-4-yl and $R^1$ is $CH_3$.

Preference is likewise given to the compounds of the formula I.208, particularly preferably the compounds I.208.1-I.208.2922, in particular the compounds (S,S)-I.208.1-I.208.2922, which differ from the corresponding compounds I.1.1-I.1.2922 or (S,S)-I.1.1-I.1.2922 in that the group $A^2R^dR^eR^f$ is 2-trifluoromethylpyridin-4-yl and $R^1$ is $CH_3$.

Preference is likewise given to the compounds of the formula I.209, particularly preferably the compounds I.209.1-I.209.2922, in particular the compounds (S,S)-I.209.1-I.209.2922, which differ from the corresponding compounds I.1.1-I.1.2922 or (S,S)-I.1.1-I.1.12922 in that the group $A^2R^dR^eR^f$ is 3-trifluoromethylpyridin-4-yl and $R^1$ is $CH_3$.

Preference is likewise given to the compounds of the formula I.210, particularly preferably the compounds I.210.1-I.210.2922, in particular the compounds (S,S)-I.210.1-I.210.2922, which differ from the corresponding compounds I.1.1-I.1.2922 or (S,S)-I.1.1-I.1.2922 in that the group $A^2R^dR^eR^f$ is 2-chloropyridin-4-yl and $R^1$ is $CH_3$.

Preference is likewise given to the compounds of the formula I.211, particularly preferably the compounds I.211.1-I.211.2922, in particular the compounds (S,S)-I.211.1-I.211.2922, which differ from the corresponding compounds I.1.1-I.1.2922 or (S,S)-I.1.1-I.1.2922 in that the group $A^2R^dR^dR^f$ is 3-chloropyridin-4-yl and $R^1$ is $CH_3$.

Preference is likewise given to the compounds of the formula I.212, particularly preferably the compounds I.212.1-I.212.2922, in particular the compounds (S,S)-I.212.1-I.212.2922, which differ from the corresponding compounds I.1.1-I.1.2922 or (S,S)-I.1.1-I.1.2922 in that the group $A^2R^dR^eR^f$ is thiophen-2-yl and $R^1$ is $CH_3$.

Preference is likewise given to the compounds of the formula I.213, particularly preferably the compounds I.213.1-I.213.2922, in particular the compounds (S,S)-I.213.1-I.213.2922, which differ from the corresponding compounds I.1.1-I.1.2922 or (S,S)-I.1.1-I.1.2922 in that the group $A^2R^dR^eR^f$ is 3-chlorothiophen-2-yl and $R^1$ is $CH_3$.

Preference is likewise given to the compounds of the formula I.2147 particularly preferably the compounds I.214.1-I.214.2922, in particular the compounds (S,S)-I.214.1-I.214.2922, which differ from the corresponding compounds I.1.1-I.1.2922 or (S,S)-I.1.1-I.1.2922 in that the group $A^2R^dR^eR^f$ is 4-chlorothiophen-2-yl and $R^1$ is $CH_3$.

Preference is likewise given to the compounds of the formula I.215, particularly preferably the compounds I.215.1-I.215.2922, in particular the compounds (S,S)-I.215.1-I.215.2922, which differ from the corresponding compounds I.1.1-I.1.2922 or (S,S)-I.1.1-I.1.2922 in that the group $A^2R^dR^eR^f$ is 5-chlorothiophen-2-yl and $R^1$ is $CH_3$.

Preference is likewise given to the compounds of the formula I.216, particularly preferably the compounds I.216.1-I.216.2922, in particular the compounds (S,S)-I.216.1-I.216.2922, which differ from the corresponding compounds I.1.1-I.1.2922 or (S,S)-I.1.1-I.1.2922 in that the group $A^2R^dR^eR^f$ is 3-trifluoromethylthiophen-2-yl and $R^1$ is $CH_3$.

Preference is likewise given to the compounds of the formula I.217, particularly preferably the compounds I.217.1-I.217.2922, in particular the compounds (S,S)-I.217.1-I.217.2922, which differ from the corresponding compounds I.1.1-I.1.2922 or (S,S)-I.1.1-I.1.2922 in that the group $A^2R^dR^eR^f$ is 4-trifluoromethylthiophen-2-yl and $R^1$ is $CH_3$.

Preference is likewise given to the compounds of the formula I.218, particularly preferably the compounds I.218.1-I.218.2922, in particular the compounds (S,S)-I.218.1-I.218.2922, which differ from the corresponding compounds I.1.1-I.1.2922 or (S,S)-I.1.1-I.1.2922 in that the group $A^2R^dR^eR^f$ is 5-trifluoromethylthiophen-2-yl and $R^1$ is $CH_3$.

Preference is likewise given to the compounds of the formula I.219, particularly preferably the compounds I.219.1-I.219.2922, in particular the compounds (S,S)-I.219.1-I.219.2922, which differ from the corresponding compounds I.1.1-I.1.2922 or (S,S)-I.1.1-I.1.2922 in that the group $A^2R^dR^eR^f$ is 3-methoxythiophen-2-yl and $R^1$ is $CH_3$.

Preference is likewise given to the compounds of the formula I.220, particularly preferably the compounds I.220.1-I.220.2922, in particular the compounds (S,S)-I.220.1-I.220.2922, which differ from the corresponding compounds I.1.1-I.1.2922 or (S,S)-I.1.1-I.1.2922 in that the group $A^2R^dR^eR^f$ is 4-methoxythiophen-2-yl and $R^1$ is $CH_3$.

Preference is likewise given to the compounds of the formula I.221, particularly preferably the compounds I.221.1-I.221.2922, in particular the compounds (S,S)-I.221.1-I.221.2922, which differ from the corresponding compounds I.1.1-I.1.2922 or (S,S)-I.1.1-I.1.2922 in that the group $A^2R^dR^eR^f$ is 5-methoxythiophen-2-yl and $R^1$ is $CH_3$.

Preference is likewise given to the compounds of the formula I.222, particularly preferably the compounds I.222.1-I.222.2922, in particular the compounds (S,S)-I.222.1-I.222.2922, which differ from the corresponding compounds I.1.1-I.1.2922 or (S,S)-I.1.1-I.1.2922 in that the group $A^2R^dR^eR^f$ is 3-fluorothiophen-2-yl and $R^1$ is $CH_3$.

Preference is likewise given to the compounds of the formula I.223, particularly preferably the compounds I.223.1-I.223.2922, in particular the compounds (S,S)-I.223.1-I.223.2922, which differ from the corresponding compounds I.1.1-I.1.2922 or (S,S)-I.1.1-I 1.2922 in that the group $A^2R^dR^eR^f$ is 4-fluorothiophen-2-yl and $R^1$ is $CH_3$.

Preference is likewise given to the compounds of the formula I.224, particularly preferably the compounds I.224.1-I.224.2922, in particular the compounds (S,S)-I.224.1-I.224.2922, which differ from the corresponding compounds I.1.1-I.1.2922 or (S,S)-I.1.1-I.1.2922 in that the group $A^2R^dR^eR^f$ is 5-fluorothiophen-2-yl and $R^1$ is $CH_3$.

Preference is likewise given to the compounds of the formula I.225, particularly preferably the compounds I.225.1-I.225.2922, in particular the compounds (S,S)-I.225.1-I.225.2922, which differ from the corresponding compounds I.1.1-I.1.2922 or (S,S)-I.1.1-I.1.2922 in that the group $A^2R^dR^eR^f$ is thiophen-3-yl and $R^1$ is $CH_3$.

Preference is likewise given to the compounds of the formula I.226, particularly preferably the compounds I.226.1-I.226.2922, in particular the compounds (S,S)-I.226.1-I.226.2922, which differ from the corresponding compounds I.1.1-I.1.2922 or (S,S)-I.1.1-I.1.2922 in that the group $A^2R^dR^eR^f$ is 2-chlorothiophen-3-yl and $R^1$ is $CH_3$.

Preference is likewise given to the compounds of the formula I.227, particularly preferably the compounds I.227.1-I.227.2922, in particular the compounds (S,S)-I.227.1-I.227.2922, which differ from the corresponding compounds I.1.1-I.1.2922 or (S,S)-I.1.1-I.1.2922 in that the group $A^2R^dR^dR^f$ is 4-chlorothiophen-3-yl and $R^1$ is $CH_3$.

Preference is likewise given to the compounds of the formula I.228, particularly preferably the compounds I.228.1-I.228.2922, in particular the compounds (S,S)-I228.1-I.228.2922, which differ from the corresponding compounds I.1.1-I.1.2922 or (S,S)-I.1.1-I.1.2922 in that the group $A^2R^dR^eR^f$ is 5-chlorothiophen-3-yl and $R^1$ is $CH_3$.

Preference is likewise given to the compounds of the formula I.229, particularly preferably the compounds I.229.1-I.229.2922, in particular the compounds (S,S)-I.229.1-I.229.2922, which differ from the corresponding compounds I.1.1-I.1.2922 or (S,S)-I.1.1-I.1.2922 in that the group $A^2R^dR^eR^f$ is 2-fluorothiophen-3-yl and $R^1$ is $CH_3$.

Preference is likewise given to the compounds of the formula I.230, particularly preferably the compounds I.230.1-I.230.2922, in particular the compounds (S,S)-I.230.1-I.230.2922, which differ from the corresponding compounds I.1.1-I.1.2922 or (S,S)-I.1.1-I.1.2922 in that the group $A^2R^dR^eR^f$ is 4-fluorothiophen-3-yl and $R^1$ is $CH_3$.

Preference is likewise given to the compounds of the formula I.231, particularly preferably the compounds I.231.1-I.231.2922, in particular the compounds (S,S)-I.231.1-I.231.2922, which differ from the corresponding compounds I.1.1-I.1.2922 or (S,S)-I.1.1-I.1.2922 in that the group $A^2R^dR^eR^f$ is 5-fluorothiophen-3-yl and $R^1$ is $CH_3$.

Preference is likewise given to the compounds of the formula I.232, particularly preferably the compounds I.232.1-I.232.2922, in particular the compounds (S,S)-I.232.1-I.232.2922, which differ from the corresponding compounds I.1.1-I.1.2922 or (S,S)-I.1.1-I.1.2922 in that the group $A^2R^dR^eR^f$ is 2-methoxythiophen-3-yl and $R^1$ is $CH_3$.

Preference is likewise given to the compounds of the formula I.233, particularly preferably the compounds I.233.1-I.233.2922, in particular the compounds (S,S)-I.233.1-I.233.2922, which differ from the corresponding compounds I.1,1-I.1.2922 or (S,S)-I.1.1-I.1.2922 in that the group $A^2R^dR^eR^f$ is 4-methoxythiophen-3-yl and $R^1$ is $CH_3$.

Preference is likewise given to the compounds of the formula I.234, particularly preferably the compounds I.234.1-I.234.2922, in particular the compounds (S,S)-I.234.1-I.2342922, which differ from the corresponding compounds I.1.1-I.1.2922 or (S,S)-I.1.1-I.1.2922 in that the group $A^2R^dR^eR^f$ is 5-methoxythiophen-3-yl and $R^1$ is $CH_3$.

Preference is likewise given to the compounds of the formula I.235, particularly preferably the compounds I.235.1-I.235.2922, in particular the compounds (S,S)-I.235.1-I.235.2922, which differ from the corresponding compounds I.1.1-I.1.2922 or (S,S)-I.1.1-I.1.2922 in that the group $A^2R^dR^eR^f$ is 2-trifluoromethylthiophen-3-yl and $R^1$ is $CH_3$.

Preference is likewise given to the compounds of the formula I.236, particularly preferably the compounds I.236.1-I.236.2922, in particular the compounds (S,S)-I.236.1-I.236.2922, which differ from the corresponding compounds I.1.1-I.1.2922 or (S,S)-I.1.1-I.1.2922 in that the group $A^2R^dR^eR^f$ is 4-trifluoromethylthiophen-3-yl and $R^1$ is $CH_3$.

Preference is likewise given to the compounds of the formula I.237, particularly preferably the compounds I.237.1-I.237.2922, in particular the compounds (S,S)-I.237.1-I.237.2922, which differ from the corresponding compounds I.1.1-I.1.2922 or (S,S)-I.1.1-I.1.2922 in that the group $A^2R^dR^eR^f$ is 5-trifluoromethylthiophen-3-yl and $R^1$ is $CH_3$.

Preference is likewise given to the compounds of the formula I.238, particularly preferably the compounds I.238.1-I.238.2922, in particular the compounds (S,S)-I.238.1-I.238.2922, which differ from the corresponding compounds I.1.1-I.1.2922 or (S,S)-I.1.1-I.1.2922 in that the group $A^2R^dR^eR^f$ is furan-2-yl and $R^1$ is $CH_3$.

Preference is likewise given to the compounds of the formula I.239, particularly preferably the compounds I.239.1-I.239.2922, in particular the compounds (S,S)-I.239.1-I.239.2922, which differ from the corresponding compounds I.1.1-I.1.2922 or (S,S)-I.1.1-I.1.2922 in that the group $A^2R^dR^eR^f$ is 3-chlorofuran-2-yl and $R^1$ is $CH_3$.

Preference is likewise given to the compounds of the formula I.240, particularly preferably the compounds I.240.1-I.240.2922, in particular the compounds (S,S)-I.240.1-I.240.2922, which differ from the corresponding compounds I.1.1-I.1.2922 or (S,S)-I.1.1-I.1.2922 in that the group $A^2R^dR^eR^f$ is 4-chlorofuran-2-yl and $R^1$ is $CH_3$.

Preference is likewise given to the compounds of the formula I.241, particularly preferably the compounds I.241.1-I.241.2922, in particular the compounds (S,S)-I.241.1-I.241.2922, which differ from the corresponding compounds I.1.1-I.1.2922 or (S,S)-I.1.1-I.1.2922 in that the group $A^2R^dR^eR^f$ is 5-chlorofuran-2-yl and $R^1$ is $CH_3$.

Preference is likewise given to the compounds of the formula I.242, particularly preferably the compounds I.242.1-I.242.2922, in particular the compounds (S,S)-I.242.1-I.242.2922, which differ from the corresponding compounds I.1.1-I.1.2922 or (S,S)-I.1.1-I.1.2922 in that the group $A^2R^dR^eR^f$ is 3-fluorofuran-2-yl and $R^1$ is $CH_3$.

Preference is likewise given to the compounds of the formula I.243, particularly preferably the compounds I.243.1-I.243.2922, in particular the compounds (S,S)-I.243.1-I.243.2922, which differ from the corresponding compounds I.1.1-I.1.2922 or (S,S)-I.1.1-I.1.2922 in that the group $A^2R^dR^eR^f$ is 4-fluorofuran-2-yl and $R^1$ is $CH_3$.

Preference is likewise given to the compounds of the formula I.244, particularly preferably the compounds I.244.1-I.244.2922, in particular the compounds (S,S)-I.244.1-I.244.2922, which differ from the corresponding compounds I.1.1-I.1.2922 or (S,S)-I.1.1-I.1.2922 in that the group $A^2R^dR^eR^f$ is 5-fluorofuran-2-yl and $R^1$ is $CH_3$.

Preference is likewise given to the compounds of the formula I.245, particularly preferably the compounds I.245.1-I.245.2922, in particular the compounds (S,S)-I.245.1-I.245.2922, which differ from the corresponding compounds I.1.1-I.1.2922 or (S,S)-I.1.1-I.1.2922 in that the group $A^2R^dR^eR^f$ is furan-3-yl and $R^1$ is $CH_3$.

Preference is likewise given to the compounds of the formula I.246, particularly preferably the compounds I.246.1-I.246.2922, in particular the compounds (S,S)-I.246.1-I.246.2922, which differ from the corresponding compounds I.1.1-I.1.2922 or (S,S)-I.1.1-I.1.2922 in that the group $A^2R^dR^eR^f$ is 2-chlorofuran-3-yl and $R^1$ is $CH_3$.

Preference is likewise given to the compounds of the formula I.247, particularly preferably the compounds I.247.1-I.247.2922, in particular the compounds (S,S)-I.247.1-I.247.2922, which differ from the corresponding compounds I.1.1-I.1.2922 or (S,S)-I.1.1-I.1.2922 in that the group $A^2R^dR^eR^f$ is 4-chlorofuran-3-yl and $R^1$ is $CH_3$.

Preference is likewise given to the compounds of the formula I.248, particularly preferably the compounds I.248.1-I.248.2922, in particular the compounds (S,S)-I.248.1-I.248.2922, which differ from the corresponding compounds I.1.1-I.1.2922 or (S,S)-I.1.1-I.1.2922 in that the group $A^2R^dR^eR^f$ is 5-chlorofuran-3-yl and $R^1$ is $CH_3$.

Preference is likewise given to the compounds of the formula I.249, particularly preferably the compounds I.249.1-I.249.2922, in particular the compounds (S,S)-I.249.1-I.249.2922, which differ from the corresponding compounds I.1.1-I.1.2922 or (S,S)-I.1.1-I.1.2922 in that the group $A^2R^dR^eR^f$ is 2-fluorofuran-3-yl and $R^1$ is $CH_3$.

Preference is likewise given to the compounds of the formula I.250, particularly preferably the compounds I.250.1-I.250.2922, in particular the compounds (S,S)-I.250.1-I.250.2922, which differ from the corresponding compounds I.1.1-I.1.2922 or (S,S)-I.1.1-I.1.2922 in that the group $A^2R^dR^eR^f$ is 4-fluorofuran-3-yl and $R^1$ is $CH_3$.

Preference is likewise given to the compounds of the formula I.251, particularly preferably the compounds I.251.1-I.251.2922, in particular the compounds (S,S)-I.251.1-I.251.2922, which differ from the corresponding compounds I.1.1-I.1.2922 or (S,S)-I.1.1-I.1.2922 in that the group $A^2R^dR^eR^f$ is 5-fluorofuran-3-yl and $R^1$ is $CH_3$.

Preference is likewise given to the compounds of the formula I.252, particularly preferably the compounds I.252.1-I.252.2922, in particular the compounds (S,S)-I.252.1-I.252.2922, which differ from the corresponding compounds I.1.1-I.1.2922 or (S,S)-I.1.1-I.1.2922 in that the group $A^2R^dR^eR^f$ is 5-fluorofuran-3-yl and $R^1$ is $CH_3$.

The piperazine compounds of the formula I can be prepared by standard methods for synthesizing organic compounds by various routes, for example by the processes illustrated in more detail below:

Process A

The compounds of the formula I can be prepared, for example, analogously to processes known from the literature by cyclizing corresponding dipeptide precursors of the formula II, for example analogously to the method described by T. Kawasaki et al., Org. Lett. 2(19) (2000), 3027-3029, Igor L. Rodionov et al., Tetrahedron 58(42) (2002), 8515-8523 or A. L. Johnson et al., Tetrahedron 60 (2004), 961-965. Hereinbelow, the cyclization of dipeptides of the formula II to the compounds according to the invention is also referred to as process A and is illustrated in the scheme below.

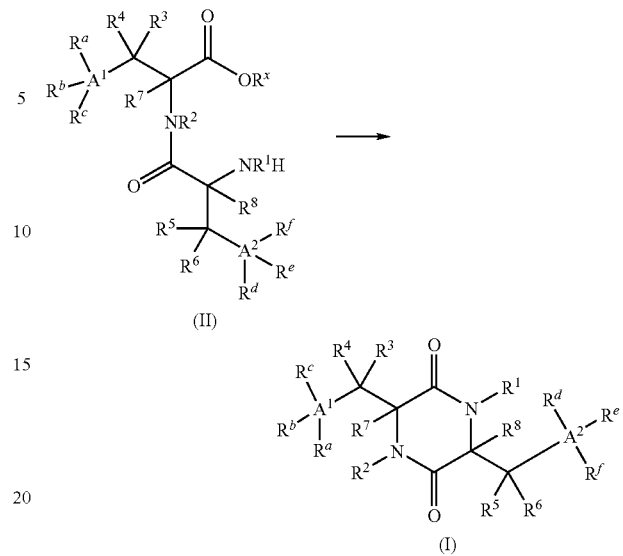

In formula II, the variables $A^1$, $A^2$, $R^1$-$R^8$, $R^a$, $R^b$, $R^c$, $R^d$, $R^e$ and $R^f$ are as defined for formula I. The group $OR^x$ is a suitable leaving group attached via oxygen. Here, $R^x$ is, for example, $C_1$-$C_6$-alkyl, in particular methyl or ethyl, or phenyl-$C_1$-$C_6$-alkyl, for example benzyl. Dipeptides of the general formula II are novel and also form part of the subject matter of the present invention.

The cyclization can be carried out, for example, by reacting a dipeptide of the formula II either in the presence of acid or base (acidic or basic cyclization) or by heating of the reaction mixture (thermal cyclization).

The bases or acids are added to the dipeptide II either in equimolar amounts or in excess. In a particular embodiment of the process according to the invention, the bases or acids are employed in excess, based on the dipeptide.

The reaction of the dipeptide II in the presence of a base is generally carried out at temperatures in the range from 0° C. to the boiling point of the reaction mixture, preferably from 10° C. to 50° C., particularly preferably from 15° C. to 35° C. In general, the reaction is carried out in a solvent, preferably in an inert organic solvent.

Suitable inert organic solvents include aliphatic hydrocarbons, such as pentane, hexane, cyclohexane and mixtures of $C_5$-$C_8$-alkanes, aromatic hydrocarbons, such as toluene, o-, m- and p-xylene, halogenated hydrocarbons, such as dichloromethane, dichloroethane, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol; n-butanol, tert-butanol, water and also dimethyl sulfoxide, dimethylformamide and dimethylacetamide and also morpholine and N-methyl-morpholine. It is also possible to use mixtures of the solvents mentioned.

In a preferred embodiment of the invention, the reaction is carried out in a tetrahydrofuran-water mixture using, for example, a mixing ratio of 1:10 to 10:1 (parts by volume).

Suitable bases are, in general, inorganic compounds, such as alkali metal and alkaline earth metal hydroxides, such as lithium hydroxide, sodium hydroxide, potassium hydroxide or calcium hydroxide, an aqueous solution of ammonia, alkali metal or alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, for example lithium diisopropylamide, sodium amide and potassium amide, alkali metal and alkaline earth metal carbonates, such as lithium carbonate, potassium carbonate, cesium carbonate and calcium carbonate and also alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and also alkali metal and alkaline earth metal alkoxides, such as sodium methoxide, sodium ethoxide, potassium ethoxide, potassium tert-butoxide, potassium tert-pentoxide and dimethoxymagnesium, moreover organic bases, for example tertiary amines, such as trimethylamine, triethylamine, diisopropylethylamine, 2-hydroxypyridine and N-methylpiperidine, pyridine, substituted pyridines, such as collidine, lutidine and 4-dimethylaminopyridine, and also bicyclic amines. It is, of course, also possible to use a mixture of different bases.

In one embodiment of the process according to the invention, the reaction of II is carried out in the presence of bases, preferably in the presence of the bases potassium tert-butoxide, 2-hydroxypyridine or an aqueous solution of ammonia or a mixture of these bases. Preference is given to using only one of these bases. In a particularly preferred embodiment, the reaction is carried out in an aqueous solution of ammonia which, for example, may be from 10 to 50% strength (w/v).

The reaction of II in the presence of an acid is usually carried out at temperatures in the range from 10° C. to the boiling point of the reaction mixture, preferably from 50° C. to the boiling point, particularly preferably at the boiling point under reflux. In general, the reaction is carried out in a solvent, preferably in an inert organic solvent.

In principle, suitable solvents are all those solvents which can also be used for the basic cyclization, in particular alcohols. In a preferred embodiment, the reaction is carried out in n-butanol.

In principle, suitable acids for the cyclization of II are both Brönstedt and Lewis acids. In particular, it is possible to employ inorganic acids, for example hydrohalic acids, such as hydrofluoric acid, hydrochloric acid, hydrobromic acid, inorganic oxo acids, such as sulfuric acid and perchloric acid, furthermore inorganic Lewis acids, such as boron trifluoride, aluminum trichloride, iron(III) chloride, tin(IV) chloride, titanium(IV) chloride and zinc(II) chloride, and also organic acids, for example carboxylic acids and hydroxycarboxylic acids, such as formic acid, acetic acid, propionic acid, oxalic acid, citric acid and trifluoroacetic acid, and also organic sulfonic acids, such as toluenesulfonic acid, benzenesulfonic acid, camphorsulfonic acid and the like. It is, of course, also possible to use a mixture of different acids.

In one embodiment of the process according to the invention, the reaction is carried out in the presence of organic acids, for example in the presence of carboxylic acids, such as formic acid, acetic acid or trifluoroacetic acid or a mixture of these acids. Preferably, only one of these acids is used. In a preferred embodiment, the reaction is carried out in acetic acid.

A particularly preferred embodiment of the acidic cyclization is carried out in the presence of n-butanol, N-methylmorpholine and acetic acid under reflux conditions.

In a further embodiment of the invention, the reaction is carried out just by heating the reaction mixture (thermal cyclization). Here, the reaction is usually carried out at temperatures in the range from 10° C. to the boiling point of the reaction mixture, preferably from 50° C. to the boiling point of the reaction mixture, particularly preferably at the boiling point of the reaction mixture under reflux. In general, the reaction is carried out in a solvent, preferably in an inert organic solvent.

In principle, suitable solvents are those solvents which can be used for the basic cyclization. Preference is given to polar aprotic solvents, for example dimethyl sulfoxide or dimethylformamide or mixtures thereof. In a preferred embodiment, the reaction is carried out in dimethyl sulfoxide.

The reaction mixtures obtained according to one of the processes A according to the invention can, for example, be worked-up in a customary manner. This may take place, for example, by mixing with water, separating the phases and, if appropriate, chromatographic purification of the crude products. Some of the intermediates and end products are obtained in the form of viscous oils which can generally be purified or freed from volatile components under reduced pressure and at moderately elevated temperature. If the intermediates and end products are obtained as solids, the purification can also be carried out by recrystallisation or digestion.

Process B

According to a further process according to the invention (process B), the compounds of the formula I where $R^1 \neq$ hydrogen can also be prepared by reacting a piperazine compound of the formula I in which $R^1$ is hydrogen with an alkylating agent or an acylating agent which contains the radical $R^1$ different from hydrogen. Such reactions can be carried out analogously to processes known from the literature, for example according to the methods described by I. O. Donkor et al., Bioorg. Med. Chem. Lett. 11 (19) (2001), 2647-2649, B. B. Snider et al., Tetrahedron 57 (16) (2001), 3301-3307, I. Yasuhiro et al., J. Am. Chem. Soc. 124(47) (2002), 14017-14019, or M. Falorni et al., Europ. J. Org. Chem. (8) (2000), 1669-1675.

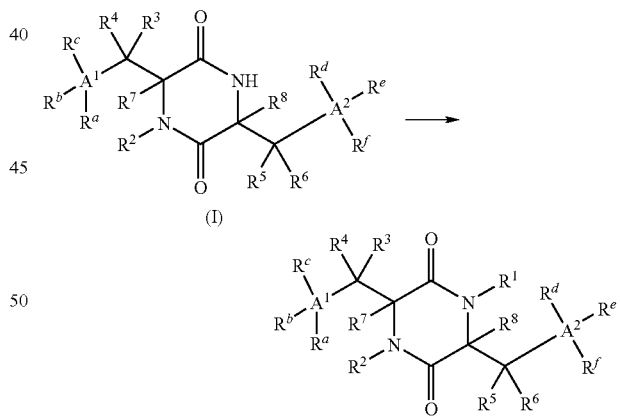

According to process B, a piperazine compound of the formula I where $R^1$ hydrogen is reacted with a suitable alkylating agent, hereinbelow compound $X^1$—$R^1$, or acylating agent, hereinbelow compound $X^2$—$R^1$, which gives a piperazine compound of the formula I where $R^1 \neq$ hydrogen.

In the alkylating agents $X^1$—$R^1$, $X^1$ can be halogen or O—$SO_2$—$R^m$ where $R^m$ has the meaning $C_1$-$C_4$-alkyl or aryl, which are optionally substituted by halogen, $C_1$-$C_4$-alkyl or halo-$C_1$-$C_4$-alkyl. In the acylating agents $X^2$—$R^1$, $X^2$ may be halogen, in particular Cl. Here, $R^1 \neq$ hydrogen and is as defined above and is in particular $C_1$-$C_6$-alkyl, $C_3$-$C_6$-cycloalkyl, $C_3$-$C_6$-alkenyl, $C_3$-$C_6$-cycloalkenyl, $C_3$-$C_6$-alkynyl, $C_3$-$C_6$-cycloalkynyl, phenyl-($C_1$-$C_6$)-alkyl, heterocyclyl, heterocyclyl-($C_1$-$C_6$)-alkyl; phenyl-[$C_1$-$C_6$-alkoxycarbonyl]-($C_1$-$C_6$)-alkyl or phenylheterocyclyl-($C_1$-$C_6$)-alkyl; or $COR^{21}$ or $SO_2R^{25}$, where the above-mentioned aliphatic, cyclic or aromatic moieties of $R^1$ may be partially or fully halogenated and/or may carry one to three of the following groups: cyano, hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-alkylthio, [di-($C_1$-$C_4$)-alkyl]-amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, [di-($C_1$-$C_4$)-alkyl]aminocarbonyl or $C_1$-$C_4$-alkylcarbonyloxy.

The reaction is usually carried out at temperatures in the range from −78° C. to the boiling point of the reaction mixture, preferably from −50° C. to 65° C., particularly preferably from −30° C. to 65° C. In general, the reaction is carried out in a solvent, preferably in an inert organic solvent.

Suitable solvents are the compounds cited under process A, inter alia, toluene, dichloromethane, tetrahydrofuran or dimethylformamide or mixtures thereof.

In a preferred embodiment of the invention, the reaction is carried out in tetrahydrofuran.

In a preferred embodiment, the compound I where $R^1$=H is reacted with the alkylating or acylating agent in the presence of a base. Suitable bases are the compounds cited under process A. In general, the bases are employed in equimolar amounts. They can also be employed in excess or even as solvent. In a preferred embodiment of the process according to the invention, the base is added in an equimolar amount or in a substantially equimolar amount. In a further preferred embodiment, the base employed is sodium hydride.

Work-up is generally carried out analogously to the procedure described under process A.

Process C

Analogously to the procedure described under process B, it is possible to react compounds I in which $R^2$ is hydrogen with alkylating agents $R^2$—$X^1$ or acylating agents $R^2$—$X^2$, giving compounds of the formula I where $R^2$ is hydrogen (process C). The reaction conditions of the process C according to the invention correspond to those of process B.

Process D

According to the process illustrated in the scheme below, it is possible to prepare the compounds of the formula I by conversion of the substituent $R^a$, for example analogously to the methods described by J. Tsuji, Top. Organomet. Chem. (14) (2005), 332 pp., or J. Tsuji, Organic Synthesis with Palladium Compounds. (1980), 207 pp. and Organikum, 21st edition, 2001, Wiley and literature cited therein.

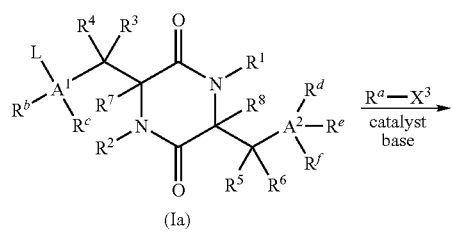

(Ia)

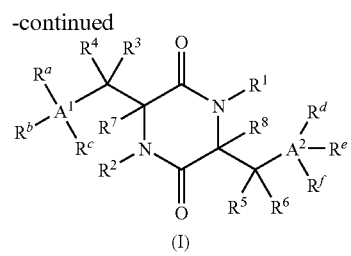

(I)

To this end, a piperazine compound of the formula Ia which, instead of the substituent $R^a$, has a suitable leaving group L is converted by reaction with a coupling reagent which contains a group $R^a$ (compound $R^a$-$X^3$) into another piperazine derivative of the formula I.

The reaction is usually carried out in the presence of a catalyst, preferably in the presence of a transition metal catalyst. In general, the reaction is carried out in the presence of a base.

This reaction sequence is illustrated below using the example of the substituent $R^a$ and can of course be employed in an analogous manner for converting the substituents $R^b$ and $R^c$.

Suitable leaving groups L are, for example, halogen, in particular chlorine, bromine or iodine, or $S(O)_nR^k$, where n=0, 1, 2 and $R^k$ is $C_1$-$C_6$-alkyl, halo-($C_1$-$C_6$)-alkyl or optionally halogenated or $C_1$-$C_4$-alkyl-substituted aryl.

Suitable coupling reagents $X^3$—$R^a$ are in particular those compounds in which $X^3$, if $R^a$ is $C_1$-$C_6$-alkyl, $C_2$-$C_6$-alkenyl, aryl or heteroaryl, denotes one of the following groups:

Zn—$R^l$ where $R^l$ is halogen, $C_1$-$C_6$-alkyl, $C_2$-$C_6$-alkenyl, aryl or heteroaryl;

$B(OR^m)_2$ where $R^m$ is H or $C_1$-$C_6$-alkyl, where two alkyl substituents together may form a $C_2$-$C_4$-alkylene chain; or $SnR^n_3$ where $R^n$ is $C_1$-$C_6$-alkyl or aryl.

If $R^a$ is $C_2$-$C_6$-alkynyl, $X^3$ may also be hydrogen.

To prepare the compound I in which $R^a$ is CN it is also possible to react the compound Ia in which L is bromine or iodine with copper cyanide analogously to known methods (see, for example, Organikum, 21st edition, 2001, Wiley, p. 404 and literature cited therein).

Here, according to a preferred embodiment, L or $R^a$ in the compounds of the formula I are attached in the ortho-position to the point of attachment of $A^1$ to a carbon atom of $A^1$.

This reaction is usually carried out at temperatures in the range from −78° C. to the boiling point of the reaction mixture, preferably from −30° C. to 65° C., particularly preferably at temperatures from 30° C. to 65° C. In general, the reaction is carried out in an inert organic solvent in the presence of a base.

Suitable solvents are the compounds cited under process A. In one embodiment of the process according to the invention, use is made of tetrahydrofuran with a catalytic amount of water; in another embodiment, only tetrahydrofuran is used.

Suitable bases are the compounds cited under process A.

The bases are generally employed in equimolar amounts. They can also be employed in excess or even as solvent.

In a preferred embodiment of the process according to the invention, the base is added in an equimolar amount. In a further preferred embodiment, the base used is triethylamine or cesium carbonate, particularly preferably cesium carbonate.

Suitable catalysts for the process according to the invention are, in principle, compounds of the transition metals Ni, Fe, Pd, or Cu. It is possible to use organic or inorganic compounds. $Pd(PPh_3)_2Cl_2$, $Pd(OAc)_2$, $PdCl_2$ or $Na_2PdCl_4$ may be mentioned by way of example. Here, Ph is phenyl.

The different catalysts can be employed either individually or else as mixtures. In a preferred embodiment of the invention, $Pd(PPh_3)_2Cl_2$ is used.

The work-up can be carried out analogously to the procedure described for process A.

Step 2:

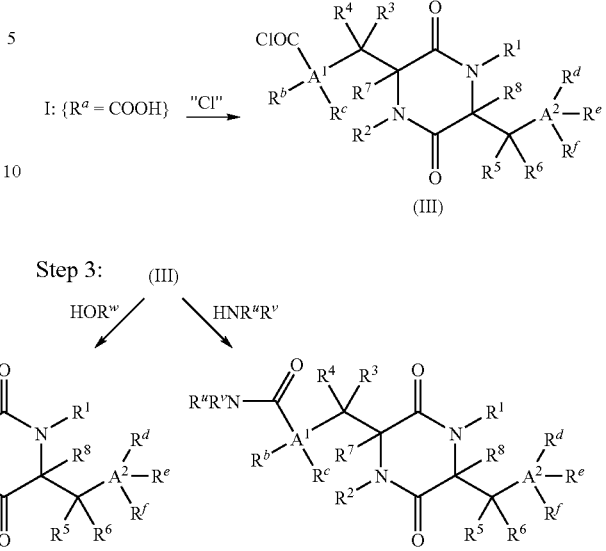

Step 3:

Process E piperazine compounds of the formula I in which one of the groups $R^a$, $R^b$ or $R^c$ is COOH can furthermore be prepared from piperazine compounds of the formula I in which $R^a$, $R^b$ or $R^c$ is $COOR^z$, where $R^z$ is alkyl, for example $CH_3$, by hydrolysis of the ester group. The hydrolysis can be performed, for example, by reaction with $(H_3C)_3SnOH$, for example according to K. C. Nicolaou et al., Angew. Chem. Int. Ed. Engl. (44) (2005), 1378. The carboxylic acid obtained in this manner can then be converted by standard methods of organic synthesis, if appropriate after conversion into the acid chloride, by reaction with an amine $HNR^uR^v$ or an alcohol $HOR^w$, into the corresponding ester or the amide Organikum, Autorenkollektiv, Leipzig 1993, 19th edition, pp. 424-429. This reaction sequence is illustrated hereinbelow using the example of the substituent $R^a$, but it is, of course, also possible to employ this sequence in an analogous manner for converting the substituents $R^b$ and $R^c$.

Step 1:

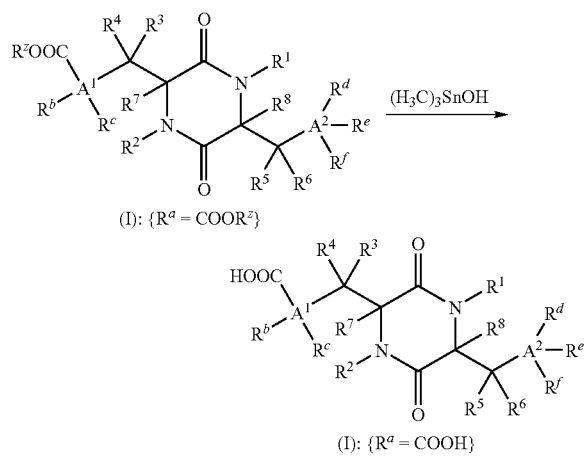

In this scheme, the variables $A^1$, $A^2$, $R^1$-$R^8$, $R^b$, $R^c$, $R^d$, $R^e$ and $R^f$ have the meanings given above. $R^u$ and $R^v$ independently of one another are hydrogen, $C_1$-$C_6$-alkyl, $C_2$-$C_6$-alkenyl, $C_2$-$C_6$-alkynyl, $C_1$-$C_6$-alkoxy, $C_1$-$C_6$-alkylsulfonyl, $C_1$-$C_6$-alkylaminosulfonyl, [di-($C_1$-$C_6$)-alkylamino]sulfonyl or optionally substituted phenyl. $R^w$ is $C_1$-$C_6$-alkyl, $C_3$-$C_6$-alkenyl or $C_3$-$C_6$-alkynyl.

In a first step, the ester group in the piperazine compound I $\{R^a = COOR^z\}$ is hydrolyzed. The hydrolysis can be performed, for example, by reaction with $(H_3C)_3SnOH$, which gives the free acid of I $\{R^a = COOH\}$. The conversion into the free acid is usually carried out using an excess of $(H_3C)_3SnOH$. In general, the reaction is carried out in an inert organic solvent. Suitable solvents include in particular dichloroethane. In general, the reaction is carried out at elevated temperature, for example at about 80° C.

In a second step, the acid I $\{R^a = COOH\}$ is converted into its acid chloride of the formula III. The conversion into the acid chloride is usually carried out at temperatures of from 10° C. to 50° C., preferably at room temperature, for example at 25° C. In general, the reaction is carried out in an inert organic solvent. The most suitable solvents include in particular dichloromethane. In a preferred embodiment, the reaction is carried out in dichloromethane and catalytic amounts of dimethylformamide. A large number of reagents are suitable for the chlorination, for example oxalyl chloride or thionyl chloride. Preference is given to using substantially equimolar amounts of the chlorinating reagent, in particular oxalyl chloride.

The reaction with an amine $NHR^uR^v$ in the subsequent reaction is usually carried out by adding an excess of the amine in question. The reaction can be carried out in a temperature range of from 0° C. to 40° C., preferably at room temperature, for example at 25° C.

The reaction with an alcohol $HOR^w$ in the subsequent reaction is usually carried out by adding an excess both of the alcohol in question and of triethylamine.

The reaction can be carried out in a temperature range of from 0° C. to 40° C., preferably at room temperature, for example at 25° C.

The work-up can be carried out analogously to the procedure described for process A.

Process F

The compounds of the formula I can be prepared according to the synthesis shown below by coupling piperazine compounds of the general formula IV with compounds V. The coupling of IV with V can be performed analogously to processes known from the literature, for example according to G. Porzi, et al., Tetrahedron Asymmetry 9 (19), (1998), 3411-3420, or C. I. Harding et al., Tetrahedron 60 (35), (2004), 7679-7692, or C. J. Chang et al., J. Chem. Soc. Perk. T. 1 (24), (1994), 3587-3593.

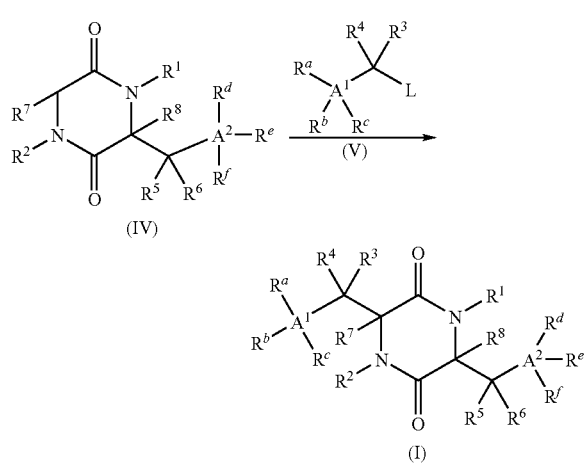

In the scheme, $A^1$, $A^2$, $R^1$-$R^8$, $R^a$, $R^b$, $R^c$, $R^d$, $R^e$ and $R^f$ are as defined above. L is a suitable leaving group, such as halogen or $OSO_2R^m$, where $R^m$ is $C_1$-$C_4$-alkyl, aryl, or aryl which is mono- to trisubstituted by $C_1$-$C_4$-alkyl.

In general, the reaction is carried out at temperatures in the range from −78° C. to the boiling point of the reaction mixture, preferably in the range from −78° C. to 40° C., particularly preferably in the range from −78° C. to 30° C.

In general, the reaction is carried out in an inert organic solvent in the presence of a base. Suitable solvents are the compounds cited under process A. In a preferred embodiment of the process according to the invention, use is made of tetrahydrofuran.

Suitable bases are the compounds cited under process A. In a further preferred embodiment, the base used is lithium diisopropylamide, particularly preferably in a substantially equimolar amount, in particular in an equimolar amount.

Some compounds of the formula V are commercially available or can be prepared by transformations, described in the literature, of the corresponding commercially available precursors.

The work-up can be carried out analogously to the procedure described for process A.

Some of the precursors and intermediates required for preparing the compounds of the formula I are commercially available, known from the literature or can be prepared by processes known from the literature.

The dipeptide compounds of the formula II can be prepared, for example, from N-protected dipeptides of the general formula VI analogously to processes known from the literature, for example according to Glenn L. Stahl et al., J. Org. Chem. 43(11), (1978), 2285-6 or A. K. Ghosh et al., Org. Lett. 3(4), (2001), 635-638.

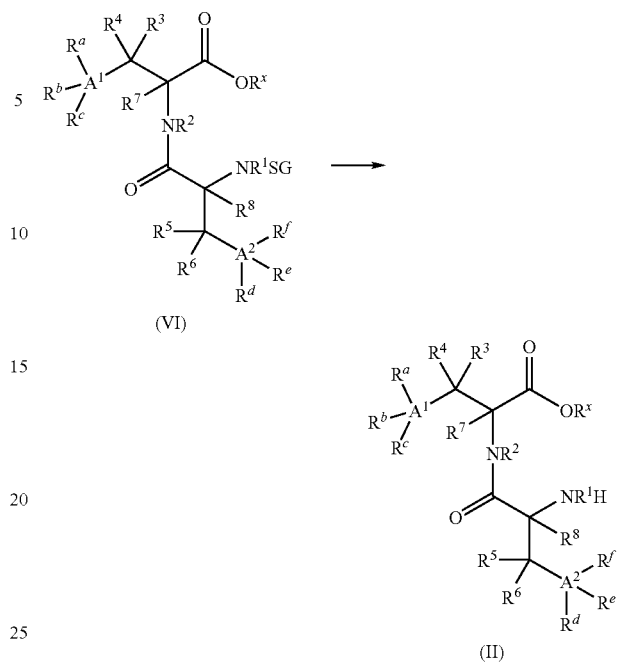

In the formulae II and VI, the variables $A^1$, $A^2$, $R^1$-$R^8$, $R^a$, $R^b$, $R^c$, $R^d$, $R^e$ and $R^f$ are as defined for formula I, SG is a nitrogen protective group, such as Boc (=tert-butoxy-carbonyl), and $OR^x$ is a leaving group attached via an oxygen atom. Of course, in each case the preferred meanings for the compounds of the formula I apply correspondingly to the compounds of the formula II or IV. With respect to the leaving group $OR^x$, what was stated above for the dipeptides of the formula II applies.

Thus, for example, a dipeptide of the formula VI in which SG is Boc and $OR^x$ is a suitable leaving group, where $R^x$ is, for example, $C_1$-$C_6$-alkyl, in particular methyl, ethyl or benzyl, can be converted in the presence of an acid into a compound of the formula II.

The reaction is usually carried out at temperatures in the range from −30° C. to the boiling point of the reaction mixture, preferably from 0° C. to 50° C., particularly preferably from 20° C. to 35° C.

The reaction can take place in a solvent, in particular in an inert organic solvent. Suitable solvents are, in principle, the compounds cited for the basic cyclization, in particular tetrahydrofuran or dichloromethane or mixtures thereof. In a preferred embodiment, the reaction is carried out in dichloromethane.

The acids used are the acids cited for process A.

In one embodiment of the process according to the invention, the reaction is carried out in the presence of organic acids, for example in the presence of strong organic acids, such as formic acid, acetic acid or trifluoroacetic acid or mixtures thereof. In a preferred embodiment, the reaction is carried out in the presence of trifluoroacetic acid.

The work-up can be carried out analogously to the procedure described for process A.

The protected dipeptides of the formula VI can be prepared analogously to processes known from the literature, for example according to Wilford L. Mendelson et al., Int. J. Peptide & Protein Research 35(3), (1990), 249-257. A typical route is the amidation of a Boc-protected amino acid VIII with an amino acid ester of the formula VII, as shown in the scheme below:

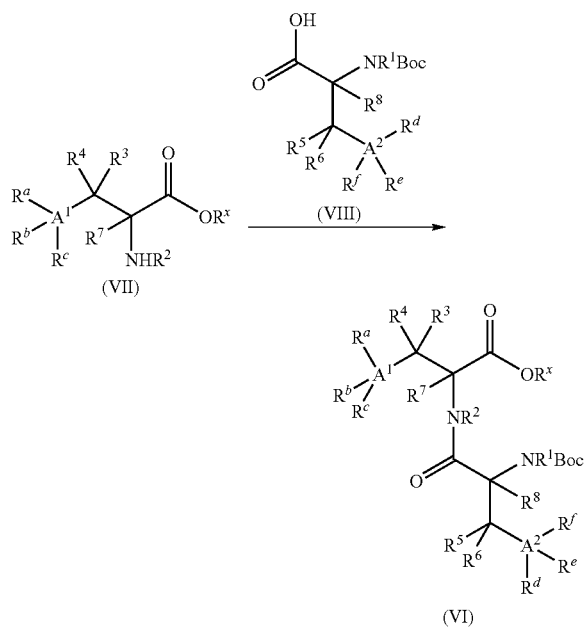

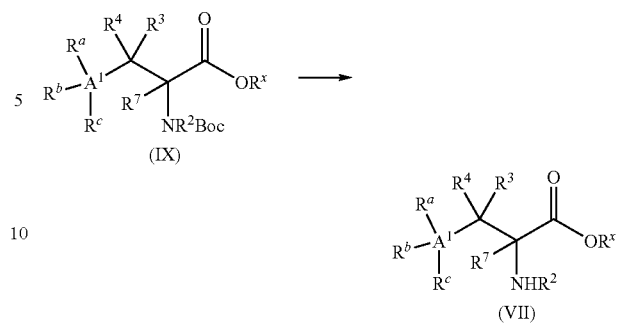

In this scheme, the variables are as defined above. Instead of Boc, it is also possible to use other amino protective groups.

In general, the reaction of VII with VIII is carried out at temperatures in a range from −30° C. to the boiling point of the reaction mixture, preferably from 0° C. to 50° C., particularly preferably from 20° C. to 35° C. The reaction can be carried out in a solvent, preferably in an inert organic solvent. Suitable solvents are the solvents mentioned for process A in connection with the basic cyclization.

In general, the reaction requires the presence of an activating agent. Suitable activating agents are condensing agents, such as, for example, polystyrene- or non-polystyrene-supported dicyclohexylcarbodiimide (DCC), diisopropylcarbodiimide, 1-ethyl-3-(dimethylaminopropyl)carbodiimide (EDAC), carbonyldiimidazole, chlorocarbonic esters, such as methyl chloroformate, ethyl chloroformate, isopropyl chloroformate, isobutyl chloroformate, sec-butyl chloroformate or allyl chloroformate, pivaloyl chloride, polyphosphoric acid, propanephosphonic anhydride, bis(2-oxo-3-oxazolidinyl)-phosphoryl chloride (BOPCl) or sulfonyl chlorides, such as methanesulfonyl chloride, toluenesulfonyl chloride or benzenesulfonyl chloride. According to one embodiment, a preferred activating agent is EDAC or DCC.

The reaction of VII with VIII is preferably carried out in the presence of a base. Suitable bases are the compounds cited under process A. In one embodiment, the base used is triethylamine or N-ethyldiisopropylamine or mixtures thereof, particularly preferably N-ethyldiisopropylamine.

The work-up can be carried out analogously to the procedure described for process A.

For their part, the compounds of the formula VII can be prepared by deprotecting corresponding protected amino acid compounds IX analogously to processes known from the literature, for example according to Glenn L. Stahl et al., J. Org. Chem. 43(11), (1978) 2285-6 or A. K. Ghosh et al. Org. Lett. 3(4), (2001), 635-638. The preparation of VII from a Boc-protected amino acid compound IX is shown in the scheme below. Instead of the Boc group, it is also possible to use other amino protective groups.

The reaction of a compound of the formula IX into the compound VII is typically carried out in the presence of an acid at temperatures in a range from −30° C. to the boiling point of the reaction mixture, preferably from 0° C. to 50° C., particularly preferably from 20° C. to 35° C. The reaction can be carried out in a solvent, preferably in an inert organic solvent.

Suitable solvents are, in principle, the compounds mentioned under the basic cyclization, in particular tetrahydrofuran or dichloromethane or mixtures thereof. In a preferred embodiment, the reaction is carried out in dichloromethane.

The acids and acidic catalysts used are the compounds cited for process A.

In one embodiment of the process according to the invention, the reaction is carried out in the presence of organic acids, for example in the presence of strong organic acids, such as formic acid, acetic acid or trifluoroacetic acid or mixtures thereof. In a preferred embodiment, the reaction is carried out in the presence of trifluoroacetic acid.

The work-up can be carried out analogously to the procedure described for process A.

The compounds of the formula IX can be prepared according to the reaction shown in the scheme below. The reaction of compound V with the protected amino acid compound X can be carried out analogously to processes known from the literature, for example according to I. Ojima et al., J. Am. Chem. Soc., 109(21), (1987), 6537-6538 or J. M. McIntosh et al., Tetrahedron 48(30), (1992), 6219-6224.

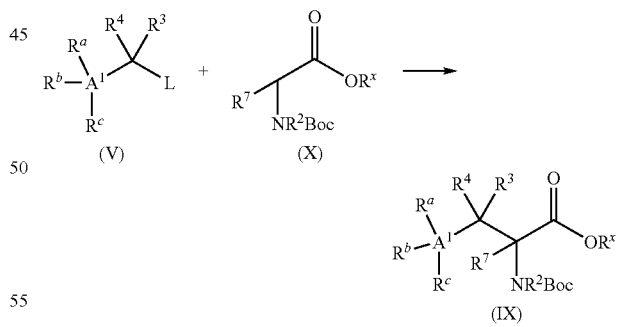

In this scheme, the variables are as defined above. L is a leaving group, for example one of the leaving groups mentioned for process F. Instead of Boc, it is also possible to use other amino protective groups.

The reaction of V with X is generally carried out in the presence of base. Suitable bases are the compounds cited under process A. In a further preferred embodiment, the base used is lithium diisopropylamide, particularly preferably in a substantially equimolar amount, in particular in an equimolar amount.

Usually, the reaction is carried out at temperatures in the range from −78° C. to the boiling point of the reaction mixture, preferably from 78° C. to the boiling point, particularly preferably from −78° C. to 30° C.

The reaction can be carried out in a solvent, preferably in an inert organic solvent. Suitable solvents are, in principle, the solvents mentioned under the basic cyclization, in particular dichloromethane or tetrahydrofuran or mixtures thereof. In a preferred embodiment, the reaction is carried out in tetrahydrofuran.

The work-up can be carried out analogously to the procedure described for process A.

Some of the compounds of the formula V are commercially available or can be prepared by transformations, described in the literature, of the corresponding commercially available precursors.

Some of the amino acid derivates of the formula VIII or X or the derivative XV described below are likewise commercially available or can be prepared by transformations, described in the literature, of the corresponding commercially available precursors.

The compounds of the formula IV where $R^1 \neq$ hydrogen can be prepared by reacting a piperazine compound of the formula IV in which $R^1$ is hydrogen with an alkylating agent or acylating agent which contains the radical $R^1$ different from hydrogen. In an analogous manner, it is possible to prepare compounds IV where $R^2 \neq$ hydrogen by reacting a piperazine compound of the formula IV in which $R^2$ is hydrogen with an alkylating agent or acylating agent which contains the radical $R^2$ different from hydrogen, Such reactions can be carried out analogously to processes known from the literature, for example according to the methods described by I. O. Donkor et al., Bioorg. Med. Chem. Lett. 11 (19) (2001), 2647-2649, B. B. Snider et al., Tetrahedron 57 (16) (2001), 3301-3307, I. Yasuhiro et al., J. Am. Chem. Soc. 124(47) (2002), 14017-14019, or M. Falorni et al., Europ. J. Org. Chem. (8) (2000), 1669-1675.

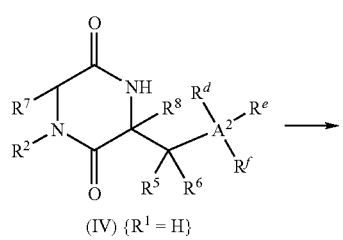

(IV) {$R^1$ = H}

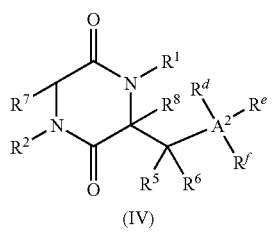

(IV)

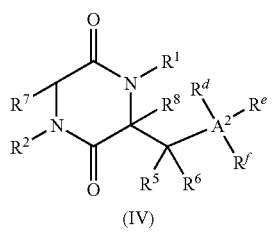

(IV) {$R^2$ = H}

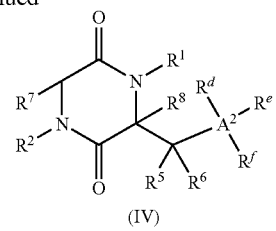

(IV)

With respect to the alkylating agent or a cycling agent, what was stated for the processes B and C applies in the same manner. With respect to the reaction conditions of these reactions, what was stated for the processes B and C likewise applies. The compounds of the formula IV can also be prepared by intramolecular cyclization of compounds of the general formula XIII analogously to further processes known from the literature, for example according to T. Kawasaki et al., Org. Lett. 2(19) (2000), 3027-3029, 3027-3029, Igor L. Rodionov et al., Tetrahedron 58(42) (2002), 8515-8523 or A. L. Johnson et alt, Tetrahedron 60 (2004), 961-965.

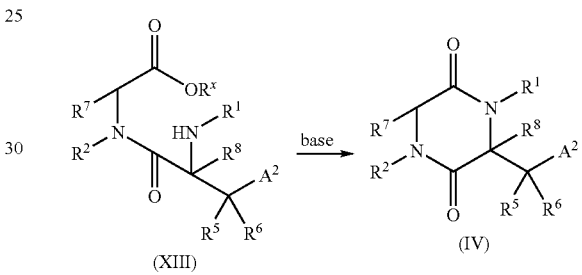

(XIII) → (IV)

Here, $OR^x$ is a suitable leaving group, and $R^x$ is, for example, $C_1$-$C_6$-alkyl, in particular methyl, ethyl or benzyl.

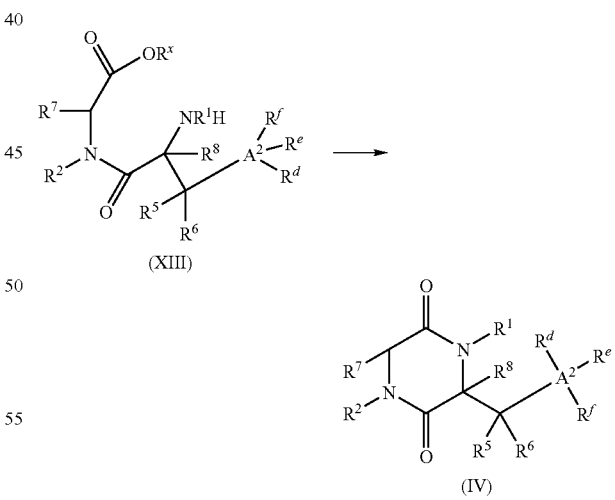

(XIII) → (IV)

In formula XIII, the variables $R^x, A^2, R^1, R^2, R^5, R^6, R^7, R^8, R^d, R^e$ and $R^f$ are as defined for formula II. The group $OR^x$ is a suitable leaving group attached via oxygen. Here, $R^x$ is, for example, $C_1$-$C_6$-alkyl, in particular methyl or ethyl, or phenyl-$C_1$-$C_6$-alkyl, for example benzyl.

The cyclization of the compounds of the formula XIII can be carried out in the presence of a base. In this case, the reaction is generally carried out at temperatures in the range from 0° C. to the boiling point of the reaction mixture, preferably from 10° C. to 50° C., particularly preferably from 15° C. to 35° C. The reaction can be carried out in a solvent, preferably in an inert organic solvent.

Suitable solvents are, in principle, the compounds cited under the thermal cyclization, in particular a tetrahydrofuran-water mixture having a mixing ratio of from 1:10 to 10:1.

Suitable bases are the bases mentioned for the basic cyclization according to process A, in particular potassium tert-butoxide, 2-hydroxypyridine or an aqueous solution of ammonia or a mixture of these bases. Preferably, only one of these bases is used. In a particularly preferred embodiment, the reaction is carried out in the presence of an aqueous solution of ammonia which, for example, may be from 10 to 50% strength (w/v).

For their part, the compounds of the formula XIII can be prepared by the synthesis illustrated in the scheme below, analogously to processes known from the literature, for example according to Wilford L. Mendelson et al., Int. J. Peptide & Protein Research 35(3), (1990), 249-257, Glenn L. Stahl et al., J. Org. Chem. 43(11), (1978), 2285-2286 or A. K. Ghosh et al., Org. Lett. 3(4), (2001), 635-638.

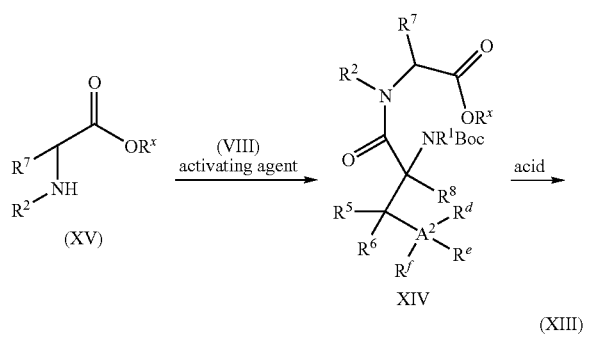

In the scheme, the variables $R^x$, $A^2$, $R^1$, $R^2$, $R^5$, $R^6$, $R^7$, $R^8$, $R^d$, $R^e$ and $R^f$ are as defined for formula II or XII. In a first step, the synthesis comprises the coupling of amino acid compounds XV with Boc-protected amino acids VIII in the presence of an activating agent.

The reaction of a compound of the formula XV with a compound of the formula VIII is usually carried out at temperatures in the range from −30° C. to the boiling point of the reaction mixture, preferably from 0° C. to 50° C., particularly preferably from 20° C. to 35° C. The reaction can be carried out in a solvent, preferably in an inert organic solvent. For further details, reference is made to the preparation of compound VI by amidation of the amino acid compound VIII with the compound VII.

In general, the reaction requires the presence of an activating agent. Suitable activating agents are condensing agents, such as, for example, polystyrene- or non-polystyrene-supported dicyclohexylcarbodiimide (DCC), diisopropylcarbodiimide, 1-ethyl-3-(dimethylaminopropyl)carbodiimide (EDAC), carbonyldiimidazole, chlorocarbonic esters, such as methyl chloroformate, ethyl chloroformate, isopropyl chloroformate, isobutyl chloroformate, sec-butyl chloroformate or allyl chloroformate, pivaloyl chloride, polyphosphoric acid, propanephosphonic anhydride, bis(2-oxo-3-oxazolidinyl)-phosphoryl chloride (BOPCl) or sulfonyl chlorides, such as methanesulfonyl chloride, toluenesulfonyl chloride or benzenesulfonyl chloride. According to one embodiment, a preferred activating agent is EDAC or DCC.

The reaction of XV with VIII is preferably carried out in the presence of a base.

Suitable bases are the compounds cited under process A. In one embodiment, the base used is triethylamine or N-ethyldiisopropylamine or mixtures thereof, particularly preferably N-ethyldiisopropylamine.

The work-up can be carried out analogously to the procedure described for process A.

The deprotection of the compound XIV to give the compound XIII is typically carried out by treatment with an acid. The reaction is usually carried out at temperatures in the range from −30° C. to the boiling point of the reaction mixture, preferably from 0° C. to 50° C., particularly preferably from 20° C. to 35° C. The reaction can be carried out in a solvent, preferably in an inert organic solvent.

Suitable solvents are, in principle, the solvents mentioned under process A in connection with the basic cyclization, in particular tetrahydrofuran or dichloromethane or mixtures thereof. In a preferred embodiment, the reaction is carried out in dichloromethane.

The acids used are the acids mentioned for process A. For further details, reference is also made to the deprotection of VI to give compound II. The reaction conditions mentioned there are also suitable for deprotecting compound XIV. In one embodiment of the process according to the invention, the reaction is carried out in the presence of organic acids, in particular strong organic acids, for example in the presence of formic acid, acetic acid or trifluoroacetic acid or mixtures thereof. In a preferred embodiment, the reaction is carried out in the presence of trifluoroacetic acid.

The work-up can be carried out analogously to the procedure described for process A.

PREPARATION EXAMPLE

Example 1

3-Benzyl-6-(2-ethynylbenzyl)-1,4-dimethylpiperazine-2,5-dione

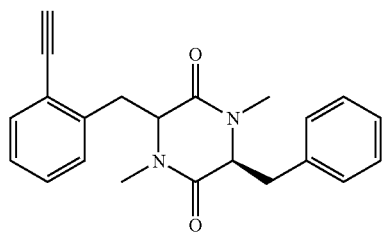 [SMILES: C#Cc1ccccc1CC1C(=O)N(C)[C@@H](Cc2ccccc2)C(=O)N1C]

1.1) Ethyl 2-(tert-butoxycarbonylmethylamino)-3-(2-iodophenyl)propionate

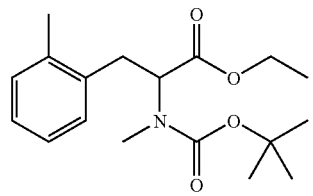 [SMILES: CCOC(=O)C(Cc1ccccc1C)N(C)C(=O)OC(C)(C)C]

At −78° C., lithium diisopropylamide solution (2 M in THF/n-heptane, 17 ml, 34 mmol) was slowly added dropwise to ethyl(tert-butoxycarbonylmethylamino)acetate (7.4 g, 34 mmol) in tetrahydrofuran (abs., 50 ml). The mixture was stirred at this temperature for 2 h. 1-Bromomethyl-2-iodobenzene (10.0 g, 46 mmol) was then slowly added dropwise, and the mixture was stirred at −78° C. for 1 h. The reaction solution was slowly (12 h) warmed to room temperature and then concentrated on a rotary evaporator. The residue was taken up in ethyl acetate, washed, dried and concentrated. The residue obtained in this manner was then purified by column chromatography (SiO$_2$, hexane/ethyl acetate). This gave 6.4 g (43%) of the target compound.

M+Na (m/z): 456.

1.2) Ethyl 3-(2-iodophenyl)-2-methylaminopropionate

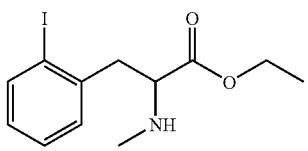 [SMILES: CCOC(=O)C(Cc1ccccc1I)NC]

Trifluoroacetic acid (25 ml) was added to ethyl 2-(tert-butoxycarbonylmethylamino)-3-(2-iodophenyl)propionate (6.4 g, 15 mmol) in CH$_2$Cl$_2$ (35 ml). The mixture was stirred at room temperature for 2 h. The reaction solution was concentrated on a rotary evaporator, the residue was taken up in ethyl acetate, washed (NaHCO$_3$ sat.), dried and concentrated. The residue obtained in this manner (3.9 g, 79%) was reacted further as a crude product.

M+1 (m/z): 334.

1.3) Ethyl 2-{[2-(tert-butoxycarbonylmethylamino)-3-phenylpropionyl]methylamino}3-(2-iodophenyl)propionate

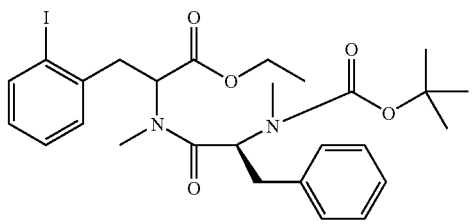 [SMILES: CCOC(=O)C(Cc1ccccc1I)N(C)C(=O)[C@H](Cc1ccccc1)N(C)C(=O)OC(C)(C)C]

Ethyl 3-(2-iodophenyl)-2-methylaminopropionate (3.94 g, 12 mmol), 2-(tert-butoxycarbonylmethylamino)-3-phenylpropionic acid (3.7 g, 13 mmol), N-ethyldiisopropylamine (7.8 g, 61 mmol) and EDAC (4.6 g, 24 mmol) were stirred in THF (abs., 50 ml) for 16 h. The reaction solution was concentrated on a rotary evaporator. The residue was taken up in ethyl acetate, washed, dried and concentrated. Purification by column chromatography (SiO$_2$, hexane/ethyl acetate) gave 4.0 g (56%) of the target compound.

M+Na (m/z): 617.

1.4) Ethyl 3-(2-iodophenyl)-2-[methyl-(2-methylamino-3-phenylpropionyl)amino]propionate

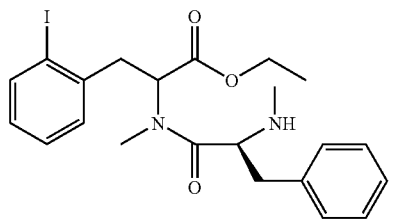 [SMILES: CCOC(=O)C(Cc1ccccc1I)N(C)C(=O)[C@H](Cc1ccccc1)NC]

Trifluoroacetic acid (10 ml) was added to ethyl 2-{[2-(tert-butoxycarbonylmethylamino)-3-phenylpropionyl]methylamino}-3-(2-iodophenyl)propionate (2.5 g, 4.2 mmol) in CH$_2$Cl$_2$ (10 ml). The mixture was stirred at room temperature for 2 h and then concentrated on a rotary evaporator. The residue was purified by column chromatography (SiO$_2$, hexane/ethyl acetate).

M+1 (m/z): 495.

1.5) 3-Benzyl-6-(2-iodobenzyl)-1,4-dimethylpiperazine-2,5-dione

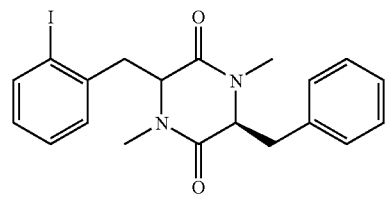 [SMILES: CN1C(=O)[C@H](Cc2ccccc2)N(C)C(=O)C1Cc1ccccc1I]

Ethyl 3-(2-iodophenyl)-2-[methyl-(2-methylamino-3-phenylpropionyl)amino]propionate (2.1 g, 4.2 mmol) was taken up in THF (30 ml), and NH$_4$OH (25% (w/v) in H$_2$O, 20 ml) was added. The mixture was stirred at room temperature for 12 h and then concentrated on a rotary evaporator. The residue obtained in this manner was purified by column chromatography (SiO$_2$, hexane/ethyl acetate). This gave 0.4 g (21%) of a non-polar isomer and 0.6 g (31%) of a polar isomer.

M+1 (m/z): 449.

1.6) 3-Benzyl-1,4-dimethyl-6-(2-trimethylsilanylethynylbenzyl)piperzine-2,5-dione

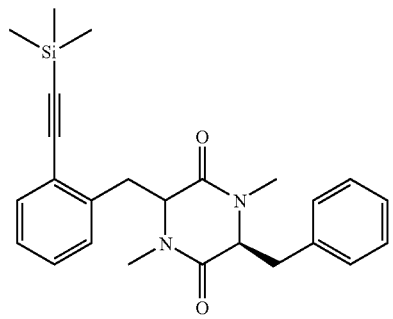 [SMILES: CN1C(=O)[C@H](Cc2ccccc2)N(C)C(=O)C1Cc1ccccc1C#C[Si](C)(C)C]

Under argon, 3-benzyl-6-(2-iodobenzyl)-1,4-dimethylpiperazine-2,5-dione (polar isomer from 1.5, 100 mg, 0.22 mmol) was stirred together with diisopropylamide (0.5 ml), trimethylsilylacetylene (40 mg, 0.4 mmol), Pd(PPh$_3$)$_4$ (60 mg, 0.05 mmol) and CuI (10 mg, 0.05 mmol) in DMF (abs., 5 ml) at 80° C. for 12 h. After cooling and addition of H$_2$O, the mixture was extracted with methyl tert-butyl ether and the organic phases were dried and concentrated. Purification by column chromatography gave 21 mg (23%) of the target compound as a colorless oil.

M+1 (m/z): 419.

1.7) 3-Benzyl-6-(2-ethynylbenzyl)-1,4-dimethylpiperazine-2,5-dione

At 0° C., tetrabutylammonium fluoride (1 mM in THF, 0.5 ml, 0.5 mmol) was added dropwise to 3-benzyl-1,4-dimethyl-6-(2-trimethylsilanylethynylbenzyl)piperazine-2,5-dione (140 mg, 0.22 mmol) in THF (abs., 5 ml). The mixture was stirred at this temperature for 1 h. After addition of NH$_4$Cl solution (saturated, aq.), the mixture was extracted with ethyl acetate and the organic phases were dried and concentrated. Purification by column chromatography gave 50 mg (65%) of the target compound as a yellow oil.

M+1 (m/z): 346.

$^1$H-NMR (CDCl$_3$): δ=2.41 (d, 2H), 2.72 (s, 3H), 2.87 (s, 3H), 3.00 (dm, 1H), 3.12 (dm, 1H), 3.31 (s, 1H), 4.16 (m, 2H), 6.94 (dm, 1H), 7.14-7.31 (brm, 5H), 7.35 (m, 2H), 7.45 (m, 1H).

Further compounds of the formula I were prepared in an analogous manner, where the structural elements of Table II below serve as legend for Tables A.1 to A.4 below.

TABLE II

1)

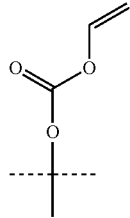

2)

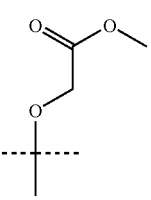

3)

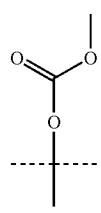

4)

TABLE II-continued

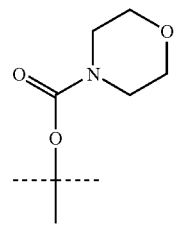

5)

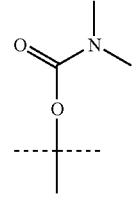

6)

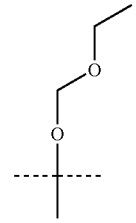

7)

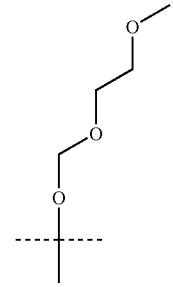

8)

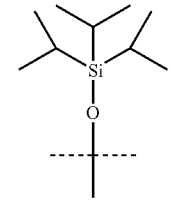

9)

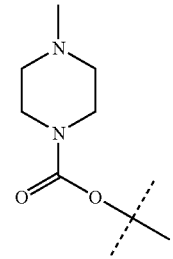

TABLE II-continued
10) 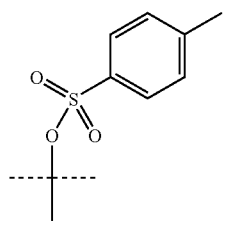
11) 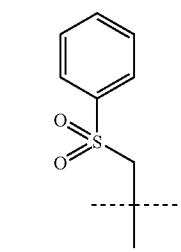
12) 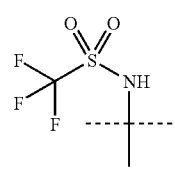
13) 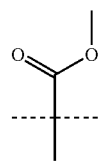
14) 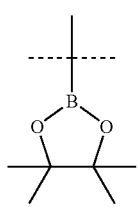
15) 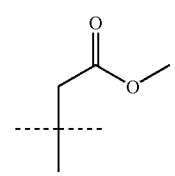
16) 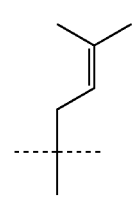
TABLE II-continued
17) 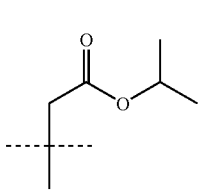
18) 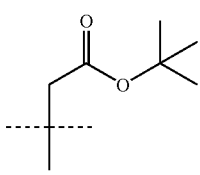
19) 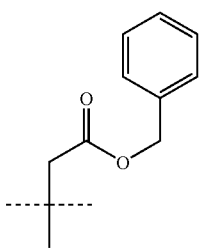
20) 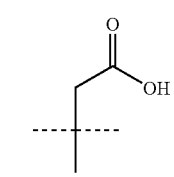
21) 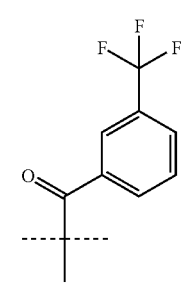
22) 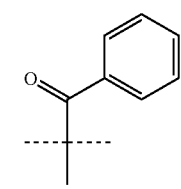
23) 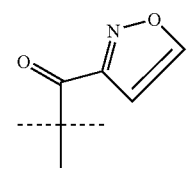

TABLE II-continued
24) 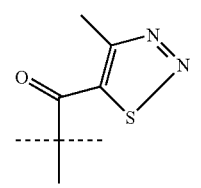
25) 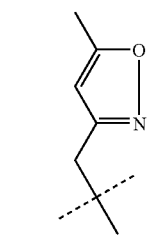
26) 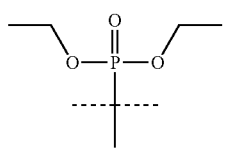
27) 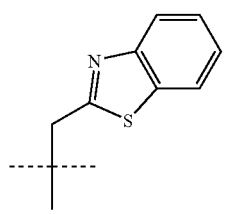
28) 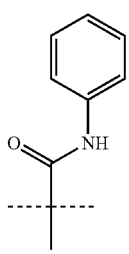
29) 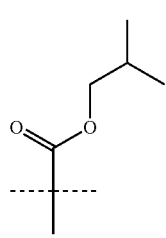
30) 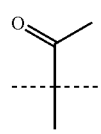
TABLE II-continued
31) 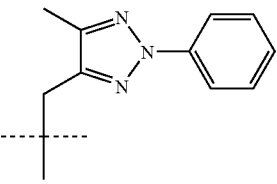
32) 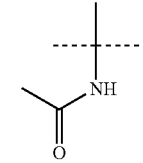
33) 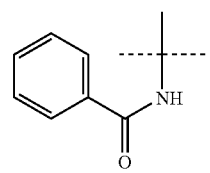
34) 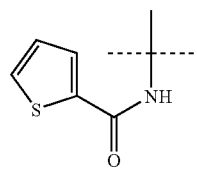
35) 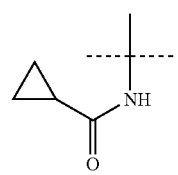
36) 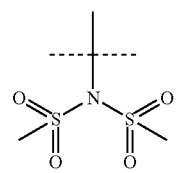
37) 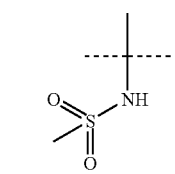
38) 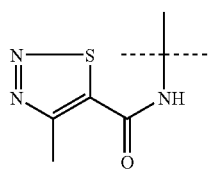

TABLE II-continued
39) 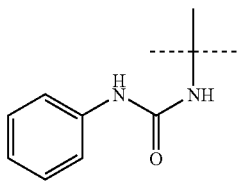
40) 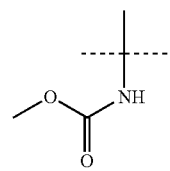
41) 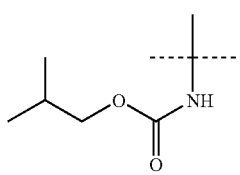
42) 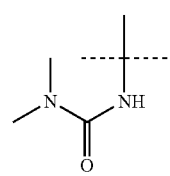
43) 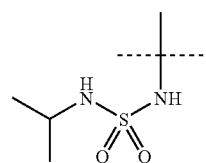
44) 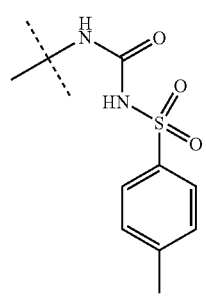
45) 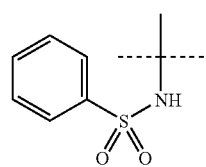
TABLE II-continued
46) 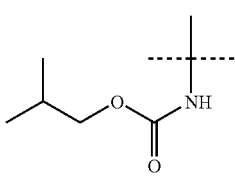
47) 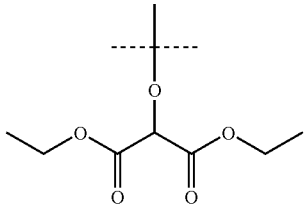
48) 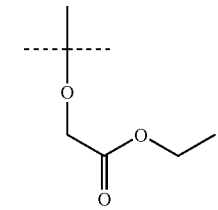
49) 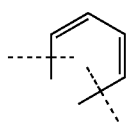
50) 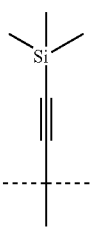
51) 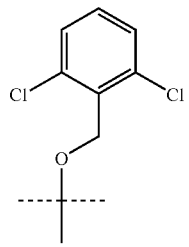
52) 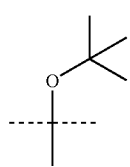

TABLE II-continued
53) 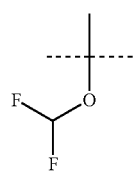
54) 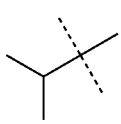
55) 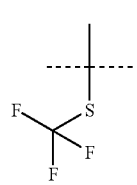
56) 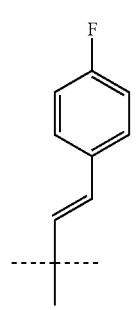
57) 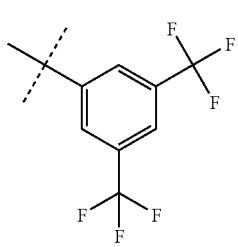
58) 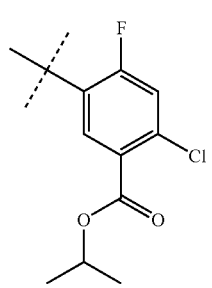
59) 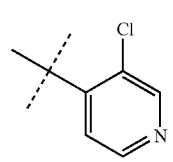
TABLE II-continued
60) 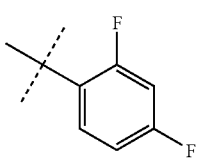
61) 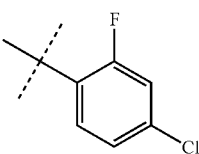
62) 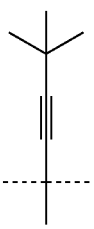
63) 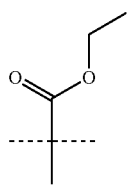
64) 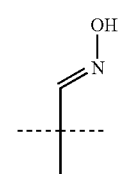
65) 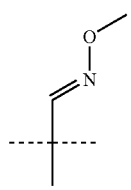
66) 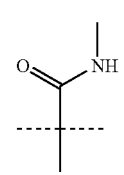

TABLE II-continued
67) 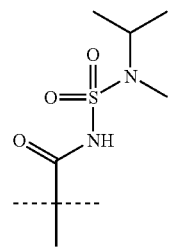
68) 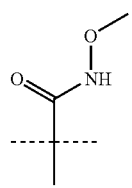
69) 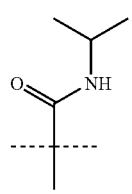
70) 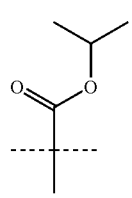
71) 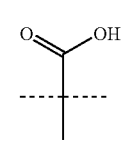
72) 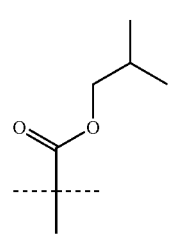
73) 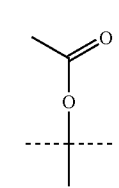
TABLE II-continued
74) 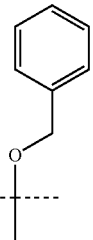
75) 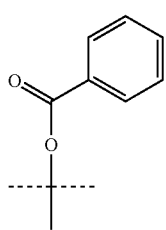
76) 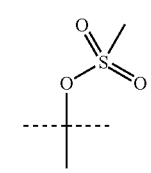
77) 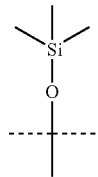
78) 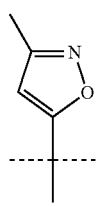
79) 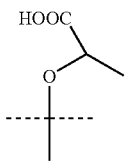
80) 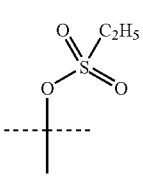

TABLE A.1

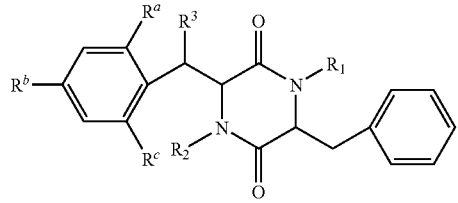

A.1

| No. | $R^a$ | $R^b$ | $R^c$ | $R^1$ | $R^2$ | $R^3$ | RT HPLC/MS or m.p. | diast. |
|---|---|---|---|---|---|---|---|---|
| A.1.1 | $NO_2$ | $CF_3$ | H | $CH_3$ | $CH_3$ | H | 3.187 min m/z = 435.9 $[M + H]^+$ | diast. 2 |
| A.1.2 | $NO_2$ | $CF_3$ | H | $CH_3$ | $CH_3$ | H | 3.079 min m/z = 435.9 $[M + H]^+$ | diast. 1 |
| A.1.3 | F | F | H | $CH_3$ | $CH_3$ | H | 2.702 min m/z = 359.1 $[M + H]^+$ | diast. 1 |
| A.1.4 | Cl | F | H | $CH_3$ | $CH_3$ | H | 2.962 min m/z = 375.3 $[M + H]^+$ | diast. 1 |
| A.1.5 | F | F | F | $CH_3$ | $CH_3$ | H | 2.737 min m/z = 377.2 $[M + H]^+$ | diast. 1 |
| A.1.6 | F | F | H | $CH_3$ | $CH_3$ | H | 2.808 min m/z = 359.1 $[M + H]^+$ | diast. 2 |
| A.1.7 | Cl | F | H | $CH_3$ | $CH_3$ | H | 3.042 min m/z = 375.4 $[M + H]^+$ | diast. 2 |
| A.1.8 | F | F | F | $CH_3$ | $CH_3$ | H | 2.950 min m/z = 377.1 $[M + H]^+$ | diast. 2 |
| A.1.9 | $NO_2$ | F | H | $CH_3$ | $CH_3$ | H | 2.808 min m/z = 386.0 $[M + H]^+$ | diast. 2 |
| A.1.10 | $NO_2$ | Cl | H | $CH_3$ | $CH_3$ | H | 3.068 min m/z = 402.0 $[M + H]^+$ | diast. 2 |
| A.1.11 | $NO_2$ | F | H | $CH_3$ | $CH_3$ | H | 2.716 min m/z = 386.0 $[M + H]^+$ | diast. 1 |
| A.1.12 | $NO_2$ | Cl | H | $CH_3$ | $CH_3$ | H | 2.938 min m/z = 402.0 $[M + H]^+$ | diast. 1 |
| A.1.13 | $NO_2$ | 79) | H | $CH_3$ | $CH_3$ | H | 2.324 min m/z = 455 $[M^+]$ | |

TABLE A.2

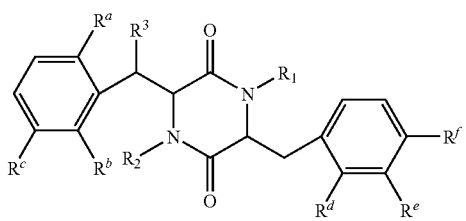

| Nr. | $R^a$ | $R^b$ | $R^c$ | $R^1$ | $R^2$ | $R^3$ | $R^d$ | $R^e$ | $R^f$ | RT HPLC/MS or m.p. | diast. |
|---|---|---|---|---|---|---|---|---|---|---|---|
| A.2.1 | $NO_2$ | H | H | $CH_3$ | $CH_3$ | 1) | H | H | H | 65° C. | |
| A.2.2 | $NO_2$ | H | H | $CH_3$ | $CH_3$ | 2) | H | H | H | 130° C. | |
| A.2.3 | $NO_2$ | H | H | $CH_3$ | $CH_3$ | 3) | H | H | H | 74° C. | |
| A.2.4 | $NO_2$ | H | H | $CH_3$ | $CH_3$ | 4) | H | H | H | 207° C. | |
| A.2.5 | $NO_2$ | H | H | $CH_3$ | $CH_3$ | 5) | H | H | H | 176° C. | |
| A.2.6 | $NO_2$ | H | H | $CH_3$ | $CH_3$ | 6) | H | H | H | 117° C. | |
| A.2.7 | $NO_2$ | H | H | $CH_3$ | $CH_3$ | 7) | H | H | H | m/z = 472.1 $[M + h]^+$ | |
| A.2.8 | $NO_2$ | H | H | $CH_3$ | $CH_3$ | 8) | H | H | H | 155° C. | |
| A.2.9 | $NO_2$ | H | H | $CH_3$ | $CH_3$ | 9) | H | H | H | 201° C. | |
| A.2.10 | $NO_2$ | H | H | $NH_2$ | $CH_3$ | H | H | H | H | 2.483 min 162° C. m/z = 369.2 $[M + h]^+$ 177° C. | Diast. 1 |
| A.2.11 | $NO_2$ | H | H | $CH_3$ | $CH_3$ | 1) | H | H | H | 120° C. | |
| A.2.12 | $NO_2$ | H | H | $CH_3$ | $CH_3$ | 3) | H | H | H | 124° C. | |
| A.2.13 | $NO_2$ | H | H | $CH_3$ | $CH_3$ | 4) | H | H | H | 184° C. | |

TABLE A.2-continued

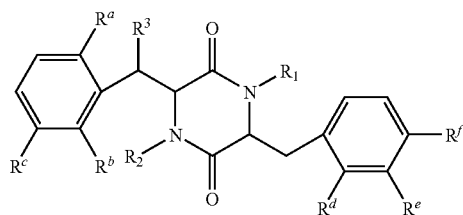

| Nr. | $R^a$ | $R^b$ | $R^c$ | $R^1$ | $R^2$ | $R^3$ | $R^d$ | $R^e$ | $R^f$ | RT HPLC/MS or m.p. | diast. |
|---|---|---|---|---|---|---|---|---|---|---|---|
| A.2.14 | NO$_2$ | H | H | CH$_3$ | CH$_3$ | 5) | H | H | H | 118° C. | |
| A.2.15 | NO$_2$ | H | H | CH$_3$ | CH$_3$ | 5) | H | H | H | 68° C. | |
| A.2.16 | NO$_2$ | H | H | CH$_3$ | CH$_3$ | 4) | H | H | H | 162° C. | |
| A.2.17 | NO$_2$ | H | H | CH$_3$ | CH$_3$ | 3) | H | H | H | 140° C. | |
| A.2.18 | NO$_2$ | H | H | CH$_3$ | CH$_3$ | 1) | H | H | H | 139° C. | |
| A.2.19 | NO$_2$ | H | H | CH$_3$ | CH$_3$ | 5) | H | H | H | 68° C. | |
| A.2.20 | NO$_2$ | H | H | CH$_3$ | CH$_3$ | 4) | H | H | H | 162° C. | |
| A.2.21 | NO$_2$ | H | H | CH$_3$ | CH$_3$ | 1) | H | H | H | 129° C. | |
| A.2.22 | NO$_2$ | H | H | CH$_3$ | CH$_3$ | 10) | H | H | H | 3.378 min m/z = 538.0 [M + H]$^+$ | diast. 2 |
| A.2.23 | NO$_2$ | H | H | CH$_3$ | CH$_3$ | 10) | H | H | H | 3.352 min m/z = 538.0 [M + H]$^+$ | diast. 1 |
| A.2.24 | NO$_2$ | H | H | CH$_3$ | CH$_3$ | 10) | H | H | H | 3.354 min m/z = 538.0 [M + H]$^+$ | diast. 3 |
| A.2.25 | NO$_2$ | H | H | H | CH$_3$ | H | H | H | H | 2.579 min m/z = 354.0 [M + H]$^+$ | diast. 1 |
| A.2.26 | NO$_2$ | H | H | H | CH$_3$ | H | H | H | H | 2.651 min m/z = 354.0 [M + H]$^+$ | diast. 2 |
| A.2.27 | F | H | H | CH$_3$ | CH$_3$ | H | H | H | H | 2.867 min m/z = 341.1 [M + H]$^+$ | |
| A.2.28 | Cl | H | H | CH$_3$ | CH$_3$ | H | H | H | H | 3.134 min m/z = 357.2 [M + H]$^+$ | |
| A.2.29 | Ph | H | H | CH$_3$ | CH$_3$ | H | H | H | H | 3.400 min m/z = 399.1 [M + H]$^+$ | diast. 1 |
| A.2.30 | 11) | H | H | CH$_3$ | CH$_3$ | H | H | H | H | 2.873 min m/z = 477.1 [M + H]$^+$ | diast. 2 |
| A.2.31 | Ph | H | H | CH$_3$ | CH$_3$ | H | H | H | H | 3.416 min m/z = 399.1 [M + H]$^+$ | diast. 2 |
| A.2.32 | 11) | H | H | CH$_3$ | CH$_3$ | H | H | H | H | 2.823 min m/z = 477.1 [M + H]$^+$ | diast. 1 |
| A.2.33 | NO$_2$ | H | H | CH$_3$ | CH$_3$ | H | H | H | H | 2.536 min m/z = 368.0 [M + H]$^+$ | diast. 1 |
| A.2.34 | NO$_2$ | H | H | CH$_3$ | CH$_3$ | H | H | H | H | 2.640 min m/z = 368.0 [M + H]$^+$ | diast. 2 |
| A.2.35 | NO$_2$ | F | H | CH$_3$ | CH$_3$ | H | H | H | H | 2.733 min m/z = 386.1 [M + H]$^+$ | diast. 2 |
| A.2.36 | NO$_2$ | H | H | H | CH$_3$ | H | F | H | H | 2.496 min m/z = 371.9 [M + H]$^+$ | diast. 2 |
| A.2.37 | NO$_2$ | H | H | CH$_3$ | CH$_3$ | H | F | H | H | 2.688 min m/z = 386.0 [M + H]$^+$ | |
| A.2.38 | NH$_2$ | H | H | CH$_3$ | CH$_3$ | H | H | H | H | 2.026 min m/z = 338.0 [M + H]$^+$ | |
| A.2.39 | F | H | H | H | CH$_3$ | H | CF$_3$ | H | H | 2.872 min m/z = 394.9 [M + H]$^+$ | diast. 1 |
| A.2.40 | 12) | H | H | CH$_3$ | CH$_3$ | H | H | H | H | 3.186 min m/z = 469.9 [M + H]$^+$ | |
| A.2.41 | NO$_2$ | H | H | H | CH$_3$ | H | NO$_2$ | H | H | 2.479 min m/z = 398.9 [M + H]$^+$ | diast. 2 |
| A.2.42 | F | H | H | CH$_3$ | CH$_3$ | H | CF$_3$ | H | H | 3.160 min m/z = 409.4 [M + H]$^+$ | |
| A.2.43 | NO$_2$ | H | H | H | CH$_3$ | H | H | F | H | 2.561 min m/z = 371.9 [M + H]$^+$ | diast. 2 |
| A.2.44 | NO$_2$ | H | H | CH$_3$ | CH$_3$ | H | H | F | H | 2.729 min m/z = 385.9 [M + H]$^+$ | |
| A.2.45 | NO$_2$ | F | H | CH$_3$ | CH$_3$ | H | H | H | H | 2.624 min m/z = 386.1 [M + Na]$^+$ | diast. 1 |
| A.2.46 | NO$_2$ | H | H | H | CH$_3$ | H | F | H | H | 2.468 min m/z = 371.9 [M + H]$^+$ | diast. 1 |
| A.2.47 | NO$_2$ | H | CH$_3$O— | CH$_3$ | CH$_3$ | H | H | H | H | 2.571 min m/z = 428.0 [M + H]$^+$ | diast. 1 |
| A.2.48 | NO$_2$ | H | H | CH$_3$ | CH$_3$ | H | F | H | H | 2.694 min m/z = 385.9 [M + H]$^+$ | |
| A.2.49 | F | H | H | H | CH$_3$ | H | CF$_3$ | H | H | 2.921 min m/z = 394.9 [M + H]$^+$ | diast. 2 |

TABLE A.2-continued

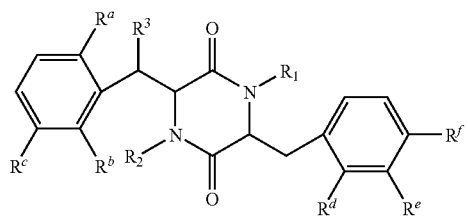

| Nr. | $R^a$ | $R^b$ | $R^c$ | $R^1$ | $R^2$ | $R^3$ | $R^d$ | $R^e$ | $R^f$ | RT HPLC/MS or m.p. | diast. |
|---|---|---|---|---|---|---|---|---|---|---|---|
| A.2.50 | NO$_2$ | H | H | H | CH$_3$ | H | NO$_2$ | H | H | 2.464 min<br>m/z = 398.9 [M + H]$^+$ | diast. 1 |
| A.2.51 | F | H | H | CH$_3$ | CH$_3$ | H | CF$_3$ | H | H | 3.071 min<br>m/z = 408.9 [M + H]$^+$ | |
| A.2.52 | NO$_2$ | H | H | H | CH$_3$ | H | H | F | H | 2.509 min<br>m/z = 371.9 [M + H]$^+$ | diast. 1 |
| A.2.53 | NO$_2$ | H | H | CH$_3$ | CH$_3$ | H | H | F | H | 2.630 min<br>m/z = 385.9 [M + H]$^+$ | |
| A.2.54 | 13) | H | H | CH$_3$ | CH$_3$ | H | H | H | H | 2.547 min<br>m/z = 381.0 [M + H]$^+$ | diast. 1 |
| A.2.55 | 13) | H | H | CH$_3$ | CH$_3$ | H | H | H | H | 2.769 min<br>m/z = 381.0 [M + H]$^+$ | diast. 2 |
| A.2.56 | 14) | H | H | CH$_3$ | CH$_3$ | H | H | H | H | m/z = 449.1 [M + H}$^+$ | diast. 2 |
| A.2.57 | NO$_2$ | H | H | PhCH$_2$— | CH$_3$ | H | H | H | H | 3.398 min<br>m/z = 444.1 [M + H]$^+$ | diast. 1 |
| A.2.58 | NO$_2$ | H | H | 15) | CH$_3$ | H | H | H | H | 2.932 min<br>m/z = 426.1 [M + H]$^+$ | diast. 2 |
| A.2.59 | NO$_2$ | H | H | 16) | CH$_3$ | H | H | H | H | 3.361 min<br>m/z = 422.2 [M + H]$^+$ | diast. 1 |
| A.2.60 | NO$_2$ | H | H | 17) | CH$_3$ | H | H | H | H | 3.337 min<br>m/z = 454.1 [M + H]$^+$ | diast. 2 |
| A.2.61 | 14) | H | H | CH$_3$ | CH$_3$ | H | H | H | H | m/z = 448.9 [M + H]$^+$ | diast. 1 |
| A.2.62 | NO$_2$ | H | H | PhCH$_2$— | CH$_3$ | H | H | H | H | 3.459 min<br>m/z = 444.1 [M + H]$^+$ | diast.2 |
| A.2.63 | NO$_2$ | H | H | 15) | CH$_3$ | H | H | H | H | 2.928 min<br>m/z = 426.1 [M + H]$^+$ | diast. 1 |
| A.2.64 | NO$_2$ | H | H | 16) | CH$_3$ | H | H | H | H | 3.420 min<br>m/z = 422.1 [M + H]$^+$ | diast. 2 |
| A.2.65 | NO$_2$ | H | H | 17) | CH$_3$ | H | H | H | H | 3.285 min<br>m/z = 454.1 [M + H]$^+$ | diast. 1 |
| A.2.66 | NO$_2$ | H | H | 18) | CH$_3$ | H | H | H | H | 3.528 min<br>m/z = 490.1 [M + Na]$^+$ | diast. 2 |
| A.2.67 | NO$_2$ | H | H | 18) | CH$_3$ | H | H | H | H | 3.458 min<br>m/z = 490.1 [M + Na]$^+$ | diast. 1 |
| A.2.68 | NO$_2$ | H | H | 19) | CH$_3$ | H | H | H | H | 3.578 min<br>m/z = 502.5 [M + H]$^+$ | diast. 2 |
| A.2.69 | NO$_2$ | H | H | 20) | CH$_3$ | H | H | H | H | 2.634 min<br>m/z = 421.1 [M + H]$^+$ | |
| A.2.70 | NO$_2$ | H | H | 19) | CH$_3$ | H | H | H | H | 3.547 min<br>m/z = 502.5 [M + H]$^+$ | diast. 1 |
| A.2.71 | NO$_2$ | H | H | 20) | CH$_3$ | H | H | H | H | 2.634 min<br>m/z = 412.1 [M + H]$^+$ | |
| A.2.72 | NO$_2$ | H | H | 21) | CH$_3$ | H | H | H | H | 3.844 min<br>m/z = 526.5 [M + H]$^+$ | |
| A.2.73 | NO$_2$ | H | H | 22) | CH$_3$ | H | H | H | H | 3.516 min<br>m/z = 458.4 [M + H]$^+$ | diast. 2 |
| A.2.74 | NH$_2$ | H | H | CH$_3$ | CH$_3$ | H | H | H | H | 1.801 min<br>m/z = 338.2 [M + H]$^+$ | diast. 1 |
| A.2.75 | NO$_2$ | H | H | 22) | CH$_3$ | H | H | H | H | 3.511 min<br>m/z = 458.4 [M + H]$^+$ | diast. 1 |
| A.2.76 | NO$_2$ | H | H | 21) | CH$_3$ | H | H | H | H | 3.844 min<br>m/z = 526.5 [M + H]$^+$ | diast. 2 |
| A.2.77 | NO$_2$ | H | H | 23) | CH$_3$ | H | H | H | H | 3.252 min<br>m/z = 449.1 [M + H]$^+$ | |
| A.2.78 | NO$_2$ | H | H | 24) | CH$_3$ | H | H | H | H | 3.411 min<br>m/z = 480.4 [M + H]$^+$ | |
| A.2.79 | NO$_2$ | H | H | 25) | CH$_3$ | H | H | H | H | 3.022 min<br>m/z = 449.1 [M + H]$^+$, 137° C. | diast. 1 |
| A.2.80 | NO$_2$ | H | H | 25) | CH$_3$ | H | H | H | H | 3.076 min<br>m/z = 449.1 [M + H]$^+$ | diast. 2 |
| A.2.81 | CN | H | H | CH$_3$ | CH$_3$ | H | H | H | H | m/z = 348.1 [M + H]$^+$ | diast. 1 |
| A.2.82 | CN | H | H | CH$_3$ | CH$_3$ | H | H | H | H | m/z = 348.1 [M + H]$^+$ | diast. 2 |
| A.2.83 | NO$_2$ | H | H | H | CH$_3$ | H | Br | H | H | m/z = 433.8 [M + H]$^+$ | diast. 1 |

TABLE A.2-continued

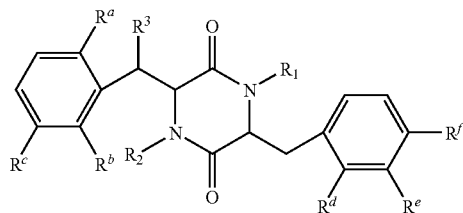

| Nr. | $R^a$ | $R^b$ | $R^c$ | $R^1$ | $R^2$ | $R^3$ | $R^d$ | $R^e$ | $R^f$ | RT HPLC/MS or m.p. | diast. |
|---|---|---|---|---|---|---|---|---|---|---|---|
| A.2.84 | NO$_2$ | H | H | H | CH$_3$ | H | H | Br | H | m/z = 433.8 [M + H]$^+$ | diast. 1 |
| A.2.85 | NO$_2$ | H | H | H | CH$_3$ | H | Br | H | H | m/z = 433.8 [M + H]$^+$ | diast. 2 |
| A.2.86 | NO$_2$ | H | H | H | CH$_3$ | H | H | Br | H | m/z = 433.8 [M + H]$^+$ | diast. 2 |
| A.2.87 | 26) | H | H | CH$_3$ | CH$_3$ | H | H | H | H | 2.749 min m/z = 459.1 [M + H]$^+$ | |
| A.2.88 | NO$_2$ | H | H | 13) | CH$_3$ | H | H | H | H | 2.969 min m/z = 412.1 [M + H]$^+$ | |
| A.2.89 | NO$_2$ | H | H | HO—CH$_2$— | CH$_3$ | H | H | H | H | 2.565 min m/z = 384.1 [M + H]$^+$ | |
| A.2.90 | NO$_2$ | H | H | 27) | CH$_3$ | H | H | H | H | 3.419 min m/z = 501.1 [M + H]$^+$, 164° C. | |
| A.2.91 | NO$_2$ | H | H | 28) | CH$_3$ | H | H | H | H | 3.011 min m/z = 473.1 [M + H]$^+$ | |
| A.2.92 | NO$_2$ | H | H | 29) | CH$_3$ | H | H | H | H | 3.562 min m/z = 454.1 [M + H]$^+$ | |
| A.2.93 | NO$_2$ | H | H | 30) | CH$_3$ | H | H | H | H | 3.115 min m/z = 396.1 [M + H]$^+$ | |
| A.2.94 | NO$_2$ | H | H | 31) | CH$_3$ | H | H | H | H | 3.728 min m/z = 525.2 [M + H]$^+$ | |
| A.2.95 | NO$_2$ | H | H | 13) | CH$_3$ | H | H | H | H | 2.998 min m/z = 412.1 [M + H]$^+$ | |
| A.2.96 | NO$_2$ | H | H | HO—CH$_2$— | CH$_3$ | H | H | H | H | 2.637 min m/z = 384.4 [M + H]$^+$ | |
| A.2.97 | I | H | H | CH$_3$ | CH$_3$ | H | H | H | H | 3.101 min m/z = 449.0 [M + H]$^+$ | |
| A.2.98 | B(OH)$_2$ | H | H | CH$_3$ | CH$_3$ | H | H | H | H | 2.260 min m/z = 367.1 [M + H]$^+$ | |
| A.2.99 | NH$_2$ | H | H | CH$_3$ | CH$_3$ | H | H | H | H | 2.188 min m/z = 380.1 [M + H]$^+$, 161° C. | |
| A.2.100 | 32) | H | H | CH$_3$ | CH$_3$ | H | H | H | H | 2.251 min m/z = 380.1 [M + H]$^+$, 145° C. | |
| A.2.101 | 33) | H | H | CH$_3$ | CH$_3$ | H | H | H | H | 2.876 min m/z = 442.1 [M + H]$^+$, 186° C. | |
| A.2.102 | 34) | H | H | CH$_3$ | CH$_3$ | H | H | H | H | 2.838 min m/z = 448.1 [M + H]$^+$, 99° C. | |
| A.2.103 | 35) | H | H | CH$_3$ | CH$_3$ | H | H | H | H | 2.549 min m/z = 406.1 [M + H]$^+$ | |
| A.2.104 | 36) | H | H | CH$_3$ | CH$_3$ | H | H | H | H | 2.662 min m/z = 494.0 [M + H]$^+$ | |
| A.2.105 | 37) | H | H | CH$_3$ | CH$_3$ | H | H | H | H | 2.431 min m/z = 416.1 [M + H]$^+$ | |
| A.2.106 | 38) | H | H | CH$_3$ | CH$_3$ | H | H | H | H | 2.781 min m/z = 464.1 [M + H]$^+$ | |
| A.2.107 | 39) | H | H | CH$_3$ | CH$_3$ | H | H | H | H | 3.053 min m/z = 457.1 [M + H]$^+$, 182° C. | |
| A.2.108 | 40) | H | H | CH$_3$ | CH$_3$ | H | H | H | H | 2.573 min m/z = 396.1 [M + H]$^+$ | |
| A.2.109 | 41) | H | H | CH$_3$ | CH$_3$ | H | H | H | H | 3.227 min m/z = 438.2 [M + H]$^+$ | |
| A.2.110 | 42) | H | H | CH$_3$ | CH$_3$ | H | H | H | H | 2.310 min m/z = 409.2 [M + H]$^+$ | |
| A.2.111 | 43) | H | H | CH$_3$ | CH$_3$ | H | H | H | H | 2.842 min m/z = 459.1 [M + H]$^+$ | |
| A.2.112 | 44) | H | H | CH$_3$ | CH$_3$ | H | H | H | H | 2.988 min m/z = 535.1 [M + H]$^+$ | |
| A.2.113 | 45) | H | H | CH$_3$ | CH$_3$ | H | H | H | H | 3.070 min m/z = 478.0 [M + H]$^+$, 227° C. | |

TABLE A.2-continued

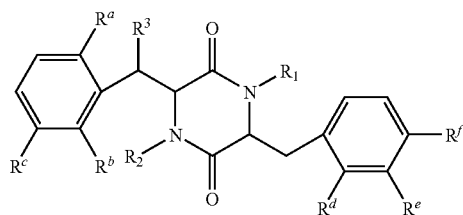

| Nr. | $R^a$ | $R^b$ | $R^c$ | $R^1$ | $R^2$ | $R^3$ | $R^d$ | $R^e$ | $R^f$ | RT HPLC/MS or m.p. | diast. |
|---|---|---|---|---|---|---|---|---|---|---|---|
| A.2.114 | 46) | H | H | $CH_3$ | $CH_3$ | H | H | H | H | 3.297 min<br>m/z = 438.2 [M + H]$^+$ | |
| A.2.115 | $NO_2$ | H | H | N≡C— | $CH_3$ | H | H | H | H | 3.079 min<br>m/z = 401.1 [M + H]$^+$ | |
| A.2.116 | $NO_2$ | H | H | N≡C—CH— | $CH_3$ | H | H | H | H | 2.876 min<br>m/z = 393.1 [M + H]$^+$ | |
| A.2.117 | $NO_2$ | H | H | 23) | $CH_3$ | H | H | H | H | 3.290 min<br>m/z = 449.2 [M + H]$^+$ | |
| A.2.118 | $NO_2$ | H | H | 24) | $CH_3$ | H | H | H | H | 3.373 min<br>m/z = 480.0 [M + H]$^+$ | |
| A.2.119 | HO— | H | H | $CH_3$ | $CH_3$ | H | H | H | H | 2.460 min<br>m/z = 339.1 [M + H]$^+$ | |
| A.2.120 | 47) | H | H | $CH_3$ | $CH_3$ | H | H | H | H | 3.207 min<br>m/z = 497.1 [M + H]$^+$ | |
| A.2.121 | 48) | H | H | $CH_3$ | $CH_3$ | H | H | H | H | 2.975 min<br>m/z = 425.2 [M + H]$^+$ | |
| A.2.122 | $NO_2$ | H | H | $CH_3$ | $CH_3$ | H | Br | H | H | 2.979 min<br>m/z = 448.1 [M + H]$^+$ | diast. 1 |
| A.2.123 | $NO_2$ | H | H | $CH_3$ | $CH_3$ | H | H | Br | H | 3.055 min<br>m/z = 448.1 [M + H]$^+$ | diast. 2 |
| A.2.124 | 73) | H | H | $CH_3$ | $CH_3$ | H | H | H | H | 2.629 min<br>m/z = 381.1 [M + H]$^+$ | |
| A.2.125 | HO— | H | H | $CH_3$ | $CH_3$ | H | H | H | H | 2.330 min<br>m/z = 339.1 [M + H]$^+$ | |
| A.2.126 | $NO_2$ | H | H | $CH_3$ | $CH_3$ | H | Br | H | H | 2.984 min<br>m/z = 448.1 [M + H]$^+$ | diast. 2 |
| A.2.127 | $NO_2$ | H | H | $CH_3$ | $CH_3$ | H | H | Br | H | 2.989 min<br>m/z = 448.1 [M + H]$^+$ | diast. 1 |
| A.2.128 | $NO_2$ | H | H | H | $CH_3$ | H | 49) | 49) | H | 2.994 min<br>m/z = 404.1 [M + H]$^+$ | diast. 2 |
| A.2.129 | $NO_2$ | H | H | H | $CH_3$ | H | H | CN | H | 2.471 min<br>m/z = 379.1 [M + H]$^+$ | diast. 1 |
| A.2.130 | $NO_2$ | H | H | H | $CH_3$ | H | H | $NO_2$ | H | 2.541 min<br>m/z = 399.1 [M + H]$^+$ | diast. 1 |
| A.2.131 | $NO_2$ | H | H | H | $CH_3$ | H | H | H | H | 2.543 min<br>m/z = 399.1 [M + H]$^+$ | diast. 1 |
| A.2.132 | $NO_2$ | H | H | $CH_3$ | $CH_3$ | H | 26) | H | H | 2.779 min<br>m/z = 504.1 [M + H]$^+$ | |
| A.2.133 | $NO_2$ | Br | H | $CH_3$ | $CH_3$ | H | H | H | H | 3.034 min<br>m/z = 446.1 [M + H]$^+$ | diast. 2 |
| A.2.134 | 50) | H | H | $CH_3$ | $CH_3$ | H | H | H | H | 3.886 min<br>m/z = 419.2 [M + H]$^+$ | |
| A.2.135 | HC≡C— | H | H | $CH_3$ | $CH_3$ | H | H | H | H | 2.860 min<br>m/z = 347.0 [M + H]$^+$ | |
| A.2.136 | $NO_2$ | Br | H | $CH_3$ | $CH_3$ | H | H | H | H | 2.901 min<br>m/z = 445.9 [M + H]$^+$ | diast. 1 |
| A.2.137 | $NO_2$ | H | H | H | $CH_3$ | H | 49) | 49) | H | 2.934 min<br>m/z = 404.1 [M + H]$^+$ | diast. 1 |
| A.2.138 | $NO_2$ | H | H | H | $CH_3$ | H | H | CN | H | 2.435 min<br>m/z = 379.1 [M + H]$^+$ | diast. 1 |
| A.2.139 | $NO_2$ | H | H | H | $CH_3$ | H | H | $NO_2$ | H | 2.569 min<br>m/z = 399.1 [M + H]$^+$ | diast. 2 |
| A.2.140 | $NO_2$ | H | H | H | $CH_3$ | H | H | H | $NO_2$ | 2.549 min<br>m/z = 399.1 [M + H]$^+$ | diast. 2 |
| A.2.141 | $NO_2$ | H | H | H | $CH_3$ | H | H | H | 51) | 3.473 min<br>m/z = 527.9 [M + H]$^+$ | diast. 2 |
| A.2.142 | $NO_2$ | H | H | H | $CH_3$ | H | H | H | I | 2.951 min<br>m/z = 479.8 [M + H]$^+$ | diast. 1 |
| A.2.143 | $NO_2$ | H | H | H | $CH_3$ | H | H | H | F | 2.553 min<br>m/z = 372.0 [M + H]$^+$ | diast. 1 |
| A.2.144 | $NO_2$ | H | H | H | $CH_3$ | H | H | H | 52) | 2.027 min<br>m/z = 370.0 [M + H]$^+$<br>tert-butyl radical | diast. 2 |
| A.2.145 | $NO_2$ | H | H | H | $CH_3$ | H | H | $CH_3$ | H | 2.698 min<br>m/z = 368.0 [M + H]$^+$ | diast. 1 |

TABLE A.2-continued

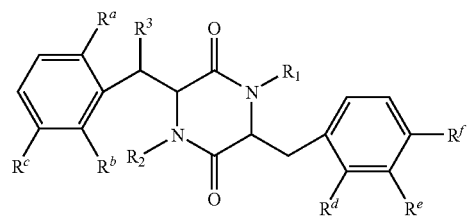

| Nr. | $R^a$ | $R^b$ | $R^c$ | $R^1$ | $R^2$ | $R^3$ | $R^d$ | $R^e$ | $R^f$ | RT HPLC/MS or m.p. | diast. |
|---|---|---|---|---|---|---|---|---|---|---|---|
| A.2.146 | NO$_2$ | H | H | H | CH$_3$ | H | Cl | H | H | 2.758 min<br>m/z = 388.1 [M + H]$^+$ | diast. 2 |
| A.2.147 | NO$_2$ | H | H | H | CH$_3$ | H | H | 49) | 49) | 2.969 min<br>m/z = 404.2 [M + H]$^+$ | diast. 2 |
| A.2.148 | NO$_2$ | H | H | H | CH$_3$ | H | H | H | Cl | 2.812 min<br>m/z = 388.1 [M + H]$^+$ | diast. 1 |
| A.2.149 | NO$_2$ | H | H | H | CH$_3$ | H | H | H | CH$_3$ | 2.734 min<br>m/z = 368.2 [M + H]$^+$ | diast. 1 |
| A.2.150 | NO$_2$ | H | H | H | CH$_3$ | H | I | H | H | 2.736 min<br>m/z = 368.2 [M + H]$^+$ | diast. 2 |
| A.2.151 | 53) | H | H | CH$_3$ | CH$_3$ | H | H | H | H | 2.866 min<br>m/z = 389.1 [M + H]$^+$ | diast. 1 |
| A.2.152 | Cl | H | Cl | CH$_3$ | CH$_3$ | H | H | H | H | 3.168 min<br>m/z = 391.1 [M + H]$^+$ | diast. 1 |
| A.2.153 | Cl | Cl | H | CH$_3$ | CH$_3$ | H | H | H | H | 3.129 min<br>m/z = 391.4 [M + H]$^+$ | diast. 1 |
| A.2.154 | Cl | H | CF$_3$ | CH$_3$ | CH$_3$ | H | H | H | H | 3.308 min<br>m/z = 425.0 [M + H]$^+$ | diast. 1 |
| A.2.155 | F | H | Cl | CH$_3$ | CH$_3$ | H | H | H | H | 2.933 min<br>m/z = 375.1 [M + H]$^+$ | diast. 1 |
| A.2.156 | Br | H | F | CH$_3$ | CH$_3$ | H | H | H | H | 3.038 min<br>m/z = 421.1 [M + H]$^+$ | diast. 1 |
| A.2.157 | F | Cl | F | CH$_3$ | CH$_3$ | H | H | H | H | 2.965 min<br>m/z = 393.3 [M + H]$^+$ | diast. 1 |
| A.2.158 | 55) | H | H | CH$_3$ | CH$_3$ | H | H | H | H | 3.324 min<br>m/z = 423.2 [M + H]$^+$ | diast. 1 |
| A.2.159 | F | F | CH$_3$ | CH$_3$ | CH$_3$ | H | H | H | H | 2.859 min<br>m/z = 373.2 [M + H]$^+$ | diast. 1 |
| A.2.160 | F | H | CF$_3$ | CH$_3$ | CH$_3$ | H | H | H | H | 3.116 min<br>m/z = 409.2 [M + H]$^+$ | diast. 1 |
| A.2.161 | F | Cl | CH$_3$ | CH$_3$ | CH$_3$ | H | H | H | H | 3.137 min<br>m/z = 389.4 [M + H]$^+$ | diast. 1 |
| A.2.162 | F | F | H | CH$_3$ | CH$_3$ | H | H | H | H | 2.625 min<br>m/z = 359.2 [M + H]$^+$ | diast. 1 |
| A.2.163 | F | Cl | H | CH$_3$ | CH$_3$ | H | H | H | H | 2.959 min<br>m/z = 375.3 [M + H]$^+$ | diast. 1 |
| A.2.164 | I | H | H | CH$_3$ | CH$_3$ | H | H | H | H | 3.046 min<br>m/z = 448.9 [M + H]$^+$ | diast. 1 |
| A.2.165 | NO$_2$ | H | H | H | CH$_3$ | H | H | H | 51) | 3.366 min<br>m/z = 527.9 [M + H]$^+$ | diast. 1 |
| A.2.166 | NO$_2$ | H | H | H | CH$_3$ | H | H | H | I | 2.929 min<br>m/z = 479.8 [M + H]$^+$ | diast. 2 |
| A.2.167 | NO$_2$ | H | H | H | CH$_3$ | H | H | H | F | 2.585 min<br>m/z = 372.0 [M + H]$^+$ | diast. 2 |
| A.2.168 | NO$_2$ | H | H | H | CH$_3$ | H | H | H | 52) | 2.013 min<br>m/z = 370.0 [M + H]$^+$ | diast. 2 |
| A.2.169 | NO$_2$ | H | H | H | CH$_3$ | H | H | CH$_3$ | H | 2.724 min<br>m/z = 368.0 [M + H]$^+$ | diast. 2 |
| A.2.170 | NO$_2$ | H | H | H | CH$_3$ | H | Cl | H | H | 2.707 min<br>m/z = 388.1 [M + H]$^+$ | diast. 1 |
| A.2.171 | NO$_2$ | H | H | H | CH$_3$ | H | H | 49) | 49) | 2.941 min<br>m/z = 404.2 [M + H]$^+$ | diast. 1 |
| A.2.172 | NO$_2$ | H | H | H | CH$_3$ | H | H | H | Cl | 2.823 min<br>m/z = 388.1 [M + H]$^+$ | diast. 2 |
| A.2.173 | NO$_2$ | H | H | H | CH$_3$ | H | H | H | CH$_3$ | 2.759 min<br>m/z = 368.2 [M + H]$^+$ | diast. 2 |
| A.2.174 | NO$_2$ | H | H | H | CH$_3$ | H | I | H | H | 2.720 min<br>m/z = 368.2 [M + H]$^+$ | diast. 1 |
| A.2.175 | 53) | H | H | CH$_3$ | CH$_3$ | H | H | H | H | 2.931 min<br>m/z = 389.1 [M + H]$^+$ | diast. 2 |
| A.2.176 | F | H | H | CH$_3$ | CH$_3$ | H | H | H | H | 2.808 min<br>m/z = 359.1 [M + H]$^+$ | diast. 2 |
| A.2.177 | Cl | H | Cl | CH$_3$ | CH$_3$ | H | H | H | H | 3.251 min<br>m/z = 391.1 [M + H]$^+$ | diast. 2 |
| A.2.178 | Cl | Cl | H | CH$_3$ | CH$_3$ | H | H | H | H | 3.189 min<br>m/z = 391.4 [M + H]$^+$ | diast. 2 |

TABLE A.2-continued

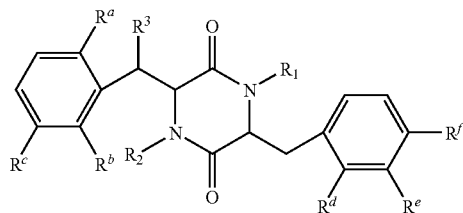

| Nr. | $R^a$ | $R^b$ | $R^c$ | $R^1$ | $R^2$ | $R^3$ | $R^d$ | $R^e$ | $R^f$ | RT HPLC/MS or m.p. | diast. |
|---|---|---|---|---|---|---|---|---|---|---|---|
| A.2.179 | Cl | H | CF$_3$ | CH$_3$ | CH$_3$ | H | H | H | H | 3.376 min m/z = 424.9 [M + H]$^+$ | diast. 2 |
| A.2.180 | F | H | Cl | CH$_3$ | CH$_3$ | H | H | H | H | 3.068 min m/z = 375.1 [M + H]$^+$ | diast. 2 |
| A.2.181 | Br | H | F | CH$_3$ | CH$_3$ | H | H | H | H | 3.089 min m/z = 421.1 [M + H]$^+$ | diast. 2 |
| A.2.182 | F | Cl | F | CH$_3$ | CH$_3$ | H | H | H | H | 3.062 min m/z = 393.3 [M + H]$^+$ | diast. 2 |
| A.2.183 | 55) | H | H | CH$_3$ | CH$_3$ | H | H | H | H | 3.327 min m/z = 432.1 [M + H]$^+$ | diast. 2 |
| A.2.184 | F | F | CH$_3$ | CH$_3$ | CH$_3$ | H | H | H | H | 3.056 min m/z = 373.2 [M + H]$^+$ | diast. 2 |
| A.2.185 | F | H | CF$_3$ | CH$_3$ | CH$_3$ | H | H | H | H | 3.226 min m/z = 409.2 [M + H]$^+$ | diast. 2 |
| A.2.186 | F | Cl | CH$_3$ | CH$_3$ | CH$_3$ | H | H | H | H | 3.240 min m/z = 389.4 [M + H]$^+$ | diast. 2 |
| A.2.187 | F | F | H | CH$_3$ | CH$_3$ | H | H | H | H | 2.832 min m/z = 359.2 [M + H]$^+$ | diast. 2 |
| A.2.188 | F | Cl | H | CH$_3$ | CH$_3$ | H | H | H | H | 3.042 min m/z = 375.4 [M + H]$^+$ | diast. 2 |
| A.2.189 | I | H | H | CH$_3$ | CH$_3$ | H | H | H | H | 3.071 min m/z = 448.9 [M + H]$^+$ | diast. 2 |
| A.2.190 | NO$_2$ | H | H | H | CH$_3$ | H | CF$_3$ | H | H | 2.814 min m/z = 422.4 [M + H]$^+$ | diast. 1 |
| A.2.191 | NO$_2$ | H | H | H | CH$_3$ | H | CF$_3$ | H | H | 2.956 min m/z = 422.3 [M + H]$^+$ | diast. 2 |
| A.2.192 | 56) | H | H | CH$_3$ | CH$_3$ | H | H | H | H | 3.625 min m/z = 465.0 [M + Na]$^+$ | |
| A.2.193 | PO(OH)$_2$ | H | H | CH$_3$ | CH$_3$ | H | H | H | H | 1.942 min m/z = 403.0 [M + H]$^+$ | |
| A.2.194 | 56) | H | H | CH$_3$ | CH$_3$ | H | H | H | H | 3.665 min m/z = 443.0 [M + H]$^+$ | |
| A.2.195 | NO$_2$ | H | H | H | CH$_3$ | H | CN | H | H | 2.475 min m/z = 379.1 [M + H]$^+$ | diast. 2 |
| A.2.196 | NO$_2$ | H | H | H | CH$_3$ | H | CN | H | H | 2.346 min m/z = 379.0 [M + H]$^+$ | diast. 1 |
| A.2.197 | NO$_2$ | H | H | H | CH$_3$ | H | 57) | H | H | 3.709 min m/z = 566.2 [M + H]$^+$ | diast. 1 |
| A.2.198 | NO$_2$ | H | H | H | CH$_3$ | H | 58) | H | H | 3.597 min m/z = 568.2 [M + H]$^+$ | diast. 1 |
| A.2.199 | NO$_2$ | H | H | H | CH$_3$ | H | 59) | H | H | 126° C. | |
| A.2.200 | NO$_2$ | H | H | H | CH$_3$ | H | 60) | H | H | 3.145 min m/z = 466.2 [M + H]$^+$ | |
| A.2.201 | NO$_2$ | H | H | H | CH$_3$ | H | H | 60) | H | 3.215 min m/z = 466.0 [M + H]$^+$ | diast. 1 |
| A.2.202 | NO$_2$ | H | H | H | CH$_3$ | H | H | 57) | H | 3.793 min m/z = 566.2 [M + H]$^+$ | diast. 1 |
| A.2.203 | NO$_2$ | H | H | H | CH$_3$ | H | H | 61) | H | 2.433 min m/z = 481.9 [M + H]$^+$ | diast. 1 |
| A.2.204 | NO$_2$ | H | H | H | CH$_3$ | H | H | 58) | H | 3.692 min m/z = 590.2 [M + Na]$^+$ | diast. 1 |
| A.2.205 | NO$_2$ | H | H | H | CH$_3$ | H | H | 59) | H | 2.503 min m/z = 465.2 [M + H]$^+$ | diast. 2 |
| A.2.206 | 59) | H | H | CH$_3$ | CH$_3$ | H | H | H | H | 2.883 min m/z = 434.1 [M + H]$^+$ | |
| A.2.207 | 61) | H | H | CH$_3$ | CH$_3$ | H | H | H | H | 3.499 min m/z = 451.2 [M + H]$^+$ | |
| A.2.208 | 58) | H | H | CH$_3$ | CH$_3$ | H | H | H | H | 3.813 min m/z = 537.2 [M + H]$^+$ | |
| A.2.209 | NO$_2$ | H | H | H | CH$_3$ | H | 57) | H | H | 3.777 min m/z = 565.9 [M + H]$^+$ | diast. 2 |
| A.2.210 | NO$_2$ | H | H | H | CH$_3$ | H | 60) | H | H | 121° C. | |
| A.2.211 | NO$_2$ | H | H | H | CH$_3$ | H | H | 60) | H | 3.229 min m/z = 466.0 [M + H]$^+$ | diast. 2 |

TABLE A.2-continued

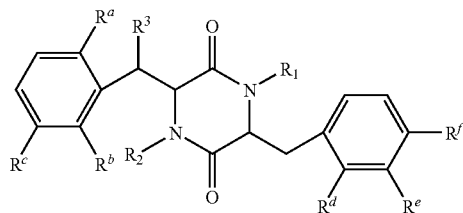

| Nr. | $R^a$ | $R^b$ | $R^c$ | $R^1$ | $R^2$ | $R^3$ | $R^d$ | $R^e$ | $R^f$ | RT HPLC/MS or m.p. | diast. |
|---|---|---|---|---|---|---|---|---|---|---|---|
| A.2.212 | NO$_2$ | H | H | H | CH$_3$ | H | H | 57) | H | 3.853 min<br>m/z = 566.2 [M + H]$^+$ | diast. 2 |
| A.2.213 | NO$_2$ | H | H | H | CH$_3$ | H | H | 61) | H | 2.485 min<br>m/z = 482.2 [M + H]$^+$ | diast. 2 |
| A.2.214 | NO$_2$ | H | H | H | CH$_3$ | H | H | 58) | H | 3.697 min<br>m/z = 590.1 [M + Na]$^+$ | diast. 2 |
| A.2.215 | NO$_2$ | H | H | H | CH$_3$ | H | H | 59) | H | 2.406 min<br>m/z = 465.2 [M + H]$^+$ | diast. 1 |
| A.2.216 | 60) | H | H | CH$_3$ | CH$_3$ | H | H | H | H | 3.352 min<br>m/z = 435.2 [M + H]$^+$ | diast. 2 |
| A.2.217 | 61) | H | H | CH$_3$ | CH$_3$ | H | H | H | H | 3.576 min<br>m/z = 451.2 [M + H]$^+$ | diast. 2 |
| A.2.218 | 58) | H | H | CH$_3$ | CH$_3$ | H | H | H | H | 3.864 min<br>m/z = 537.2 [M + H]$^+$ | diast. 2 |
| A.2.219 | 62) | H | H | CH$_3$ | CH$_3$ | H | H | H | H | 3.695 min<br>m/z = 403.1 [M + H]$^+$ | |
| A.2.220 | I | H | H | CH$_3$ | CH$_3$ | H | H | H | H | 3.014 min<br>m/z = 448.9 [M + H]$^+$ | diast. 1 |
| A.2.221 | I | H | H | CH$_3$ | CH$_3$ | H | H | H | H | 3.041 min<br>m/z = 448.9 [M + H]$^+$ | diast. 2 |
| A.2.222 | NO$_2$ | H | Cl | CH$_3$ | CH$_3$ | H | H | H | H | 3.035 min<br>m/z = 402.1 [M + H]$^+$ | diast. 2 |
| A.2.223 | 63) | H | H | CH$_3$ | CH$_3$ | H | H | H | H | 3.009 min<br>m/z = 395.1 [M + H]$^+$ | diast. 2 |
| A.2.224 | NO$_2$ | H$_2$C=CH— | H | CH$_3$ | CH$_3$ | H | H | H | H | 2.981 min<br>m/z = 394.0 [M + H]$^+$ | |
| A.2.225 | NO$_2$ | H | H | CH$_3$ | CH$_3$ | H | CN | H | H | 2.592 min<br>m/z = 393.2 [M + H]$^+$ | diast. 2 |
| A.2.226 | NO$_2$ | H | Cl | CH$_3$ | CH$_3$ | H | H | H | H | 2.919 min<br>m/z = 402.1 [M + H]$^+$ | diast. 1 |
| A.2.227 | 63) | H | H | CH$_3$ | CH$_3$ | H | H | H | H | 2.864 min<br>m/z = 395.2 [M + H]$^+$ | diast. 1 |
| A.2.228 | NO$_2$ | H | H | CH$_3$ | CH$_3$ | H | CN | H | H | 2.525 min<br>m/z = 393.2 [M + H]$^+$, 184° C. | diast. 1 |
| A.2.229 | NO$_2$ | H | H | H$_2$N— | CH$_3$ | H | H | H | H | 2.599 min<br>m/z = 369.2 [M + H]$^+$, 115° C. | diast. 2 |
| A.2.230 | NO$_2$ | Cl | 63) | CH$_3$ | CH$_3$ | H | H | H | H | 3.095 min<br>m/z = 474.1 [M + H]$^+$ | diast. 1 |
| A.2.231 | NO$_2$ | Cl | 13) | CH$_3$ | CH$_3$ | H | H | H | H | 2.882 min<br>m/z = 460.1 [M + H]$^+$ | diast. 1 |
| A.2.232 | NO$_2$ | H | H | CH$_3$ | CH$_3$ | H | C(O)NH$_3$ | H | H | 2.051 min<br>m/z = 411.0 [M + H]$^+$ | |
| A.2.233 | NO$_2$ | H | H | CH$_3$ | CH$_3$ | H | COOH | H | H | 2.401 min<br>m/z = 412.0 [M + H]$^+$ | |
| A.2.234 | NO$_2$ | Cl | 63) | CH$_3$ | CH$_3$ | H | H | H | H | 3.172 min<br>m/z = 474.1 [M + H]$^+$ | diast. 2 |
| A.2.235 | NO$_2$ | Cl | 13) | CH$_3$ | CH$_3$ | H | H | H | H | 2.970 min<br>m/z = 460.0 [M + H]$^+$ | diast. 2 |
| A.2.236 | C(O)H | H | H | CH$_3$ | CH$_3$ | H | H | H | H | 2.317 min<br>m/z = 351.0 [M + H]$^+$ | diast. 1 |
| A.2.237 | 64) | H | H | CH$_3$ | CH$_3$ | H | H | H | H | 2.184 min<br>m/z = 366.1 [M + H]$^+$ | diast. 1 |
| A.2.238 | 65) | H | H | CH$_3$ | CH$_3$ | H | H | H | H | 2.774 min<br>m/z = 380.1 [M + H]$^+$ | diast. 1 |
| A.2.239 | C(O)H | H | H | CH$_3$ | CH$_3$ | H | H | H | H | 2.564 min<br>m/z = 351.2 [M + H]$^+$ | diast. 2 |
| A.2.240 | 64) | H | H | CH$_3$ | CH$_3$ | H | H | H | H | 2.473 min<br>m/z = 366.1 [M + H]$^+$ | diast. 2 |
| A.2.241 | 65) | H | H | CH$_3$ | CH$_3$ | H | H | H | H | 2.943 min<br>m/z = 380.1 [M + H]$^+$ | diast. 2 |
| A.2.242 | 66) | H | H | CH$_3$ | CH$_3$ | H | H | H | H | 1.828 min<br>m/z = 336.0<br>1.920 min | |

TABLE A.2-continued

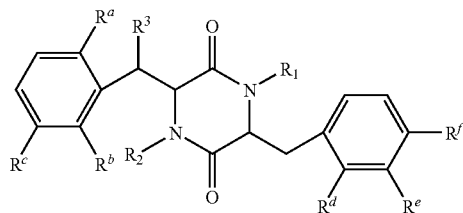

| Nr. | $R^a$ | $R^b$ | $R^c$ | $R^1$ | $R^2$ | $R^3$ | $R^d$ | $R^e$ | $R^f$ | RT HPLC/MS or m.p. | diast. |
|---|---|---|---|---|---|---|---|---|---|---|---|
| A.2.243 | 67) | H | H | CH₃ | CH₃ | H | H | H | H | m/z = 336.0 [M + H]⁺ 2.864 min | |
| A.2.244 | 68) | H | H | CH₃ | CH₃ | H | H | H | H | m/z = 501.0 [M + H]⁺ 2.152 min | |
| A.2.245 | 69) | H | H | CH₃ | CH₃ | H | H | H | H | m/z = 396.0 [M + H]⁺ 2.512 min | |
| A.2.246 | 70) | H | H | CH₃ | CH₃ | H | H | H | H | m/z = 408.0 [M + H]⁺ 3.307 min | |
| A.2.247 | 71) | H | H | CH₃ | CH₃ | H | H | H | H | m/z = 409.5 [M + H]⁺ 2.402 min | |
| A.2.248 | 72) | H | H | CH₃ | CH₃ | H | H | H | H | m/z = 367.0 [M + H]⁺ 3.528 min | |
| A.2.249 | NO₂ | H | H | CH₃ | CH₃ | 73) | H | H | H | m/z = 423.1 [M + H]⁺ 2.778 min | |
| A.2.250 | NO₂ | H | H | CH₃ | CH₃ | 73) | H | H | H | m/z = 426.1 [M + H]⁺ 2.828 min | |
| A.2.251 | NO₂ | H | H | CH₃ | CH₃ | 73) | H | H | H | m/z = 426.4 [M + H]⁺ 2.851 min | |
| A.2.252 | NO₂ | H | H | CH₃ | CH₃ | 73) | H | H | H | m/z = 426.4 [M + H]⁺ 2.827 min | |
| A.2.253 | NO₂ | H | H | CH₃ | CH₃ | 74) | H | H | H | m/z = 426.4 [M + H]⁺ 3.426 min | |
| A.2.254 | NO₂ | H | H | CH₃ | CH₃ | 74) | H | H | H | m/z = 474.2 [M + H]⁺ 3.481 min | |
| A.2.255 | NO₂ | H | H | CH₃ | CH₃ | 74) | H | H | H | m/z = 474.5 [M + H]⁺ 3.483 min | |
| A.2.256 | NO₂ | H | H | CH₃ | CH₃ | 74) | H | H | H | m/z = 474.5 [M + H]⁺ 3.479 min | |
| A.2.257 | 75) | NO₂ | H | CH₃ | CH₃ | H | H | H | H | m/z = 474.5 [M + H]⁺ 181° C. | |
| A.2.258 | 75) | NO₂ | H | CH₃ | CH₃ | H | H | H | H | 73° C. | |
| A.2.259 | 75) | NO₂ | H | CH₃ | CH₃ | H | H | H | H | 108° C. | |
| A.2.260 | 75) | NO₂ | H | CH₃ | CH₃ | H | H | H | H | 108° C. | |
| A.2.261 | NO₂ | H | H | CH₃ | CH₃ | HO— | H | H | H | 2.548 min m/z = 384.4 [M + H]⁺ | diast. 2 |
| A.2.262 | NO₂ | H | H | CH₃ | CH₃ | HO— | H | H | H | 2.483 min m/z = 384.4 [M + H]⁺ | diast. 1 |
| A.2.263 | NO₂ | H | H | CH₃ | CH₃ | HO— | H | H | H | 2.548 min m/z = 384.4 [M + H]⁺ | diast. 3 |
| A.2.264 | NO₂ | H | H | CH₃ | CH₃ | HO— | H | H | H | 2.484 min m/z = 384.4 [M + H]⁺ | diast. 4 |
| A.2.265 | NO₂ | H | H | CH₃ | CH₃ | 76) | H | H | H | 2.687 min m/z = 462.0 [M + H]⁺ | diast. 3 |
| A.2.266 | NO₂ | H | H | CH₃ | CH₃ | 76) | H | H | H | 2.700 min m/z = 461.9 [M + H]⁺ | diast. 4 |
| A.2.267 | NO₂ | H | H | CH₃ | CH₃ | 76) | H | H | H | 2.740 min m/z = 462.1 [M + H]⁺ | diast. 1 |
| A.2.268 | NO₂ | H | H | CH₃ | CH₃ | 76) | H | H | H | 2.754 min m/z = 462.2 [M + H]⁺ | diast. 2 |
| A.2.269 | NO₂ | H | H | H | CH₃ | 76) | H | H | H | 2.475 min m/z = 447.9 2.593 min m/z = 447.9 [M + H]⁺ | |
| A.2.270 | NO₂ | H | H | CH₃ | CH₃ | 77) | H | H | H | 109° C. | diast. 1 |
| A.2.271 | NO₂ | H | H | CH₃ | CH₃ | 77) | H | H | H | 109° C. | diast. 2 |
| A.2.272 | NO₂ | H | H | CH₃ | CH₃ | 77) | H | H | H | 144° C. | diast. 3 |
| A.2.273 | 78) | H | H | CH₃ | CH₃ | H | H | H | H | m/z = 404.05 [M]⁺ | |
| A.2.274 | CH=CH₂ | H | H | CH₃ | CH₃ | H | H | H | H | 2.980 m/z = 349.1 [M + H]⁺ | |
| A.2.275 | NO₂ | H | H | CH₃ | CH₃ | 80) | H | H | H | 145° C. | |
| A.2.276 | Br | F | F | CH₃ | CH₃ | 76) | H | H | H | 3.030 m/z = 531.0 [M]⁺ | |

TABLE A.3

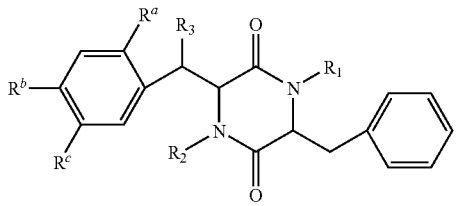

(A.3)

| No. | $R^a$ | $R^b$ | $R^c$ | $R^1$ | $R^2$ | $R^3$ | RT HPLC/MS or m.p. | diast. |
|---|---|---|---|---|---|---|---|---|
| A.3.1 | NO$_2$ | CH$_3$O— | CH$_3$O— | CH$_3$ | CH$_3$ | H | 2.668 min<br>m/z = 428.0 [M + H]$^+$ | diast. 2 |
| A.3.2 | NO$_2$ | CH$_3$O— | CH$_3$O— | CH$_3$ | CH$_3$ | H | 2.571 min<br>m/z = 428.0 [M + H]$^+$ | diast. 1 |

TABLE A.4

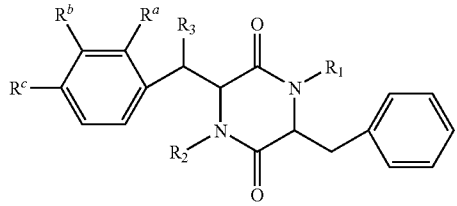

(A.4)

| No. | $R^a$ | $R^b$ | $R^c$ | $R^1$ | $R^2$ | $R^3$ | RT HPLC/MS or m.p. | diast. |
|---|---|---|---|---|---|---|---|---|
| A.4.1 | Cl | CH$_3$ | H$_3$CS— | CH$_3$ | CH$_3$ | H | 3.354 min<br>m/z = 417.0 [M + H]$^+$ | diast. 1 |
| A.4.2 | Cl | CH$_3$ | H$_3$CS— | CH$_3$ | CH$_3$ | H | 3.397 min<br>m/z = 417.0 [M + H]$^+$ | diast. 2 |
| A.4.3 | Cl | 54) | H | CH$_3$ | CH$_3$ | H | 3.513 min<br>m/z = 399.2 [M + H]$^+$ | diast. 1 |
| A.4.4 | Cl | CF$_3$ | H | CH$_3$ | CH$_3$ | H | 3.281 min<br>m/z = 425.4 [M + H]$^+$ | |
| A.4.5 | Cl | CH$_3$ | H$_3$CS— | CH$_3$ | CH$_3$ | H | 3.389 min<br>m/z = 417.2 [M + H]$^+$ | diast. 1 |
| A.4.6 | F | Cl | H | CH$_3$ | CH$_3$ | H | 2.927 min<br>m/z = 375.4 [M + H]$^+$ | diast. 1 |
| A.4.7 | F | F | H | CH$_3$ | CH$_3$ | H | 2.739 min<br>m/z = 359.4 [M + H]$^+$ | diast. 1 |
| A.4.8 | F | CF$_3$ | H | CH$_3$ | CH$_3$ | H | 3.096 min<br>m/z = 409.2 [M + H]$^+$ | diast. 1 |
| A.4.9 | Cl | Cl | H$_3$CO— | CH$_3$ | CH$_3$ | H | 3.088 min<br>m/z = 421.4 [M + H]$^+$ | diast. 1 |
| A.4.10 | F | F | F | CH$_3$ | CH$_3$ | H | 2.872 min<br>m/z = 377.2 [M + H]$^+$ | diast. 1 |
| A.4.11 | Cl | 54) | H | CH$_3$ | CH$_3$ | H | 3.557 min<br>m/z = 399.2 [M + H]$^+$ | diast. 2 |
| A.4.12 | Cl | CH$_3$ | H$_3$CS— | CH$_3$ | CH$_3$ | H | 3.428 min<br>m/z = 417.1 [M + H]$^+$ | diast. 2 |
| A.4.13 | F | Cl | H | CH$_3$ | CH$_3$ | H | 3.052 min<br>m/z = 375.3 [M + H]$^+$ | diast. 2 |
| A.4.14 | F | F | H | CH$_3$ | CH$_3$ | H | 2.965 min<br>m/z = 359.4 [M + H]$^+$ | diast. 2 |
| A.4.15 | F | CF$_3$ | H | CH$_3$ | CH$_3$ | H | 3.209 min<br>m/z = 409.2 [M + H]$^+$ | diast. 2 |
| A.4.16 | Cl | Cl | H$_3$CO— | CH$_3$ | CH$_3$ | H | 3.102 min<br>m/z = 421.1 [M + H]$^+$ | diast. 2 |
| A.4.17 | F | F | F | CH$_3$ | CH$_3$ | H | 2.999 min<br>m/z = 377.1 [M + H]$^+$ | diast. 2 |
| A.4.18 | Cl | Cl | H$_3$CO— | CH$_3$ | CH$_3$ | H | 3.138 min<br>m/z = 421.3 [M + H]$^+$ | |
| A.4.19 | NO$_2$ | 13) | H | CH$_3$ | CH$_3$ | H | 2.764 min<br>m/z = 426.0 [M + H]$^+$ | diast. 2 |
| A.4.20 | NO$_2$ | 13) | H | CH$_3$ | CH$_3$ | H | 2.754 min<br>m/z = 426.0 [M + H]$^+$ | diast. 1 |

Further compounds of the formula II which are listed in Table A.5 below, were prepared in an analogous manner.

TABLE A.5

| No. | Name | RT HPLC/MS or m.p. | diast. |
|---|---|---|---|
| A.5.1 | 1-methyl-6-(2-nitrobenzyl)-3-thiophen-2-yl-methylpiperazine-2,5-dione | 2.474 min<br>m/z = 360.3 [M + H]$^+$ | diast. 1 |
| A.5.2 | 1,4-dimethyl-3-(2-nitrobenzyl)-6-thiophen-2-ylmethylpiperazine-2,5-dione | 2.564 min<br>m/z = 373.9 [M + H]$^+$ | diast. 1 |
| A.5.3 | 1-methyl-6-(2-nitrobenzyl)-3-thiophen-2-yl-methylpiperazine-2,5-dione | 2.374 min<br>m/z = 360.3 [M + H]$^+$ | diast. 2 |
| A.5.4 | 1,4-dimethyl-3-(2-nitrobenzyl)-6-thiophen-2-ylmethylpiperazine-2,5-dione | 2.418 min<br>m/z = 373.9 [M + H]$^+$ | diast. 2 |
| A.5.5 | 1,4-dimethyl-3,6-bis-(2-nitrobenzyl)-piperazine-2,5-dione | 2.666 min<br>m/z = 412.9 [M + H]$^+$ | |
| A.5.6 | 3-benzyl-1,4-dimethyl-6-(2-nitrobenzyl)-piperazine-2,5-dione | 2.868 min<br>m/z = 382.1<br>3.192 min<br>m/z = 382.1 [M + H]$^+$ | |
| A.5.7 | 1-methyl-6-(2-nitrobenzyl)-3-tetrazol-2-yl-methylpiperazine-2,5-dione | 1.753 min<br>m/z = 346.1 [M + H]$^+$ | diast. 1 |
| A.5.8 | 1-methyl-6-(2-nitrobenzyl)-3-tetrazol-2-ylmethylpiperazine-2,5-dione | 1.829 min<br>m/z = 346.1 [M + H]$^+$ | diast. 2 |
| A.5.9 | 1-methyl-6-(2-nitrobenzyl)-3-[1,2,4]triazol-1-ylmethylpiperazine-2,5-dione | 1.669 min<br>m/z = 345.1 [M + H]$^+$ | diast. 1 |
| A.5.10 | N-{2-[2-(5-benzyl-1,4-dimethyl-3,6-dioxo-piperazine-2-yl)-acetyl]-3-nitrophenyl}-formamide | 2.504 min<br>m/z = 461.1 [M + Na]$^+$ | |
| A.5.11 | 1-methyl-6-(2-nitrobenzyl)-3-[1,2,4]triazol-1-ylmethylpiperazine-2,5-dione | 1.671 min<br>m/z = 345.1 [M + H]$^+$ | diast. 2 |
| A.5.12 | 3-benzyl-1,3-dimethyl-6-(2-nitrobenzyl)-piperazine-2,5-dione | 2.652 min<br>m/z = 368.0 [M + H]$^+$ | diast. 1 |
| A.5.13 | 3-benzyl-1,3-dimethyl-6-(2-nitrobenzyl)-piperazine-2,5-dione | 2.696 min<br>m/z = 368.0 [M + H]$^+$ | diast. 2 |
| A.5.14 | 1-methyl-6-(2-nitrobenzyl)-3-pyridin-3-yl-methylpiperazine-2,5-dione | 1.555 min<br>m/z = 355.0 [M + H]$^+$ | diast. 1 |
| A.5.15 | 1-methyl-6-(2-nitrobenzyl)-3-pyridin-3-yl-methylpiperazine-2,5-dione | 1.580 min<br>m/z = 355.0 [M + H]$^+$ | diast. 2 |
| A.5.16 | methyl (5-benzyl-1,4-dimethyl-3,6-dioxopiperazin-2-yl)-(2-bromopyridin-3-yl)methanesulfonate | 2.530 min<br>m/z = 498 [M + H]+ | |
| A.5.17 | methyl [1,4-dimethyl-3,6-dioxo-5-(thiophen-2-ylmethyl)piperazin-2-yl]-(2-nitrophenyl) methanesulfonate | 2.575 min<br>m/z = 468.1 [M + H]+ | |

The products were characterized by HPLC/MS (High Performance Liquid Chromatography combined with Mass Spectrometry), by NMR or by their melting point. HPLC column; RP-18 column (Chromolith Speed ROD from Merck KgaA, Germany) Eluent: acetonitrile+0.1% trifluoroacetic acid (TFA)/water+0.1% TEA in a gradient from 5:95 to 95:5 in 5 minutes at 40° C.

MS: Quadrupol electrospray ionisation, 80 V (positive mode)

The compounds I and their agriculturally useful salts are suitable, both in the form of isomer mixtures and in the form of the pure isomers, as herbicides. They are suitable as such or as an appropriately formulated composition. The herbicidal compositions comprising the compound I or Ia control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds I or Ia, or compositions comprising them, can additionally be employed in a further number of crop plants for eliminating undesirable plants. Examples of suitable crops are the following:

Allium cepa, Ananas comosus, Arachis hypogaea, Asparagus officinalis, Avena sativa, Beta vulgaris spec. altissima, Beta vulgaris spec. rapa, Brassica napus var. napus, Brassica napus var. napobrassica, Brassica rapa var. silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N. rustica), Olea europaea, Oryza sativa, Phaseolus lunatus, Phaseolus vulgaris, Picea abies, Pinus spec., Pistacia vera, Pisum sativum, Prunus avium, Prunus persica, Pyrus communis, Prunus armeniaca, Prunus cerasus, Prunus dulcis and Prunus domestica, Ribes sylvestre, Ricinus communis, Saccharum officinarum, Secale cereale, Sinapsis alba, Solanum tuberosum, Sorghum bicolor (S. vulgare), Theobroma cacao, Trifolium pratense, Triticale, Triticum aestivum, Triticum durum, Vicia faba, Vitis vinifera and Zea mays.

In addition, the compounds of the formula I may also be used in crops which tolerate the action of herbicides owing to breeding, including genetic engineering methods.

In addition, the compounds I can also be used in crops which tolerate insects or fungal attack as the result of breeding, including genetic engineering methods.

Furthermore, it has been found that the compounds of the formula I are also suitable for the defoliation and/or desiccation of plant parts, for which crop plants such as cotton, potato, oilseed rape, sunflower, soybean or field beans, in particular cotton, are suitable. In this regard, there have been found compositions for the desiccation and/or defoliation of plants, processes for preparing these compositions and methods for desiccating and/or defoliating plants using the compounds of the formula I.

As desiccants, the compounds of the formula I are particularly suitable for desiccating the above-ground parts of crop plants such as potato, oilseed rape, sunflower and soybean, but also cereals. This makes possible the fully mechanical harvesting of these important crop plants.

Also of economic interest is to facilitate harvesting, which is made possible by concentrating within a certain period of time the dehiscence, or reduction of adhesion to the tree, in citrus fruit, olives and other species and varieties of pernicious fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

The compounds I, or the herbicidal compositions comprising them, can be used, for example, in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading or watering or treatment of the seed or mixing with the seed. The use forms depend on the intended purpose; in any case, they should ensure the finest possible distribution of the active ingredients according to the invention.

The herbicidal compositions comprise a herbicidally effective amount of at least one compound of the formula I or an agriculturally useful salt of I, and auxiliaries which are customary for the formulation of crop protection agents.

Examples of auxiliaries customary for the formulation of crop protection agents are inert auxiliaries, solid carriers, surfactants (such as dispersants, protective colloids, emulsifiers, wetting agents and tackifiers), organic and inorganic thickeners, bactericides, antifreeze agents, antifoams, optionally colorants and, for seed formulations, adhesives.

Examples of thickeners (i.e. compounds which impart to the formulation modified flow properties, i.e. high viscosity in the state of rest and low viscosity in motion) are polysaccharides, such as xanthan gum (Keizan® from Kelco), Rhodopol® 23 (Rhone Poulenc) or Veegum® (from R.T. Vanderbilt), and also organic and inorganic sheet minerals, such as Attaclay® (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on dichlorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15.1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following:

Mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, for example amines such as N-methylpyrrolidone, and water.

Solid carriers are mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF AG), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF AG, Sokalan types), polyalkoxylates, polyvinylamine (BASF AG, Lupamine types), polyethyleneimine (BASF AG, Lupasol types), polyvinylpyrrolidone and copolymers thereof.

Powders, materials for broadcasting and dusts can be prepared by mixing or grinding the active ingredients together with a solid carrier.

Granules, for example coated granules, impregnated granules and homogeneous granules, can be prepared by binding the active ingredients to solid carriers.

Aqueous use forms can be prepared from emulsion concentrates, suspensions, pastes, wettable powders or water-dispersible granules by adding water. To prepare emulsions, pastes or oil dispersions, the compounds of the formula 1 or 1a, either as such or dissolved in an oil or solvent, can be homogenized in water by means of a wetting agent, tackifier, dispersant or emulsifier. Alternatively, it is also possible to prepare concentrates comprising active substance, wetting agent, tackifier, dispersant or emulsifier and, if desired, solvent or oil, which are suitable for dilution with water.

The concentrations of the compounds of the formula I in the ready-to-use preparations can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

The compounds I of the invention can for example be formulated as follows:

1. Products for Dilution with Water

A Water-Soluble Concentrates 10 parts by weight of active substance are dissolved in 90 parts by weight of water or a water-soluble solvent. As an alternative, wetters or other adjuvants are added The active substance dissolves upon dilution with water. This gives a formulation with an active substance content of 10% by weight.

B Dispersible Concentrates 20 parts by weight of active substance are dissolved in 70 parts by weight of cyclohexanone with addition of 10 parts by weight of a dispersant, for example polyvinylpyrrolidone. Dilution with water gives a dispersion. The active substance content is 20% by weight C Emulsifiable Concentrates 15 parts by weight of active substance are dissolved in 75 parts by weight of an organic solvent (eg. alkylaromatics) with addition of calcium dodecylbenzenesulfonate and castor oil ethoxylate (in each case 5 parts by weight). Dilution with water gives an emulsion. The formulation has an active substance content of 15% by weight.

D Emulsions 25 parts by weight of active substance are dissolved in 35 parts by weight of an organic solvent (eg. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active substance content of 25% by weight.

E Suspensions

In an agitated ball mill, 20 parts by weight of active substance are comminuted with addition of 10 parts by weight of dispersants and wetters and 70 parts by weight of water or an organic solvent to give a fine active substance suspension. Dilution with water gives a stable suspension of the active substance. The active substance content in the formulation is 20% by weight.

F Water-Dispersible Granules and Water-Soluble Granules 50 parts by weight of active substance are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active substance. The formulation has an active substance content of 50% by weight.

G Water-Dispersible Powders and Water-Soluble Powders 75 parts by weight of active substance are ground in a rotor-stator mill with addition of 25 parts by weight of dispersants, wetters and silica gel. Dilution with water gives a stable dispersion or solution of the active substance. The active substance content of the formulation is 75% by weight.

H Gel Formulations

In a ball mill, 20 parts by weight of active substance, 10 parts by weight of dispersant, 1 part by weight of gelling agent and 70 parts by weight of water or of an organic solvent are mixed to give a fine suspension. Dilution with water gives a stable suspension with active substance content of 20% by weight.

2. Products to be Applied Undiluted

I. Dusts 5 parts by weight of active substance are ground finely and mixed intimately with 95 parts by weight of finely divided kaolin. This gives a tracking powder with an active substance content of 5% by weight.

J Granules (GR, FG, GG, MG)

0.5 parts by weight of active substance are ground finely and associated with 95.5 parts by weight of carriers. Current methods here are extrusion, spray-drying or the fluidized bed. This gives granules to be applied undiluted with an active substance content of 0.5% by weight.

K ULV Solutions (UL)

10 parts by weight of active substance are dissolved in 90 pads by weight of an organic solvent, for example xylene. This gives a product to be applied undiluted with an active substance content of 10% by weight.

Specific Formulations are Indicated Below.

I 20 parts by weight of the compound of the formula I are dissolved in a mixture composed of 80 parts by weight of alkylated benzene, 10 parts by weight of the adduct of from 8 to 10 mol of ethylene oxide to 1 mol of oleic acid N-mono-ethanolamide, 5 parts by weight of calcium dodecylbenzenesulfonate and 5 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active compound.

II 20 parts by weight of the compound of the formula I are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active compound.

III 20 parts by weight of the compound of the formula I are dissolved in a mixture composed of 25 parts by weight of cyclohexanone, 65 parts by weight of a mineral oil fraction of boiling point 210 to 280° C. and 10 parts by weight of the adduct of 40 mot of ethylene oxide to 1 mol of castor oil. Pouring the solution into 100 000 parts by weight of water and finely distributing it therein gives an aqueous dispersion which comprises 0.02% by weight of the active compound.

IV 20 parts by weight of the compound of the formula I are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20 000 parts by weight of water gives a spray mixture which comprises 0.1% by weight of the active compound.

V 3 parts by weight of the compound of the formula I are mixed with 97 parts by weight of finely divided kaolin. This gives a dust which comprises 3% by weight of the active compound.

VI 20 parts by weight of the compound of the formula I are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII 1 part by weight of the compound of the formula I is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of the compound of the formula I is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The compounds I or the herbicidal compositions comprising them can be applied pre- or post-emergence, or together with the seed of a crop plant. It is also possible to apply the herbicidal composition or active compounds by applying seed, pretreated with the herbicidal compositions or active compounds, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the compounds of the formula I or the herbicidal compositions can be applied by treating seed.

The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the compounds of the formula I according to the invention or the compositions prepared therefrom. Here, the herbicidal compositions can be applied diluted or undiluted.

The term seed comprises seed of all types, such as, for example, corns, seeds, fruits, tubers, seedlings and similar forms. Here, preferably, the term seed describes corns and seeds.

The seed used can be seed of the useful plants mentioned above, but also the seed of transgenic plants or plants obtained by customary breeding methods.

The rates of application of the active compound are from 0.001 to 3.0, preferably 0.01 to 1.0, kg/ha of active substance (a.s.), depending on the control target, the season, the target plants and the growth stage. To treat the seed, the compounds I are generally employed in amounts of from 0.001 to 10 kg per 100 kg of seed.

To widen the spectrum of action and to achieve synergistic effects, the compounds of the formula I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, 2-hetaroyl-1,3-cyclohexane-diones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides, uracils, phenyl pyrazolines and isoxazolines and derivatives thereof.

It may furthermore be beneficial to apply the compounds I alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

Part B

Use Examples

The herbicidal activity of the compounds of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this has been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

137

The plants used in the greenhouse experiments belonged to the following species:

| Scientific name | Common name |
|---|---|
| *Amaranthus retroflexus* (AMARE) | pig weed |
| *Chenopodium album* (CHEAL) | lambsquaters |
| *Setaria viridis* (SETVI) | green foxtail |
| *Setaria faberi* (SETFA) | giant foxtail |
| *Echinochloa crus galli* (ECHCG) | barnyard grass |
| *Alopecurus myosuroides* (ALOMY) | black grass |
| *Avena fatua* (AVEFA) | wild oat |
| *Lolium multiflorum* (LOLMU) | raygrass |
| *Apera spica-venti* (APESV) | windgrass |

The compounds A.1.10, A.1.11, A.2.81, A.2.97, A.2.135, A.2.136, A2.222, A2.223, A.2.224, A.2.226 and A.2.267 exhibit a very good herbicidal activity when applied by the post-emergence method.

At an application rate of 1 kg/ha, the compounds A.1.10, A.1.11, A.2.135, A.2.222, A.2.223 and A.2.224 had very good herbicidal post-emergence activity against CHEAL.

At an application rate of 1 kg/ha, the compounds A.1.10, A.1.11, A.2.135, A.2.222, A.2.223, A.2.224, A.2.226 and A.2.267 had very good herbicidal post-emergence activity against AMARE.

At an application rate of 1 kg/ha, the compounds A.1.10, A.1.11, A.2.97, A.2.136, A.2.222, A.2.223 and A.2.226 had very good herbicidal post-emergence activity against SETVI.

At an application rate of 1 kg/ha, the compounds A.2.97, A.2.136 and A.2.224 had very good herbicidal post-emergence activity against LOLMU.

At an application rate of 3 kg/ha, the compound A.2.81 had very good herbicidal post-emergence activity against ECHCG. At an application rate of 1 kg/ha, the compounds A.2.226 and A.2.267 had very good herbicidal post-emergence activity against ECHCG.

At an application rate of 3 kg/ha, the compound A.2.105 had very good herbicidal post-emergence activity against ALOMY and AVEFA.

At an application rate of 3 kg/ha, the compounds A.2.64, A.2.65, A.2.133, A.2.135, A.2.251, A.2.255, A.2.265, A.2.267, A.2.273, A.2.274 and A.2.275 had good to very good herbicidal post-emergence activity against SETFA. At an application rate of 1 kg/ha, the compound A.2.224 had good to very good herbicidal post-emergence activity against SETFA.

At an application rate of 3 kg/ha, the compounds A.2.64, A.2.105, A.2.133, A.2.135, A.2.265, A.2.267, A.2.273, A.2.274 and A.2.275 had good to very good herbicidal pre-emergence activity against ECHCG.

At an application rate of 3 kg/ha, the compounds A.1.13, A.5.16, A.2.135, A.2.265, A.2.267, A.2.271, A.2.273 and A.2.276 had good to very good herbicidal pre-emergence activity against SETIT.

At an application rate of 1 kg/ha, the compounds A.2.97, A+2.136, A.2.224 and A.2.267 had very good herbicidal pre-emergence activity against APESV.

At an application rate of 3 kg/ha, the compound A.2.81 had very good herbicidal pre-emergence activity against SETFA.

At an application rate of 0.5 kg/ha, the compound A.5.17 had good and very good herbicidal pre-emergence activity against APESV and AMARE, respectively.

138

The invention claimed is:

1. A method for controlling unwanted vegetation comprising treating a plant, a plant seed, and/or a plant habitat with a herbicidally effective amount of at least one piperazine compound of formula (I)

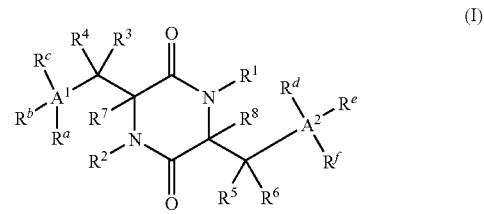

or an agriculturally useful salt thereof, wherein:

$R^1$ and $R^2$ are, independently of one another, cyano, $C_3$-$C_6$-cycloalkyl, $C_3$-$C_6$-alkenyl, $C_3$-$C_6$-cycloalkenyl, $C_3$-$C_6$-alkynyl, $C_3$-$C_6$-cycloalkynyl, phenyl, phenyl-($C_1$-$C_6$)-alkyl, heterocyclyl, heterocyclyl-($C_1$-$C_6$)-alkyl; phenyl-[($C_1$-$C_6$-alkoxycarbonyl]-($C_1$-$C_6$)-alkyl; phenylheterocyclyl-($C_1$-$C_6$)-alkyl; or $COR^{21}$, wherein $R^{21}$ is hydrogen, $C_1$-$C_6$-alkyl, $C_3$-$C_6$-cycloalkyl, $C_2$-$C_6$-alkenyl, $C_3$-$C_6$-cycloalkenyl, $C_2$-$C_6$-alkynyl, $C_3$-$C_6$-cycloalkynyl, hydroxyl, $C_1$-$C_6$-alkoxy, $C_3$-$C_6$-alkenyloxy, $C_3$-$C_6$-alkynyloxy, amino, $C_1$-$C_6$-alkylamino, [di-($C_1$-$C_6$)-alkyl]amino, $C_3$-$C_6$-alkenylamino, $C_3$-$C_6$-alkynylamino, $C_1$-$C_6$-alkylsulfonylamino, N—($C_2$-$C_6$-alkenyl)-N—($C_1$-$C_6$-alkyl)amino, N—($C_2$-$C_6$-alkynyl)-N—($C_1$-$C_6$-alkyl)amino, N—($C_1$-$C_6$-alkoxy)-N—($C_1$-$C_6$-alkyl)amino, N—($C_2$-$C_6$-alkenyl)-N—($C_1$-$C_6$-alkoxy)amino, N—($C_2$-$C_6$-alkynyl)-N—($C_1$-$C_6$-alkoxy)amino, phenyl, phenylamino, phenoxy, naphthyl, or heterocyclyl; or $NR^{22}R^{23}$, wherein $R^{22}$ and $R^{23}$ are, independently of one another, hydrogen, $C_1$-$C_6$-alkyl, $C_3$-$C_6$-cycloalkyl, $C_3$-$C_6$-alkenyl, $C_3$-$C_6$-cycloalkenyl, $C_3$-$C_6$-alkynyl, $C_3$-$C_6$-cycloalkynyl, or $C_1$-$C_6$-alkylcarbonyl; or $OR^{24}$, wherein $R^{24}$ is $C_1$-$C_6$-alkyl, $C_3$-$C_6$-cycloalkyl, $C_3$-$C_6$-alkenyl, $C_3$-$C_6$-cycloalkenyl, $C_3$-$C_6$-alkynyl, $C_3$-$C_6$-cycloalkynyl, phenyl, or phenyl-($C_1$-$C_6$)-alkyl; or $SO_2R^{25}$, wherein $R^{25}$ is $C_1$-$C_6$-alkyl or phenyl;

wherein, when $R^1$ and $R^2$ are aliphatic, cyclic, or aromatic substituents, said aliphatic, cyclic, or aromatic substituents are optionally partially or fully halogenated and/or are optionally mono-, di, or tri-substituted with cyano, hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-alkylthio, [di-($C_1$-$C_4$)-alkyl]amino, $C_1$-$C_4$-alkylcarbonyl, hydroxycarbonyl, alkoxycarbonyl, aminocarbonyl, $C_1$-$C_4$-alkylaminocarbonyl, [di-($C_1$-$C_4$)-alkyl]aminocarbonyl, $C_1$-$C_4$-alkylcarbonyloxy, or combinations thereof, and wherein $R^1$ is optionally hydrogen;

$R^3$ is a radical $R^{26}$, $OR^{27}$, $SR^{28}$, $NR^{29}R^{30}$, or $N(OR^{31})R^{32}$, wherein $R^{26}$, $R^{27}$, $R^{28}$, $R^{29}$, and $R^{32}$ are, independently of one another, hydrogen, $C_1$-$C_6$-alkyl, $C_3$-$C_6$-cycloalkyl, $C_3$-$C_6$-alkenyl, $C_3$-$C_6$-alkynyl, $C_3$-$C_6$-haloalkynyl, formyl, $C_1$-$C_6$-alkylcarbonyl, $C_3$-$C_6$-cycloalkylcarbonyl, $C_2$-$C_6$-alkenylcarbonyl, $C_2$-$C_6$-alkynylcarbonyl, $C_1$-$C_6$-alkoxy-($C_1$-$C_6$)-alkyl, $C_1$-$C_6$-alkoxycarbonyl, $C_2$-$C_6$-alkenyloxycarbonyl, $C_3$-$C_6$-alkynyloxycarbonyl, $C_1$-$C_6$-alkylaminocarbonyl, $C_3$-$C_6$-alkenylaminocarbonyl, $C_3$-$C_6$-alkynylaminocarbonyl, $C_1$-$C_6$-alkylsulfonyl-aminocarbonyl, $C_1$-$C_6$-alkylaminocarbonyl, [di-($C_1$-$C_6$)-alkylamino]carbonyl, N—($C_3$-$C_6$-alkenyl)-N—($C_1$-$C_6$-alkyl)-aminocarbonyl, N—($C_3$-$C_6$-alkynyl)-N—($C_1$-$C_6$-alkyl)-aminocarbonyl, N—($C_1$-$C_6$-alkoxy)-N—($C_1$-$C_6$-alkyl)-amino-carbonyl, N—($C_3$-$C_6$-alkenyl)-N—($C_1$-$C_6$-alkoxy)-aminocarbonyl, N—($C_3$-$C_6$-alkynyl)-N—($C_1$-$C_6$-alkoxy)-aminocarbonyl, di-($C_1$-$C_6$-alkyl)-aminothiocarbonyl, $C_1$-$C_6$-alkylcarbonyl-$C_1$-$C_6$-alkyl, $C_1$-$C_6$-alkoxyimino-$C_1$-$C_6$-alkyl, N—($C_1$-$C_6$-alkylamino)imino-$C_1$-$C_6$-alkyl, N-(di-$C_1$-$C_6$-alkylamino)imino-$C_1$-$C_6$-alkyl or [tri-($C_1$-$C_4$)-alkyl]silyl, wherein the aliphatic or isocyclic moieties of the substituents are optionally partially or fully halogenated and/or are optionally mono-, di, or tri-substituted with cyano, hydroxyl, $C_1$-$C_4$-alkyl, $C_1$-$C_4$-haloalkyl, $C_3$-$C_6$-cycloalkyl, $C_1$-$C_4$-alkoxy, [di-($C_1$-$C_4$)-alkyl]amino, $C_1$-$C_4$-alkylcarbonyl, hydroxycarbonyl, $C_1$-$C_4$-alkoxycarbonyl, aminocarbonyl, $C_1$-$C_4$-alkyl-aminocarbonyl, [di-($C_1$-$C_4$)-alkyl]aminocarbonyl, $C_1$-$C_4$-alkylcarbonyloxy, or combinations thereof; or phenyl, phenyl-$C_1$-$C_6$-alkyl, phenylcarbonyl, phenylcarbonyl-$C_1$-$C_6$-alkyl, phenoxycarbonyl, phenylaminocarbonyl, phenylsulfonylaminocarbonyl, N—($C_1$-$C_6$-alkyl)-N-(phenyl)aminocarbonyl, phenyl-$C_1$-$C_6$-alkylcarbonyl, heterocyclyl, heterocyclyl-$C_1$-$C_6$-alkyl, heterocyclylcarbonyl, heterocyclylcarbonyl-$C_1$-$C_6$-alkyl, heterocyclyloxycarbonyl, heterocyclylaminocarbonyl, heterocyclylsulfonylaminocarbonyl, N—($C_1$-$C_6$-alkyl)-N-(heterocyclyl)aminocarbonyl, or heterocyclyl-$C_1$-$C_6$-alkylcarbonyl, wherein the phenyl or heterocyclyl moieties of these substituents are optionally partially or fully halogenated and/or are optionally mono-, di, or tri-substituted with nitro, cyano, $C_1$-$C_4$-alkyl, $C_1$-$C_4$-haloalkyl, $C_1$-$C_4$-alkoxy, $C_1$-$C_4$-haloalkoxy, or combinations thereof; or $S(O)_nR^{33}$, wherein n is 1 or 2; and $R^{33}$ is $C_1$-$C_6$-alkyl, $C_1$-$C_6$-haloalkyl or phenyl, wherein phenyl is optionally partially or fully halogenated and/or are optionally mono-, di, or tri-substituted with nitro, cyano, $C_1$-$C_4$-alkyl, $C_1$-$C_4$-haloalkyl, $C_1$-$C_4$-alkoxy, $C_1$-$C_4$-haloalkoxy, or combinations thereof; and $R^{30}$ and $R^{31}$ are, independently of one another, hydrogen, $C_1$-$C_6$-alkyl, $C_3$-$C_6$cycloalkyl, $C_2$-$C_6$-alkenyl, or $C_2$-$C_6$-alkynyl, wherein the aliphatic or isocyclic moieties of these substituents are optionally partially or fully halogenated and/or are optionally mono-, di, or tri-substituted with cyano, hydroxyl, $C_1$-$C_4$-alkyl, $C_1$-$C_4$haloalkyl, $C_3$-$C_6$-cycloalkyl, $C_1$-$C_4$-alkoxy, $C_1$-$C_4$-alkylthio, [di-($C_1$-$C_4$)-alkyl]amino, $C_1$-$C_4$alkylcarbonyl, hydroxycarbonyl, $C_1$-$C_4$alkoxycarbonyl, aminocarbonyl, $C_1$-$C_4$-alkylaminocarbonyl, [di-($C_1$-$C_4$)-alkyl]aminocarbonyl, $C_1$-$C_4$-alkylcarbonyloxy, or combinations thereof; or phenyl, phenyl-$C_1$-$C_6$-alkyl, heterocyclyl, or heterocyclyl-$C_1$-$C_6$-alkyl, wherein the phenyl or heterocyclyl moieties of these substituents are optionally partially or fully halogenated and/or are optionally mono-, di, or tri-substituted with nitro, cyano, $C_1$-$C_4$-haloalkyl, $C_1$-$C_4$-alkoxy, $C_1$-$C_4$-haloalkoxy, or combinations thereof;

$R^4$, $R^5$, and $R^6$ are, independently of one another, hydrogen, $C_1$-$C_6$-alkyl, or $C_1$-$C_6$-alkoxy, wherein the aliphatic moieties of these substituents are optionally partially or fully halogenated and/or are optionally mono-, di, or tri-substituted with cyano, hydroxyl, $C_1$-$C_4$-alkyl, $C_1$-$C_4$-haloalkyl, $C_3$-$C_6$-cycloalkyl, $C_1$-$C_4$alkoxy, $C_1$-$C_4$-alkylthio, [di-($C_1$-$C_4$)-alkyl]amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, [di-($C_1$-$C_4$)-alkyl]aminocarbonyl, $C_1$-$C_4$-alkylcarbonyloxy, or combinations thereof; and wherein $R^3$ and $R^4$ together are optionally a keto group;

$R^7$ and $R^8$ are, independently of one another, hydrogen, hydroxyl, $C_1$-$C_6$-alkyl optionally partially or fully halogenated and/or optionally mono-, di, or tri-substituted with cyano, hydroxyl, $C_1$-$C_4$alkyl, $C_1$-$C_4$-haloalkyl, $C_3$-$C_6$-cycloalkyl, $C_1$-$C_4$-alkoxy, $C_1$-$C_4$-alkylthio, [di-($C_1$-$C_4$)-alkyl]amino, $C_1$-$C_4$alkylcarbonyl, hydroxycarbonyl, $C_1$-$C_4$alkoxycarbonyl, aminocarbonyl, $C_1$-$C_4$-alkylaminocarbonyl, [di-($C_1$-$C_4$)-alkyl]aminocarbonyl, $C_1$-$C_4$-alkylcarbonyloxy, or combinations thereof;

$A^1$ and $A^2$ are, independently of one another, aryl or heteroaryl, with the proviso that neither $A^1$ nor $A^2$ is indolyl, and wherein $R^a$ is attached in the ortho-position to the point of attachment of $A^1$ to a carbon atom or a nitrogen atom of $A^1$;

$R^a$ is halogen, cyano, nitro, $C_1$-$C_6$-alkyl, $C_3$-$C_6$-cycloalkyl, $C_2$-$C_6$-alkenyl, $C_3$-$C_6$-cycloalkenyl, $C_4$-$C_{10}$-alkadienyl, $C_2$-$C_6$-alkynyl, [tri-($C_1$-$C_6$)-alkylsilyl]-($C_2$-$C_6$)-alkynyl, $C_3$-$C_6$-cycloalkynyl, $C_1$-$C_6$-alkylthio, $C_1$-$C_6$-alkylsulfinyl, aryl, phenyl-phenyl-($C_2$-$C_6$)-alkenyl, phenylsulfonyl-($C_1$-$C_6$)-alkyl, heterocyclyl, heterocyclyl-($C_1$-$C_6$)-alkyl, phenyl-[$C_1$-$C_6$-alkoxycarbonyl]-($C_1$-$C_6$)-alkyl; or $Z^1P(O)(OR^9)_2$ or $Z^2B(OR^{10})_2$, wherein $R^9$ and $R^{10}$ are each, independently of one another, hydrogen or $C_1$-$C_6$-alkyl and wherein both $R^{10}$ moieties in $Z^2B(OR^{10})_2$ together optionally define a $C_2$-$C_4$-alkylene chain; or $Z^3COR^{11}$, wherein $R^{11}$ is hydrogen, $C_1$-$C_6$-alkyl, $C_3$-$C_6$-cycloalkyl, $C_2$-$C_6$-alkenyl, $C_3$-$C_6$-cycloalkenyl, $C_2$-$C_6$-alkynyl, $C_3$-$C_6$-cycloalkynyl, hydroxyl, $C_1$-$C_6$-alkoxy, $C_3$-$C_6$-alkenyloxy, $C_3$-$C_6$-alkynyloxy, amino, $C_1$-$C_6$-alkylamino, [th-($C_1$-$C_6$)-alkyl]amino, $C_1$-$C_6$-alkoxyamino, [di-($C_1$-$C_6$)-alkoxy]amino, $C_1$-$C_6$-alkylsulfonylamino, $C_1$-$C_6$-alkylaminosulfonylamino, [di-($C_1$-$C_6$)-alkylamino]sulfonylamino, $C_3$-$C_6$-alkenylamino, $C_3$-$C_6$-alkynylamino, N—($C_2$-$C_6$-alkenyl)-N—($C_1$-$C_6$-alkyl)amino, N—($C_2$-$C_6$-alkynyl)-N—($C_1$-$C_6$-alkyl)amino, N—($C_1$-$C_6$-alkoxy)-N—($C_1$-$C_6$-alkyl)amino, N—($C_2$-$C_6$-alkenyl)-N—($C_1$-$C_6$-alkoxy)amino, N—($C_2$-$C_6$-alkynyl)-N—($C_1$-$C_6$-alkoxy)amino, phenyl, phenoxy, phenylamino, naphthyl, or heterocyclyl; or $Z^4NR^{12}R^{13}$, wherein $R^{12}$ and $R^{13}$ are, independently of one another, hydrogen, $C_1$-$C_6$-alkyl, $C_3$-$C_6$-cycloalkyl, $C_3$-$C_6$-alkenyl, $C_3$-$C_6$-cycloalkenyl, $C_3$-$C_6$-alkynyl, $C_3$-$C_6$-cycloalkynyl, $C_1$-$C_6$-alkylcarbonyl, $C_3$-$C_6$-cycloalkylcarbonyl, [di-($C_1$-$C_6$)-alkylamino]carbonyl, $C_1$-$C_6$-alkoxycarbonyl, $C_1$-$C_6$-alkoxycarbonyl-($C_1$-$C_6$)-alkyl, $C_1$-$C_6$-alkylsulfonyl, $C_1$-$C_6$-alkylaminosulfonyl, [di-($C_1$-$C_6$)-alkylamino]sulfonyl, phenylcarbonyl, phenylaminocarbonyl, phenylsulfonyl, phenylsulfonylaminocarbonyl, or heterocyclylcarbonyl; or $Z^5CH{=}N{-}O{-}R^{14}$, wherein $R^{14}$ is hydrogen or $C_1$-$C_6$-alkyl; or $Z^6OR^{15}$, wherein
  $R^{15}$ is hydrogen, $C_1$-$C_6$-alkyl, $C_3$-$C_6$-cycloalkyl, $C_3$-$C_6$-alkenyl, $C_3$-$C_6$-cycloalkenyl, $C_3$-$C_6$-alkynyl, $C_3$-$C_6$-cycloalkynyl, $C_1$-$C_6$-alkylcarbonyl, $C_1$-$C_6$-alkoxycarbonyl-($C_1$-$C_6$)-alkyl, [di-($C_1$-$C_6$)-alkoxycarbonyl]-($C_1$-$C_6$)-alkyl, phenyl, or phenyl-($C_1$-$C_6$)-alkyl; or $Z^7SO_2R^{16}$, wherein $R^{16}$ is $C_1$-$C_6$-alkyl or phenyl;
wherein
$Z^1, Z^2, Z^3, Z^4, Z^5, Z^6$, and $Z^7$
are, independently of one another, a bond, $-CH_2-$, $-CH_2-CH_2-$, $-O-CH(R^{17})-$, $-S-CH(R^{18})-$, $-S(O)-CH(R^{19})-$, or $-SO_2CH(R^{20})-$, wherein $R^{17}, R^{18}, R^{19}$, and $R^{20}$ are, independently of one another, hydrogen or $C_1$-$C_6$-alkyl; and wherein, when $R^a$ is an aliphatic, cyclic, or aromatic substituent, said aliphatic, cyclic, or aromatic substituent is optionally partially or fully halogenated and/or is optionally mono-, di, or tri-substituted with cyano, hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-alkylthio, [di-($C_1$-$C_4$)-alkyl]amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, [di-($C_1$-$C_4$)-alkyl]aminocarbonyl, $C_1$-$C_4$-alkylcarbonyloxy, or combinations thereof;

$R^b, R^c, R^d, R^e$, and $R^f$
are, independently of one another, hydrogen or a substituent as defined in $R^a$; and wherein any two of $R^a, R^b$, or $R^c$ attached to adjacent ring atoms of $A^1$ or any two of $R^d, R^e$, or $R^f$ attached to adjacent ring atoms of $A^2$ are optionally straight-chain $C_3$-$C_6$-alkylene optionally partially or fully halogenated and/or optionally mono-, di, or tri-substituted with cyano, hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-alkylthio, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, [di-($C_1$-$C_4$)-alkyl]aminocarbonyl, $C_1$-$C_4$-alkylcarbonyloxy, or combinations thereof, wherein one $CH_2$ group in $C_3$-$C_6$-alkylene is optionally replaced by a carbonyl group, thiocarbonyl group, or sulfonyl group and wherein one or two non-adjacent $CH_2$ groups in $C_3$-$C_6$-alkylene are optionally replaced by oxygen, sulfur, or a group $NR^{34}$, where $R^{34}$ is a substituent as defined in $R^{12}$.

2. The method of claim 1, wherein $A^1$ and $A^2$ are, independently of one another, selected from the group consisting of phenyl, naphthyl, furyl, thienyl, pyrrolyl, pyrazolyl, thiazolyl, isothiazolyl, oxazolyl, isoxazolyl, triazolyl, tetrazolyl, pyridinyl, pyridazinyl, pyrimidinyl, pyrazinyl, triazinyl, and tetrazinyl.

3. The method of claim 1, wherein $A^1$ and $A^2$ are, independently of one another, selected from the group consisting of phenyl, furyl, thienyl, triazolyl, tetrazolyl, and pyridinyl.

4. The method of claim 1, wherein $A^1$ is phenyl or pyridinyl.

5. The method of claim 1, wherein $A^2$ is phenyl or thienyl.

6. The method of claim 1, wherein
$R^a$ is selected from the group consisting of halogen, cyano, nitro, $C_2$-$C_6$-alkenyl, $C_2$-$C_6$-alkynyl, $Z^1P(O)(OR^9)_2$, $Z^3COR^{11}$, $Z^4NR^{12}R^{13}$, $Z^5CH{=}N{-}O{-}R^{14}$, $Z^6OR^{15}$, $Z^7SO_2R^{16}$, $C_1$-$C_6$-alkylthio, $C_1$-$C_6$-alkylsulfinyl, aryl, and heterocyclyl, wherein
  $Z^1$ is a bond or $CH_2$ and each $R^9$ is, independently of one another, hydrogen or $C_1$-$C_6$-alkyl;
  $Z^3$ is a bond and $R^{11}$ is hydrogen, $C_1$-$C_6$-alkyl, hydroxyl, $C_1$-$C_6$-alkoxy, $C_3$-$C_6$-alkenyloxy, $C_3$-$C_6$-alkynyloxy, amino, $C_1$-$C_6$-alkylamino, [di-($C_1$-$C_6$)-alkyl]amino, $C_1$-$C_6$-alkoxyamino, $C_1$-$C_6$-alkylsulfonylamino, $C_1$-$C_6$-alkylaminosulfonylamino, [di-($C_1$-$C_6$)-alkylamino]sulfonylamino, phenyl, phenoxy, phenylamino, naphthyl, or heterocyclyl;
  $Z^4$ is a bond or $CH_2$ and $R^{12}$ and $R^{13}$ are, independently of one another, hydrogen, $C_1$-$C_6$-alkyl, $C_3$-$C_6$-cycloalkyl, $C_3$-$C_6$-alkenyl, $C_3$-$C_6$-alkynyl, $C_1$-$C_6$-alkylcarbonyl, [di-($C_1$-$C_6$)-alkylamino]carbonyl, $C_1$-$C_6$-alkoxycarbonyl, $C_1$-$C_6$-alkylsulfonyl, phenylcarbonyl, phenylsulfonyl, or heterocyclylcarbonyl;
  $Z^5$ is a bond or $CH_2$ and $R^{14}$ is hydrogen or $C_1$-$C_6$-alkyl;
  $Z^6$ is a bond or $CH_2$ and $R^{15}$ is hydrogen, $C_1$-$C_6$-alkyl, $C_3$-$C_6$-cycloalkyl, $C_3$-$C_6$-alkenyl, $C_3$-$C_6$-alkynyl, $C_1$-$C_6$-alkylcarbonyl, $C_1$-$C_6$-alkoxycarbonyl-($C_1$-$C_6$)-alkyl, phenyl, or phenyl-($C_1$-$C_6$)-alkyl; and
  $Z^7$ is a bond and $R^{16}$ is $C_1$-$C_6$-alkyl or phenyl;
and wherein
$R^b, R^c, R^d, R^e$, and $R^f$
are, independently of one another, hydrogen, a substituent as defined in $R^a$, $C_1$-$C_6$-alkyl, $C_3$-$C_6$-cycloalkyl, [tri-($C_1$-$C_6$)-alkylsilyl]-($C_2$-$C_6$)-alkynyl, and
wherein, when $R^a, R^b, R^c, R^d, R^e$, and $R^f$ are aliphatic, cyclic or aromatic substituents, said aliphatic, cyclic, or aromatic substituents are optionally partially or fully halogenated.

7. The method of claim 1, wherein $R^1$ is hydrogen or $C_1$-$C_6$-alkyl and $R^2$ is $C_1$-$C_6$alkyl, wherein $C_1$-$C_6$-alkyl in $R^1$ and $R^2$ is optionally partially or fully halogenated.

8. The method of claim 1, wherein
$R^3$ is $R^{26}$ or $OR^{27}$, wherein $R^{26}$ and $R^{27}$ are, independently of one another, hydrogen, $C_1$-$C_6$-alkyl, $C_1$-$C_6$-alkylcarbonyl, phenyl-$C_1$-$C_6$-alkyl, or phenylcarbonyl, wherein the aliphatic or aromatic moieties of these substituents are optionally partially or fully halogenated, or $SO_2R^{31}$, wherein
  $R^{31}$ is $C_1$-$C_6$-alkyl or phenyl, wherein phenyl is optionally partially or fully halogenated and/or are optionally mono-, di, or tri-substituted with $C_1$-$C_6$-alkyl groups.

9. The method of claim 1, wherein $R^4, R^5, R^6, R^7$, and $R^8$ are hydrogen.

10. The method of claim 1, wherein the two centers of chirality in the piperazine ring have the (S,S)-configuration.

* * * * *